(12) United States Patent
Paullin et al.

(10) Patent No.: US 11,535,683 B2
(45) Date of Patent: *Dec. 27, 2022

(54) OXIDIZED DEXTRAN

(71) Applicant: NUTRITION & BIOSCIENCES USA 4, INC., Rochester, NY (US)

(72) Inventors: Jayme L. Paullin, Claymont, DE (US); Rakesh Nambiar, West Chester, PA (US)

(73) Assignee: NUTRITION & BIOSCIENCES USA 4, INC., Rochester, NY (US)

( * ) Notice: Subject to any disclaimer, the term of this patent is extended or adjusted under 35 U.S.C. 154(b) by 0 days.

This patent is subject to a terminal disclaimer.

(21) Appl. No.: 17/029,516

(22) Filed: Sep. 23, 2020

(65) Prior Publication Data

US 2021/0155719 A1    May 27, 2021

Related U.S. Application Data

(63) Continuation of application No. 15/550,883, filed as application No. PCT/US2016/024580 on Mar. 28, 2016, now Pat. No. 10,787,524.

(60) Provisional application No. 62/142,649, filed on Apr. 3, 2015.

(51) Int. Cl.
| | | |
|---|---|---|
| *C08B 37/02* | (2006.01) | |
| *A23L 29/269* | (2016.01) | |
| *C11D 3/22* | (2006.01) | |
| *C11D 3/00* | (2006.01) | |
| *C12N 9/10* | (2006.01) | |
| *C08B 31/18* | (2006.01) | |
| *A61K 31/721* | (2006.01) | |
| *C08L 5/02* | (2006.01) | |

(52) U.S. Cl.
CPC ........ *C08B 37/0021* (2013.01); *A23L 29/273* (2016.08); *A61K 31/721* (2013.01); *C08B 31/18* (2013.01); *C08L 5/02* (2013.01); *C11D 3/0036* (2013.01); *C11D 3/223* (2013.01); *C12N 9/1048* (2013.01); *A23V 2002/00* (2013.01)

(58) Field of Classification Search
CPC ... C08B 37/0021; C08B 31/18; A23L 29/273; A61K 31/721; C08L 5/02; C11D 3/0036; C12N 9/1048; A23V 2002/00
USPC ........................................................ 536/112
See application file for complete search history.

(56) References Cited

U.S. PATENT DOCUMENTS

| | | | |
|---|---|---|---|
| 10,787,524 B2 * | 9/2020 | Paullin | A23L 29/273 |
| 2005/0059633 A1 * | 3/2005 | Van Geel-Schuten | C12P 19/08 514/54 |

OTHER PUBLICATIONS

Bragd et al. TEMPO-mediated oxidation of polysaccharides: survey of methods and applications. Topics in Catalysis vol. 27, Nos. 1-4, p. 49-66 Feb. 2004. (Year: 2004).*
NCBI Blast:Protein Sequence, BLAST ®» blastp suite » results for RID-WFBGR363014. (Nov. 10, 2019) (Year: 2019).*

* cited by examiner

*Primary Examiner* — Yih-Horng Shiao

(57) ABSTRACT

Compositions comprising oxidized dextran compounds are disclosed herein. Oxidized dextran compounds are produced by contacting dextran under aqueous conditions with at least one N-oxoammonium salt, at least one periodate compound, and/or at least one peroxide compound.

21 Claims, 4 Drawing Sheets

Figure 1:
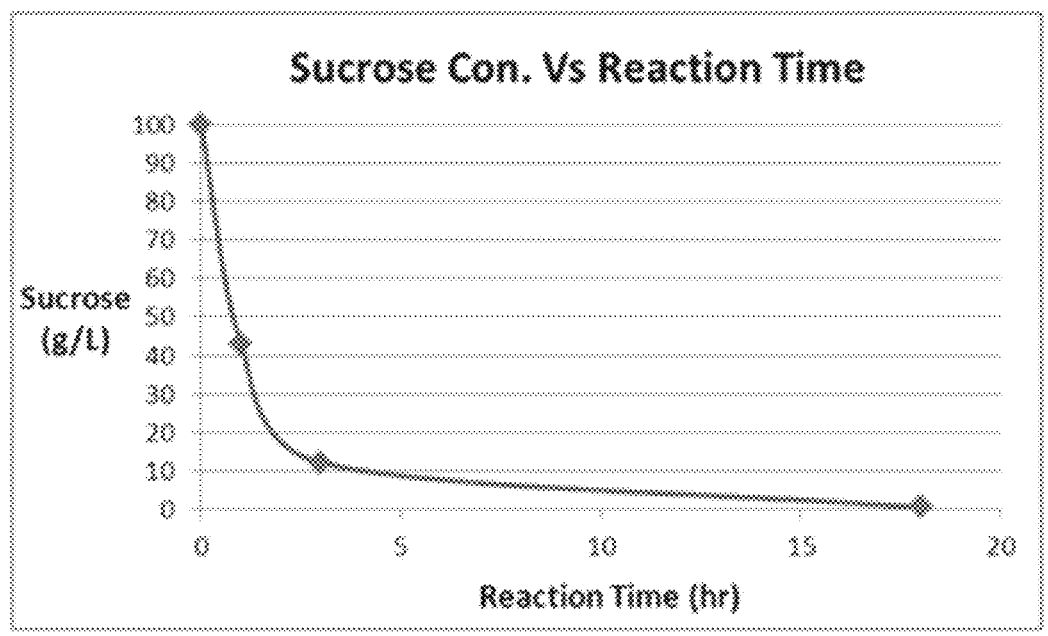

Specification includes a Sequence Listing.

OXIDIZED DEXTRAN

This application is a continuation of U.S. application Ser. No. 15/550,883 (filed Aug. 14, 2017, now U.S. patent Ser. No. 10/787,524), which is the National Stage application of International Application No. PCT/US2016/24580 (filed Mar. 28, 2016), which claims the benefit of U.S. Provisional Application No. 62/142,649 (filed Apr. 3, 2015), all of which prior applications are incorporated herein by reference in their entirety.

FIELD OF INVENTION

The present disclosure is in the field of polysaccharide derivatives. For example, the disclosure pertains to oxidized dextran compounds and methods of preparation thereof.

REFERENCE TO SEQUENCE LISTING SUBMITTED ELECTRONICALLY

The official copy of the sequence listing is transferred into the instant application from parent application Ser. No. 15/550,883. This sequence listing was submitted electronically in the parent application on Aug. 14, 2017 via EFS-Web as an ASCII-formatted sequence listing with a file having a size of about 164 kilobytes. The sequence listing contained in this transferred ASCII-formatted document is part of the specification and is herein incorporated by reference in its entirety.

BACKGROUND

Driven by a desire to find new structural polysaccharides using enzymatic syntheses or genetic engineering of microorganisms, researchers have discovered polysaccharides that are biodegradable and can be made economically from renewably sourced feedstocks. One such family of polysaccharides are alpha-glucans, which are polymers comprising glucose monomers linked by alpha-glycosidic bonds.

Dextrans represent a family of complex, branched alpha-glucans generally comprising chains of alpha-1,6-linked glucose monomers, with periodic side chains (branches) linked to the straight chains by alpha-1,3-linkage (Ioan et al., *Macromolecules* 33:5730-5739). Production of dextrans is typically done through fermentation of sucrose with bacteria (e.g., *Leuconostoc* or *Streptococcus* species), where sucrose serves as the source of glucose for dextran polymerization (Naessens et al., *J. Chem. Technol. Biotechnol.* 80:845-860; Sarwat et al., *Int. J. Biol. Sci.* 4:379-386; Onilude et al., *Int. Food Res. J.* 20:1645-1651). Although dextrans are used in several applications given their high solubility in water (e.g., adjuvants, stabilizers), this high solubility can negatively affect their general utility as thickening agents in hydrocolloid applications.

Thus, there is interest in developing new dextran polymers and derivatives thereof. These types of compounds, such as those now disclosed herein, have potential utility in various applications.

SUMMARY OF INVENTION

In one embodiment, the disclosure concerns a composition comprising an oxidized dextran compound, wherein the oxidized dextran compound is produced by contacting dextran under aqueous conditions with at least one N-oxoammonium salt, at least one periodate compound, and/or at least one peroxide compound, wherein the dextran comprises: (i) about 87-93 wt % glucose linked at positions 1 and 6; (ii) about 0.1-1.2 wt % glucose linked at positions 1 and 3; (iii) about 0.1-0.7 wt % glucose linked at positions 1 and 4; (iv) about 7.7-8.6 wt % glucose linked at positions 1, 3 and 6; and (v) about 0.4-1.7 wt % glucose linked at: (a) positions 1, 2 and 6, or (b) positions 1, 4 and 6; and wherein the weight-average molecular weight (Mw) of the dextran is about 50-200 million Daltons and the z-average radius of gyration of the dextran is about 200-280 nm.

In another embodiment, the dextran comprises: (i) about 89.5-90.5 wt % glucose linked at positions 1 and 6; (ii) about 0.4-0.9 wt % glucose linked at positions 1 and 3; (iii) about 0.3-0.5 wt % glucose linked at positions 1 and 4; (iv) about 8.0-8.3 wt % glucose linked at positions 1, 3 and 6; and (v) about 0.7-1.4 wt % glucose linked at: (a) positions 1, 2 and 6, or (b) positions 1, 4 and 6.

In another embodiment, the dextran comprises chains linked together within a branching structure, wherein chains are similar in length and comprise substantially alpha-1,6-glucosidic linkages. The average length of the chains is about 10-50 monomeric units in another embodiment.

In another embodiment, the dextran is a product of a glucosyltransferase enzyme comprising an amino acid sequence that is at least 90% identical to SEQ ID NO:1, SEQ ID NO:2, SEQ ID NO:5, SEQ ID NO:9, SEQ ID NO:13, or SEQ ID NO:17.

In another embodiment, the dextran is contacted with the periodate compound.

In another embodiment, the dextran is first contacted with the periodate compound, and then contacted with the N-oxoammonium salt.

In another embodiment, the N-oxoammonium salt comprises a TEMPO oxoammonium salt. The N-oxoammonium salt comprises a 4-acetamido-TEMPO oxoammonium salt in another embodiment.

In another embodiment, the dextran is contacted with the peroxide compound. The peroxide compound can be hydrogen peroxide in another embodiment.

In another embodiment, the composition is a household product, personal care product, industrial product, pharmaceutical product, or food product. The composition is a detergent composition in another embodiment. A detergent composition is preferably a household product, for example.

In another embodiment, the disclosure concerns a method for producing an oxidized dextran compound. This method comprises: contacting dextran under aqueous conditions with at least one N-oxoammonium salt, at least one periodate compound, and/or at least one peroxide compound, wherein the dextran is oxidized by the N-oxoammonium salt, periodate compound, and/or peroxide compound thereby producing an oxidized dextran compound. Dextran used in such a method can be as disclosed herein such as in the above embodiments. The oxidized dextran compound produced by this method can optionally be isolated.

In another embodiment of the method, the dextran is contacted with the periodate. In another embodiment, the dextran is first contacted with the periodate compound, and then contacted with the N-oxoammonium salt.

In another embodiment of the method, the N-oxoammonium salt comprises a TEMPO oxoammonium salt. The N-oxoammonium salt can comprise a 4-acetamido-TEMPO oxoammonium salt in another embodiment. In another embodiment, the TEMPO oxoammonium salt or 4-acetamido-TEMPO oxoammonium salt is provided in the method by oxidizing an agent comprising TEMPO under the aqueous conditions. The agent comprising TEMPO is 4-acetamido-TEMPO in another embodiment.

In another embodiment of the method, the dextran is contacted with the peroxide compound. The peroxide compound can be hydrogen peroxide in another embodiment.

In another embodiment, the aqueous conditions of the method are acidic or basic.

In another embodiment, the disclosure concerns a method of preparing an aqueous composition having increased builder and/or anti-redeposition capacity. This method comprises: contacting an oxidized dextran compound produced according to the present disclosure with an aqueous composition, wherein the builder and/or anti-redeposition capacity of the aqueous composition is increased by the oxidized dextran compound compared to the builder and/or anti-redeposition capacity of the aqueous composition as it existed before the contacting step.

In another embodiment, the disclosure concerns a method of treating a material. This method comprises: contacting a material with an aqueous composition comprising an oxidized dextran compound as presently disclosed.

BRIEF DESCRIPTION OF THE DRAWINGS AND SEQUENCES

FIG. 1: HPLC analysis of sucrose consumption by a glucosyltransferase reaction comprising 100 g/L sucrose and a 0768 gtf (SEQ ID NO:1). Refer to Example 2.

Figure 2A:
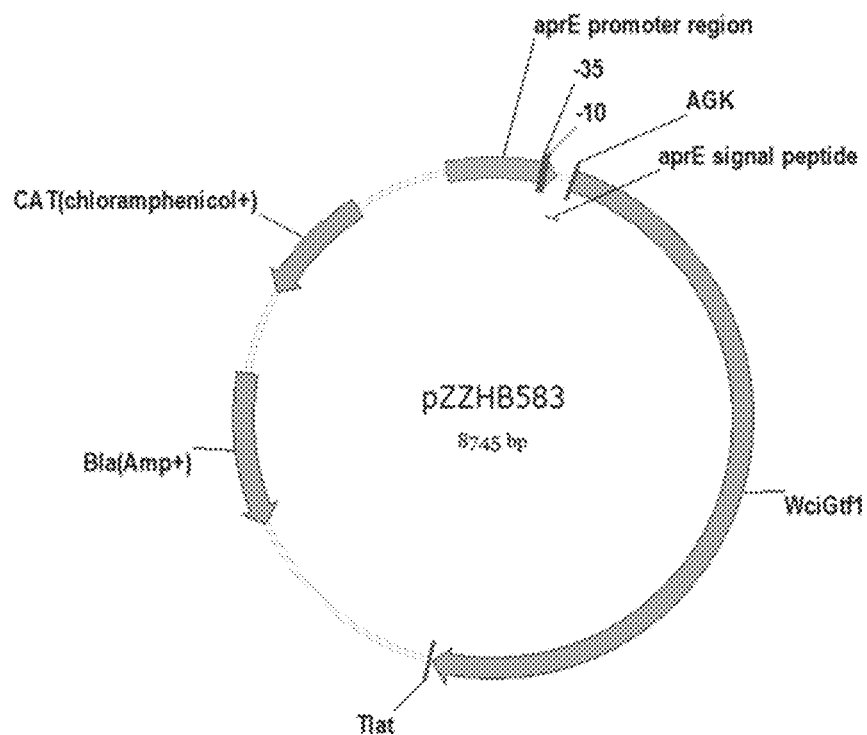

FIG. 2A: Map of plasmid pZZHB583 used to express 2919 gtf (SEQ ID NO:5) in *B. subtilis*. Refer to Example 3.

Figure 2B:
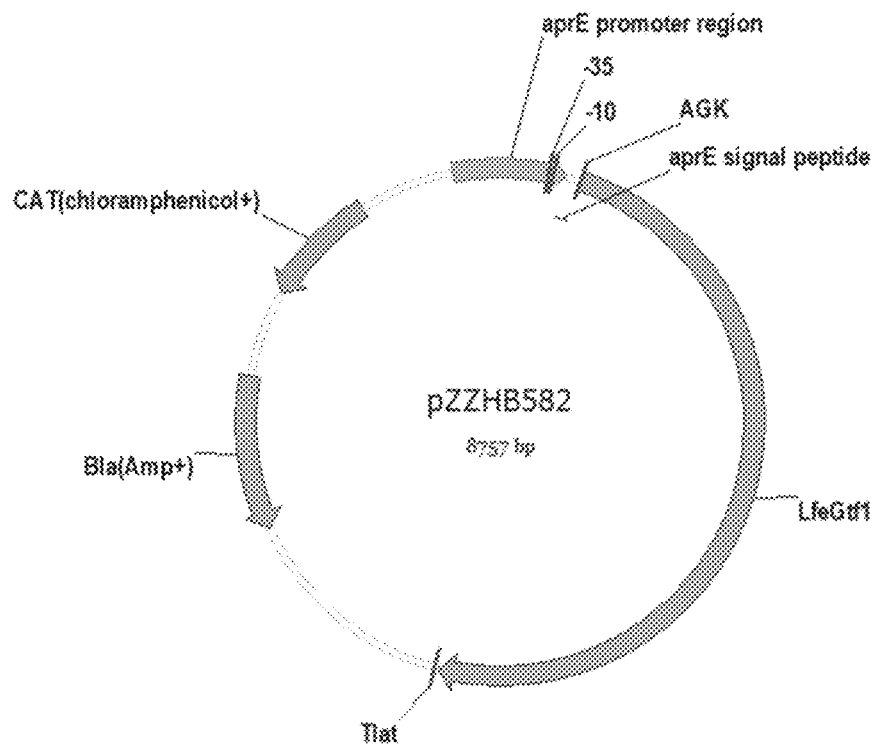

FIG. 2B: Map of plasmid pZZHB582 used to express 2918 gtf (SEQ ID NO:9) in *B. subtilis*. Refer to Example 4.

Figure 2C:
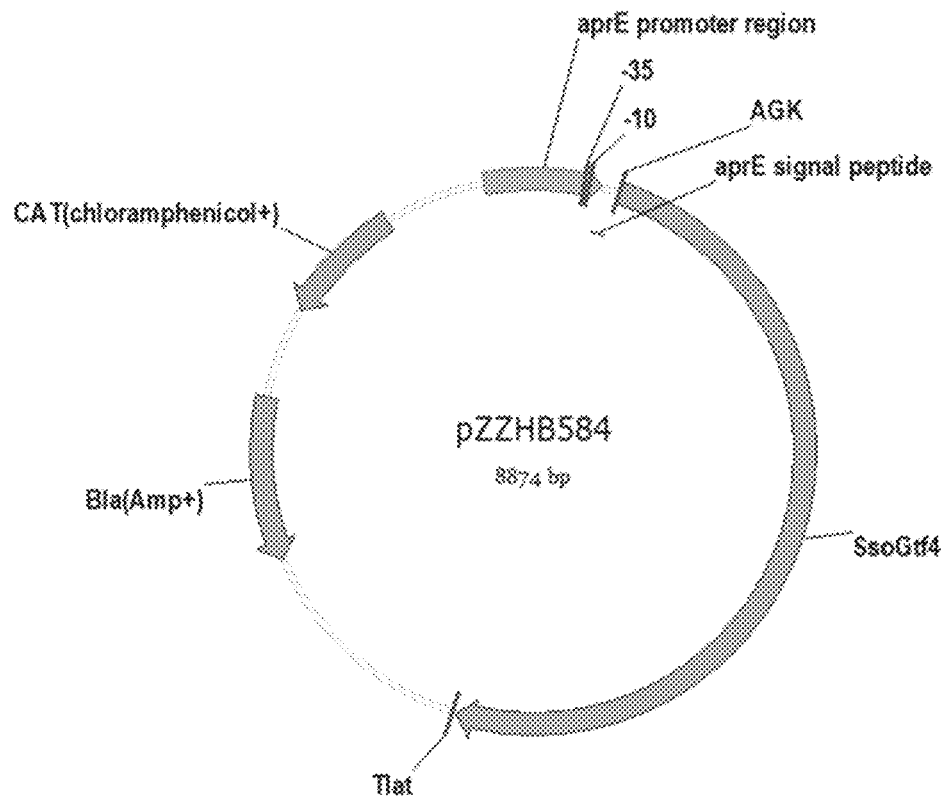

FIG. 2C: Map of plasmid pZZHB584 used to express 2920 gtf (SEQ ID NO:13) in *B. subtilis*. Refer to Example 5.

Figure 2D:
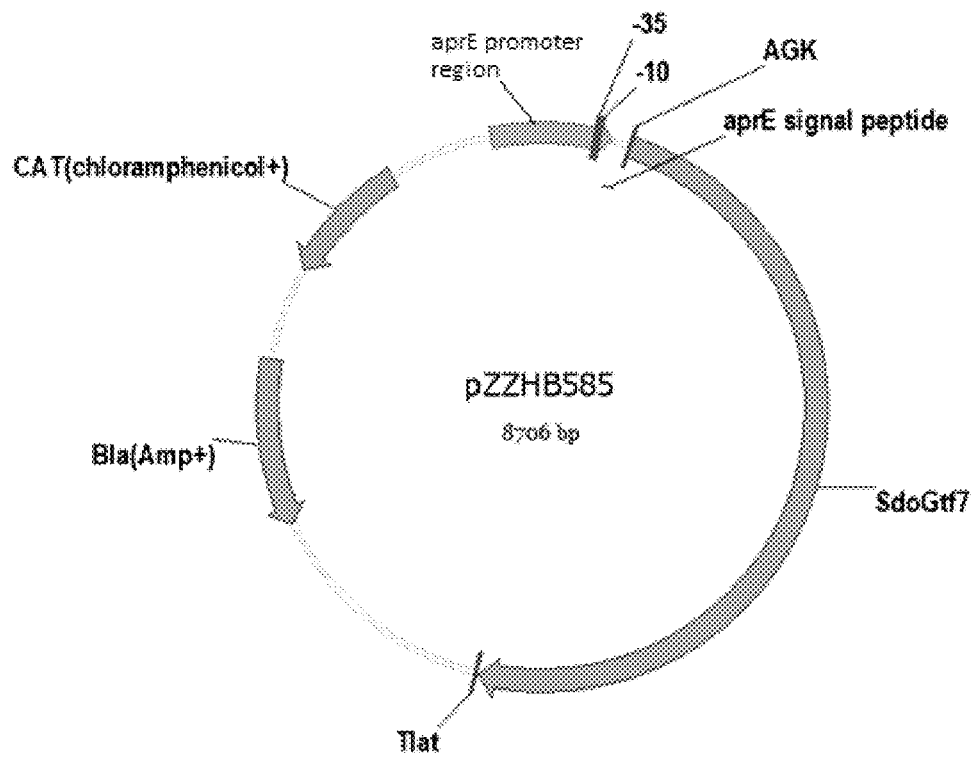

FIG. 2D: Map of plasmid pZZHB585 used to express 2921 gtf (SEQ ID NO:17) in *B. subtilis*. Refer to Example 6.

Figure 3:
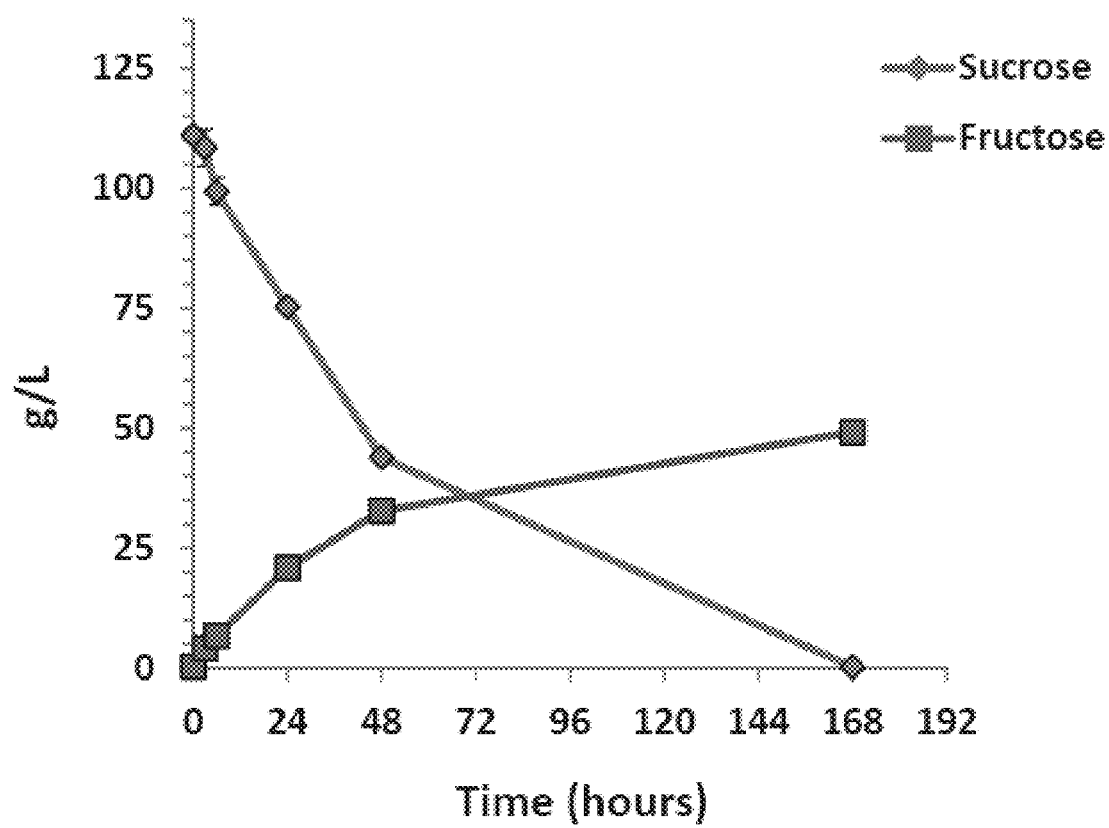

FIG. 3: HPLC analysis of sucrose consumption by a reaction comprising a commercially available dextran sucrase. Refer to Example 7.

TABLE 1

Summary of Nucleic Acid and Protein SEQ ID Numbers

| Description | Nucleic acid SEQ ID NO. | Protein SEQ ID NO. |
|---|---|---|
| "0768 gtf", *Leuconostoc pseudomesenteroides*. Mature form of GENBANK Identification No. 497964659. | | 1 (1447 aa) |
| "0768 gtf", *Leuconostoc pseudomesenteroides*. Mature form of GENBANK Identification No. 497964659, but including a start methionine and additional N- and C-terminal amino acids. | | 2 (1457 aa) |
| WciGtf1, *Weissella cibaria*. Full length form comprising signal sequence. GENBANK Accession No. ZP_08417432 (amino acid sequence). | 3 (4347 bases) | 4 (1448 aa) |
| "2919 gtf", *Weissella cibaria*. Mature form of GENBANK Identification No. ZP_08417432. | | 5 (1422 aa) |
| "2919 gtf", *Weissella cibaria*. Sequence optimized for expression in *B. subtilis*. Encodes 2919 gtf with a heterologous signal sequence and additional N-terminal amino acids. | 6 (4269 bases) | |
| LfeGtf1, *Lactobacillus fermentum*. Full length form comprising signal sequence. GENBANK Accession No. AAU08008 (amino acid sequence). | 7 (4392 bases) | 8 (1463 aa) |

TABLE 1-continued

Summary of Nucleic Acid and Protein SEQ ID Numbers

| Description | Nucleic acid SEQ ID NO. | Protein SEQ ID NO. |
|---|---|---|
| "2918 gtf", *Lactobacillus fermentum*. Mature form of GENBANK Identification No. AAU08008. | | 9 (1426 aa) |
| "2918 gtf", *Lactobacillus fermentum*. Sequence optimized for expression in *B. subtilis*. Encodes 2918 gtf with a heterologous signal sequence and additional N-terminal amino acids. | 10 (4281 bases) | |
| SsoGtf4, *Streptococcus sobrinus*. Full length form comprising signal sequence. GENBANK Accession No. AAX76986 (amino acid sequence). | 11 (4521 bases) | 12 (1506 aa) |
| "2920 gtf", *Streptococcus sobrinus*. Mature form of GENBANK Identification No. AAX76986. | | 13 (1465 aa) |
| "2920 gtf", *Streptococcus sobrinus*. Sequence optimized for expression in *B. subtilis*. Encodes 2920 gtf with a heterologous signal sequence and additional N-terminal amino acids. | 14 (4398 bases) | |
| SdoGtf7, *Streptococcus downei*. Full length form comprising signal sequence. GENBANK Accession No. ZP_08549987.1 (amino acid sequence). | 15 (4360 bases) | 16 (1453 aa) |
| "2921 gtf", *Streptococcus downei*. Mature form of GENBANK Identification No. ZP_08549987.1. | | 17 (1409 aa) |
| "2921 gtf", *Streptococcus downei*. Sequence optimized for expression in *B. subtilis*. Encodes 2921 gtf with a heterologous signal sequence and additional N-terminal amino acids. | 18 (4230 bases) | |

DETAILED DESCRIPTION

The disclosures of all patent and non-patent literature cited herein are incorporated herein by reference in their entirety.

Unless otherwise disclosed, the terms "a" and "an" as used herein are intended to encompass one or more (i.e., at least one) of a referenced feature.

Where present, all ranges are inclusive and combinable, except as otherwise noted. For example, when a range of "1 to 5" is recited, the recited range should be construed as including ranges "1 to 4", "1 to 3", "1-2", "1-2 & 4-5", "1-3 & 5", and the like.

The term "glucan" herein refers to a polysaccharide of D-glucose monomers that are linked by glucosidic linkages, which are a type of glycosidic linkage. An "alpha-glucan" herein refers to a glucan in which the constituent D-glucose monomers are alpha-D-glucose monomers.

The terms "dextran", "dextran polymer", "dextran compound" and the like are used interchangeably herein and refer to complex, branched alpha-glucans generally comprising chains of substantially (mostly) alpha-1,6-linked glucose monomers, with side chains (branches) linked mainly by alpha-1,3-linkage. The term "gelling dextran" herein refers to the ability of one or more dextrans disclosed herein to form a viscous solution or gel-like composition (i) during enzymatic dextran synthesis and, optionally, (ii) when such synthesized dextran is isolated (e.g., >90% pure) and then placed in an aqueous composition.

Dextran "long chains" herein can comprise "substantially [or mostly] alpha-1,6-glucosidic linkages", meaning that they can have at least about 98.0% alpha-1,6-glucosidic linkages in some aspects. Dextran herein can comprise a "branching structure" (branched structure) in some aspects. It is contemplated that in this structure, long chains branch from other long chains, likely in an iterative manner (e.g., a long chain can be a branch from another long chain, which in turn can itself be a branch from another long chain, and so on). It is contemplated that long chains in this structure can be "similar in length", meaning that the length (DP [degree of polymerization]) of at least 70% of all the long chains in a branching structure is within plus/minus 30% of the mean length of all the long chains of the branching structure.

Dextran in some embodiments can also comprise "short chains" branching from the long chains, typically being one to three glucose monomers in length, and comprising less than about 10% of all the glucose monomers of a dextran polymer. Such short chains typically comprise alpha-1,2-, alpha-1,3-, and/or alpha-1,4-glucosidic linkages (it is believed that there can also be a small percentage of such non-alpha-1,6 linkages in long chains in some aspects).

The terms "glycosidic linkage", "glycosidic bond" and the like are used interchangeably herein and refer to the covalent bond that joins a carbohydrate molecule to another carbohydrate molecule. The terms "glucosidic linkage", "glucosidic bond" and the like are used interchangeably herein and refer to a glycosidic linkage between two glucose molecules. The term "alpha-1,6-glucosidic linkage" as used herein refers to the covalent bond that joins alpha-D-glucose molecules to each other through carbons 1 and 6 on adjacent alpha-D-glucose rings. The term "alpha-1,3-glucosidic linkage" as used herein refers to the covalent bond that joins alpha-D-glucose molecules to each other through carbons 1 and 3 on adjacent alpha-D-glucose rings. The term "alpha-1,2-glucosidic linkage" as used herein refers to the covalent bond that joins alpha-D-glucose molecules to each other through carbons 1 and 2 on adjacent alpha-D-glucose rings. The term "alpha-1,4-glucosidic linkage" as used herein refers to the covalent bond that joins alpha-D-glucose molecules to each other through carbons 1 and 4 on adjacent alpha-D glucose rings. Herein, "alpha-D-glucose" will be referred to as "glucose." All glucosidic linkages disclosed herein are alpha-glucosidic linkages, except where otherwise noted.

"Glucose (glucose monomers) linked at positions 1 and 6" herein refers to a glucose monomer of dextran in which only carbons 1 and 6 of the glucose monomer are involved in respective glucosidic linkages with two adjacent glucose monomers. This definition likewise applies to glucose (i) "linked at positions 1 and 3", and (ii) "linked at positions 1 and 4", taking into account, accordingly, the different carbon positions involved in each respective linkage.

"Glucose (glucose monomers) linked at positions 1, 3 and 6" herein refers to a glucose monomer of dextran in which carbons 1, 3 and 6 of the glucose monomer are involved in respective glucosidic linkages with three adjacent glucose monomers. A glucose linked only at positions 1, 3 and 6 is a branch point. This definition likewise applies to glucose linked at (i) positions 1, 2 and 6, and (ii) positions 1, 4 and 6, but taking into account, accordingly, the different carbon positions involved in each respective linkage.

Glucose positions (glucose carbon positions) 1, 2, 3, 4 and 6 herein are as known in the art (depicted in the following structure):

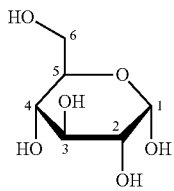

The glycosidic linkage profile of a dextran herein can be determined using any method known in the art. For example, a linkage profile can be determined using methods that use nuclear magnetic resonance (NMR) spectroscopy (e.g., $^{13}$C NMR or $^1$H NMR). These and other methods that can be used are disclosed in *Food Carbohydrates: Chemistry, Physical Properties, and Applications* (S. W. Cui, Ed., Chapter 3, S. W. Cui, Structural Analysis of Polysaccharides, Taylor & Francis Group LLC, Boca Raton, Fla., 2005), which is incorporated herein by reference.

The term "sucrose" herein refers to a non-reducing disaccharide composed of an alpha-D-glucose molecule and a beta-D-fructose molecule linked by an alpha-1,2-glycosidic bond. Sucrose is known commonly as table sugar.

The "molecular weight" of a dextran or oxidized dextran compound herein can be represented as number-average molecular weight ($M_n$) or as weight-average molecular weight ($M_w$), the units of which are in Daltons or grams/mole. Alternatively, molecular weight can be represented as $DP_w$ (weight average degree of polymerization) or $DP_n$ (number average degree of polymerization). Various means are known in the art for calculating these molecular weight measurements such as with high-pressure liquid chromatography (HPLC), size exclusion chromatography (SEC), or gel permeation chromatography (GPC).

The term "radius of gyration" (Rg) herein refers to the mean radius of dextran, and is calculated as the root-mean-square distance of a dextran molecule's components (atoms) from the molecule's center of gravity. Rg can be provided in Angstrom or nanometer (nm) units, for example. The "z-average radius of gyration" of dextran herein refers to the Rg of dextran as measured using light scattering (e.g., MALS). Methods for measuring z-average Rg are known and can be used herein, accordingly. For example, z-average Rg can be measured as disclosed in U.S. Pat. No. 7,531,073, U.S. Patent Appl. Publ. Nos. 2010/0003515 and 2009/0046274, Wyatt (*Anal. Chim. Acta* 272:1-40), and Mori and Barth (Size Exclusion Chromatography, Springer-Verlag, Berlin, 1999), all of which are incorporated herein by reference.

The terms "glucosyltransferase enzyme", "gtf enzyme", "gtf enzyme catalyst", "gtf", "glucansucrase" and the like are used interchangeably herein. The activity of a gtf enzyme herein catalyzes the reaction of the substrate sucrose to make the products glucan and fructose. A gtf enzyme that produces a dextran (a type of glucan) can also be referred to as a dextransucrase. Other products (byproducts) of a gtf reaction can include glucose (where glucose is hydrolyzed from the glucosyl-gtf enzyme intermediate complex), and various soluble oligosaccharides (e.g., DP2-DP7) such as leucrose. Wild type forms of glucosyltransferase enzymes generally contain (in the N-terminal to C-terminal direction) a signal peptide, a variable domain, a catalytic domain, and a glucan-binding domain. A gtf herein is classified under the glycoside hydrolase family 70 (GH70) according to the CAZy (Carbohydrate-Active Enzymes) database (Cantarel et al., *Nucleic Acids Res.* 37:D233-238, 2009).

The terms "glucosyltransferase catalytic domain" and "catalytic domain" are used interchangeably herein and refer to the domain of a glucosyltransferase enzyme that provides glucan-producing activity to the glucosyltransferase enzyme.

The terms "gtf reaction", "gtf reaction solution", "glucosyltransferase reaction", "enzymatic reaction", "dextran synthesis reaction", "dextran reaction" and the like are used interchangeably herein and refer to a reaction that is performed by a glucosyltransferase enzyme. A gtf reaction as used herein generally refers to a reaction initially comprising at least one active glucosyltransferase enzyme in a solution comprising sucrose and water, and optionally other components. Other components that can be in a gtf reaction after it has commenced include fructose, glucose, soluble oligosaccharides (e.g., DP2-DP7) such as leucrose, and dextran products. It is in a gtf reaction where the step of contacting water, sucrose and a glucosyltransferase enzyme is performed. The term "under suitable gtf reaction conditions" as used herein, refers to gtf reaction conditions that support conversion of sucrose to dextran via glucosyltransferase enzyme activity. A gtf reaction herein is not naturally occurring.

A "control" gtf reaction as used herein can refer to a reaction using a glucosyltransferase not comprising an amino acid sequence that is at least 90% identical to SEQ ID NO:1, SEQ ID NO:2, SEQ ID NO:5, SEQ ID NO:9, SEQ ID NO:13, or SEQ ID NO:17. All the other features (e.g., sucrose concentration, temperature, pH, time) of a control reaction solution can be the same as the reaction to which it is being compared.

The "percent dry solids" of a gtf reaction refers to the wt % of all the sugars in a gtf reaction. The percent dry solids of a gtf reaction can be calculated, for example, based on the amount of sucrose used to prepare the reaction.

The "yield" of dextran by a gtf reaction herein represents the weight of dextran product expressed as a percentage of the weight of sucrose substrate that is converted in the reaction. For example, if 100 g of sucrose in a reaction solution is converted to products, and 10 g of the products is dextran, the yield of the dextran would be 10%. This yield calculation can be considered as a measure of selectivity of the reaction toward dextran.

The terms "polynucleotide", "polynucleotide sequence", and "nucleic acid sequence" are used interchangeably herein. These terms encompass nucleotide sequences and the like. A polynucleotide may be a polymer of DNA or RNA that is single- or double-stranded, that optionally contains synthetic, non-natural or altered nucleotide bases. A polynucleotide may be comprised of one or more segments of cDNA, genomic DNA, synthetic DNA, or mixtures thereof.

The terms "sequence identity" or "identity" as used herein with respect to polynucleotide or polypeptide sequences refer to the nucleic acid bases or amino acid residues in two sequences that are the same when aligned for maximum correspondence over a specified comparison window. Thus, "percentage of sequence identity" or "percent identity" refers to the value determined by comparing two optimally aligned sequences over a comparison window, wherein the portion of the polynucleotide or polypeptide sequence in the comparison window may comprise additions or deletions (i.e., gaps) as compared to the reference sequence (which does not comprise additions or deletions) for optimal alignment of the two sequences. The percentage is calculated by determining the number of positions at which the identical nucleic acid base or amino acid residue occurs in both sequences to yield the number of matched positions, dividing the number of matched positions by the total number of positions in the window of comparison and multiplying the results by 100 to yield the percentage of sequence identity. It would be understood that, when calculating sequence identity between a DNA sequence and an RNA sequence, T residues of the DNA sequence align with, and can be considered "identical" with, U residues of the RNA sequence. For purposes of determining percent complementarity of first and second polynucleotides, one can obtain this by determining (i) the percent identity between the first polynucleotide and the complement sequence of the second polynucleotide (or vice versa), for example, and/or (ii) the percentage of bases between the first and second polynucleotides that would create canonical Watson and Crick base pairs.

The Basic Local Alignment Search Tool (BLAST) algorithm, which is available online at the National Center for Biotechnology Information (NCBI) website, may be used, for example, to measure percent identity between or among two or more of the polynucleotide sequences (BLASTN algorithm) or polypeptide sequences (BLASTP algorithm) disclosed herein. Alternatively, percent identity between sequences may be performed using a Clustal algorithm (e.g., ClustalW, ClustalV, or Clustal-Omega). For multiple alignments using a Clustal method of alignment, the default values may correspond to GAP PENALTY=10 and GAP LENGTH PENALTY=10. Default parameters for pairwise alignments and calculation of percent identity of protein sequences using a Clustal method may be KTUPLE=1, GAP PENALTY=3, WINDOW=5 and DIAGONALS SAVED=5. For nucleic acids, these parameters may be KTUPLE=2, GAP PENALTY=5, WINDOW=4 and DIAGONALS SAVED=4. Alternatively still, percent identity between sequences may be performed using an EMBOSS algorithm (e.g., needle) with parameters such as GAP OPEN=10, GAP EXTEND=0.5, END GAP PENALTY=false, END GAP OPEN=10, END GAP EXTEND=0.5 using a BLOSUM matrix (e.g., BLOSUM62).

Various polypeptide amino acid sequences and polynucleotide sequences are disclosed herein as features of certain embodiments. Variants of these sequences that are at least about 70-85%, 85-90%, or 90%-95% identical to the sequences disclosed herein can be used. Alternatively, a variant amino acid sequence or polynucleotide sequence can have at least 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98% or 99% identity with a sequence disclosed herein. The variant amino acid sequence or polynucleotide sequence may have the same function/activity of the disclosed sequence, or at least about 85%, 86%, 87%, 88%, 89%, 90%, 91%, 92%, 93%, 94%, 95%, 96%, 97%, 98%, or 99% of the function/activity of the disclosed sequence.

The terms "oxidized dextran compound", "oxidized dextran derivative", "oxidized dextran" and the like are used interchangeably herein. An oxidized dextran compound herein is a compound resulting from oxidation of one or more of the hydroxyl groups of the glucose monomeric units of a dextran. This oxidation may independently convert each of these hydroxyl groups to an aldehyde, ketone, or carboxylic group. Dextran can be oxidized herein by contacting it with one or more oxidizing/oxidation agents (e.g., an N-oxoammonium salt, periodate compound, and/or peroxide compound) under aqueous conditions, for example. It is believed that oxidized dextran as disclosed herein can also be prepared via application of other oxidation processes, if desired, such as processes disclosed in Canadian Patent Publ. Nos. 2028284 and 2038640, and U.S. Pat. Nos. 4,985,553, 2,894,945, 5,747,658 and 7,595,392, all of which are incorporated herein by reference.

The term "oxidized" as used herein characterizes a compound, or atom within a compound, from which electrons have been removed. The carbon of a primary alcohol group ($R-CH_2-OH$) in a glucose monomeric unit (position 6) in a dextran herein (e.g., in a side-chain in which a glucose may be linked by an alpha-1,2-, alpha-1,3-, or alpha-1,4-glucosidic linkage) can be oxidized to an aldehyde ($R-CHO$) or carboxylic acid (R—COOH). The carbon of a secondary alcohol group ($R_1R_2$CH—OH) in a glucose monomeric unit of a dextran herein can be oxidized to a ketone ($R_1R_2$CH=OH). Alternatively, a secondary alcohol group ($R_1R_2$CH—OH) in a glucose monomeric unit of a dextran herein can be oxidized to an aldehyde or carboxylic acid group, in which case the glucose monomeric ring unit of dextran is opened (i.e., no longer cyclic).

An "agent for oxidizing dextran" (and similar terms) herein can comprise an N-oxoammonium salt, a periodate, and/or a peroxide compound, for example.

The terms "N-oxoammonium salt" and "oxoammonium salt" are used interchangeably herein. An N-oxoammonium salt herein refers to the following structure:

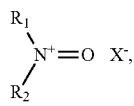
(structure I)

where $R^1$ and $R^2$ each represent the same or different organic groups (e.g., a linear or branched carbon chain), and $X^-$ is a counterion. Alternatively, $R^1$ and $R^2$ can each be part of the same group bound to the $N^+$, in which case $N^+$ is part of a ring structure. An example herein of an N-oxoammonium salt having a ring structure (i.e., a "cyclic N-oxoammonium salt") is a TEMPO oxoammonium salt.

The term "TEMPO oxoammonium salt" herein refers to the following structure:

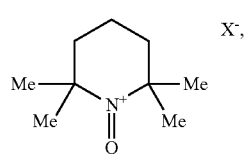
(structure II)

where each Me represents a methyl group and $X^-$ is a counterion. An example of an N-oxoammonium salt comprising TEMPO oxoammonium salt is 4-acetamido-TEMPO oxoammonium salt.

The terms "4-acetamido-TEMPO oxoammonium salt", "4-acimido-TEMPO oxoammonium salt" and the like are used interchangeably herein. 4-acetamido-TEMPO oxoammonium salt herein refers to the following structure:

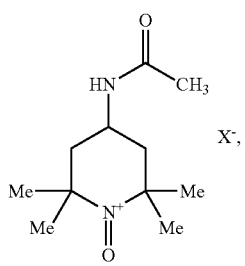
(structure III)

where each Me represents a methyl group and $X^-$ is a counterion.

An "agent comprising TEMPO" herein refers to an agent/compound comprising 2,2,6,6-tetramethylpiperidine 1-oxyl (TEMPO). TEMPO has the following structure:

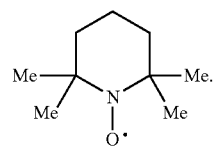
(structure IV)

Examples of agents comprising TEMPO are TEMPO itself and 4-acetamido-TEMPO. "4-acetamido-TEMPO" (alternatively referred to as "4-acimido-TEMPO") has the following structure:

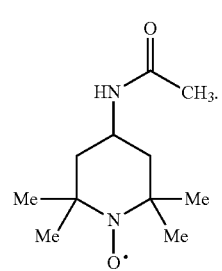
(structure V)

An agent comprising TEMPO can be oxidized to its corresponding N-oxoammonium salt. For example, TEMPO can be oxidized to TEMPO oxoammonium salt, and 4-acetamido-TEMPO can be oxidized to 4-acetamido-TEMPO oxoammonium salt. Thus, a "precursor of an N-oxoammonium salt" such as TEMPO or 4-acetamido-TEMPO, can be used to provide an N-oxoammonium salt in an oxidation reaction as disclosed herein.

The terms "periodate", "periodate compound" and the like are used interchangeably herein and refer to a salt of periodic acid containing the monovalent anion $IO^-$. An example of a periodate herein is sodium periodate (e.g., sodium metaperiodate[$NaIO_4$]).

The terms "peroxide", "peroxide compound" and the like are used interchangeably herein and refer to a compound containing an oxygen-oxygen (O—O) single bond or a peroxide anion ($O_2^{-2}$). The O—O group is called the peroxide group (peroxo group). Hydrogen peroxide ($H_2O_2$) is an example of a peroxide compound herein.

The terms "oxidation reaction", "oxidation reaction preparation", "oxidation reaction composition" and the like are used interchangeably herein and refer to a reaction under aqueous conditions comprising at least dextran and an N-oxoammonium salt, a periodate, and/or a peroxide. A reaction preparation herein typically begins and ends as a solution, given that dextran and oxidized dextran compounds disclosed herein are soluble in aqueous compositions. An oxidation reaction is conducted under suitable conditions (e.g., time, temperature, pH) for the N-oxoammonium salt, periodate, and/or a peroxide to oxidize one or more hydroxyl groups of the glucose monomeric units of dextran, thereby yielding an oxidized dextran compound.

The terms "aqueous conditions", "aqueous reaction conditions", "aqueous setting", "aqueous system" and the like are used interchangeably herein. Aqueous conditions herein refer to a solution or mixture in which the solvent is at least about 60 wt % water, for example. An oxidation reaction herein can be performed under aqueous conditions. Aqueous conditions can be acidic or basic, for example.

The terms "acidic", "acidic conditions", "acidic aqueous conditions" and the like are used interchangeably herein. Acidic conditions herein can refer to a solution or mixture pH of 5.5 or less, for example. Acidic conditions can be prepared by any means known in the art, such as by adding acetic acid and/or an acetate salt to a solution or mixture.

The terms "basic", "basic conditions", "basic aqueous conditions", "alkaline" and the like are used interchangeably herein. Basic conditions herein can refer to a solution or mixture pH of 8.5 or more, for example. Basic conditions can be prepared by any means known in the art, such as by adding sodium hydroxide to a solution or mixture.

An "aqueous composition" herein has a liquid component that comprises at least about 10 wt % water, for example. Examples of aqueous compositions include mixtures, solutions, dispersions (e.g., colloidal dispersions), suspensions and emulsions, for example. Aqueous compositions in certain embodiments comprise oxidized dextran that is (i) dissolved in the aqueous composition (i.e., in solution), or (ii) not dissolved in the aqueous composition (e.g., present as a colloidal dispersion).

As used herein, the term "colloidal dispersion" refers to a heterogeneous system having a dispersed phase and a dispersion medium, i.e., microscopically dispersed insoluble particles (e.g., some forms of oxidized dextran herein) are suspended throughout another substance (e.g., an aqueous composition such as water or aqueous solution). An example of a colloidal dispersion herein is a hydrocolloid. All, or a portion of, the particles of a colloidal dispersion such as a hydrocolloid can comprise certain oxidized dextran compounds of the present disclosure. The terms "dispersant" and "dispersion agent" are used interchangeably herein to refer to a material that promotes the formation and/or stabilization of a dispersion.

The terms "hydrocolloid" and "hydrogel" are used interchangeably herein. A hydrocolloid refers to a colloid system in which water or an aqueous solution is the dispersion medium.

The term "aqueous solution" herein refers to a solution in which the solvent comprises water. An aqueous solution can serve as a dispersant in certain aspects herein. Oxidized dextran compounds in certain embodiments can be dissolved, dispersed, or mixed within an aqueous solution.

The term "viscosity" as used herein refers to the measure of the extent to which a fluid or an aqueous composition resists a force tending to cause it to flow. Various units of viscosity that can be used herein include centipoise (cPs) and Pascal-second (Pa.$). One poise is equal to 0.100 kg·m$^{-1}$·s$^{-1}$, or 1 mPa·s. Thus, the terms "viscosity modifier" and "viscosity-modifying agent" as used herein refer to anything that can alter/modify the viscosity of a fluid or aqueous composition.

The term "shear thinning behavior" as used herein refers to a decrease in the viscosity of an aqueous composition as shear rate increases. The term "shear thickening behavior" as used herein refers to an increase in the viscosity of an aqueous composition as shear rate increases. "Shear rate" herein refers to the rate at which a progressive shearing deformation is applied to an aqueous composition. A shearing deformation can be applied rotationally, for example.

The term "contacting" as used herein with respect to methods of increasing the builder capacity and/or anti-redeposition capacity of an aqueous composition refers to any action that results in bringing together an aqueous composition with at least one oxidized dextran compound as presently disclosed. Contacting can be performed by any means known in the art, such as mixing, shaking, or homogenization, for example.

The terms "fabric", "textile", "cloth" and the like are used interchangeably herein to refer to a woven material having a network of natural and/or artificial fibers. Such fibers can be in the form of thread or yarn, for example.

A "fabric care composition" herein is any composition suitable for treating fabric in some manner. Examples of such a composition include laundry detergents and fabric softeners.

The terms "heavy duty detergent", "all-purpose detergent" and the like are used interchangeably herein to refer to a detergent useful for regular washing of white and colored textiles at any temperature. The terms "low duty detergent", "fine fabric detergent" and the like are used interchangeably herein to refer to a detergent useful for the care of delicate fabrics such as viscose, wool, silk, microfiber or other fabric requiring special care. "Special care" can include conditions of using excess water, low agitation, and/or no bleach, for example.

A "detergent composition" herein typically comprises at least one surfactant (detergent compound) and/or at least one builder. A "surfactant" herein refers to a substance that tends to reduce the surface tension of a liquid in which the substance is dissolved. A surfactant may act as a detergent, wetting agent, emulsifier, foaming agent, and/or dispersant, for example.

The terms "builder", "builder agent" and the like herein refer to compositions such as oxidized dextran that, for example, can complex with hard water cations such as calcium and magnesium cations. Such complex formation is believed to prevent the formation of water-insoluble salt(s) by the cation(s). While not intending to be held to any particular theory, it is believed that oxidized dextran herein orchestrates builder activity through cation sequestration (chelation) or cation exchange. In the context of a detergent composition for cleaning applications, a builder added thereto typically can enhance or maintain the cleaning efficiency of a surfactant present in the detergent composition. The terms "builder capacity", "builder activity" and the like are used interchangeably herein and refer to the ability of an aqueous composition to exhibit features endowed by one or more builders (e.g., oxidized dextran) present in the aqueous composition.

The terms "anti-redeposition agent", "anti-soil redeposition agent", "anti-greying agent" and the like herein refer to agents that help keep soils from redepositing onto clothing in laundry wash water after these soils have been removed, therefore preventing greying/discoloration of laundry. Anti-redeposition agents can function by helping keep soil dispersed in wash water and/or by blocking attachment of soil onto fabric surfaces.

An "oral care composition" herein is any composition suitable for treating a soft or hard surface in the oral cavity such as dental (teeth) and/or gum surfaces.

The term "adsorption" herein refers to the adhesion of a compound (e.g., oxidized dextran herein) to the surface of a material.

The terms "cellulase", "cellulase enzyme" and the like are used interchangeably herein to refer to an enzyme that hydrolyzes beta-1,4-D-glucosidic linkages in cellulose, thereby partially or completely degrading cellulose. Cellulase can alternatively be referred to as "beta-1,4-glucanase", for example, and can have endocellulase activity (EC 3.2.1.4), exocellulase activity (EC 3.2.1.91), or cellobiase activity (EC 3.2.1.21). "Cellulose" refers to an insoluble polysaccharide having a linear chain of beta-1,4-linked D-glucose monomeric units.

The terms "percent by volume", "volume percent", "vol %", "v/v %" and the like are used interchangeably herein. The percent by volume of a solute in a solution can be determined using the formula: [(volume of solute)/(volume of solution)]×100%.

The terms "percent by weight", "weight percentage (wt %)", "weight-weight percentage (% w/w)" and the like are used interchangeably herein. Percent by weight refers to the percentage of a material on a mass basis as it is comprised in a composition, mixture or solution.

The term "increased" as used herein can refer to a quantity or activity that is at least about 1%, 2%, 3%, 4%, 5%, 6%, 7%, 8%, 9%, 10%, 11%, 12%, 13%, 14%, 15%, 16%, 17%, 18%, 19%, 20%, 50%, 100%, or 200% more than the quantity or activity for which the increased quantity or activity is being compared. The terms "increased", "elevated", "enhanced", "greater than", "improved" and the like are used interchangeably herein.

The term "isolated" as used herein refers to material (e.g., oxidized dextran) that has been completely or partially purified. Oxidized dextran compounds of the present disclosure are synthetic, man-made compounds. Such compounds are believed (i) not to occur in nature, and/or (ii) to have properties that do not occur naturally.

There is interest in developing new dextran polymers and oxidized derivatives thereof. These types of compounds, such as those now disclosed herein, have potential utility in various applications.

Embodiments of the present disclosure concern a composition comprising an oxidized dextran compound produced by contacting dextran under aqueous conditions with at least one N-oxoammonium salt, at least one periodate compound, and/or at least one peroxide, wherein the dextran comprises:
  (i) about 87-93 wt % glucose linked at positions 1 and 6;
  (ii) about 0.1-1.2 wt % glucose linked at positions 1 and 3;
  (iii) about 0.1-0.7 wt % glucose linked at positions 1 and 4;
  (iv) about 7.7-8.6 wt % glucose linked at positions 1, 3 and 6;
  (v) about 0.4-1.7 wt % glucose linked at: (a) positions 1, 2 and 6, or (b) positions 1, 4 and 6; and
  (vi) a degree of substitution (DoS) with at least one organic group of about 0.0025 to about 3.0;
  wherein the weight-average molecular weight (Mw) of the dextran is about 50-200 million Daltons and the z-average radius of gyration of the dextran is about 200-280 nm.

Thus, oxidized dextran is disclosed. Significantly, such compounds are typically soluble in aqueous compositions, and can, for example, be used to provide builder activity and/or anti-redeposition activity to detergent compositions.

An oxidized dextran compound herein is a compound resulting from oxidation of one or more of the hydroxyl groups of the glucose monomeric units of dextran. Such oxidation may occur in all, or in at least 60%, 65%, 70%, 75%, 80%, 85%, 90%, 95%, 96%, 97%, 98%, or 99% (or any integer between 60% and 100%), of the constituent glucose monomeric units of dextran, for example.

It is believed that oxidation occurring at a primary alcohol group of a glucose monomeric unit of dextran herein converts the hydroxyl group to an aldehyde or carboxylic group. Typically, enhanced oxidation conditions (e.g., increased oxidation reaction time and/or amount of N-oxoammonium salt) may lead to conversion of a primary alcohol group to a carboxylic group, whereas weaker oxidation conditions may lead to conversion of a primary alcohol group to an aldehyde group. Given the structure of dextran as presently disclosed, it is contemplated that oxidation events at primary alcohol groups occur largely within side-chains, which can comprise alpha-1,2-, alpha-1,3-, and/or alpha-1,4-glucosidic linkages (such linked glucose units would have a position 6 hydroxyl group, which represents a primary alcohol group. The glucose units of the main chain of dextran herein are mostly alpha-1,6-linked and therefore have few or no hydroxyl groups at position 6 (i.e., few or no primary alcohol groups).

It is believed that oxidation occurring at a secondary alcohol group of a glucose monomeric unit of dextran herein converts the hydroxyl group to a ketone, aldehyde, or carboxylic group. Typically, enhanced oxidation conditions (e.g., increased oxidation reaction time and/or amount of N-oxoammonium salt) may lead to conversion of a secondary alcohol group to a carboxylic group. Weaker oxidation conditions may lead to conversion of a secondary alcohol group to an aldehyde group or ketone group, which are both less oxidized than a carboxylic group.

Oxidation of a secondary alcohol group of a glucose monomeric unit of dextran to an aldehyde group or carboxylic acid group would open the glucose monomeric ring (i.e., the glucose unit would no longer be cyclic). Such ring opening would be attributable to breaking a carbon-carbon bond. Oxidation of secondary alcohol groups of dextran to aldehyde and/or carboxylic groups may produce an oxidized dextran product in which all or at least about 50%, 60%, 70%, 80%, or 90% (or any integer between 50% and 100%) of the constituent glucose monomeric ring units of the dextran have been opened, for example. In general, as more glucose monomeric ring units are opened by oxidation, the molecular weight of the oxidized product decreases, since there is an increased chance of polymer fission (breakdown) by the ring-opening events.

An oxidized dextran compound is produced herein, for example, by contacting dextran as presently disclosed with at least one N-oxoammonium salt. In certain embodiments, the N-oxoammonium salt comprises a TEMPO oxoammonium salt. Examples of such an N-oxoammonium salt include TEMPO oxoammonium salt itself (structure II) and 4-acetamido-TEMPO oxoammonium salt (structure III). Structure II is comprised within structure III.

Noting that structures II and III are cyclic, an N-oxoammonium salt herein can be a "cyclic N-oxoammonium salt" (or "cyclic oxoammonium salt"). A cyclic N-oxoammonium salt herein can be represented by the following structure:

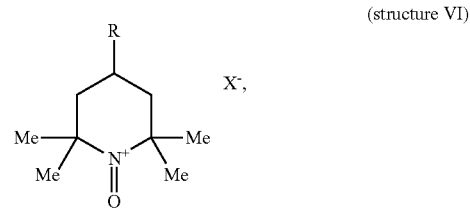

(structure VI)

where each Me represents a methyl group, X⁻ is a counterion, and R is a hydrogen (H), acetamido group (—NH—CO—CH$_3$), hydroxyl (—OH), amino (—NH$_2$), carboxyl (—COOH), methoxy (—OCH$_3$), cyano (—CN), oxo (═O), phosphonooxy [—O—PO(OH)$_2$], acetoxy (—O—CO—CH$_3$), benzoyloxy, acetamino, maleimido, or isothiocyanato group. It would be understood that where R in structure VI is an H, the cyclic N-oxoammonium salt is TEMPO oxoammonium salt. Examples of structure VI in which R is a moiety other than an H represent TEMPO oxoammonium salt that is substituted at carbon position 4 (where the N$^+$ in structure VI is position 1 in the ring). For example, where R is an acetamido group, the cyclic N-oxoammonium salt of structure VI is 4-acetamido-TEMPO oxoammonium salt. Thus, for example, an N-oxoammonium salt herein can be TEMPO oxoammonium salt having a substitution at carbon position 4 (where the N$^+$ in the ring of the TEMPO oxoammonium salt is position 1).

A TEMPO oxoammonium salt can be provided in certain embodiments by oxidizing an agent comprising TEMPO in the aqueous conditions in which the TEMPO oxoammonium salt is contacted with dextran. An agent comprising TEMPO is an agent/compound comprising structure IV. Examples of an agent comprising TEMPO are TEMPO itself (structure IV) and 4-acetamido-TEMPO (structure V). Other examples of agents comprising TEMPO can be represented by the following structure:

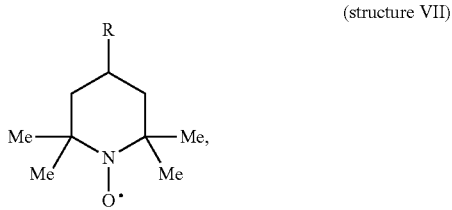

(structure VII)

where each Me represents a methyl group and R is a hydrogen (H), acetamido group (—NH—CO—CH$_3$), hydroxyl (—OH), amino (—NH$_2$), carboxyl (—COOH), methoxy (—OCH$_3$), cyano (—CN), oxo (=O), phosphonooxy [—O—PO(OH)$_2$], acetoxy (—O—CO—CH$_3$), benzoyloxy, acetamino, maleimido, or isothiocyanato group. Each of these agents can be converted to its corresponding oxoammonium salt, as represented by structure VI, by contacting it with one or more oxidation agents under aqueous conditions. Thus, structure VI can also be considered as a precursor of an N-oxoammonium salt. TEMPO and its derivatives, such as above (e.g., 4-acetamido-TEMPO), are examples of cyclic nitroxyl compounds. Thus, a cyclic nitroxyl compound can be used to provide a TEMPO oxoammonium salt herein.

An agent comprising TEMPO can be oxidized under aqueous conditions herein to its corresponding oxoammonium salt by contacting the agent with one or more "oxidation agents" (or "oxidant"). This contacting can be performed in the same aqueous conditions in which dextran is contacted with an N-oxoammonium salt. In some embodiments, a reaction herein for oxidizing dextran can initially be prepared to comprise, under aqueous conditions, at least dextran, an agent comprising TEMPO (e.g., structure VII), and one or more oxidation agents. The oxidation agent(s) can convert the agent comprising TEMPO to its corresponding oxoammonium salt (e.g., structure VI), which in turn can oxidize the dextran.

Non-limiting examples of an oxidation agent include one or more "inorganic oxidation agents" (or "inorganic oxidant"). An inorganic oxidation agent herein is not an oxoammonium salt such as a TEMPO oxoammonium salt since such compounds contain organic components (refer to structures I-III, for example). Examples of oxidation agents that may be used to convert an agent comprising TEMPO to its corresponding oxoammonium salt include one or more of a halite (e.g., a chlorite, such as sodium chlorite [NaClO$_2$]) or a hypohalite (e.g., a hypochlorite, such as sodium hypochlorite [NaClO]). Other examples of oxidation agents (inorganic or organic) that may be used to convert an agent comprising TEMPO to its corresponding oxoammonium salt include one or more of a halide salt such as KCl, KBr, NaCl, NaBr, or NaI; a hypohalite such as NaOBr; metals such as Fe(III), Mn(II), Mn(III), or Cu(II); KMnO$_4$; Mn(OAc)$_3$; Mn$_2$O$_3$; MnO$_2$; Mn(NO$_3$)$_2$; MgCl$_2$; Mg(OAc)$_2$; or Cu(NO$_3$)$_2$; iodobenzene diacetate [PhI(OAc)$_2$]; Ca(ClO)$_2$; t-BuOCl; CuCl—O$_2$; NaBrO$_2$; Cl$_2$; Br$_2$; and trichloroisocyanuric acid.

An oxidized dextran compound can be produced herein, for example, by contacting dextran as presently disclosed with at least one periodate compound. A periodate compound can be a metal periodate (e.g., sodium periodate or potassium periodate), for example. A periodate compound can be a metaperiodate (e.g., NaIO$_4$) or an orthoperiodate in some aspects. Conditions for oxidizing dextran with a periodate compound can follow those conditions as disclosed in U.S. Pat. Nos. 3,086,969, 6,800,753, 5,747,658 and/or 6635755, which are all disclosed herein by reference, and/or as disclosed in Examples 10 and 11 below, for example.

In some aspects herein, an oxidized dextran compound is produced by first contacting dextran with a periodate compound, followed by contacting the periodate-oxidized dextran with an N-oxoammonium salt. Such a sequential oxidation treatment can follow any of the processes disclosed herein, such as in Example 11 below.

An dextran compound can be produced herein, for example, by contacting dextran with at least one peroxide compound. A peroxide compound can be hydrogen peroxide, for example. In some aspects, a peroxide compound can be an inorganic peroxide compound or an organic peroxide compound. Suitable peroxide compounds herein further include perborate-monohydrate, perborate-tetrahydrate, percarbonates, alkali persulphates, persilicates, and percitrates, in which sodium or calcium is the preferred cation, as well as hydrogen peroxide adducts of urea or amine oxides, for example.

In some aspects herein, an oxidized dextran compound is produced by first contacting dextran with a peroxide compound, followed by contacting the peroxide-oxidized dextran with an N-oxoammonium salt.

A dextran in certain embodiments can be contacted with a peroxide compound in the absence of a chelating agent (e.g., EDTA), whereas in other embodiments a chelating agent can optionally be present.

Aqueous conditions are used in reactions disclosed herein for oxidizing dextran. Aqueous conditions herein refer to a solution or mixture in which the solvent is at least about 60 wt % water. Alternatively, aqueous conditions herein are at least about 65, 70, 75, 80, 85, 90, or 95 wt % water (or any integer value between 60 and 95 wt %), for example. Aqueous conditions herein can comprise a buffer, such as an acidic, neutral, or alkaline buffer, at a suitable concentration and selected based on the pH range provided by the buffer. Examples of buffers include citric acid, acetic acid, KH$_2$PO$_4$, CHES and borate.

Aqueous conditions herein can be acidic, having a pH of 5.5 or less, for example. Alternatively, the pH may be about 2.0, 2.5, 3.0, 3.5, 4.0, 4.5, 5.0, or 5.5, for example. Acidic conditions can be prepared by any means known in the art, such as by adding acetic acid and/or an acetate salt to a solution or mixture. For example, a sodium acetate buffer (acetate buffer) (pH 4-5) (e.g., 0.2-0.3 M solution) can provide acidic conditions.

Aqueous conditions herein can be basic, having a pH of 8.5 or more, for example. Alternatively, the pH may be about 8.5, 9.0, 9.5, 10.0, 10.5, 11.0, 11.5, or 12, for example. Basic conditions can be prepared by any means known in the art, such as by adding an alkaline hydroxide (e.g., sodium hydroxide) to a solution or mixture.

Dextran herein can be included in an oxidation reaction at about, or at least about, 0.1, 0.25, 0.5, 0.75, 1, 2, 3, 4, 5, 6, 7, 8, 9, 10, 11, or 12 wt % of the reaction, for example. Dextran can be mixed or dissolved in aqueous conditions before or after an agent comprising a periodate compound, peroxide compound, TEMPO and/or an oxidation agent (which converts the agent comprising TEMPO to its corresponding oxoammonium salt) is added to the aqueous conditions. The oxidation agent in these particular embodiments can be sodium chlorite and/or sodium hypochlorite, for example.

An agent comprising TEMPO, such as TEMPO and/or 4-acetamido-TEMPO, can be included in an oxidation reaction herein at about, or at least about, 0.05, 0.075, 0.1, 0.25, 0.5, 0.75, 1, or 2 wt % of the reaction, for example. In certain embodiments, an agent comprising TEMPO can be added to a reaction in which dextran has already been mixed or dissolved. Such addition may be made before, after, or at the time an oxidation agent is added to the reaction.

An oxidation agent such as sodium chlorite, sodium bromide, and/or sodium hypochlorite can be included in a reaction herein at about, or at least about, 0.1, 0.25, 0.5, 0.75, 1, 2, 3, 4, 5, 10, 15, 20, 25, 30, 35, 40, 45, or 50 wt % of the reaction, for example. In certain embodiments, an oxidation agent(s) can be added to a reaction in which dextran has already been mixed or dissolved.

An oxidation reaction in certain embodiments may initially contain dextran, an agent comprising TEMPO (e.g., 4-acetamido-TEMPO), and one or more oxidation agents (e.g., sodium chlorite, sodium bromide, and/or sodium hypochlorite) dissolved in a buffer solution (e.g., sodium acetate buffer at a pH of about 4-5) or other solution (e.g., sodium hydroxide solution at a pH of about 10.5-11.5). Optionally, no additional components are included in preparing this particular reaction.

A dextran herein that can be oxidized to produce an oxidized dextran compound may comprise (i) about 87-93 wt % glucose linked only at positions 1 and 6; (ii) about 0.1-1.2 wt % glucose linked only at positions 1 and 3; (iii) about 0.1-0.7 wt % glucose linked only at positions 1 and 4; (iv) about 7.7-8.6 wt % glucose linked only at positions 1, 3 and 6; and (v) about 0.4-1.7 wt % glucose linked only at: (a) positions 1, 2 and 6, or (b) positions 1, 4 and 6. In certain embodiments, a dextran can comprise (i) about 89.5-90.5 wt % glucose linked only at positions 1 and 6; (ii) about 0.4-0.9 wt % glucose linked only at positions 1 and 3; (iii) about 0.3-0.5 wt % glucose linked only at positions 1 and 4; (iv) about 8.0-8.3 wt % glucose linked only at positions 1, 3 and 6; and (v) about 0.7-1.4 wt % glucose linked only at: (a) positions 1, 2 and 6, or (b) positions 1, 4 and 6.

Dextran in some aspects can comprise about 87, 87.5, 88, 88.5, 89, 89.5, 90, 90.5, 91, 91.5, 92, 92.5, or 93 wt % glucose linked only at positions 1 and 6. There can be about 87-92.5, 87-92, 87-91.5, 87-91, 87-90.5, 87-90, 87.5-92.5, 87.5-92, 87.5-91.5, 87.5-91, 87.5-90.5, 87.5-90, 88-92.5, 88-92, 88-91.5, 88-91, 88-90.5, 88-90, 88.5-92.5, 88.5-92, 88.5-91.5, 88.5-91, 88.5-90.5, 88.5-90, 89-92.5, 89-92, 89-91.5, 89-91, 89-90.5, 89-90, 89.5-92.5, 89.5-92, 89.5- 91.5, 89.5-91, or 89.5-90.5 wt % glucose linked only at positions 1 and 6, in some instances.

Dextran in some aspects can comprise about 0.1, 0.2, 0.3, 0.4, 0.5, 0.6, 0.7, 0.8, 0.9, 1.0, 1.1, or 1.2 wt % glucose linked only at positions 1 and 3. There can be about 0.1-1.2, 0.1-1.0, 0.1-0.8, 0.3-1.2, 0.3-1.0, 0.3-0.8, 0.4-1.2, 0.4-1.0, 0.4-0.8, 0.5-1.2, 0.5-1.0, 0.5-0.8, 0.6-1.2, 0.6-1.0, or 0.6-0.8 wt % glucose linked only at positions 1 and 3, in some instances.

Dextran in some aspects can comprise about 0.1, 0.2, 0.3, 0.4, 0.5, 0.6, or 0.7 wt % glucose linked only at positions 1 and 4. There can be about 0.1-0.7, 0.1-0.6, 0.1-0.5, 0.1-0.4, 0.2-0.7, 0.2-0.6, 0.2-0.5, 0.2-0.4, 0.3-0.7, 0.3-0.6, 0.3-0.5, or 0.3-0.4 wt % glucose linked only at positions 1 and 4, in some instances.

Dextran in some aspects can comprise about 7.7, 7.8, 7.9, 8.0, 8.1, 8.2, 8.3, 8.4, 8.5, or 8.6 wt % glucose linked only at positions 1, 3 and 6. There can be about 7.7-8.6, 7.7-8.5, 7.7-8.4, 7.7-8.3, 7.7-8.2, 7.8-8.6, 7.8-8.5, 7.8-8.4, 7.8-8.3, 7.8-8.2, 7.9-8.6, 7.9-8.5, 7.9-8.4, 7.9-8.3, 7.9-8.2, 8.0-8.6, 8.0-8.5, 8.0-8.4, 8.0-8.3, 8.0-8.2, 8.1-8.6, 8.1-8.5, 8.1-8.1, 8.1-8.3, or 8.1-8.2 wt % glucose linked only at positions 1, 3 and 6, in some instances.

Dextran in some aspects can comprise about 0.4, 0.5, 0.6, 0.7, 0.8, 0.9, 1.0, 1.1, 1.2, 1.3, 1.4, 1.5, 1.6, or 1.7 wt % glucose linked only at (a) positions 1, 2 and 6, or (b) positions 1, 4 and 6. There can be about 0.4-1.7, 0.4-1.6, 0.4-1.5, 0.4-1.4, 0.4-1.3, 0.5-1.7, 0.5-1.6, 0.5-1.5, 0.5-1.4, 0.5-1.3, 0.6-1.7, 0.6-1.6, 0.6-1.5, 0.6-1.4, 0.6-1.3, 0.7-1.7, 0.7-1.6, 0.7-1.5, 0.7-1.4, 0.7-1.3, 0.8-1.7, 0.8-1.6, 0.8-1.5, 0.8-1.4, 0.8-1.3 wt % glucose linked only at (a) positions 1, 2 and 6, or (b) positions 1, 4 and 6, in some instances.

The linkage profile of dextran in some aspects can be determined following any protocol disclosed herein. An example of a suitable linkage determination protocol can be similar to, or the same as, the protocol disclosed in Example 9: For example, an 0768 gtf enzyme reaction that has been deactivated by heating the reaction at about 70-90° C. (e.g., 80° C.) for about 5-30 minutes (e.g., 10 minutes) is placed into dialysis tubing (e.g., made with regenerated cellulose) with an MWCO of 12-14 kDa (e.g., Spectra/Por® 4 Dialysis Tubing, Part No. 132706, Spectrum Laboratories, Inc.). The deactivated reaction is then dialyzed against a large volume of water (e.g., 3-5 L) at about 20-25° C. (room temp) over about 4-10 days (e.g., 7 days); this water can be exchanged every day during the dialysis. The dextran product is then (i) precipitated by mixing the dialyzed deactivated reaction with about 1-2×(1.5×) reaction volume of 100% methanol, (ii) washed at least two times with the same volume of 100% methanol, and (iii) dried at about 40-50° C. (e.g., 45° C.) (optionally under a vacuum). A dissolvable amount of dry dextran is dissolved in dimethyl sulfoxide (DMSO) or DMSO/5% LiCl, after which all free hydroxyl groups are methylated (e.g., by sequential addition of a NaOH/DMSO slurry followed with iodomethane). The methylated dextran is then extracted (e.g., into methylene chloride) and hydrolyzed to monomeric units using aqueous trifluoroacetic acid (TFA) at about 110-125° C. (e.g., 120° C.). The TFA is then evaporated and reductive ring opening is done using sodium borodeuteride. The hydroxyl groups created by hydrolyzing the glycosidic linkages are then acetylated by treating with acetyl chloride and TFA at a temperature of about 40-60° C. (e.g., 50° C.). Next, the derivatizing reagents are evaporated and the resulting methylated/acetylated monomers are reconstituted in acetonitrile; this preparation is then analyzed by GC/MS using an appropriate column (e.g., biscyanopropyl cyanopropylphenyl polysiloxane). The relative positioning of the methyl and acetyl functionalities render species with distinctive retention time indices and mass spectra that can be compared to published databases. In this way, the derivatives of the monomeric units indicate how each monomer was originally linked in the dextran polymer.

Dextran used to produce an oxidized dextran compound herein is contemplated to have a branched structure in which there are long chains (containing mostly or all alpha-1,6-linkages) that iteratively branch from each other (e.g., a long chain can be a branch from another long chain, which in turn can itself be a branch from another long chain, and so on). The branched structure may also comprise short branches from the long chains; these short chains are believed to mostly comprise alpha-1,3 and -1,4 linkages, for example. Branch points in the dextran, whether from a long chain branching from another long chain, or a short chain branching from a long chain, appear to comprise alpha-1,3, -1,4, or -1,2 linkages off of a glucose involved in alpha-1,6 linkage. On average, about 20%, 21%, 22%, 23%, 24%, 25%, 26%, 27%, 28%, 29%, 30%, 15-35%, 15-30%, 15-25%, 15-20%, 20-35%, 20-30%, 20-25%, 25-35%, or 25-30% of all branch points of dextran in some embodiments branch into long chains. Most (>98% or 99%) or all the other branch points branch into short chains.

The long chains of a dextran branching structure can be similar in length in some aspects. By being similar in length, it is meant that the length (DP) of at least 70%, 75%, 80%, 85%, or 90% of all the long chains in a branching structure is within plus/minus 15% (or 10%, 5%) of the mean length of all the long chains of the branching structure. In some aspects, the mean length (average length) of the long chains is about 10-50 DP (i.e., 10-50 glucose monomers). For example, the mean individual length of the long chains can be about 10, 15, 16, 17, 18, 19, 20, 21, 22, 23, 24, 25, 30, 35, 40, 45, 50, 10-50, 10-40, 10-30, 10-25, 10-20, 15-50, 15-40, 15-30, 15-25, 15-20, 20-50, 20-40, 20-30, or 20-25 DP.

Dextran long chains in certain embodiments can comprise substantially alpha-1,6-glucosidic linkages and a small amount (less than 2.0%) of alpha-1,3- and/or alpha-1,4-glucosidic linkages. For example, dextran long chains can comprise about, or at least about, 98%, 98.25%, 98.5%, 98.75%, 99%, 99.25%, 99.5%, 99.75%, or 99.9% alpha-1,6-glucosidic linkages. A dextran long chain in certain embodiments does not comprise alpha-1,4-glucosidic linkages (i.e., such a long chain has mostly alpha-1,6 linkages and a small amount of alpha-1,3 linkages). Conversely, a dextran long chain in some embodiments does not comprise alpha-1,3-glucosidic linkages (i.e., such a long chain has mostly alpha-1,6 linkages and a small amount of alpha-1,4 linkages). Any dextran long chain of the above embodiments may further not comprise alpha-1,2-glucosidic linkages, for example. Still in some aspects, a dextran long chain can comprise 100% alpha-1,6-glucosidic linkages (excepting the linkage used by such long chain to branch from another chain).

Short chains of dextran in some aspects are one to three glucose monomers in length and comprise less than about 5-10% of all the glucose monomers of the dextran polymer. At least about 90%, 91%, 92%, 93%, 94%, 95%, 96%, 97%, 98%, 99%, or all of, short chains herein are 1-3 glucose monomers in length. The short chains of dextran can comprise less than about 10%, 9%, 8%, 7%, 6%, 5%, 4%, 3%, 2%, or 1% of all the glucose monomers of the dextran, for example.

Short chains of dextran in some aspects can comprise alpha-1,2-, alpha-1,3-, and/or alpha-1,4-glucosidic linkages. Short chains, when considered all together (not individually) may comprise (i) all three of these linkages, or (ii) alpha-1,3- and alpha-1,4-glucosidic linkages, for example. It is believed that short chains of dextran herein can be heterogeneous (i.e., showing some variation in linkage profile) or homogeneous (i.e., sharing similar or same linkage profile) with respect to the other short chains of the dextran.

Dextran used to produce an oxidized dextran compound in certain embodiments can have an Mw of about, or at least about, 50, 55, 60, 65, 70, 75, 80, 85, 90, 95, 100, 105, 110, 115, 120, 125, 130, 135, 140, 145, 150, 155, 160, 165, 170, 175, 180, 185, 190, 195, or 200 million (or any integer between 50 and 200 million) (or any range between two of these values). The Mw of dextran can be about 50-200, 60-200, 70-200, 80-200, 90-200, 100-200, 110-200, 120-200, 50-180, 60-180, 70-180, 80-180, 90-180, 100-180, 110-180, 120-180, 50-160, 60-160, 70-160, 80-160, 90-160, 100-160, 110-160, 120-160, 50-140, 60-140, 70-140, 80-140, 90-140, 100-140, 110-140, 120-140, 50-120, 60-120, 70-120, 80-120, 90-120, 100-120, 110-120, 50-110, 60-110, 70-110, 80-110, 90-110, 100-110, 50-100, 60-100, 70-100, 80-100, 90-100, or 95-105 million, for example.

Dextran used to produce an oxidized dextran compound in certain embodiments can have a z-average radius of gyration (Rg) of about 200-280 nm. For example, the z-average Rg can be about 200, 205, 210, 215, 220, 225, 230, 235, 240, 245, 250, 255, 260, 265, 270, 275, or 280 nm (or any integer between 200-280 nm). As other examples, the z-average Rg can be about 200-280, 200-270, 200-260, 200-250, 200-240, 200-230, 220-280, 220-270, 220-260, 220-250, 220-240, 220-230, 230-280, 230-270, 230-260, 230-250, 230-240, 240-280, 240-270, 240-260, 240-250, 250-280, 250-270, or 250-260 nm.

The Mw and/or z-average Rg of dextran in some aspects can be measured following a protocol similar to, or the same as, the protocol disclosed in Example 9. For example, a Mw and/or z-average Rg herein can be measured by first dissolving dextran produced by an 0768 gtf at 0.4-0.6 mg/mL (e.g., ~0.5 mg/mL) in 0.05-1.0 M (e.g., ~0.075 M) Tris (hydroxymethyl)aminomethane buffer with 150-250 ppm (e.g., ~200 ppm) $NaN_3$. Solvation of dry dextran can be achieved by shaking for 12-18 hours at 45-55° C. (e.g., ~50° C.). The resulting dextran solution can be entered into a suitable flow injection chromatographic apparatus comprising a separation module (e.g., Alliance™ 2695 separation module from Waters Corporation, Milford, Mass.) coupled with three online detectors: a differential refractometer (e.g., Waters 2414 refractive index detector), a multiangle light scattering (MALS) photometer (e.g., Heleos™-2 18-angle multiangle MALS photometer) equipped with a quasielastic light scatering (QELS) detector (e.g., QELS detector from Wyatt Technologies, Santa Barbara, Calif.), and a differential capillary viscometer (e.g., ViscoStar™ differential capillary viscometer from Wyatt). Two suitable size-exclusion columns (e.g., AQUAGEL-OH GUARD columns from Agilent Technologies, Santa Clara, Calif.) can be used to separate the dextran polymer peak from the injection peak, where the mobile phase can be the same as the sample solvent (above), the flow rate can be about 0.2 mL/min, the injection volumes can be about 0.1 mL, and column temperature can be about 30° C. Suitable software can be used for data acquisition (e.g., Empower™ version 3 software from Waters) and for multidetector data reduction (Astra™ version 6 software from Wyatt). MALS data can provide Mw and z-average Rg, and QELS data can provide z-average hydrodynamic radius, for example.

A dextran from which an oxidized dextran compound herein can be produced can be a product of a glucosyltransferase enzyme comprising, or consisting of, an amino acid sequence that is 100% identical to, or at least 90%, 91%, 92%, 93%, 94%, 95%, 96%, 97%, 98%, or 99% identical to, SEQ ID NO:1, SEQ ID NO:2, SEQ ID NO:5, SEQ ID NO:9, SEQ ID NO:13, or SEQ ID NO:17 (and have gtf activity). Non-limiting examples of a glucosyltransferase enzyme comprising SEQ ID NO:1 (or a related sequence) include glucosyltransferase enzymes comprising, or consisting of, an amino acid sequence that is 100% identical to, or at least 90%, 91%, 92%, 93%, 94%, 95%, 96%, 97%, 98%, or 99% identical to, SEQ ID NO:2 (and have gtf activity). Production of dextran can be accomplished with a gtf reaction as disclosed herein, for example. Dextran as disclosed in the instant detailed description (e.g., molecular weight, linkage and branching profile) can optionally be characterized as a product of a glucosyltransferase enzyme comprising or consisting of SEQ ID NO:1 or 2 (or a related sequence thereof that is at least 90% identical [above]). In some other aspects, a glucosyltransferase enzyme comprises or consists of an amino acid sequence that is 100% identical to, or at least 90%, 91%, 92%, 93%, 94%, 95%, 96%, 97%, 98%, or 99% identical to, the secreted portion (i.e., signal peptide removed) of the amino acid sequence encoded by SEQ ID NO:6, 10, 14, or 18.

A glucosyltransferase enzyme herein may be from various microbial sources, such as a bacteria or fungus. Examples of bacterial glucosyltransferase enzymes are those derived from a *Streptococcus* species, *Leuconostoc* species, *Lactobacillus* species, or *Weissella* species. Examples of *Streptococcus* species include *S. sobrinus, S. downei, S. salivarius, S. dentirousetti, S. mutans, S. oralis, S. gallolyticus* and *S. sanguinis*. Examples of *Leuconostoc* species include *L. pseudomesenteroides, L. amelibiosum, L. argentinum, L. carnosum, L. citreum, L. cremoris, L. dextranicum* and *L. fructosum*. Examples of *Lactobacillus* species include *L. fermentum, L. acidophilus, L. delbrueckii, L. helveticus, L. salivarius, L. casei, L. curvatus, L. plantarum, L. sakei, L. brevis, L. buchneri* and *L. reuteri*. Examples of *Weissella* species include *W. cibaria, W. confusa, W. halotolerans, W. hellenica, W. kandleri, W. kimchii, W. koreensis, W. minor, W. paramesenteroides, W. soli* and *W. thailandensis*. A glucosyltransferase in some aspects is not from *L. mesenteroides*; thus in some aspects dextran used to produce an oxidized dextran compound is not a product of a *Leuconostoc mesenteroides* glucosyltransferase enzyme.

Examples of glucosyltransferase enzymes herein can be any of the amino acid sequences disclosed herein and that further include 1-300 (or any integer there between [e.g., 10, 15, 20, 25, 30, 35, 40, 45, or 50]) residues on the N-terminus and/or C-terminus. Such additional residues may be from a corresponding wild type sequence from which the glucosyltransferase enzyme is derived, or may be a heterologous sequence such as an epitope tag (at either N- or C-terminus) or a heterologous signal peptide (at N-terminus), for example.

A glucosyltransferase enzyme used to produce dextran herein is typically in a mature form lacking an N-terminal signal peptide. An expression system for producing a mature glucosyltransferase enzyme herein may employ an enzyme-encoding polynucleotide that further comprises sequence encoding an N-terminal signal peptide to direct extra-cellular secretion. The signal peptide in such embodiments is cleaved from the enzyme during the secretion process. The signal peptide may either be native or heterologous to the glucosyltransferase. An example of a signal peptide useful herein is one from a bacterial (e.g., a *Bacillus* species such as *B. subtilis*) or fungal species. An example of a bacterial signal peptide is an aprE signal peptide, such as one from *Bacillus* (e.g., *B. subtilis*, see Vogtentanz et al., *Protein Expr. Purif.* 55:40-52, which is incorporated herein by reference).

SEQ ID NO:1, SEQ ID NO:5, SEQ ID NO:9, SEQ ID NO:13 and SEQ ID NO:17 are examples of mature glucosyltransferase enzymes that lack an N-terminal signal peptide. Since these and related amino acid sequences do not begin with a methionine residue, it would be understood that an N-terminal start-methionine is preferably added to the sequence (directly or via an intervening heterologous amino acid sequence such as an epitope) if expressing any of these enzymes without using a signal peptide (such as with an expression system where the enzyme is expressed intracellularly and obtained from a cell lysate).

A glucosyltransferase enzyme in certain embodiments can be produced by any means known in the art. For example, a glucosyltransferase enzyme can be produced recombinantly in a heterologous expression system, such as a microbial heterologous expression system. Examples of heterologous expression systems include bacterial (e.g., *E. coli* such as TOP10, MG1655, or BL21 DE3; *Bacillus* sp. such as *B. subtilis*) and eukaryotic (e.g., yeasts such as *Pichia* sp. and *Saccharomyces* sp.) expression systems.

A glucosyltransferase enzyme disclosed herein may be used in any purification state (e.g., pure or non-pure). For example, the glucosyltransferase enzyme may be purified and/or isolated prior to its use. Examples of glucosyltransferase enzymes that are non-pure include those in the form of a cell lysate. A cell lysate or extract may be prepared from a bacteria (e.g., *E. coli*) used to heterologously express the enzyme. For example, the bacteria may be subjected to disruption using a French pressure cell. In alternative embodiments, bacteria may be homogenized with a homogenizer (e.g., APV, Rannie, Gaulin). A glucosyltransferase enzyme is typically soluble in these types of preparations. A bacterial cell lysate, extract, or homogenate herein may be used at about 0.15-0.3% (v/v) in a reaction for producing dextran from sucrose.

The activity of a glucosyltransferase enzyme herein can be determined using any method known in the art. For example, glucosyltransferase enzyme activity can be determined by measuring the production of reducing sugars (fructose and glucose) in a reaction containing sucrose (~50 g/L), dextran T10 (~1 mg/mL) and potassium phosphate buffer (~pH 6.5, 50 mM), where the solution is held at ~22-25° C. for ~24-30 hours. The reducing sugars can be measured by adding 0.01 mL of the reaction to a mixture containing ~1 N NaOH and ~0.1% triphenyltetrazolium chloride and then monitoring the increase in absorbance at $OD_{480nm}$ for ~five minutes. Also for instance, a unit of an enzyme such as gtf 0768 (comprising SEQ ID NO:1) herein can be defined as the amount of enzyme required to consume 1 g of sucrose in 1 hour at 26° C., pH 6.5, and with 100 g/L of sucrose.

An oxidized dextran compound herein can be derived from a dextran that is a product of a glucosyltransferase as comprised in a glucosyltransferase reaction. The temperature of a gtf reaction herein can be controlled, if desired. In certain embodiments, the temperature is between about 5° C. to about 50° C. The temperature in certain other embodiments is between about 20° C. to about 40° C. Alternatively, the temperature may be about 20, 21, 22, 23, 24, 25, 26, 27, 28, 29, 30, 31, 32, 33, 34, 35, 36, 37, 38, 39, or 40° C. The temperature of a gtf reaction herein may be maintained using various means known in the art. For example, the temperature can be maintained by placing the vessel containing the reaction in an air or water bath incubator set at the desired temperature.

The initial concentration of sucrose in a gtf reaction herein can be about 20 g/L to 900 g/L, 20 g/L to 400 g/L, 75 g/L to 175 g/L, or 50 g/L to 150 g/L. The initial concentration of sucrose can be about 20, 30, 40, 50, 60, 70, 80, 90, 100, 110, 120, 130, 140, 150, 160, 200, 300, 400, 500, 600, 700, 800, 900, 50-150, 75-125, 90-110, 50-500, 100-500, 200-500, 300-500, 400-500, 50-400, 100-400, 200-400, 300-400, 50-300, 100-300, 200-300, 50-200, 100-200, or 50-100 g/L (or any integer between 20 and 900 g/L), for example. "Initial concentration of sucrose" refers to the sucrose concentration in a gtf reaction just after all the reaction components have been added (at least water, sucrose, gtf enzyme).

The pH of a gtf reaction in certain embodiments can be between about 4.0 to about 8.0. Alternatively, the pH can be about 4.0, 4.5, 5.0, 5.5, 6.0, 6.5, 7.0, 7.5, or 8.0. The pH can be adjusted or controlled by the addition or incorporation of a suitable buffer, including but not limited to: phosphate, tris, citrate, or a combination thereof. Buffer concentration in a gtf reaction can be from 0 mM to about 100 mM, or about 10, 20, or 50 mM, for example.

A gtf reaction herein can optionally be agitated via stirring or orbital shaking, for example. Such agitation can be at about 50, 60, 70, 80, 90, 100, 110, 120, 130, 140, 150, 50-150, 60-140, 70-130, 80-120, or 90-110 rpm, for example.

The concentration of gtf enzyme in a reaction can be at least about 15, 20, 25, 30, 35, or 40 U/L, for example. In some aspects, 15-35, 15-30, 15-25, 20-35, 20-30, 20-25, 25-35, 25-30, or 30-35 U/L of glucosyltransferase can be used.

A gtf reaction herein can take about 2, 3, 4, 5, 6, 7, 8, 9, 10, 12, 18, 24, 30, 36, 48, 60, 72, 84, 96, 18-30, 20-28, or 22-26 hours to complete. Reaction time may depend, for example, on certain parameters such as the amount of sucrose and gtf enzyme used in the reaction.

All the features herein defining a glucosyltransferase reaction can be combined, accordingly. Simply as an example, a reaction using an 0768 gtf (comprising SEQ ID NO:1 or related sequence thereof) can initially contain 90-110 g/L (e.g., ~100 g/L) sucrose, 10-30 mM (e.g., ~20 mM) sodium phosphate buffer at pH 6.0-7.0 (e.g., ~pH 6.5), and 20-30 U/L (e.g., ~25 U/L) enzyme. Such a reaction can be held for about 20-28 hours (e.g., ~24 hours) with 50-150 rpm (e.g., ~100 rpm) shaking at 24-28° C. (e.g., ~26° C.).

Still in additional embodiments, conditions for performing a gtf reaction as disclosed in the below Examples can be used to prepare dextran from which an oxidized dextran compound herein can be derived.

A composition comprising an oxidized dextran compound herein can be non-aqueous (e.g., a dry composition). Examples of such embodiments include powders, granules, microcapsules, flakes, or any other form of particulate matter. Other examples include larger compositions such as pellets, bars, kernels, beads, tablets, sticks, or other agglomerates. A non-aqueous or dry composition herein typically has less than 3, 2, 1, 0.5, or 0.1 wt % water comprised therein. The amount of oxidized dextran herein in a non-aqueous or dry composition can be about, or at least about, 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 99.5, or 99.9 wt %, for example. A non-aqueous composition herein can be in the form of a household product, personal care product, pharmaceutical product, industrial product, or food product, for example.

In certain embodiments, a composition comprising an oxidized dextran compound can be an aqueous composition, with or without a detectable amount of viscosity. It is believed that an aqueous composition comprising oxidized dextran can, in some aspects, have a viscosity of about, or at least about, 3, 4, 5, 10, 15, 20, 25, 30, 35, 40, 45, or 50 cPs (or any integer between 3 and 50 cPs). Examples of aqueous compositions herein include aqueous mixtures, colloidal dispersions (e.g., hydrocolloid), and aqueous solutions.

Viscosity can be measured with an aqueous composition herein at any temperature between about 3° C. to about 110° C. (or any integer between 3 and 110° C.). Alternatively, viscosity can be measured at a temperature between about 4° C. to 30° C., or about 20° C. to 25° C., for example. Viscosity can be measured at atmospheric pressure (about 760 torr) or any other higher or lower pressure.

The viscosity of an aqueous composition herein can be measured using a viscometer or rheometer, or using any other means known in the art. The viscosity in such embodiments can be measured at a rotational shear rate of about 0.1 to 1000 rpm (revolutions per minute), for example. In other examples, viscosity can be measured at a rotational shear rate of about 10, 60, 150, 250, or 600 rpm.

The pH of an aqueous composition herein can be between about 2.0 to about 12.0, for example. Alternatively, pH can be about 2.0, 3.0, 4.0, 5.0, 6.0, 7.0, 8.0, 9.0, 10.0, 11.0, 12.0; or between 5.0 to about 12.0; or between about 4.0 and 8.0; or between about 5.0 and 8.0, for example.

An aqueous composition herein can comprise a solvent having at least about 10 wt % water. In other embodiments, a solvent is at least about 20, 30, 40, 50, 60, 70, 80, 90, or 100 wt % water (or any integer value between 10 and 100 wt %), for example.

An oxidized dextran compound herein can be present in an aqueous composition at a wt % of about, or at least about, 0.01, 0.05, 0.1, 0.2, 0.3, 0.4, 0.5, 0.6, 0.7, 0.8, 0.9, 1.0, 1.2, 1.4, 1.6, 1.8, 2.0, 2.5, 3.0, 3.5, 4.0, 4.5, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, or 90 wt %, for example.

An aqueous composition herein can comprise other components in addition to an oxidized dextran compound. For example, an aqueous composition can comprise one or more salts such as a sodium salt (e.g., NaCl, $Na_2SO_4$). Other non-limiting examples of salts include those having (i) an aluminum, ammonium, barium, calcium, chromium (II or III), copper (I or II), iron (II or III), hydrogen, lead (II), lithium, magnesium, manganese (II or III), mercury (I or II), potassium, silver, sodium strontium, tin (II or IV), or zinc cation, and (ii) an acetate, borate, bromate, bromide, carbonate, chlorate, chloride, chlorite, chromate, cyanamide, cyanide, dichromate, dihydrogen phosphate, ferricyanide, ferrocyanide, fluoride, hydrogen carbonate, hydrogen phosphate, hydrogen sulfate, hydrogen sulfide, hydrogen sulfite, hydride, hydroxide, hypochlorite, iodate, iodide, nitrate, nitride, nitrite, oxalate, oxide, perchlorate, permanganate, peroxide, phosphate, phosphide, phosphite, silicate, stannate, stannite, sulfate, sulfide, sulfite, tartrate, or thiocyanate anion. Thus, any salt having a cation from (i) above and an anion from (ii) above can be in an aqueous composition, for example. A salt can be present in an aqueous composition herein at a wt % of about 0.01 to about 10.00 (or any hundredth increment between 0.01 and 10.00), for example.

A composition herein may optionally contain one or more active enzymes. Non-limiting examples of suitable enzymes include proteases, cellulases, hemicellulases, peroxidases, lipolytic enzymes (e.g., metallolipolytic enzymes), xylanases, lipases, phospholipases, esterases (e.g., arylesterase, polyesterase), perhydrolases, cutinases, pectinases, pectate lyases, mannanases, keratinases, reductases, oxidases (e.g., choline oxidase), phenoloxidases, lipoxygenases, ligninases, pullulanases, tannases, pentosanases, malanases, beta-glucanases, arabinosidases, hyaluronidases, chondroitinases, laccases, metalloproteinases, amadoriases, glucoamylases, arabinofuranosidases, phytases, isomerases, transferases and amylases. If an enzyme(s) is included, it may be comprised in a composition herein at about 0.0001-0.1 wt % (e.g., 0.01-0.03 wt %) active enzyme (e.g., calculated as pure enzyme protein), for example.

A cellulase herein can have endocellulase activity (EC 3.2.1.4), exocellulase activity (EC 3.2.1.91), or cellobiase activity (EC 3.2.1.21). A cellulase herein is an "active cellulase" having activity under suitable conditions for maintaining cellulase activity; it is within the skill of the art to determine such suitable conditions. Besides being able to degrade cellulose, a cellulase in certain embodiments can also degrade cellulose ether derivatives such as carboxymethyl cellulose. Examples of cellulose ether derivatives which are expected to not be stable to cellulase are disclosed in U.S. Pat. Nos. 7,012,053, 7,056,880, 6,579,840, 7,534,759 and 7,576,048.

A cellulase herein may be derived from any microbial source, such as a bacteria or fungus. Chemically-modified cellulases or protein-engineered mutant cellulases are included. Suitable cellulases include, but are not limited to, cellulases from the genera *Bacillus, Pseudomonas, Streptomyces, Trichoderma, Humicola, Fusarium, Thielavia* and *Acremonium*. As other examples, a cellulase may be derived from *Humicola insolens, Myceliophthora thermophila* or *Fusarium oxysporum*; these and other cellulases are disclosed in U.S. Pat. Nos. 4,435,307, 5,648,263, 5,691,178, 5,776,757 and 7,604,974, which are all incorporated herein by reference. Exemplary *Trichoderma reesei* cellulases are disclosed in U.S. Pat. Nos. 4,689,297, 5,814,501, 5,324,649, and International Patent Appl. Publ. Nos. WO92/06221 and WO92/06165, all of which are incorporated herein by reference. Exemplary *Bacillus* cellulases are disclosed in U.S. Pat. No. 6,562,612, which is incorporated herein by reference. A cellulase, such as any of the foregoing, preferably is in a mature form lacking an N-terminal signal peptide. Commercially available cellulases useful herein include CELLUZYME® and CAREZYME® (Novozymes A/S); CLAZINASE® and PURADAX® HA (DuPont Industrial Biosciences), and KAC-500(B)® (Kao Corporation).

One or more cellulases can be directly added as an ingredient when preparing a composition disclosed herein. Alternatively, one or more cellulases can be indirectly (inadvertently) provided in the disclosed composition. For example, cellulase can be provided in a composition herein by virtue of being present in a non-cellulase enzyme preparation used for preparing a composition. Cellulase in compositions in which cellulase is indirectly provided thereto can be present at about 0.1-10 ppb (e.g., less than 1 ppm), for example. A contemplated benefit of a composition herein, by virtue of employing an oxidized dextran compound instead of a cellulose-based compound, is that non-cellulase enzyme preparations that might have background cellulase activity can be used without concern that the desired effects of the oxidized dextran compound will be negated by the background cellulase activity.

A cellulase in certain embodiments can be thermostable. Cellulase thermostability refers to the ability of the enzyme to retain activity after exposure to an elevated temperature (e.g. about 60-70° C.) for a period of time (e.g., about 30-60 minutes). The thermostability of a cellulase can be measured by its half-life (t½) given in minutes, hours, or days, during which time period half the cellulase activity is lost under defined conditions.

A cellulase in certain embodiments can be stable to a wide range of pH values (e.g. neutral or alkaline pH such as pH of ~7.0 to ~11.0). Such enzymes can remain stable for a predetermined period of time (e.g., at least about 15 min., 30 min., or 1 hour) under such pH conditions.

At least one, two, or more cellulases may be included in a composition herein. The effective concentration of cellulase in an aqueous composition in which a fabric is treated can be readily determined by a skilled artisan. In fabric care processes, cellulase can be present in an aqueous composition (e.g., wash liquor) in which a fabric is treated in a concentration that is minimally about 0.01-0.1 ppm total cellulase protein, or about 0.1-10 ppb total cellulase protein (e.g., less than 1 ppm), to maximally about 100, 200, 500, 1000, 2000, 3000, 4000, or 5000 ppm total cellulase protein, for example.

Oxidized dextran compounds herein are mostly or completely stable (resistant) to being degraded by cellulase. For example, the percent degradation of an oxidized dextran compound by one or more cellulases is less than 10%, 9%, 8%, 7%, 6%, 5%, 4%, 3%, 2%, or 1%, or is 0%. Such percent degradation can be determined, for example, by comparing the molecular weight of oxidized dextran before and after treatment with a cellulase for a period of time (e.g., ~24 hours).

Aqueous compositions in certain embodiments are believed to have either shear thinning behavior or shear thickening behavior. Shear thinning behavior is observed as a decrease in viscosity of the aqueous composition as shear rate increases, whereas shear thickening behavior is observed as an increase in viscosity of the aqueous composition as shear rate increases. Modification of the shear thinning behavior or shear thickening behavior of an aqueous composition herein is due to the admixture of an oxidized dextran compound to the aqueous composition. Thus, one or more oxidized dextran compounds herein can be added to an aqueous composition to modify its rheological profile (i.e., the flow properties of an aqueous liquid, solution, or mixture are modified) in some aspects. Also, one or more oxidized dextran compounds can be added to an aqueous composition to modify its viscosity in some aspects.

The rheological properties of aqueous compositions herein can be observed by measuring viscosity over an increasing rotational shear rate (e.g., from about 0.1 rpm to about 1000 rpm). For example, shear thinning behavior of an aqueous composition can be observed as a decrease in viscosity (cPs) by at least about 5%, 10%, 15%, 20%, 25%, 30%, 35%, 40%, 45%, 50%, 55%, 60%, 65%, 70%, 75%, 80%, 85%, 90%, or 95% (or any integer between 5% and 95%) as the rotational shear rate increases from about 10 rpm to 60 rpm, 10 rpm to 150 rpm, 10 rpm to 250 rpm, 60 rpm to 150 rpm, 60 rpm to 250 rpm, or 150 rpm to 250 rpm. As another example, shear thickening behavior of an aqueous composition can be observed as an increase in viscosity (cPs) by at least about 5%, 10%, 15%, 20%, 25%, 30%, 35%, 40%, 45%, 50%, 55%, 60%, 65%, 70%, 75%, 80%, 85%, 90%, 95%, 100%, 125%, 150%, 175%, or 200% (or any integer between 5% and 200%) as the rotational shear rate increases from about 10 rpm to 60 rpm, 10 rpm to 150 rpm, 10 rpm to 250 rpm, 60 rpm to 150 rpm, 60 rpm to 250 rpm, or 150 rpm to 250 rpm.

An aqueous composition disclosed herein can be in the form of, and/or comprised in, a household product, personal care product, industrial product, pharmaceutical product, or food product, for example, such as any of those products described below. Oxidized dextran compounds herein can optionally be used as builder agents and/or anti-redeposition agents in one or more of these type of products—such use, which depends in part on the application of the product, can be contemplated by a skilled artisan, especially in view of some of the embodiments disclosed herein. In other embodiments, oxidized dextran compounds herein are believed to have some use as thickening agents in one or more of these products. Such a thickening agent may be used in conjunction with one or more other types of thickening agents if desired, such as those disclosed in U.S. Pat. No. 8,541,041, which is incorporated herein by reference.

Personal care products herein are not particularly limited and include, for example, skin care compositions, cosmetic compositions, antifungal compositions, and antibacterial compositions. Personal care products herein may be in the form of, for example, lotions, creams, pastes, balms, ointments, pomades, gels, liquids, combinations of these and the like. The personal care products disclosed herein can include at least one active ingredient, if desired. An active ingredient is generally recognized as an ingredient that causes an intended pharmacological effect. A personal care product herein can be used in personal care cleaning applications in certain embodiments.

In certain embodiments, a skin care product can be applied to skin for addressing skin damage related to a lack of moisture. A skin care product may also be used to address the visual appearance of skin (e.g., reduce the appearance of flaky, cracked, and/or red skin) and/or the tactile feel of the skin (e.g., reduce roughness and/or dryness of the skin while improved the softness and subtleness of the skin). A skin care product typically may include at least one active ingredient for the treatment or prevention of skin ailments, providing a cosmetic effect, or for providing a moisturizing benefit to skin, such as zinc oxide, petrolatum, white petrolatum, mineral oil, cod liver oil, lanolin, dimethicone, hard fat, vitamin A, allantoin, calamine, kaolin, glycerin, or colloidal oatmeal, and combinations of these. A skin care product may include one or more natural moisturizing factors such as ceramides, hyaluronic acid, glycerin, squalane, amino acids, cholesterol, fatty acids, triglycerides, phospholipids, glycosphingolipids, urea, linoleic acid, glycosaminoglycans, mucopolysaccharide, sodium lactate, or sodium pyrrolidone carboxylate, for example. Other ingredients that may be included in a skin care product include, without limitation, glycerides, apricot kernel oil, canola oil, squalane, squalene, coconut oil, corn oil, jojoba oil, jojoba wax, lecithin, olive oil, safflower oil, sesame oil, shea butter, soybean oil, sweet almond oil, sunflower oil, tea tree oil, shea butter, palm oil, cholesterol, cholesterol esters, wax esters, fatty acids, and orange oil.

A personal care product herein can also be in the form of makeup, lipstick, mascara, rouge, foundation, blush, eyeliner, lip liner, lip gloss, other cosmetics, sunscreen, sun block, nail polish, nail conditioner, bath gel, shower gel, body wash, face wash, lip balm, skin conditioner, cold cream, moisturizer, body spray, soap, body scrub, exfoliant, astringent, scruffing lotion, depilatory, permanent waving solution, antidandruff formulation, antiperspirant composition, deodorant, shaving product, pre-shaving product, after-shaving product, cleanser, skin gel, rinse, dentifrice composition, toothpaste, or mouthwash, for example.

A personal care product in some aspects can be a hair care product. Examples of hair care products herein include shampoo, hair conditioner (leave-in or rinse-out), cream rinse, hair dye, hair coloring product, hair shine product, hair serum, hair anti-frizz product, hair split-end repair product, mousse, hair spray, and styling gel. A hair care product can be in the form of a liquid, paste, gel, solid, or powder in some embodiments. A hair care product as presently disclosed typically comprises one or more of the following ingredients, which are generally used to formulate hair care products: anionic surfactants such as polyoxyethylenelauryl ether sodium sulfate; cationic surfactants such as stearyltrimethylammonium chloride and/or distearyltrimethylammonium chloride; nonionic surfactants such as glyceryl monostearate, sorbitan monopalmitate and/or polyoxyethylenecetyl ether; wetting agents such as propylene glycol, 1,3-butylene glycol, glycerin, sorbitol, pyroglutamic acid salts, amino acids and/or trimethylglycine; hydrocarbons such as liquid paraffins, petrolatum, solid paraffins, squalane and/or olefin oligomers; higher alcohols such as stearyl alcohol and/or cetyl alcohol; superfatting agents; antidandruff agents; disinfectants; anti-inflammatory agents; crude drugs; water-soluble polymers such as methylcellulose, hydroxycellulose and/or partially deacetylated chitin; antiseptics such as paraben; ultra-violet light absorbers; pearling agents; pH adjustors; perfumes; and pigments.

A pharmaceutical product herein can be in the form of an emulsion, liquid, elixir, gel, suspension, solution, cream, or ointment, for example. Also, a pharmaceutical product herein can be in the form of any of the personal care products disclosed herein, such as an antibacterial or antifungal composition. A pharmaceutical product can further comprise one or more pharmaceutically acceptable carriers, diluents, and/or pharmaceutically acceptable salts. An oxidized dextran compound disclosed herein can also be used in capsules, encapsulants, tablet coatings, and excipients for medicaments and drugs.

Non-limiting examples of food products herein include vegetable, meat, and soy patties; reformed seafood; reformed cheese sticks; cream soups; gravies and sauces; salad dressing; mayonnaise; onion rings; jams, jellies, and syrups; pie filling; potato products such as French fries and extruded fries; batters for fried foods, pancakes/waffles and cakes; pet foods; confectioneries (candy); beverages; frozen desserts; ice cream; cultured dairy products such as cottage cheese, yogurt, cheeses, and sour creams; cake icing and glazes; whipped topping; leavened and unleavened baked goods; bars; and the like.

In certain embodiments, an oxidized dextran compound can be comprised in a foodstuff or any other ingestible material (e.g., enteral pharmaceutical preparation) in an amount that provides the desired degree of thickening and/or dispersion. For example, the concentration or amount of an oxidized dextran compound in a product can be about 0.1-3 wt %, 0.1-4 wt %, 0.1-5 wt %, or 0.1-10 wt %.

A household and/or industrial product herein can be in the form of drywall tape-joint compounds; mortars; grouts; cement plasters; spray plasters; cement stucco; adhesives; pastes; wall/ceiling texturizers; binders and processing aids for tape casting, extrusion forming, injection molding and ceramics; spray adherents and suspending/dispersing aids for pesticides, herbicides, and fertilizers; fabric care products such as fabric softeners and laundry detergents; dishwashing detergents, hard surface cleaners; air fresheners; polymer emulsions; gels such as water-based gels; surfactant solutions; paints such as water-based paints; protective coatings; adhesives; sealants and caulks; inks such as water-based ink; metal-working fluids; or emulsion-based metal cleaning fluids used in electroplating, phosphatizing, galvanizing and/or general metal cleaning operations, for example. A household product or industrial product herein can be used in cleaning applications in certain embodiments, and as such can be comprised in detergent compositions, for example.

Oxidized dextran compounds disclosed herein are believed to be useful for providing one or more of the following physical properties to a personal care product, pharmaceutical product, household product, industrial product, or food product: thickening, freeze/thaw stability, lubricity, moisture retention and release, texture, consistency, shape retention, emulsification, binding, suspension, dispersion, gelation, reduced mineral hardness, for example. Examples of a concentration or amount of an oxidized dextran compound in a product can be any of the weight percentages provided above, for example.

A food product herein can be in the form of a confectionery, for example. A confectionary herein can contain one or more sugars (e.g., sucrose, fructose, dextrose) for sweetening, or otherwise be sugar-free.

Examples of confectioneries herein include boiled sugars (hard boiled candies [i.e., hard candy]), dragees, jelly candies, gums, licorice, chews, caramels, toffee, fudge, chewing gums, bubble gums, nougat, chewy pastes, halawa, tablets, lozenges, icing, frosting, pudding, and gels (e.g., fruit gels, gelatin dessert). Other examples of confectioneries include aerated confectioneries such as marshmallows, and baked confectioneries.

A confectionery herein can optionally be prepared with chocolate, in any form (e.g., bars, candies, bonbons, truffles, lentils). A confectionary can be coated with chocolate, sugar-coated, candied, glazed, and/or film-coated, for example. Film-coating processes typically comprise applying to the surface of a confectionery a film-forming liquid composition which becomes, after drying, a protective film. This film-coating serves, for example, to protect the active principles contained in the confectionery; to protect the confectionery itself from moisture, shocks, and/or friability; and/or to confer the confectionery attractive visual properties (e.g., shine, uniform color, smooth surface).

In certain embodiments, a confectionery can be filled with a filling that is liquid, pasty, solid, or powdered. An oxidized dextran compound herein can be comprised in such a filling, in which case the compound is optionally also included in the confectionery component being filled.

A confectionery herein is optionally sugar-free, comprising no sugar and typically instead having one or more artificial and/or non-sugar sweeteners (optionally non-caloric) (e.g., aspartame, saccharin, STEVIA, SUCRALOSE). A sugar-free confectionery in certain embodiments can comprise one or more polyols (e.g., erythritol, glycerol, lactitol, mannitol, maltitol, xylitol), soluble fibers, and/or proteins in place of sugar.

A food product herein can be in the form of a pet food, for example. A pet food herein can be a food for a domesticated animal such as a dog or cat (or any other companion animal), for example. A pet food in certain embodiments provides to a domestic animal one or more of the following: necessary dietary requirements, treats (e.g., dog biscuits), food supplements. Examples of pet food include dry pet food (e.g., kernels, kibbles), semi-moist compositions, wet pet food (e.g., canned pet food), or any combination thereof. Wet pet food typically has a moisture content over 65%. Semi-moist pet food typically has a moisture content of 20-65% and can include humectants such as propylene glycol, potassium sorbate, and ingredients that prevent microbial growth (bacteria and mold). Dry pet food typically has a moisture content less than 20% and its processing usually includes extruding, drying and/or baking. A pet food can optionally be in the form of a gravy, yogurt, powder, suspension, chew, or treat (e.g., biscuits); all these compositions can also be used as pet food supplements, if desired. Pet treats can be semi-moist chewable treats; dry treats; chewable bones; baked, extruded or stamped treats; or confection treats, for example. Examples of pet food compositions/formulations in which an oxidized dextran compound herein can be added include those disclosed in U.S. Patent Appl. Publ. Nos. 2013/0280352 and 2010/0159103, and U.S. Pat. No. 6,977,084, which are all incorporated herein by reference.

Compositions disclosed herein can be in the form of a fabric care composition. A fabric care composition herein can be used for hand wash, machine wash and/or other purposes such as soaking and/or pretreatment of fabrics, for example. A fabric care composition may take the form of, for example, a laundry detergent; fabric conditioner; any wash-, rinse-, or dryer-added product; unit dose or spray. Fabric care compositions in a liquid form may be in the form of an aqueous composition as disclosed herein. In other aspects, a fabric care composition can be in a dry form such as a granular detergent or dryer-added fabric softener sheet. Other non-limiting examples of fabric care compositions herein include: granular or powder-form all-purpose or heavy-duty washing agents; liquid, gel or paste-form all-purpose or heavy-duty washing agents; liquid or dry fine-fabric (e.g., delicates) detergents; cleaning auxiliaries such as bleach additives, "stain-stick", or pre-treatments; substrate-laden products such as dry and wetted wipes, pads, or sponges; sprays and mists.

A detergent composition herein may be in any useful form, e.g., as powders, granules, pastes, bars, unit dose, or liquid. A liquid detergent may be aqueous, typically containing up to about 70 wt % of water and 0 wt % to about 30 wt % of organic solvent. It may also be in the form of a compact gel type containing only about 30 wt % water.

A detergent composition herein typically comprises one or more surfactants, wherein the surfactant is selected from nonionic surfactants, anionic surfactants, cationic surfactants, ampholytic surfactants, zwitterionic surfactants, semi-polar nonionic surfactants and mixtures thereof. In some embodiments, the surfactant is present at a level of from about 0.1% to about 60%, while in alternative embodiments the level is from about 1% to about 50%, while in still further embodiments the level is from about 5% to about 40%, by weight of the detergent composition. A detergent will usually contain 0 wt % to about 50 wt % of an anionic surfactant such as linear alkylbenzenesulfonate (LAS), alpha-olefinsulfonate (AOS), alkyl sulfate (fatty alcohol sulfate) (AS), alcohol ethoxysulfate (AEOS or AES), secondary alkanesulfonates (SAS), alpha-sulfo fatty acid methyl esters, alkyl- or alkenylsuccinic acid, or soap. In addition, a detergent composition may optionally contain 0 wt % to about 40 wt % of a nonionic surfactant such as alcohol ethoxylate (AEO or AE), carboxylated alcohol ethoxylates, nonylphenol ethoxylate, alkylpolyglycoside, alkyldimethylamineoxide, ethoxylated fatty acid monoethanolamide, fatty acid monoethanolamide, or polyhydroxy alkyl fatty acid amide (as described for example in WO92/06154, which is incorporated herein by reference).

A detergent composition herein typically comprises one or more detergent builders or builder systems. One or more oxidized dextran compounds can be included as a builder, for example. In some aspects, oxidized dextran can be included as a co-builder, in which it is used together with one or more additional builders such as any disclosed herein. In some embodiments incorporating at least one builder, the cleaning compositions comprise at least about 1%, from about 3% to about 60%, or even from about 5% to about 40%, builder by weight of the composition. Builders (in addition to oxidized dextran herein) include, but are not limited to, alkali metal, ammonium and alkanolammonium salts of polyphosphates, alkali metal silicates, alkaline earth and alkali metal carbonates, aluminosilicates, polycarboxylate compounds, ether hydroxypolycarboxylates, copolymers of maleic anhydride with ethylene or vinyl methyl ether, 1,3,5-trihydroxy benzene-2,4,6-trisulphonic acid, and carboxymethyloxysuccinic acid, various alkali metal, ammonium and substituted ammonium salts of polyacetic acids such as ethylenediamine tetraacetic acid and nitrilotriacetic acid, as well as polycarboxylates such as mellitic acid, succinic acid, citric acid, oxydisuccinic acid, polymaleic acid, benzene 1,3,5 tricarboxylic acid, carboxymethyloxysuccinic acid, and soluble salts thereof. Indeed, it is contemplated that any suitable builder will find use in various embodiments of the present disclosure. Additional examples of a detergent builder or complexing agent include zeolite, diphosphate, triphosphate, phosphonate, citrate, nitrilotriacetic acid (NTA), ethylenediaminetetraacetic acid (EDTA), diethylenetriaminepentaacetic acid (DTMPA), alkyl- or alkenylsuccinic acid, soluble silicates or layered silicates (e.g., SKS-6 from Hoechst).

In some embodiments, builders form water-soluble hardness ion complexes (e.g., sequestering builders), such as citrates and polyphosphates (e.g., sodium tripolyphosphate and sodium tripolyphospate hexahydrate, potassium tripolyphosphate, and mixed sodium and potassium tripolyphosphate, etc.). It is contemplated that any suitable builder will find use in the present disclosure, including those known in the art (See, e.g., EP2100949).

In some embodiments, suitable builders can include phosphate builders and non-phosphate builders. In some embodiments, a builder is a phosphate builder. In some embodiments, a builder is a non-phosphate builder. A builder can be used in a level of from 0.1% to 80%, or from 5% to 60%, or from 10% to 50%, by weight of the composition. In some embodiments, the product comprises a mixture of phosphate and non-phosphate builders. Suitable phosphate builders include mono-phosphates, di-phosphates, tri-polyphosphates or oligomeric-polyphosphates, including the alkali metal salts of these compounds, including the sodium salts. In some embodiments, a builder can be sodium tripolyphosphate (STPP). Additionally, the composition can comprise carbonate and/or citrate, preferably citrate that helps to achieve a neutral pH composition. Other suitable non-phosphate builders include homopolymers and copolymers of polycarboxylic acids and their partially or completely neutralized salts, monomeric polycarboxylic acids and hydroxycarboxylic acids and their salts. In some embodiments, salts of the above mentioned compounds include ammonium and/or alkali metal salts, i.e., lithium, sodium, and potassium salts, including sodium salts. Suitable polycarboxylic acids include acyclic, alicyclic, hetero-cyclic and aromatic carboxylic acids, wherein in some embodiments, they can contain at least two carboxyl groups which are in each case separated from one another by, in some instances, no more than two carbon atoms.

A detergent composition herein can comprise at least one chelating agent. Suitable chelating agents include, but are not limited to, copper, iron and/or manganese chelating agents and mixtures thereof. In embodiments in which at least one chelating agent is used, the composition comprises from about 0.1% to about 15%, or even from about 3.0% to about 10%, chelating agent by weight of the composition.

A detergent composition herein can comprise at least one deposition aid. Suitable deposition aids include, but are not limited to, polyethylene glycol, polypropylene glycol, polycarboxylate, soil release polymers such as polytelephthalic acid, clays such as kaolinite, montmorillonite, atapulgite, illite, bentonite, halloysite, and mixtures thereof.

A detergent composition herein can comprise one or more dye transfer inhibiting agents. Suitable polymeric dye transfer inhibiting agents include, but are not limited to, polyvinylpyrrolidone polymers, polyamine N-oxide polymers, copolymers of N-vinylpyrrolidone and N-vinylimidazole, polyvinyloxazolidones and polyvinylimidazoles or mixtures thereof. Additional dye transfer inhibiting agents include manganese phthalocyanine, peroxidases, polyvinylpyrrolidone polymers, polyamine N-oxide polymers, copolymers of N-vinylpyrrolidone and N-vinylimidazole, polyvinyloxazolidones and polyvinylimidazoles and/or mixtures thereof; chelating agents examples of which include ethylene-diamine-tetraacetic acid (EDTA); diethylene triamine penta methylene phosphonic acid (DTPMP); hydroxy-ethane diphosphonic acid (HEDP); ethylenediamine N,N'-disuccinic acid (EDDS); methyl glycine diacetic acid (MGDA); diethylene triamine penta acetic acid (DTPA); propylene diamine tetracetic acid (PDT A); 2-hydroxypyridine-N-oxide (HPNO); or methyl glycine diacetic acid (MGDA); glutamic acid N,N-diacetic acid (N,N-dicarboxymethyl glutamic acid tetrasodium salt (GLDA); nitrilotriacetic acid (NTA); 4,5-dihydroxy-m-benzenedisulfonic acid; citric acid and any salts thereof; N-hydroxyethyl ethylenediaminetriacetic acid (HEDTA), triethylenetetraaminehexaacetic acid (TTHA), N-hydroxyethyliminodiacetic acid (HEIDA), dihydroxyethylglycine (DHEG), ethylenediaminetetrapropionic acid (EDTP) and derivatives thereof, which can be used alone or in combination with any of the above. In embodiments in which at least one dye transfer inhibiting agent is used, a composition herein may comprise from about 0.0001% to about 10%, from about 0.01% to about 5%, or even from about 0.1% to about 3%, by weight of the composition.

A detergent composition herein can comprise silicates. In some of these embodiments, sodium silicates (e.g., sodium disilicate, sodium metasilicate, and/or crystalline phyllosilicates) find use. In some embodiments, silicates are present at a level of from about 1% to about 20% by weight of the composition. In some embodiments, silicates are present at a level of from about 5% to about 15% by weight of the composition.

A detergent composition herein can comprise dispersants. Suitable water-soluble organic materials include, but are not limited to the homo- or co-polymeric acids or their salts, in which the polycarboxylic acid comprises at least two carboxyl radicals separated from each other by not more than two carbon atoms.

A detergent composition herein may additionally comprise one or more enzymes. Examples of enzymes include proteases, cellulases, hemicellulases, peroxidases, lipolytic enzymes (e.g., metallolipolytic enzymes), xylanases, lipases, phospholipases, esterases (e.g., arylesterase, polyesterase), perhydrolases, cutinases, pectinases, pectate lyases, mannanases, keratinases, reductases, oxidases (e.g., choline oxidase, phenoloxidase), phenoloxidases, lipoxygenases, ligninases, pullulanases, tannases, pentosanases, malanases, beta-glucanases, arabinosidases, hyaluronidases, chondroitinases, laccases, metalloproteinases, amadoriases, glucoamylases, alpha-amylases, beta-amylases, galactosidases, galactanases, catalases, carageenases, hyaluronidases, keratinases, lactases, ligninases, peroxidases, phosphatases, polygalacturonases, pullulanases, rhamnogalactouronases, tannases, transglutaminases, xyloglucanases, xylosidases, metalloproteases, arabinofuranosidases, phytases, isomerases, transferases and/or amylases in any combination.

In some embodiments, a detergent composition can comprise one or more enzymes (e.g., any disclosed herein), each at a level from about 0.00001% to about 10% by weight of the composition and the balance of cleaning adjunct materials by weight of composition. In some other embodiments, a detergent composition can also comprise each enzyme at a level of about 0.0001% to about 10%, about 0.001% to about 5%, about 0.001% to about 2%, or about 0.005% to about 0.5%, by weight of the composition.

Enzymes that may be comprised in a detergent composition herein may be stabilized using conventional stabilizing agents, e.g., a polyol such as propylene glycol or glycerol; a sugar or sugar alcohol; lactic acid; boric acid or a boric acid derivative (e.g., an aromatic borate ester).

A detergent composition in certain embodiments may comprise one or more polymers. Examples of suitable polymers include carboxymethyl cellulose (CMC), poly (vinylpyrrolidone) (PVP), polyethylene glycol (PEG), poly (vinyl alcohol) (PVA), polycarboxylates such as polyacrylates, maleic/acrylic acid copolymers and lauryl methacrylate/acrylic acid copolymers.

A detergent composition herein may contain a bleaching system. For example, a bleaching system can comprise an $H_2O_2$ source such as perborate or percarbonate, which may be combined with a peracid-forming bleach activator such as tetraacetylethylenediamine (TAED) or nonanoyloxybenzenesulfonate (NOBS). Alternatively, a bleaching system may comprise peroxyacids (e.g., amide, imide, or sulfone type peroxyacids). Alternatively still, a bleaching system can be an enzymatic bleaching system comprising perhydrolase, for example, such as the system described in WO2005/056783.

A detergent composition herein may also contain conventional detergent ingredients such as fabric conditioners, clays, foam boosters, suds suppressors, anti corrosion agents, soil-suspending agents, anti-soil redeposition agents, dyes, bactericides, tarnish inhibiters, optical brighteners, or perfumes. The pH of a detergent composition herein (measured in aqueous solution at use concentration) is usually neutral or alkaline (e.g., pH of about 7.0 to about 11.0).

It is believed that an oxidized dextran can be included as an anti-redeposition agent and/or clay soil removal agent in a detergent composition such as a fabric care composition, if desired (such agents can optionally be characterized as whiteness maintenance agents in certain aspects). Examples of other suitable anti-redeposition and/or clay soil removal agents herein include polyethoxy zwitterionic surfactants, water-soluble copolymers of acrylic or methacrylic acid with acrylic or methacrylic acid-ethylene oxide condensates (e.g., U.S. Pat. No. 3,719,647), cellulose derivatives such as carboxymethylcellulose and hydroxypropylcellulose (e.g., U.S. Pat. Nos. 3,597,416 and 3,523,088), and mixtures comprising nonionic alkyl polyethoxy surfactant, polyethoxy alkyl quaternary cationic surfactant and fatty amide surfactant (e.g., U.S. Pat. No. 4,228,044). Non-limiting examples of other suitable anti-redeposition and clay soil removal agents are disclosed in U.S. Pat. Nos. 4,597,898 and 4,891,160, and Int. Pat. Appl. Publ. No. WO95/32272, all of which are incorporated herein by reference.

Particular forms of detergent compositions that can be adapted for purposes disclosed herein are disclosed in, for example, US20090209445A1, US20100081598A1, U.S. Pat. No. 7,001,878B2, EP1504994B1, WO2001085888A2, WO2003089562A1, WO2009098659A1, WO2009098660A1, WO2009112992A1, WO2009124160A1, WO2009152031 A1, WO2010059483A1, WO2010088112A1, WO2010090915A1, WO2010135238A1, WO2011094687A1, WO2011094690A1, WO2011127102A1, WO2011163428A1, WO2008000567A1, WO2006045391 A1, WO2006007911 A1, WO2012027404A1, EP1740690B1, WO2012059336A1, U.S. Pat. No. 6,730,646B1, WO2008087426A1, WO2010116139A1, and WO2012104613A1, all of which are incorporated herein by reference.

Laundry detergent compositions herein can optionally be heavy duty (all purpose) laundry detergent compositions. Exemplary heavy duty laundry detergent compositions comprise a detersive surfactant (10%-40% wt/wt), including an anionic detersive surfactant (selected from a group of linear or branched or random chain, substituted or unsubstituted alkyl sulphates, alkyl sulphonates, alkyl alkoxylated sulphate, alkyl phosphates, alkyl phosphonates, alkyl carboxylates, and/or mixtures thereof), and optionally non-ionic surfactant (selected from a group of linear or branched or random chain, substituted or unsubstituted alkyl alkoxylated alcohol, e.g., C8-C18 alkyl ethoxylated alcohols and/or C6-C12 alkyl phenol alkoxylates), where the weight ratio of anionic detersive surfactant (with a hydrophilic index (HIc) of from 6.0 to 9) to non-ionic detersive surfactant is greater than 1:1. Suitable detersive surfactants also include cationic detersive surfactants (selected from a group of alkyl pyridinium compounds, alkyl quaternary ammonium compounds, alkyl quaternary phosphonium compounds, alkyl ternary sulphonium compounds, and/or mixtures thereof); zwitterionic and/or amphoteric detersive surfactants (selected from a group of alkanolamine sulpho-betaines); ampholytic surfactants; semi-polar non-ionic surfactants and mixtures thereof.

A detergent herein such as a heavy duty laundry detergent composition may optionally include, a surfactancy boosting polymer consisting of amphiphilic alkoxylated grease cleaning polymers (selected from a group of alkoxylated polymers having branched hydrophilic and hydrophobic properties, such as alkoxylated polyalkylenimines in the range of 0.05 wt %-10 wt %) and/or random graft polymers (typically comprising of hydrophilic backbone comprising monomers selected from the group consisting of: unsaturated C1-C6 carboxylic acids, ethers, alcohols, aldehydes, ketones, esters, sugar units, alkoxy units, maleic anhydride, saturated polyalcohols such as glycerol, and mixtures thereof; and hydrophobic side chain(s) selected from the group consisting of: C4-C25 alkyl group, polypropylene, polybutylene, vinyl ester of a saturated C1-C6 mono-carboxylic acid, C1-C6 alkyl ester of acrylic or methacrylic acid, and mixtures thereof.

A detergent herein such as a heavy duty laundry detergent composition may optionally include additional polymers such as soil release polymers (include anionically end-capped polyesters, for example SRP1, polymers comprising at least one monomer unit selected from saccharide, dicarboxylic acid, polyol and combinations thereof, in random or block configuration, ethylene terephthalate-based polymers and co-polymers thereof in random or block configuration, for example REPEL-O-TEX SF, SF-2 AND SRP6, TEXCARE SRA100, SRA300, SRN100, SRN170, SRN240, SRN300 AND SRN325, MARLOQUEST SL), anti-redeposition agent(s) herein (0.1 wt % to 10 wt %), include carboxylate polymers, such as polymers comprising at least one monomer selected from acrylic acid, maleic acid (or maleic anhydride), fumaric acid, itaconic acid, aconitic acid, mesaconic acid, citraconic acid, methylenemalonic acid, and any mixture thereof, vinylpyrrolidone homopolymer, and/or polyethylene glycol, molecular weight in the range of from 500 to 100,000 Da); and polymeric carboxylate (such as maleate/acrylate random copolymer or polyacrylate homopolymer).

A detergent herein such as a heavy duty laundry detergent composition may optionally further include saturated or unsaturated fatty acids, preferably saturated or unsaturated C12-C24 fatty acids (0 wt % to 10 wt %); deposition aids disclosed herein (examples for which include polysaccharides, cellulosic polymers, poly diallyl dimethyl ammonium halides (DADMAC), and co-polymers of DAD MAC with vinyl pyrrolidone, acrylamides, imidazoles, imidazolinium halides, and mixtures thereof, in random or block configuration, cationic guar gum, cationic starch, cationic polyacylamides, and mixtures thereof).

A detergent herein such as a heavy duty laundry detergent composition may optionally further include dye transfer inhibiting agents, examples of which include manganese phthalocyanine, peroxidases, polyvinylpyrrolidone polymers, polyamine N-oxide polymers, copolymers of N-vinylpyrrolidone and N-vinylimidazole, polyvinyloxazolidones and polyvinylimidazoles and/or mixtures thereof; chelating agents, examples of which include ethylene-diamine-tetraacetic acid (EDTA), diethylene triamine penta methylene phosphonic acid (DTPMP), hydroxy-ethane diphosphonic acid (HEDP), ethylenediamine N,N'-disuccinic acid (EDDS), methyl glycine diacetic acid (MGDA), diethylene triamine penta acetic acid (DTPA), propylene diamine tetracetic acid (PDTA), 2-hydroxypyridine-N-oxide (HPNO), or methyl glycine diacetic acid (MGDA), glutamic acid N,N-diacetic acid (N,N-dicarboxymethyl glutamic acid tetrasodium salt (GLDA), nitrilotriacetic acid (NTA), 4,5-dihydroxy-m-benzenedisulfonic acid, citric acid and any salts thereof, N-hydroxyethylethylenediaminetriacetic acid (HEDTA), triethylenetetraaminehexaacetic acid (TTHA), N-hydroxyethyliminodiacetic acid (HEIDA), dihydroxyethylglycine (DHEG), ethylenediaminetetrapropionic acid (EDTP), and derivatives thereof.

A detergent herein such as a heavy duty laundry detergent composition may optionally include silicone or fatty-acid based suds suppressors; hueing dyes, calcium and magnesium cations, visual signaling ingredients, anti-foam (0.001 wt % to about 4.0 wt %), and/or a structurant/thickener (0.01 wt % to 5 wt %) selected from the group consisting of diglycerides and triglycerides, ethylene glycol distearate, microcrystalline cellulose, microfiber cellulose, biopolymers, xanthan gum, gellan gum, and mixtures thereof). Such structurant/thickener would be, in certain embodiments, in addition to the one or more oxidized dextran compounds comprised in the detergent. A structurant can also be referred to as a structural agent.

A detergent herein can be in the form of a heavy duty dry/solid laundry detergent composition, for example. Such a detergent may include: (i) a detersive surfactant, such as any anionic detersive surfactant disclosed herein, any non-ionic detersive surfactant disclosed herein, any cationic detersive surfactant disclosed herein, any zwitterionic and/or amphoteric detersive surfactant disclosed herein, any ampholytic surfactant, any semi-polar non-ionic surfactant, and mixtures thereof; (ii) a builder, such as any phosphate-free builder (e.g., zeolite builders in the range of 0 wt % to less than 10 wt %), any phosphate builder (e.g., sodium tri-polyphosphate in the range of 0 wt % to less than 10 wt %), citric acid, citrate salts and nitrilotriacetic acid, any silicate salt (e.g., sodium or potassium silicate or sodium meta-silicate in the range of 0 wt % to less than 10 wt %); any carbonate salt (e.g., sodium carbonate and/or sodium bicarbonate in the range of 0 wt % to less than 80 wt %), and mixtures thereof; (iii) a bleaching agent, such as any photobleach (e.g., sulfonated zinc phthalocyanines, sulfonated aluminum phthalocyanines, xanthenes dyes, and mixtures thereof), any hydrophobic or hydrophilic bleach activator (e.g., dodecanoyl oxybenzene sulfonate, decanoyl oxybenzene sulfonate, decanoyl oxybenzoic acid or salts thereof, 3,5,5-trimethy hexanoyl oxybenzene sulfonate, tetraacetyl ethylene diamine-TAED, nonanoyloxybenzene sulfonate-NOBS, nitrile quats, and mixtures thereof), any source of hydrogen peroxide (e.g., inorganic perhydrate salts, examples of which include mono or tetra hydrate sodium salt of perborate, percarbonate, persulfate, perphosphate, or persilicate), any preformed hydrophilic and/or hydrophobic peracids (e.g., percarboxylic acids and salts, percarbonic acids and salts, perimidic acids and salts, peroxymonosulfuric acids and salts, and mixtures thereof); and/or (iv) any other components such as a bleach catalyst (e.g., imine bleach boosters examples of which include iminium cations and polyions, iminium zwitterions, modified amines, modified amine oxides, N-sulphonyl imines, N phosphonyl imines, N-acyl imines, thiadiazole dioxides, perfluoroimines, cyclic sugar ketones, and mixtures thereof), and a metal-containing bleach catalyst (e.g., copper, iron, titanium, ruthenium, tungsten, molybdenum, or manganese cations along with an auxiliary metal cations such as zinc or aluminum and a sequestrate such as EDTA, ethylenediaminetetra(methylenephosphonic acid).

Compositions disclosed herein can be in the form of a dishwashing detergent composition. Examples of dishwashing detergents include automatic dishwashing detergents (typically used in dishwasher machines) and hand-washing dish detergents. A dishwashing detergent composition can be in any dry or liquid/aqueous form as disclosed herein, for example. Components that may be included in certain embodiments of a dishwashing detergent composition include, for example, one or more of a phosphate; oxygen- or chlorine-based bleaching agent; non-ionic surfactant; alkaline salt (e.g., metasilicates, alkali metal hydroxides, sodium carbonate); any active enzyme disclosed herein; anti-corrosion agent (e.g., sodium silicate); anti-foaming agent; additives to slow down the removal of glaze and patterns from ceramics; perfume; anti-caking agent (in granular detergent); starch (in tablet-based detergents); gelling agent (in liquid/gel based detergents); and/or sand (powdered detergents).

Dishwashing detergents such as an automatic dishwasher detergent or liquid dishwashing detergent can comprise (i) a non-ionic surfactant, including any ethoxylated non-ionic surfactant, alcohol alkoxylated surfactant, epoxy-capped poly(oxyalkylated) alcohol, or amine oxide surfactant present in an amount from 0 to 10 wt %; (ii) a builder, in the range of about 5-60 wt %, including oxidized dextran and any phosphate builder (e.g., mono-phosphates, di-phosphates, tri-polyphosphates, other oligomeric-polyphosphates, sodium tripolyphosphate-STPP), any phosphate-free builder (e.g., amino acid-based compounds including methyl-glycine-diacetic acid [MGDA] and salts or derivatives thereof, glutamic-N,N-diacetic acid [GLDA] and salts or derivatives thereof, iminodisuccinic acid (IDS) and salts or derivatives thereof, carboxy methyl inulin and salts or derivatives thereof, nitrilotriacetic acid [NTA], diethylene triamine penta acetic acid [DTPA], B-alaninediacetic acid [B-ADA] and salts thereof), homopolymers and copolymers of poly-carboxylic acids and partially or completely neutralized salts thereof, monomeric polycarboxylic acids and hydroxycarboxylic acids and salts thereof in the range of 0.5 wt % to 50 wt %, or sulfonated/carboxylated polymers in the range of about 0.1 wt % to about 50 wt %; (iii) a drying aid in the range of about 0.1 wt % to about 10 wt % (e.g., polyesters, especially anionic polyesters, optionally together with further monomers with 3 to 6 functionalities—typically acid, alcohol or ester functionalities which are conducive to polycondensation, polycarbonate-, polyurethane- and/or polyurea-polyorganosiloxane compounds or precursor compounds thereof, particularly of the reactive cyclic carbonate and urea type); (iv) a silicate in the range from about 1 wt % to about 20 wt % (e.g., sodium or potassium silicates such as sodium disilicate, sodium meta-silicate and crystalline phyllosilicates); (v) an inorganic bleach (e.g., perhydrate salts such as perborate, percarbonate, perphosphate, persulfate and persilicate salts) and/or an organic bleach (e.g., organic peroxyacids such as diacyl- and tetraacylperoxides, especially diperoxydodecanedioic acid, diperoxytetradecanedioic acid, and diperoxyhexadecanedioic acid); (vi) a bleach activator (e.g., organic peracid precursors in the range from about 0.1 wt % to about 10 wt %) and/or bleach catalyst (e.g., manganese triazacyclononane and related complexes; Co, Cu, Mn, and Fe bispyridylamine and related complexes; and pentamine acetate cobalt(III) and related complexes); (vii) a metal care agent in the range from about 0.1 wt % to 5 wt % (e.g., benzatriazoles, metal salts and complexes, and/or silicates); and/or (viii) any active enzyme disclosed herein in the range from about 0.01 to 5.0 mg of active enzyme per gram of automatic dishwashing detergent composition, and an enzyme stabilizer component (e.g., oligosaccharides, polysaccharides, and inorganic divalent metal salts).

It is believed that numerous commercially available detergent formulations can be adapted to include an oxidized dextran compound as disclosed herein. Examples include PUREX® ULTRAPACKS (Henkel), FINISH® QUANTUM (Reckitt Benckiser), CLOROX™ 2 PACKS (Clorox), OXICLEAN MAX FORCE POWER PAKS (Church & Dwight), TIDE® STAIN RELEASE, CASCADE® ACTIONPACS, and TIDE® PODS™ (Procter & Gamble).

Compositions disclosed herein can be in the form of an oral care composition, for example. Examples of oral care compositions include dentifrices, toothpaste, mouth wash, mouth rinse, chewing gum, edible strips, and tooth cream/gel that provide some form of oral care (e.g., treatment or prevention of cavities [dental caries], gingivitis, plaque, tartar, and/or periodontal disease). An oral care composition can also be for treating an "oral surface", which encompasses any soft or hard surface within the oral cavity including surfaces of the tongue, hard and soft palate, buccal mucosa, gums and dental surfaces. A "dental surface" herein is a surface of a natural tooth or a hard surface of artificial dentition including a crown, cap, filling, bridge, denture, or dental implant, for example.

An oral care composition herein can comprise about 0.01-15.0 wt % (e.g., ~0.1-10 wt % or ~0.1-5.0 wt %, ~0.1-2.0 wt %) of one or more oxidized dextran compounds as disclosed herein, for example. One or more oxidized dextran compounds comprised in an oral care composition can sometimes be provided therein as a thickening agent and/or dispersion agent, which may be useful to impart a desired consistency and/or mouth feel to the composition. One or more other thickening or dispersion agents can also be provided in an oral care composition herein, such as a carboxyvinyl polymer, carrageenan (e.g., L-carrageenan), natural gum (e.g., karaya, xanthan, gum arabic, tragacanth), colloidal magnesium aluminum silicate, or colloidal silica, for example. In some embodiments, oxidized dextran can be included as a builder.

An oral care composition herein may be a toothpaste or other dentifrice, for example. Such compositions, as well as any other oral care composition herein, can additionally comprise, without limitation, one or more of an anticaries agent, antimicrobial or antibacterial agent, anticalculus or tartar control agent, surfactant, abrasive, pH-modifying agent, foam modulator, humectant, flavorant, sweetener, pigment/colorant, whitening agent, and/or other suitable components. Examples of oral care compositions to which one or more oxidized dextran compounds can be added are disclosed in U.S. Patent Appl. Publ. Nos. 2006/0134025, 2002/0022006 and 2008/0057007, which are incorporated herein by reference.

An anticaries agent herein can be an orally acceptable source of fluoride ions. Suitable sources of fluoride ions include fluoride, monofluorophosphate and fluorosilicate salts as well as amine fluorides, including olaflur (N'-octadecyltrimethylendiamine-N,N, N'-tris(2-ethanol)-dihydrofluoride), for example. An anticaries agent can be present in an amount providing a total of about 100-20000 ppm, about 200-5000 ppm, or about 500-2500 ppm, fluoride ions to the composition, for example. In oral care compositions in which sodium fluoride is the sole source of fluoride ions, an amount of about 0.01-5.0 wt %, about 0.05-1.0 wt %, or about 0.1-0.5 wt %, sodium fluoride can be present in the composition, for example.

An antimicrobial or antibacterial agent suitable for use in an oral care composition herein includes, for example, phenolic compounds (e.g., 4-allylcatechol; p-hydroxybenzoic acid esters such as benzylparaben, butylparaben, ethylparaben, methylparaben and propylparaben; 2-benzylphenol; butylated hydroxyanisole; butylated hydroxytoluene; capsaicin; carvacrol; creosol; eugenol; guaiacol; halogenated bisphenolics such as hexachlorophene and bromochlorophene; 4-hexylresorcinol; 8-hydroxyquinoline and salts thereof; salicylic acid esters such as menthyl salicylate, methyl salicylate and phenyl salicylate; phenol; pyrocatechol; salicylanilide; thymol; halogenated diphenylether compounds such as triclosan and triclosan monophosphate), copper (II) compounds (e.g., copper (II) chloride, fluoride, sulfate and hydroxide), zinc ion sources (e.g., zinc acetate, citrate, gluconate, glycinate, oxide, and sulfate), phthalic acid and salts thereof (e.g., magnesium monopotassium phthalate), hexetidine, octenidine, sanguinarine, benzalkonium chloride, domiphen bromide, alkylpyridinium chlorides (e.g. cetylpyridinium chloride, tetradecylpyridinium chloride, N-tetradecyl-4-ethylpyridinium chloride), iodine, sulfonamides, bisbiguanides (e.g., alexidine, chlorhexidine, chlorhexidine digluconate), piperidino derivatives (e.g., delmopinol, octapinol), *magnolia* extract, grapeseed extract, rosemary extract, menthol, geraniol, citral, eucalyptol, antibiotics (e.g., augmentin, amoxicillin, tetracycline, doxycycline, minocycline, metronidazole, neomycin, kanamycin, clindamycin), and/or any antibacterial agents disclosed in U.S. Pat. No. 5,776,435, which is incorporated herein by reference. One or more antimicrobial agents can optionally be present at about 0.01-10 wt % (e.g., 0.1-3 wt %), for example, in the disclosed oral care composition.

An anticalculus or tartar control agent suitable for use in an oral care composition herein includes, for example, phosphates and polyphosphates (e.g., pyrophosphates), polyaminopropanesulfonic acid (AMPS), zinc citrate trihydrate, polypeptides (e.g., polyaspartic and polyglutamic acids), polyolefin sulfonates, polyolefin phosphates, diphosphonates (e.g., azacycloalkane-2,2-diphosphonates such as azacycloheptane-2,2-diphosphonic acid), N-methyl azacyclopentane-2,3-diphosphonic acid, ethane-1-hydroxy-1,1-diphosphonic acid (EHDP), ethane-1-amino-1,1-diphosphonate, and/or phosphonoalkane carboxylic acids and salts thereof (e.g., their alkali metal and ammonium salts). Useful inorganic phosphate and polyphosphate salts include, for example, monobasic, dibasic and tribasic sodium phosphates, sodium tripolyphosphate, tetrapolyphosphate, mono-, di-, tri- and tetra-sodium pyrophosphates, disodium dihydrogen pyrophosphate, sodium trimetaphosphate, sodium hexametaphosphate, or any of these in which sodium is replaced by potassium or ammonium. Other useful anticalculus agents in certain embodiments include anionic polycarboxylate polymers (e.g., polymers or copolymers of acrylic acid, methacrylic, and maleic anhydride such as polyvinyl methyl ether/maleic anhydride copolymers). Still other useful anticalculus agents include sequestering agents such as hydroxycarboxylic acids (e.g., citric, fumaric, malic, glutaric and oxalic acids and salts thereof) and aminopolycarboxylic acids (e.g., EDTA). One or more anticalculus or tartar control agents can optionally be present at about 0.01-50 wt % (e.g., about 0.05-25 wt % or about 0.1-15 wt %), for example, in the disclosed oral care composition.

A surfactant suitable for use in an oral care composition herein may be anionic, non-ionic, or amphoteric, for example. Suitable anionic surfactants include, without limitation, water-soluble salts of $C_{8-20}$ alkyl sulfates, sulfonated monoglycerides of $C_{8-20}$ fatty acids, sarcosinates, and taurates. Examples of anionic surfactants include sodium lauryl sulfate, sodium coconut monoglyceride sulfonate, sodium lauryl sarcosinate, sodium lauryl isoethionate, sodium laureth carboxylate and sodium dodecyl benzenesulfonate. Suitable non-ionic surfactants include, without limitation, poloxamers, polyoxyethylene sorbitan esters, fatty alcohol ethoxylates, alkylphenol ethoxylates, tertiary amine oxides, tertiary phosphine oxides, and dialkyl sulfoxides. Suitable amphoteric surfactants include, without limitation, derivatives of $C_{8-20}$ aliphatic secondary and tertiary amines having an anionic group such as a carboxylate, sulfate, sulfonate, phosphate or phosphonate. An example of a suitable amphoteric surfactant is cocoamidopropyl betaine. One or more surfactants are optionally present in a total amount of about 0.01-10 wt % (e.g., about 0.05-5.0 wt % or about 0.1-2.0 wt %), for example, in the disclosed oral care composition.

An abrasive suitable for use in an oral care composition herein may include, for example, silica (e.g., silica gel, hydrated silica, precipitated silica), alumina, insoluble phosphates, calcium carbonate, and resinous abrasives (e.g., a urea-formaldehyde condensation product). Examples of insoluble phosphates useful as abrasives herein are orthophosphates, polymetaphosphates and pyrophosphates, and include dicalcium orthophosphate dihydrate, calcium pyrophosphate, beta-calcium pyrophosphate, tricalcium phosphate, calcium polymetaphosphate and insoluble sodium polymetaphosphate. One or more abrasives are optionally present in a total amount of about 5-70 wt % (e.g., about 10-56 wt % or about 15-30 wt %), for example, in the disclosed oral care composition. The average particle size of an abrasive in certain embodiments is about 0.1-30 microns (e.g., about 1-20 microns or about 5-15 microns).

An oral care composition in certain embodiments may comprise at least one pH-modifying agent. Such agents may be selected to acidify, make more basic, or buffer the pH of a composition to a pH range of about 2-10 (e.g., pH ranging from about 2-8, 3-9, 4-8, 5-7, 6-10, or 7-9). Examples of pH-modifying agents useful herein include, without limitation, carboxylic, phosphoric and sulfonic acids; acid salts (e.g., monosodium citrate, disodium citrate, monosodium malate); alkali metal hydroxides (e.g. sodium hydroxide, carbonates such as sodium carbonate, bicarbonates, sesquicarbonates); borates; silicates; phosphates (e.g., monosodium phosphate, trisodium phosphate, pyrophosphate salts); and imidazole.

A foam modulator suitable for use in an oral care composition herein may be a polyethylene glycol (PEG), for example. High molecular weight PEGs are suitable, including those having an average molecular weight of about 200000-7000000 (e.g., about 500000-5000000 or about 1000000-2500000), for example. One or more PEGs are optionally present in a total amount of about 0.1-10 wt % (e.g. about 0.2-5.0 wt % or about 0.25-2.0 wt %), for example, in the disclosed oral care composition.

An oral care composition in certain embodiments may comprise at least one humectant. A humectant in certain embodiments may be a polyhydric alcohol such as glycerin, sorbitol, xylitol, or a low molecular weight PEG. Most suitable humectants also may function as a sweetener herein. One or more humectants are optionally present in a total amount of about 1.0-70 wt % (e.g., about 1.0-50 wt %, about 2-25 wt %, or about 5-15 wt %), for example, in the disclosed oral care composition.

A natural or artificial sweetener may optionally be comprised in an oral care composition herein. Examples of suitable sweeteners include dextrose, sucrose, maltose, dextrin, invert sugar, mannose, xylose, ribose, fructose, levulose, galactose, corn syrup (e.g., high fructose corn syrup or corn syrup solids), partially hydrolyzed starch, hydrogenated starch hydrolysate, sorbitol, mannitol, xylitol, maltitol, isomalt, aspartame, neotame, saccharin and salts thereof, dipeptide-based intense sweeteners, and cyclamates. One or more sweeteners are optionally present in a total amount of about 0.005-5.0 wt %, for example, in the disclosed oral care composition.

A natural or artificial flavorant may optionally be comprised in an oral care composition herein. Examples of suitable flavorants include vanillin; sage; marjoram; parsley oil; spearmint oil; cinnamon oil; oil of wintergreen (methylsalicylate); peppermint oil; clove oil; bay oil; anise oil; *eucalyptus* oil; citrus oils; fruit oils; essences such as those derived from lemon, orange, lime, grapefruit, apricot, banana, grape, apple, strawberry, cherry, or pineapple; bean- and nut-derived flavors such as coffee, cocoa, cola, peanut, or almond; and adsorbed and encapsulated flavorants. Also encompassed within flavorants herein are ingredients that provide fragrance and/or other sensory effect in the mouth, including cooling or warming effects. Such ingredients include, without limitation, menthol, menthyl acetate, menthyl lactate, camphor, *eucalyptus* oil, eucalyptol, anethole, eugenol, *cassia*, oxanone, Insane®, propenyl guaiethol, thymol, linalool, benzaldehyde, cinnamaldehyde, N-ethyl-p- menthan-3-carboxamine, N,2,3-trimethyl-2-isopropylbutanamide, 3-(1-menthoxy)-propane-1,2-diol, cinnamaldehyde glycerol acetal (CGA), and menthone glycerol acetal (MGA). One or more flavorants are optionally present in a total amount of about 0.01-5.0 wt % (e.g., about 0.1-2.5 wt %), for example, in the disclosed oral care composition.

An oral care composition in certain embodiments may comprise at least one bicarbonate salt. Any orally acceptable bicarbonate can be used, including alkali metal bicarbonates such as sodium or potassium bicarbonate, and ammonium bicarbonate, for example. One or more bicarbonate salts are optionally present in a total amount of about 0.1-50 wt % (e.g., about 1-20 wt %), for example, in the disclosed oral care composition.

An oral care composition in certain embodiments may comprise at least one whitening agent and/or colorant. A suitable whitening agent is a peroxide compound such as any of those disclosed in U.S. Pat. No. 8,540,971, which is incorporated herein by reference. Suitable colorants herein include pigments, dyes, lakes and agents imparting a particular luster or reflectivity such as pearling agents, for example. Specific examples of colorants useful herein include talc; mica; magnesium carbonate; calcium carbonate; magnesium silicate; magnesium aluminum silicate; silica; titanium dioxide; zinc oxide; red, yellow, brown and black iron oxides; ferric ammonium ferrocyanide; manganese violet; ultramarine; titaniated mica; and bismuth oxychloride. One or more colorants are optionally present in a total amount of about 0.001-20 wt % (e.g., about 0.01-10 wt % or about 0.1-5.0 wt %), for example, in the disclosed oral care composition.

Additional components that can optionally be included in an oral composition herein include one or more enzymes (above), vitamins, and anti-adhesion agents, for example. Examples of vitamins useful herein include vitamin C, vitamin E, vitamin B5, and folic acid. Examples of suitable anti-adhesion agents include solbrol, ficin, and quorum-sensing inhibitors.

The present disclosure also concerns a method of preparing an aqueous composition having increased builder and/or anti-redeposition capacity. This method comprises contacting at least one oxidized dextran compound as disclosed herein with an aqueous composition, wherein the builder and/or anti-redeposition capacity of the aqueous composition is increased by the compound when compared to the builder and/or anti-redeposition capacity of the aqueous composition as it existed before the contacting step. An increase in anti-redeposition capacity can, in some embodiments, also refer to an increase in clay removal capacity.

An aqueous composition in this method can be any aqueous composition as disclosed herein, for example, such as a household care product, personal care product, industrial product, pharmaceutical product, or food product. Examples of suitable household care products include fabric care products such as laundry detergent and fabric softener, and dishwashing detergent. Examples of suitable personal care items include hair care products (e.g. shampoos, conditioners), dentifrice compositions (e.g., toothpaste, mouthwash), and skin care products (e.g., hand or body soap, lotion, cosmetics).

In some embodiments, an aqueous composition in this method is a detergent and/or surfactant composition. Such a composition herein can comprise at least one detergent/surfactant ingredient, such as any of the present disclosure, at about 0.01-10 wt % (e.g., about 0.05-5.0 wt % or about 0.1-2.0 wt %), for example. A skilled artisan would recognize all the various products disclosed herein that constitute examples of detergent/surfactant-comprising compositions such as certain household care products (e.g., laundry detergent, dishwashing detergent) and personal care products (e.g., hand/body soap, dentifrices), particularly those used in cleaning applications.

Contacting an aqueous composition with one or more oxidized dextran compounds herein can increase the builder and/or anti-redeposition capacity of the aqueous composition. This increase can be an increase of at least about 1%, 5%, 10%, 25%, 50%, 100%, 500%, or 1000% (or any integer between 1% and 1000%), for example, compared to the builder and/or anti-redeposition capacity of the aqueous composition before the contacting step. An increase in builder and/or anti-redeposition capacity can be determined, for example, by comparing the builder and/or anti-redeposition capacity of the aqueous composition obtained by the method (i.e., after the contacting step) with the builder and/or anti-redeposition capacity of the aqueous composition as it had existed before the method (i.e., before the contacting step). Alternatively, a control aqueous composition can be used, which is not contacted with oxidized dextran, but otherwise contains the same contents as the test composition.

The degree of anti-redeposition and/or clay removal capacity achieved using the presently disclosed subject matter can be measured following the disclosure of U.S. Pat. No. 4,597,898, for example, which is incorporated herein by reference. For example, anti-redeposition comparisons can be conducted in a 5-pot Automatic Miniwasher (AMW) employing 7-grain hardness water and a temperature of 95° F. Test swatches are washed for 10 minutes and rinsed twice with water (7-grain hardness) at 75° F. for 2 minutes. The AMW pots are filled with 6 liters of water each, after which a detergent composition to be tested (control or further containing oxidized dextran [e.g., 20 ppm]) is added and agitated for 2 minutes. A background soil mixture (200 ppm artificial body soil, 100 ppm vacuum cleaner soil and 200 ppm clay soil) is then added and agitated for an additional 3 minutes. Three 5-inch square test swatches (50% polyester/50% cotton T-shirt material) are then added, along with two 80% cotton/20% polyester terry clothes and two 11-inch square swatches of 100% polyester knit fabric. A 10-minute wash cycle is initiated at this point. Following a rinse cycle, the test swatches are dried in a mini-dryer. Gardner Whiteness meter readings (L, a and b) are then determined for the three test swatches. Anti-redeposition performance (ARD) is then calculated according to the following equation: ARD= $(7(L^2)-40(L)(b))/700$. The ARD values for the three test swatches are then averaged. The improvement in anti-redeposition performance of the detergent composition containing oxidized dextran is measured as the difference in ARD value relative to the control composition. As another example of determining degree of anti-redeposition, such can be gauged, in part, following methodology disclosed in the below Examples (adsorption studies).

The degree of increased builder capacity achieved using the presently disclosed subject matter can be measured following any number of methods. For example, increased builder capacity effected by an oxidized dextran compound can be estimated by determining the extent to which the compound supplies alkalinity to an aqueous composition, or buffers an aqueous composition to maintain alkalinity. As another example, increased builder capacity effected by an oxidized dextran compound can be estimated by determining the extent to which the compound reduces hardness in an aqueous composition (it is believed that oxidized dextran can effect this feature by sequestering or chelating hard water cations) and/or helps to remove soil in suspension (this feature typically applies to fabric care compositions). As another example, increased builder capacity can be determined following methodology disclosed in the below Examples (calcium dispersing capacity).

The contacting step in a method for increasing the builder and/or anti-redeposition capacity of an aqueous composition can be performed by mixing or dissolving any oxidized dextran compound as presently disclosed in the aqueous composition by any means known in the art. For example, mixing or dissolving can be performed manually or with a machine (e.g., industrial mixer or blender, orbital shaker, stir plate, homogenizer, sonicator, bead mill). Mixing or dissolving can comprise a homogenization step in certain embodiments. Homogenization (as well as any other type of mixing) can be performed for about 5 to 60, 5 to 30, 10 to 60, 10 to 30, 5 to 15, or 10 to 15 seconds (or any integer between 5 and 60 seconds), or longer periods of time as necessary to mix oxidized dextran with the aqueous composition. A homogenizer can be used at about 5000 to 30000 rpm, 10000 to 30000 rpm, 15000 to 30000 rpm, 15000 to 25000 rpm, or 20000 rpm (or any integer between 5000 and 30000 rpm), for example.

After an oxidized dextran compound herein is mixed with or dissolved into an aqueous composition, the resulting aqueous composition may be filtered, or may not be filtered. For example, an aqueous composition prepared with a homogenization step may or may not be filtered.

The order in which components of an aqueous composition, including oxidized dextran, are brought together to form the aqueous composition is not believed to be important. For example, oxidized dextran can be added as an ingredient at the same time as when one or more other ingredients are added. Thus, the feature of contacting oxidized dextran with an aqueous composition is not intended to refer only to embodiments in which an oxidized dextran is added to a final- or near final-prepared aqueous composition.

The present disclosure also concerns a method of treating a material. This method comprises contacting a material with an aqueous composition comprising at least one oxidized dextran compound as disclosed herein.

A material contacted with an aqueous composition in a contacting method herein can comprise a fabric in certain embodiments. A fabric herein can comprise natural fibers, synthetic fibers, semi-synthetic fibers, or any combination thereof. A semi-synthetic fiber herein is produced using naturally occurring material that has been chemically derivatized, an example of which is rayon. Non-limiting examples of fabric types herein include fabrics made of (i) cellulosic fibers such as cotton (e.g., broadcloth, canvas, chambray, chenille, chintz, corduroy, cretonne, damask, denim, flannel, gingham, jacquard, knit, matelassé, oxford, percale, poplin, plissé, sateen, seersucker, sheers, terry cloth, twill, velvet), rayon (e.g., viscose, modal, lyocell), linen, and Tencel® (ii) proteinaceous fibers such as silk, wool and related mammalian fibers; (iii) synthetic fibers such as polyester, acrylic, nylon, and the like; (iv) long vegetable fibers from jute, flax, ramie, coir, kapok, sisal, henequen, abaca, hemp and sunn; and (v) any combination of a fabric of (i)-(iv). Fabric comprising a combination of fiber types (e.g., natural and synthetic) include those with both a cotton fiber and polyester, for example. Materials/articles containing one or more fabrics herein include, for example, clothing, curtains, drapes, upholstery, carpeting, bed linens, bath linens, tablecloths, sleeping bags, tents, car interiors, etc. Other materials comprising natural and/or synthetic fibers include, for example, non-woven fabrics, paddings, paper, and foams.

An aqueous composition that is contacted with a fabric can be, for example, a fabric care composition (e.g., laundry detergent, fabric softener). Thus, a treatment method in certain embodiments can be considered a fabric care method or laundry method if employing a fabric care composition therein. A fabric care composition herein is contemplated to effect one or more of the following fabric care benefits (i.e., surface substantive effects): wrinkle removal, wrinkle reduction, wrinkle resistance, fabric wear reduction, fabric wear resistance, fabric pilling reduction, extended fabric life, fabric color maintenance, fabric color fading reduction, reduced dye transfer, fabric color restoration, fabric soiling reduction, fabric soil release, fabric shape retention, fabric smoothness enhancement, anti-redeposition of soil on fabric, anti-greying of laundry, improved fabric hand/handle, and/or fabric shrinkage reduction.

Examples of conditions (e.g., time, temperature, wash/rinse volumes) for conducting a fabric care method or laundry method herein are disclosed in WO1997/003161 and U.S. Pat. Nos. 4,794,661, 4,580,421 and 5,945,394, which are incorporated herein by reference. In other examples, a material comprising fabric can be contacted with an aqueous composition herein: (i) for at least about 5, 10, 20, 30, 40, 50, 60, 70, 80, 90, 100, 110, or 120 minutes; (ii) at a temperature of at least about 10, 15, 20, 25, 30, 35, 40, 45, 50, 55, 60, 65, 70, 75, 80, 85, 90, or 95° C. (e.g., for laundry wash or rinse: a "cold" temperature of about 15-30° C., a "warm" temperature of about 30-50° C., a "hot" temperature of about 50-95° C.); (iii) at a pH of about 2, 3, 4, 5, 6, 7, 8, 9, 10, 11, or 12 (e.g., pH range of about 2-12, or about 3-11); (iv) at a salt (e.g., NaCl) concentration of at least about 0.5, 1.0, 1.5, 2.0, 2.5, 3.0, 3.5, or 4.0 wt %; or any combination of (i)-(iv).

The contacting step in a fabric care method or laundry method can comprise any of washing, soaking, and/or rinsing steps, for example. Contacting a material or fabric in still further embodiments can be performed by any means known in the art, such as dissolving, mixing, shaking, spraying, treating, immersing, flushing, pouring on or in, combining, painting, coating, applying, affixing to, and/or communicating an effective amount of an oxidized dextran compound herein with the fabric or material. In still further embodiments, contacting may be used to treat a fabric to provide a surface substantive effect. As used herein, the term "fabric hand" or "handle" refers to a person's tactile sensory response towards fabric which may be physical, physiological, psychological, social or any combination thereof. In one embodiment, the fabric hand may be measured using a PhabrOmeter® System for measuring relative hand value (available from Nu Cybertek, Inc. Davis, Calif.) (American Association of Textile Chemists and Colorists (AATCC test method "202-2012, Relative Hand Value of Textiles: Instrumental Method")).

In certain embodiments of treating a material comprising fabric, an oxidized dextran component(s) of the aqueous composition adsorbs to the fabric. This feature is believed, in part, to render oxidized dextran compounds herein useful as anti-redeposition agents and/or anti-greying agents in fabric care compositions (in addition to their soil dispersion effect). An anti-redeposition agent or anti-greying agent herein helps keep soil from redepositing onto clothing in wash water after the soil has been removed. It is further contemplated that adsorption of one or more oxidized dextran compounds herein to a fabric enhances mechanical properties of the fabric.

Adsorption of an oxidized dextran compound to a fabric herein can be measured using a colorimetric technique (e.g., Dubois et al., 1956, Anal. Chem. 28:350-356; Zemljič et al., 2006, *Lenzinger Berichte* 85:68-76; both incorporated herein by reference), for example, or any other method known in the art.

Other materials that can be contacted in the above treatment method include surfaces that can be treated with a dish detergent (e.g., automatic dishwashing detergent or hand dish detergent). Examples of such materials include surfaces of dishes, glasses, pots, pans, baking dishes, utensils and flatware made from ceramic material, china, metal, glass, plastic (e.g., polyethylene, polypropylene, polystyrene, etc.) and wood (collectively referred to herein as "tableware"). Thus, the treatment method in certain embodiments can be considered a dishwashing method or tableware washing method, for example. Examples of conditions (e.g., time, temperature, wash volume) for conducting a dishwashing or tableware washing method herein are disclosed in U.S. Pat. No. 8,575,083, which is incorporated herein by reference. In other examples, a tableware article can be contacted with an aqueous composition herein under a suitable set of conditions such as any of those disclosed above with regard to contacting a fabric-comprising material.

Other materials that can be contacted in the above treatment method include oral surfaces such as any soft or hard surface within the oral cavity including surfaces of the tongue, hard and soft palate, buccal mucosa, gums and dental surfaces (e.g., natural tooth or a hard surface of artificial dentition such as a crown, cap, filling, bridge, denture, or dental implant). Thus, a treatment method in certain embodiments can be considered an oral care method or dental care method, for example. Conditions (e.g., time, temperature) for contacting an oral surface with an aqueous composition herein should be suitable for the intended purpose of making such contact. Other surfaces that can be contacted in a treatment method also include a surface of the integumentary system such as skin, hair or nails.

Thus, certain embodiments of the present disclosure concern material (e.g., fabric) that comprises an oxidized dextran compound herein. Such material can be produced following a material treatment method as disclosed herein, for example. A material may comprise an oxidized dextran compound in certain embodiments if the compound is adsorbed to, or otherwise in contact with, the surface of the material.

Certain embodiments of a method of treating a material herein further comprise a drying step, in which a material is dried after being contacted with the aqueous composition. A drying step can be performed directly after the contacting step, or following one or more additional steps that might follow the contacting step (e.g., drying of a fabric after being rinsed, in water for example, following a wash in an aqueous composition herein). Drying can be performed by any of several means known in the art, such as air drying (e.g., ~20-25° C.), or at a temperature of at least about 30, 40, 50, 60, 70, 80, 90, 100, 120, 140, 160, 170, 175, 180, or 200° C., for example. A material that has been dried herein typically has less than 3, 2, 1, 0.5, or 0.1 wt % water comprised therein. Fabric is a preferred material for conducting an optional drying step.

An aqueous composition used in a treatment method herein can be any aqueous composition disclosed herein. Thus, the oxidized dextran component(s) of an aqueous composition can be any as disclosed herein. Examples of aqueous compositions include detergents (e.g., laundry detergent or dish detergent) and water-containing dentifrices such as toothpaste.

The present disclosure also concerns a method for producing an oxidized dextran compound. This method comprises: contacting dextran under aqueous conditions with (i) at least one N-oxoammonium salt, (ii) at least one periodate compound, and/or (iii) at least one peroxide compound, wherein the dextran is oxidized by the N-oxoammonium salt, periodate compound, and/or peroxide compound thereby producing an oxidized dextran compound. Dextran used in this method can be as disclosed herein. The oxidized dextran compound produced by this method can optionally be isolated.

An N-oxoammonium salt in certain embodiments of an oxidation method can comprise a TEMPO oxoammonium salt. Examples of such an N-oxoammonium salt include TEMPO oxoammonium salt itself (structure II) and 4-acetamido-TEMPO oxoammonium salt (structure III). An N-oxoammonium salt herein can be a cyclic N-oxoammonium salt, for example. A cyclic N-oxoammonium salt is represented by structure VI (above) in certain embodiments. An N-oxoammonium salt in the disclosed method can be a TEMPO oxoammonium salt having a substitution at carbon position 4 (where the $N^+$ in the ring of the TEMPO oxoammonium salt is position 1).

A TEMPO oxoammonium salt can be provided in an oxidation method, for example, by oxidizing an agent comprising TEMPO under aqueous conditions in which a TEMPO oxoammonium salt is contacted with dextran. An agent comprising TEMPO is an agent/compound comprising structure IV. Examples of an agent comprising TEMPO is TEMPO itself (structure IV) and 4-acetamido-TEMPO (structure V). Other examples of agents comprising TEMPO can be represented by structure VII (above). Each of these agents can be converted to its corresponding oxoammonium salt, as represented by structure VI, by contacting it with one or more oxidation agents in aqueous conditions. Given that TEMPO and its derivatives, such as above (e.g., 4-acetamido-TEMPO), are examples of cyclic nitroxyl compounds, a cyclic nitroxyl compound can be used to provide a TEMPO oxoammonium salt herein.

An agent comprising TEMPO can be oxidized under aqueous conditions of an oxidation method to its corresponding oxoammonium salt by contacting the agent with one or more "oxidation agents" (or "oxidant"). This contacting can be performed under the same aqueous conditions in which dextran is contacted with an N-oxoammonium salt. In some embodiments, a reaction herein for oxidizing dextran can initially be prepared to comprise, under aqueous conditions, at least dextran, an agent comprising TEMPO (e.g., structure VII), and one or more oxidation agents. The oxidation agent(s) can convert the agent comprising TEMPO to its corresponding oxoammonium salt (e.g., structure VI), which in turn oxidizes the dextran.

Non-limiting examples of an oxidation agent for use in the disclosed oxidation method include one or more "inorganic oxidation agents" (or "inorganic oxidant"). Examples of oxidation agents that may be used to convert an agent comprising TEMPO to its corresponding oxoammonium salt under aqueous conditions of the method include one or more of a halite (e.g., a chlorite, such as sodium chlorite [$NaClO_2$]) or a hypohalite (e.g., a hypochlorite, such as sodium hypochlorite [NaClO]). Other examples of oxidation agents (inorganic or organic) include one or more of a halide salt such as KCl, KBr, NaCl, NaBr, or NaI; a hypohalite such as NaOBr; metals such as Fe(III), Mn(II), Mn(III), or Cu(II);

KMnO$_4$; Mn(OAc)$_3$; Mn$_2$O$_3$; MnO$_2$; Mn(NO$_3$)$_2$; MgCl$_2$; Mg(OAc)$_2$; Cu(NO$_3$)$_2$; iodobenzene diacetate [PhI(OAc)$_2$]; Ca(ClO)$_2$; t-BuOCl; CuCl—O$_2$; NaBrO$_2$; Cl$_2$; Br$_2$; and trichloroisocyanuric acid.

Aqueous conditions are used in a method for oxidizing dextran. Aqueous conditions in the method refer to a solution or mixture in which the solvent is at least about 60 wt % water, for example. Alternatively, aqueous conditions can be at least about 65, 70, 75, 80, 85, 90, or 95 wt % water (or any integer value between 60 and 95 wt %), for example. Aqueous conditions herein can comprise a buffer, such as an acidic, neutral, or alkaline buffer, at a suitable concentration and selected based on the pH range provided by the buffer. Examples of buffers include citric acid, acetic acid, KH$_2$PO$_4$, CHES and borate.

The aqueous conditions of an oxidation method herein can be acidic (e.g., pH of 5.5 or less). Alternatively, the pH may be about 2.0, 2.5, 3.0, 3.5, 4.0, 4.5, 5.0, or 5.5. Acidic conditions can be prepared by any means known in the art, such as by adding acetic acid and/or an acetate salt to a solution or mixture. For example, a sodium acetate buffer (acetate buffer) (pH 4-5) (e.g., 0.2-0.3 M solution) can provide acidic conditions.

The aqueous conditions of an oxidation method herein can be basic, having a pH of 8.5 or more, for example. Alternatively, the pH may be about 8.5, 9.0, 9.5, 10.0, 10.5, 11.0, 11.5, or 12, for example. Basic conditions can be prepared by any means known in the art, such as by adding an alkaline hydroxide (e.g., sodium hydroxide) to a solution or mixture.

A periodate compound in certain embodiments of an oxidation method can be a metal periodate (e.g., sodium periodate or potassium periodate), for example. A periodate compounds can be a metaperiodate (e.g., NaIO$_4$) or an orthoperiodate in some aspects. Conditions for oxidizing dextran with a periodate compound can follow those as disclosed in U.S. Pat. Nos. 3,086,969, 6,800,753, 5,747,658 and/or 6635755, which are all disclosed herein by reference, and/or as disclosed in Examples 10 and 11 below, for example. Typically, a reaction employing periodate comprises providing dextran in an aqueous periodate solution. The concentration of a periodate in a reaction can be about 1, 2, 3, 4, 5, 6, 7, 8, 9, or 10 wt %, for example. The temperature of a reaction herein comprising a periodate can be between about 18° C. to about 40° C. (e.g., room temperature), for example. In certain embodiments, a reaction comprising a periodate can proceed for about 1-72 hours (e.g., ~5 hours or ~48 hours).

In some aspects of an oxidation method herein, an oxidized dextran compound is produced by first contacting dextran with a periodate compound, followed by contacting the dextran (i.e., periodate-oxidized dextran) with an N-oxoammonium salt. Such a sequential oxidation treatment can follow any of the processes disclosed herein, such as in Example 11 below. Periodate-oxidized dextran can optionally first be isolated (e.g., via alcohol precipitation) from the periodate reaction before contacting it with an N-oxoammonium salt.

A peroxide compound in certain embodiments of an oxidation method herein can be hydrogen peroxide (H$_2$O$_2$), for example. In some aspects, a peroxide compound can be an inorganic peroxide compound or an organic peroxide compound. Suitable peroxide compounds herein further include perborate-monohydrate, perborate-tetrahydrate, percarbonates, alkali persulphates, persilicates, and percitrates, in which sodium or calcium is the preferred cation, as well as hydrogen peroxide adducts of urea or amine oxides, for example.

Conditions for oxidizing dextran with a peroxide compound can follow those as disclosed in Example 14 below, for example. Typically, a reaction employing a peroxide (e.g., H$_2$O$_2$) comprises providing dextran in an aqueous peroxide solution. The amount of peroxide in a reaction can be about 1, 2, 3, 4, 5, 6, 7, 8, 9, or 10 wt %, for example, where such wt % is with respect to the amount of dextran present in the reaction. A reaction employing a peroxide compound herein can have a neutral pH (e.g., pH 6-8) in some embodiments. The temperature of a reaction comprising a peroxide can be between about 110° C. to about 140° C. (e.g., ~121° C.), for example. It would be understood that achieving such elevated reaction temperatures can involve application of pressure, such as can be provided with an autoclave or other high pressure device. In certain embodiments, a reaction comprising a peroxide can proceed for about 30 minutes to about 120 minutes (e.g., ~60 minutes).

In some aspects of an oxidation method herein, an oxidized dextran compound is produced by first contacting dextran with a peroxide compound, followed by contacting the peroxide-oxidized dextran with an N-oxoammonium salt.

Dextran in certain embodiments of an oxidation method as presently disclosed can be contacted with a peroxide compound in the absence of a chelating agent (e.g., EDTA), whereas in other embodiments a chelating agent can optionally be present.

Dextran can be included under aqueous conditions of an oxidation method at about, or at least about, 0.1, 0.25, 0.5, 0.75, 1, 2, 3, 4, 5, 6, 7, 8, 9, 10, 11, or 12 wt %, for example. Dextran can be mixed or dissolved under aqueous conditions before or after a periodate compound, peroxide compound, and/or an agent comprising TEMPO and/or an oxidation agent (which converts the agent comprising TEMPO to its corresponding oxoammonium salt) is added to the aqueous conditions. The oxidation agent in these particular embodiments can be sodium chlorite, sodium bromide, and/or sodium hypochlorite (or any other oxidation agent listed herein), for example.

An agent comprising TEMPO, such as TEMPO and/or 4-acetamido-TEMPO, can be included under aqueous conditions of the method at about, or at least about, 0.05, 0.075, 0.1, 0.25, 0.5, 0.75, 1, or 2 wt %, for example. In certain embodiments, an agent comprising TEMPO can be added to aqueous conditions in which dextran has already been mixed or dissolved. Such addition may be made before, after, or at the time an oxidation agent is added to the aqueous conditions.

An oxidation agent such as sodium chlorite, sodium bromide, and/or sodium hypochlorite (or any other oxidation agent listed herein) can be included in aqueous conditions of the method at about, or at least about, 0.1, 0.25, 0.5, 0.75, 1, 2, 3, 4, 5, 10, 15, 20, 25, 30, 35, 40, 45, or 50 wt %, for example. In certain embodiments, an oxidation agent(s) can be added to aqueous conditions in which dextran has already been mixed or dissolved.

Aqueous conditions in certain embodiments of the disclosed oxidation method may initially contain dextran, an agent comprising TEMPO (e.g., 4-acetamido-TEMPO), and one or more oxidation agents (e.g., sodium chlorite and/or sodium hypochlorite) in a buffer solution (e.g., sodium acetate buffer at a pH of about 4-5). Optionally, no additional components are included in preparing these particular aqueous conditions. These particular aqueous conditions can be maintained for about 24-96 hours (e.g., ~48 hours) at a temperature of about 18° C. to about 40° C. (e.g., room temperature).

Aqueous conditions in certain embodiments of the disclosed method may initially contain dextran, an agent comprising TEMPO (e.g., 4-acetamido-TEMPO), and one or more oxidation agents (e.g., sodium bromide and/or sodium hypochlorite) in a basic solution (e.g., sodium hydroxide solution at a pH of about 10.5-11.5). Optionally, no additional components are included in preparing these particular aqueous conditions. These particular aqueous conditions can be maintained for about 0.5-5 hours (e.g., ~1 hours) at a temperature of about 18° C. to about 40° C. (e.g., room temperature).

Dextran can be contacted with at least one periodate compound, peroxide compound, and/or N-oxoammonium salt under aqueous conditions by mixing, for example. Mixing can be performed by manual mixing, mixing using an overhead mixer, using a magnetic stir bar, or shaking, for example. Such mixing can be performed during and/or after adding each of dextran, an agent comprising TEMPO (and/or a periodate compound or peroxide compound), and one or more oxidation agents to the aqueous conditions. As described above, such aqueous conditions allow contact between the agent comprising TEMPO and one or more oxidation agents, thereby converting the agent comprising TEMPO to its corresponding N oxoammonium salt. This N-oxoammonium salt can then contact and oxidize the dextran.

The time period for which dextran herein is contacted with at least one N-oxoammonium salt, peroxide, and/or periodate under aqueous conditions can be at least about 0.5, 1, 4, 8, 12, 16, 20, 24, 28, 32, 36, 40, 44, 48, 72, or 96 hours (or any integer value between 1 to 96 hours), for example. A reaction can be maintained for about 0.5-5 hours (e.g., ~1 hour) or 24-96 hours (e.g., ~48 hours) in certain embodiments. The period of time for contacting dextran with at least one N-oxoammonium salt, peroxide, and/or periodate under aqueous conditions can be measured, for example, from the point of time after each reaction component has been dissolved and/or mixed in the aqueous conditions.

The temperature of aqueous conditions of the disclosed method can be about 18° C. to about 40° C. (or any integer value between 18 to 40° C.) in certain embodiments (e.g., when employing a periodate and/or N-oxoammonium salt). Aqueous conditions in certain embodiments of the method can be maintained at a temperature of about 20-25° C. The temperature of aqueous conditions can be maintained from the time in which each reaction component has been dissolved and/or mixed under the aqueous conditions, until the reaction is completed. Optionally, the initial aqueous conditions to which each reaction component is added may be at the temperature held for the reaction.

Optionally, a reaction herein can be maintained under an inert gas, with or without heating. As used herein, the term "inert gas" refers to a gas which does not undergo chemical reactions under a set of given conditions; such as those disclosed for preparing a reaction herein.

Upon completion of an oxidation reaction in which acidic or basic aqueous conditions are used, the pH of the reaction can optionally be neutralized. Neutralization of an acidic reaction can be performed using one or more bases (e.g., an alkali hydroxide such as sodium hydroxide). Neutralization of a basic reaction can be performed using one or more acids (e.g., an inorganic acid such as hydrochloric acid). The term "neutral pH" as used herein, refers to a pH that is neither substantially acidic or basic (e.g., a pH of about 6-8, or about 6.0, 6.2, 6.4, 6.6, 6.8, 7.0, 7.2, 7.4, 7.6, 7.8, or 8.0).

An oxidized dextran compound produced in an oxidation reaction herein can optionally be isolated. Such a product may first be precipitated from the aqueous conditions of the reaction. Precipitation can be performed by adding an excess amount (e.g., at least 2-3 times the volume of the reaction volume) of an alcohol (e.g., 100% or 95% concentration) such as ethanol or isopropanol to the reaction. A precipitated product can then be isolated using a filtration funnel, centrifuge, press filter, or any other method or equipment known in the art that allows removal of liquids from solids. For example, a vacuum filtration may be used to isolate an oxidized dextran product. The isolated compound can be dried using any method known in the art, such as vacuum drying, air drying, or freeze drying.

An oxidized dextran compound produced in an oxidation reaction herein can optionally be washed, following precipitation, one or more times with a liquid that does not readily dissolve the compound. For example, oxidized dextran can be washed with alcohol, acetone, aromatics, or any combination of these, depending on the solubility of the oxidized compound therein (where lack of solubility is desirable for washing). In general, a solvent comprising an organic solvent (e.g. 95-100%) such as alcohol is preferred for washing an oxidized dextran compound. An oxidized dextran compound can be washed one or more times with an aqueous solution containing an alcohol (e.g., methanol or ethanol), for example.

Any of the above oxidation reactions can be repeated using an oxidized dextran compound produced herein as the starting material for further modification. For example, dextran that has been periodate-oxidized can be subjected to another round of periodate oxidation, or oxidation with another agent such as an N-oxoammonium salt.

Dextran herein can optionally be provided in a pre-treated form prior to being oxidized according to the present disclosure. An example of a pre-treated form is dextran that has been treated with an oxidizing agent other than those used in embodiments of the instantly disclosed subject matter. Thus, dextran in certain aspects herein can be provided in a pre-oxidized form. It is contemplated that such pre-oxidized material in certain embodiments would comprise some amount of intact dextran polymer that was not oxidized. It is believed that pre-oxidized dextran can be prepared, for example, via application of oxidation processes as disclosed in Canadian Patent Publ. Nos. 2028284 and 2038640, and U.S. Pat. Nos. 4,985,553, 2,894,945, 5,747,658 and 7,595,392, all of which are incorporated herein by reference.

The structure and molecular weight of an oxidized dextran product can be determined using various physiochemical analyses known in the art such as NMR spectroscopy and size exclusion chromatography (SEC).

Any of the embodiments of dextran disclosed herein can be used in an oxidation reaction, for example. Dextran can be provided in some aspects of preparing an oxidation reaction in a dry form (e.g., powder, flakes), wet form (e.g., aqueous solution), or any other suitable form for preparing an oxidation reaction. As another example, dextran can be provided in the form of a dextran synthesis reaction (gtf reaction) as disclosed herein, containing at least dextran, water, fructose and a glucosyltransferase enzyme.

Non-limiting examples of compositions and methods disclosed herein include:

1. A composition comprising an oxidized dextran compound, wherein the oxidized dextran compound is produced by contacting dextran under aqueous conditions with at least one N-oxoammonium salt, at least one periodate compound, and/or at least one peroxide compound, wherein the dextran comprises:
  (i) about 87-93 wt % glucose linked at positions 1 and 6;
  (ii) about 0.1-1.2 wt % glucose linked at positions 1 and 3;
  (iii) about 0.1-0.7 wt % glucose linked at positions 1 and 4;
  (iv) about 7.7-8.6 wt % glucose linked at positions 1, 3 and 6; and
  (v) about 0.4-1.7 wt % glucose linked at:
    (a) positions 1, 2 and 6, or
    (b) positions 1, 4 and 6;
  and wherein the weight-average molecular weight (Mw) of the dextran is about 50-200 million Daltons and the z-average radius of gyration of the dextran is about 200-280 nm.
2. The composition of embodiment 1, wherein the dextran comprises: (i) about 89.5-90.5 wt % glucose linked at positions 1 and 6; (ii) about 0.4-0.9 wt % glucose linked at positions 1 and 3; (iii) about 0.3-0.5 wt % glucose linked at positions 1 and 4; (iv) about 8.0-8.3 wt % glucose linked at positions 1, 3 and 6; and (v) about 0.7-1.4 wt % glucose linked at: (a) positions 1, 2 and 6, or (b) positions 1, 4 and 6.
3. The composition of embodiment 1 or 2, wherein the dextran comprises chains linked together within a branching structure, wherein the chains are similar in length and comprise substantially alpha-1,6-glucosidic linkages.
4. The composition of embodiment 3, wherein the average length of the chains is about 10-50 monomeric units.
5. The composition of embodiment 1, 2, 3, or 4, wherein the dextran is a product of a glucosyltransferase enzyme comprising an amino acid sequence that is at least 90% identical to SEQ ID NO:1, SEQ ID NO:2, SEQ ID NO:5, SEQ ID NO:9, SEQ ID NO:13, or SEQ ID NO:17.
6. The composition of embodiment 1, 2, 3, 4, or 5, wherein the dextran is contacted with the periodate compound.
7. The composition of embodiment 1, 2, 3, 4, or 5, wherein the dextran is first contacted with the periodate compound, and then contacted with the N-oxoammonium salt.
8. The composition of embodiment 1, 2, 3, 4, 5, or 7, wherein the N-oxoammonium salt comprises a TEMPO oxoammonium salt.
9. The composition of any one of embodiments 1-8, wherein the composition is a household product, personal care product, industrial product, pharmaceutical product, or food product.
10. The composition of embodiment 9, wherein the composition is a detergent composition, and further wherein the composition is preferably a household product.
11. A method of producing an oxidized dextran compound, the method comprising: (a) contacting dextran under aqueous conditions with at least one N-oxoammonium salt, at least one periodate compound, and/or at least one peroxide compound, wherein the dextran comprises: (i) about 87-93 wt % glucose linked at positions 1 and 6; (ii) about 0.1-1.2 wt % glucose linked at positions 1 and 3; (iii) about 0.1-0.7 wt % glucose linked at positions 1 and 4; (iv) about 7.7-8.6 wt % glucose linked at positions 1, 3 and 6; and (v) about 0.4-1.7 wt % glucose linked at: (a) positions 1, 2 and 6, or (b) positions 1, 4 and 6; wherein the weight-average molecular weight (Mw) of the dextran is about 50-200 million Daltons and the z-average radius of gyration of the dextran is about 200-280 nm; wherein the dextran is oxidized by the N-oxoammonium salt, periodate compound, and/or peroxide compound thereby producing an oxidized dextran compound, and (b) optionally, isolating the oxidized dextran compound.
12. The method of embodiment 11, wherein: (I) the dextran is contacted with the periodate compound; or (II) the dextran is first contacted with the periodate compound, and then contacted with the N-oxoammonium salt.
13. The method of embodiment 11 or 12, wherein the N-oxoammonium salt comprises: (I) a TEMPO oxoammonium salt, or (II) a 4-acetamido-TEMPO oxoammonium salt; optionally wherein the TEMPO oxoammonium salt or a 4 acetamido-TEMPO oxoammonium salt is provided by oxidizing an agent comprising TEMPO under the aqueous conditions.
14. A method of increasing the builder capacity and/or anti-redeposition capacity of an aqueous composition, wherein the method comprises: contacting an oxidized dextran compound produced according to the method of any one of embodiments 11-13, or as recited in any one of embodiments 1-8, with an aqueous composition, wherein the builder and/or anti-redeposition capacity of the aqueous composition is increased by the oxidized dextran compound compared to the builder and/or anti-redeposition capacity of the aqueous composition before the contacting step.
15. A method of treating a material, the method comprising: contacting a material with an aqueous composition comprising an oxidized dextran compound (i) produced according to the method of any one of embodiments 11-13, or (ii) as recited in any one of embodiments 1-8.

EXAMPLES

The present disclosure is further exemplified in Examples 1-6 and 8-14. It should be understood that these Examples, while indicating certain preferred aspects herein, are given by way of illustration only. From the above discussion and these Examples, one skilled in the art can ascertain the essential characteristics of the disclosed embodiments, and without departing from the spirit and scope thereof, can make various changes and modifications to adapt the disclosed embodiments to various uses and conditions.

General Methods
Cloning and Expression of Glucosyltransferase Enzymes in *Bacillus subtilis*

Each glucosyltransferase used in Examples 3-6 was prepared as follows.

A plasmid encoding the gtf enzyme (pZZHB582, pZZHB583, pZZHB584, or pZZHB585, which allow for gtf expression and secretion from *B. subtilis*; see FIGS. 2A-D) was amplified using Illustra TempliPhi® 100 Amplification Kit (GE Healthcare Life Sciences, NJ). Competent *B. subtilis* cells (ΔspoIIE, ΔaprE, ΔnprE, degUHy32, ΔscoC, ΔnprB, Δvpr, Δepr, ΔwprA, Δmpr, ΔispA, Δbpr) were transformed with the amplification product. Cells were plated on Luria Agar plates supplemented with 5 ppm chloramphenicol. Colonies from the transformation plate were inoculated into 5 mL LB medium and incubated at 37° C. overnight. Aliquots (25-50 μL) from each culture were then transferred to 250-mL shake flasks containing 30 mL of Grant's II Medium supplemented with 5 ppm chloramphenicol and incubated at 30° C. with shaking (280 rpm) for 24 hours. Cells were harvested by centrifugation at 14000 rpm for 1 hour. Supernatants were analyzed by SDS-PAGE for secreted gtf product and further dialyzed three times against a solution containing 20 mM Tris, pH 7.5 for a total of 20 hours. Dialyzed samples were aliquoted at 25 mL per 50-mL conical centrifuge tube, and the tubes were placed at an angle at −80° C. for about 1 hour. Once the samples were frozen, the tube lid was removed and replaced with PARAFILM that was pierced 5-10 times with a high-gauge needle. The PARAFILM-covered frozen samples were lyophilized in a FreeZone® Freeze Dry System (Labconco Corp., Kansas City, Mo.) according to the manufacturer's instruction. Stock Solutions of Glucosyltransferase Enzymes An enzyme stock solution was made for each gtf by adding 10 mL of molecular grade $H_2O$ into each 50-mL conical centrifuge tube containing lyophilized enzyme powder.

Example 1

Expression of a Glucosyltransferase (0768) in *E. coli* and Production of Active Crude Enzyme Lysate This Example describes expression of a mature glucosyltransferase (gtf) enzyme in *E. coli*. Crude cell lysate of an *E. coli* expression strain was produced and showed gel product-forming activity in the presence of sucrose.

A putative YG repeat-containing hydrolase (categorized in GENBANK under GI number 339480768, but now having GI number 497964659) with 1484 amino acids was identified from *Leuconostoc pseudomesenteroides* strain KCTC3652 by whole genome shotgun sequencing. This putative glucosyltransferase (designated herein as gtf 0768) belongs to the GH70 family of glycosyl hydrolases containing a glucan-binding domain. The N-terminal 37 amino acid segment of gtf 0768 was deduced as the signal peptide of the enzyme by the SIGNALP 4.0 program (Petersen et al., *Nature Methods* 8:785-786). The mature form of gtf 0768 is represented by SEQ ID NO:1.

To construct a plasmid for bacterial expression of gtf 0768, a DNA sequence encoding a mature form of the gtf without the signal peptide was synthesized by GenScript USA Inc. (Piscataway, N.J.). The synthesized sequence was subcloned into the NheI and HindIII sites of the pET23D+ vector (NOVAGEN®; Merck KGaA, Darmstadt, Germany). The 0768 gtf (SEQ ID NO:2) encoded by this construct included a start methionine and 3 additional amino acids (Ala-Ser-Ala) at the N-terminus, and 6 histidine residues at the C-terminus, compared to the wild type mature (predicted) form of gtf 0768 (SEQ ID NO:1) (i.e., SEQ ID NO:1 is comprised in SEQ ID NO:2). The plasmid construct was sequence-confirmed and transformed into *E. coli* BL21 DE3 host cells with ampicillin selection, resulting in expression strain EC0052.

Cells of EC0052 and a control strain containing only empty pET23D+ vector were grown in LB medium with 100 μg/mL ampicillin to $OD_{600}$~0.5, and then induced with 1 mM IPTG at 37° C. for 3 hours or alternatively induced at 23° C. overnight. Following this induction period, cells were collected by centrifugation at 4000×g for 10 min and resuspended in PBS buffer pH 6.8. The cells were then lysed by passing through a French Press at 14,000 psi (~96.53 MPa) twice, afterwhich cell debris was pelleted by centrifugation at 15,000×g for 20 min. The supernatants of each crude cell lysate were aliquoted and frozen at −80° C.

The activity of crude cell lysate from EC0052 cells was checked by reaction with sucrose. A control reaction was set up similarly using cell lysate prepared from cells containing the empty vector. Each sucrose reaction was set up using 10% (v/v) of cell lysate with 100 g/L sucrose, 10 mM sodium citrate pH 5, and 1 mM $CaCl_2$. After incubation of the reactions at 37° C. for a few hours, a gel-like product, believed to be a dextran, was formed in the tube in which EC0052 cell lysate had been added. No gel-like product was formed in the control reaction. HPLC analysis confirmed that sucrose was consumed in the reaction containing EC0052 cell lysate, and not in the control reaction. This result suggested that the EC0052 crude cell lysate expressed active gtf 0768 enzyme, and that this gtf produced a dextran product having high viscosity.

Thus, reactions comprising water, sucrose and an enzyme comprising SEQ ID NO:1 synthesized a gelling product, believed to be a dextran. This result demonstrated that gtf 0768 likely has glucosyltransferase activity. This product can be used to prepare oxidized dextran as presently disclosed.

Example 2

Reaction of Sucrose with Gtf 0768 and Analysis of a Gelling Dextran Reaction Product This Example describes another reaction comprising water, sucrose and gtf 0768, supplementing the results provided in Example 1. Also, this Example provides glycosidic linkage analysis of the gelling product synthesized by gtf 0768, showing that this product is a type of dextran.

Reagents for preparing gtf reactions:

Sucrose (Sigma Prod. No. S-9378).

Sodium phosphate buffer stock (200 mM) (pH 5.5): prepare 250 mL in water using sodium phosphate monobasic monohydrate (Sigma Prod. No. S9638) and sodium phosphate dibasic heptahydrate (Sigma Prod. No. S9390), accordingly.

Gtf 0768 enzyme solution (cell lysate as prepared in Example 1).

Conditions of three gtf reactions:

A 1000-mL reaction was prepared containing 2.72 g of sodium phosphate buffer stock (pH 5.5), 100 g/L sucrose, and 2 mL of gtf 0768 enzyme solution. The reaction was stirred at 26° C. for 20 hours, and became viscous. The gtf enzyme was deactivated by heating the reaction at 80° C. for 10 minutes. The deactivated viscous reaction was then mixed with 3 liters of 100% methanol to precipitate the viscous product. A white precipitate was formed, which was then filtered, followed by four washes with 120 ml of 100% methanol. The solid product was dried at room temperature under vacuum in an oven for 72 hours.

A 725-mL reaction was prepared containing 1.97 g of sodium phosphate buffer, 300 g/L sucrose, and 1.45 mL of gtf 0768 enzyme solution. The reaction was stirred at 26° C. for 20 hours, and became viscous. The gtf enzyme was deactivated by adding methanol to the reaction mixture. The deactivated reaction was then mixed with 3 liters of 100% methanol to precipitate the viscous product. A white precipitate was formed, which was then filtered, followed by four washes with 120 mL of 100% methanol. The solid product was dried at room temperature under vacuum in an oven for 72 hours.

A 200-mL reaction was prepared containing 0.544 g of sodium phosphate buffer, 400 g/L sucrose, and 0.4 mL of gtf 0768 enzyme solution. The reaction was stirred at 26° C. for 20 hours, and became viscous. The gtf enzyme was deactivated by adding methanol to the reaction mixture. The deactivated reaction was then mixed with 3 liters of 100% methanol to precipitate the viscous product. A white precipitate was formed, which was then filtered, followed by four washes with 120 mL of 100% methanol. The solid product was dried at room temperature under vacuum in an oven for 72 hours.

A 200-mL reaction was prepared containing 0.544 g of sodium phosphate buffer, 800 g/L sucrose, and 0.4 mL of gtf 0768 enzyme solution. The reaction was stirred at 26° C. for 20 hours, and became viscous. The gtf enzyme was deactivated by adding methanol to the reaction mixture. The deactivated reaction was then mixed with 3 liters of 100% methanol to precipitate the viscous product. A white precipitate was formed, which was then filtered, followed by four washes with 120 ml of 100% methanol. The solid product was dried at room temperature under vacuum in an oven for 72 hours.

Samples (100 µL) of each reaction were taken at 0, 2, 4, and 18 hours, respectively. The gtf enzyme was deactivated in each sample by heating at 80° C. for 10 minutes. Each sample was then diluted 10-fold with water and centrifuged at 14,000 rpm for 5 minutes, afterwhich 200 µl of supernatant was used for HPLC analysis to measure sucrose consumption during the reaction. The following HPLC conditions were applied for analyzing each sample: column (AMINEX HPX-87C carbohydrate column, 300×7.8 mm, Bio-Rad, No. 125-0095), eluent (water), flow rate (0.6 mL/min), temperature (85° C.), refractive index detector. HPLC analysis of the samples indicated substantial sucrose consumption during the 0768 gtf reaction (FIG. 1, reaction comprising 100 g/L sucrose) (this sucrose consumption occurred significantly faster than the sucrose consumption observed in a reaction using a dextran sucrase obtained from a commercial source—refer to Example 7).

HPLC was also used to analyze other products of the reaction comprising 100 g/L sucrose. Polymer yield was back-calculated by subtracting the amount of all other saccharides left in the reaction from the amount of the starting sucrose. The back-calculated number was consistent with the viscous product dry weight analysis. Sucrose, leucrose, glucose and fructose were quantified by HPLC with an HPX-87C column (HPLC conditions as described above). DP2-7 disaccharides were quantified by HPLC with the following conditions: column (AMINEX HPX-42A carbohydrate column, 300×7.8 mm, Bio-Rad, No. 125-0097), eluent (water), flow rate (0.6 mL/min), temperature (85° C.), refractive index detector. These HPLC analyses indicated that the glucosyl-containing saccharide products of the 0768 gtf reaction consisted of 91% polymer product, 1% glucose, 6.5% leucrose, and 1.5% DP2-7 oligosaccharides.

The glycosidic linkage profile of the gelling polymer product of the reaction comprising 100 g/L sucrose was determined by $^{13}$C NMR. Dry polymer (25-30 mg) as prepared above was dissolved in 1 mL of deuterated DMSO containing 3 wt % LiCl with stirring at 50° C. Using a glass pipet, 0.8 mL of the preparation was transferred into a 5-mm NMR tube. A quantitative $^{13}$C NMR spectrum was acquired using a Bruker Avance (Billerica, Mass.) 500 MHz NMR spectrometer equipped with a CPDul cryoprobe, at a spectral frequency of 125.76 MHz, using a spectral window of 26041.7 Hz. An inverse-gated decoupling pulse sequence using waltz decoupling was used with an acquisition time of 0.629 second, an inter-pulse delay of 5 seconds, and 6000 pulses. The time domain data were transformed using an exponential multiplication of 2.0 Hz.

The NMR results indicated that the gelling polymer product comprised about 90% alpha-1,6-glucosidic linkages, about 4-5% alpha-1,3-glucosidic linkages, and about 5-6% alpha-1,4 and -1,2 glucosidic linkages. The main chain(s) of the polymer product appeared to mostly comprise alpha-1,6-glucosidic linkages, but also a very small amount of alpha-1,3 and -1,4 glucosidic linkages. Other alpha-1,3 and -1,4 glucosidic linkages, and all of the alpha-1,2-glucosidic linkages, appeared to be in branches off the main chains(s). The gelling product thus appears to be a gelling dextran.

A different protocol (not the above $^{13}$c NMR procedure) is presently recommended herein for determining the linkage profile of dextran produced by gtf 0768. This protocol is disclosed below in Example 9, indicating a linkage profile similar to that disclosed in this Example.

The number-average molecular weight ($M_n$) and weight-average molecular weight ($M_w$) of the gelling dextran product of the reaction comprising 100 g/L sucrose was determined by size-exclusion chromatography (SEC). Dry polymer as prepared above was dissolved in DMAc and 5% LiCl (0.5 mg/mL) with shaking overnight at 100° C. The chromatographic system used was an Alliance™ 2695 separation module from Waters Corporation (Milford, Mass.) coupled with three on-line detectors: a differential refractometer 2410 from Waters, a Heleos™ 8+ multiangle light scattering photometer from Wyatt Technologies (Santa Barbara, Calif.), and a ViscoStar™ differential capillary viscometer from Wyatt. Columns used for SEC were four styrene-divinyl benzene columns from Shodex (Japan) and two linear KD-806M, KD-802 and KD-801 columns to improve resolution at the low molecular weight region of a polymer distribution. The mobile phase was DMAc with 0.11% LiCl. The chromatographic conditions used were 50° C. in the column and detector compartments, 40° C. in the sample and injector compartment, a flow rate of 0.5 mL/min, and an injection volume of 100 µL. The software packages used for data reduction were Empower™ version 3 from Waters (calibration with broad glucan polymer standard) and Astra® version 6 from Wyatt (triple detection method with column calibration). It was determined from this procedure that the gelling dextran product had an $M_n$ of 2229400 and an $M_w$ of 5365700.

A different protocol (not the above SEC procedure) is presently recommended herein for determining the molecular weight of dextran produced by gtf 0768. This protocol is disclosed below in Example 9, indicating a molecular weight more than one order of magnitude greater than the molecular weight disclosed in this Example.

Thus, reactions comprising water, sucrose and an enzyme comprising SEQ ID NO:1 synthesized a gelling dextran product, as determined by the product's predominant alpha-1,6 glucosidic linkage profile. Example 8 below discloses comparing the viscosity of this product versus the viscosities of certain commercially available dextrans. Example 9 discloses further production of dextran with a gtf enzyme comprising SEQ ID NO:1, along with yield, molecular weight, and linkage analysis of the dextran. The dextran produced in this Example can be used to prepare oxidized dextran as presently disclosed.

Example 3

Expression of a Glucosyltransferase (2919) and Use Thereof to Produce a Gelling Dextran Product This Example describes expression of a mature *Weissella cibaria* glucosyltransferase (gtf) enzyme in *B. subtilis*. Also, this Example shows that this enzyme produces a gelling product, likely a dextran, when used is a reaction containing water and sucrose.

A glucosyltransferase gene, WciGtf1, was identified from *Weissella cibaria* KACC 11862. The nucleic acid sequence of this gene (positions 23315 to 27661 of GENBANK Accession No. NZ_AEKT01000035.1) is set forth in SEQ ID NO:3 and encodes the protein sequence of SEQ ID NO:4 (GENBANK Accession No. ZP_08417432). At the N-terminus of the WciGtf1 protein (SEQ ID NO:4) is a signal peptide of 26 amino acids, as predicted by the SIGNALP 4.0 program (Petersen et al., *Nature Methods* 8:785-786). This indicates that WciGtf1 (SEQ ID NO:4) is a secreted protein. The mature, secreted form of the WciGtf1 protein is herein referred to as 2919 gtf, and is set forth in SEQ ID NO:5.

The nucleotide sequence encoding 2919 gtf was optimized for expression in *B. subtilis*. The optimized sequence (SEQ ID NO:6) was synthesized by Generay (Shanghai, China), and inserted into plasmid p2JM103BBI (Vogtentanz et al., *Protein Expr. Purif.* 55:40-52), resulting in plasmid pZZHB583 (FIG. 2A). Plasmid pZZHB583 contains an aprE promoter operably linked to a sequence encoding (i) an aprE signal sequence used to direct heterologous protein (2919 gtf in this case) secretion in *B. subtilis*, (ii) Ala-Gly-Lys to facilitate the secretion, and (iii) 2919 gtf (SEQ ID NO:5) (i-iii are fused together in the amino-to-carboxy direction).

Plasmid pZZHB583 was transformed into *B. subtilis* cells for 2919 gtf expression and purification (see General Methods).

The activity of 2919 gtf (SEQ ID NO:5) was determined in a 250-mL reaction at room temperature comprising 100 g/L sucrose, 20 mM sodium phosphate buffer (pH 5.5), and 6.25 mL of enzyme stock. The reaction was carried out at room temperature with shaking (150 rpm) for 48 hours.

Samples (100 µL) were taken from the reaction at 0, 1, 3, 5, 24, and 48 hour time points, respectively. Enzyme was deactivated by heating each sample at 80° C. for 10 minutes. Samples were diluted 10-fold with water and centrifuged at 14000 rpm for 5 minutes. Supernatant (200 µL) was used for HPLC analysis.

The concentrations of leucrose, glucose, and fructose in the gtf reaction were determined using HPLC, which was performed with an Agilent 1260 chromatography system equipped with an AMINEX HPX-87C column (300×7.8 mm) placed in a thermostatted column compartment at 85° C., and a refractive index detector. HPLC elution was carried out with Milli-Q® water at 0.6 mL/min. Sucrose, leucrose, glucose, and fructose were identified by comparison with corresponding standards. Their concentrations were calculated based on a peak area standard curves. Sucrose was consumed almost completely by the end of the reaction. Aside from a viscous dextran product, 2919 gtf (SEQ ID NO:5) produced mostly fructose (~50%), and small amounts of leucrose (~5%) and glucose (~1%).

The concentration of oligosaccharides (DP2-DP7) in the gtf reaction was determined by HPLC analysis, which was performed with an Agilent 1260 chromatography system equipped with an AMINEX HPX-42A column (300×7.8 mm) placed in a thermostatted column compartment at 85° C., and a refractive index detector. HPLC elution was carried out with Milli-Q® water at 0.6 mL/min. Formation of oligosaccharides was identified by comparison with corresponding standards. The concentration of the oligosaccharides was calculated based on standard curves from peak area. 2919 gtf (SEQ ID NO:5) produced a small amount of DP2-DP7 oligosaccharides (~3%) by the end of the reaction.

Thus, reactions comprising water, sucrose and an enzyme comprising SEQ ID NO:5 synthesized a gelling product, which is believed to be a dextran polymer. This product can be used to prepare oxidized dextran as presently disclosed. Experimental results demonstrated that gtf 2919 likely has glucosyltransferase activity.

Example 4

Expression of a Glucosyltransferase (2918) and Use Thereof to Produce a Gelling Dextran Product This Example describes expression of a mature *Lactobacillus fermentum* glucosyltransferase (gtf) enzyme in *B. subtilis*. Also, this Example shows that this enzyme produces a gelling product, likely a dextran, when used is a reaction containing water and sucrose.

A glucosyltransferase gene, LfeGtf1, was identified from *Lactobacillus fermentum*. The nucleic acid sequence of this gene (positions 618 to 5009 of GENBANK Accession No. AY697433.1) is set forth in SEQ ID NO:7 and encodes protein sequence of SEQ ID NO:8 (GENBANK Accession No. AAU08008). At the N-terminus of the LfeGtf1 protein (SEQ ID NO:8) is a signal peptide of 37 amino acids, as predicted by the SIGNALP 4.0 program. This indicates that LfeGtf1 (SEQ ID NO:8) is a secreted protein. The mature, secreted form of the LfeGtf1 protein is herein referred to as 2918 gtf, and is set forth in SEQ ID NO:9.

The nucleotide sequence encoding 2918 gtf was optimized for expression in *B. subtilis*. The optimized sequence (SEQ ID NO:10) was synthesized by Generay (Shanghai, China), and inserted into plasmid p2JM103BBI, resulting in plasmid pZZHB582 (FIG. 2B). Plasmid pZZHB582 contains an aprE promoter operably linked to a sequence encoding (i) an aprE signal sequence used to direct heterologous protein (2918 gtf in this case) secretion in *B. subtilis*, (ii) Ala-Gly-Lys to facilitate the secretion, and (iii) 2918 gtf (SEQ ID NO:9) (i-iii are fused together in the amino-to-carboxy direction).

Plasmid pZZHB582 was transformed into *B. subtilis* cells for 2918 gtf expression and purification (see General Methods).

The activity of 2918 gtf (SEQ ID NO:9) was determined in a 250-mL reaction at room temperature comprising 100 g/L sucrose, 20 mM sodium phosphate buffer (pH 5.5), and 6.25 mL of enzyme stock. The reaction was carried out at room temperature with shaking (150 rpm) for 6 days.

Samples (100 µL) were taken from the reaction at 0, 1, 3, 5, 24, 48 and 144 hour time points, respectively. Enzyme was deactivated by heating each sample at 80° C. for 10 minutes. Samples were diluted 10-fold with water and centrifuged at 14000 rpm for 5 minutes. Supernatant (200 µL) was used for HPLC analysis.

The concentrations of sucrose, leucrose, glucose, fructose and oligosaccharides (DP2-DP7) in the gtf reaction were determined using HPLC procedures as described in Example 3. Sucrose was consumed almost completely by the end of the reaction. Aside from a viscous dextran product, 2918 gtf (SEQ ID NO:9) produced mostly fructose (~50%), and small amounts of leucrose (~5%) and glucose (~1%). 2918 gtf (SEQ ID NO:9) produced a small amount of DP2-DP7 oligosaccharides (~1%).

Thus, reactions comprising water, sucrose and an enzyme comprising SEQ ID NO:9 synthesized a gelling product, which is believed to be a dextran polymer. This product can be used to prepare oxidized dextran as presently disclosed. Experimental results demonstrated that gtf 2920 likely has glucosyltransferase activity.

Example 5

Expression of a Glucosyltransferase (2920) and Use Thereof to Produce a Gelling Dextran Product This Example describes expression of a mature *Streptococcus sobrinus* glucosyltransferase (gtf) enzyme in *B. subtilis*. Also, this Example shows that this enzyme produces a gelling product, likely a dextran, when used is a reaction containing water and sucrose.

A glucosyltransferase gene, SsoGtf4, was identified from *Streptococcus sobrinus* B13N. The nucleic acid sequence of this gene (positions 198 to 4718 of GENBANK Accession No. AY966490) is set forth in SEQ ID NO:11 and encodes the protein sequence of SEQ ID NO:12 (GENBANK Accession No. AAX76986). At the N-terminus of the SsoGtf4 protein (SEQ ID NO:12) is a signal peptide of 41 amino acids, as predicted by the SIGNALP 4.0 program. This indicates that SsoGtf4 (SEQ ID NO:12) is a secreted protein. The mature, secreted form of the SsoGtf4 protein is herein referred to as 2920 gtf, and is set forth in SEQ ID NO:13.

The nucleotide sequence encoding 2920 gtf was optimized for expression in *B. subtilis*. The optimized sequence (SEQ ID NO:14) was synthesized by Generay (Shanghai, China), and inserted into plasmid p2JM103BBI, resulting in plasmid pZZHB584 (FIG. 2C). Plasmid pZZHB584 contains an aprE promoter operably linked to a sequence encoding (i) an aprE signal sequence used to direct heterologous protein (2920 gtf in this case) secretion in *B. subtilis*, (ii) Ala-Gly-Lys to facilitate the secretion, and (iii) 2920 gtf (SEQ ID NO:13) (i-iii are fused together in the amino-to-carboxy direction).

Plasmid pZZHB584 was transformed into *B. subtilis* cells for 2920 gtf expression and purification (see General Methods).

The activity of 2920 gtf (SEQ ID NO:13) was determined in a 250-mL reaction at room temperature comprising 100 g/L sucrose, 20 mM sodium phosphate buffer (pH 5.5), and 6.25 mL of enzyme stock. The reaction was carried out at room temperature with shaking (150 rpm) for 6 days.

Samples (100 μL) were taken from the reaction at 0, 1, 3, 5, 24, 48, 72 and 144 hour time points, respectively. Enzyme was deactivated by heating each sample at 80° C. for 10 minutes. Samples were diluted 10-fold with water and centrifuged at 14000 rpm for 5 minutes. Supernatant (200 μL) was used for HPLC analysis.

The concentrations of sucrose, leucrose, glucose, fructose and oligosaccharides (DP2-DP7) in the gtf reaction were determined using HPLC procedures as described in Example 3. Sucrose was consumed almost completely by the end of the reaction. Aside from a viscous dextran product, 2920 gtf (SEQ ID NO:13) produced mostly fructose (~50%), leucrose (~20%), and a small amount of glucose (~3%). 2920 gtf (SEQ ID NO:13) produced a small amount of DP2-DP7 oligosaccharides (~1%).

Thus, reactions comprising water, sucrose and an enzyme comprising SEQ ID NO:13 synthesized a gelling product, which is believed to be a dextran polymer. This product can be used to prepare oxidized dextran as presently disclosed. Experimental results demonstrated that gtf 2920 likely has glucosyltransferase activity.

Example 6

Expression of a Glucosyltransferase (2921) and Use Thereof to Produce a Gelling Dextran Product This Example describes expression of a mature *Streptococcus downei* glucosyltransferase (gtf) enzyme in *B. subtilis*. Also, this Example shows that this enzyme produces a gelling product, likely a dextran, when used is a reaction containing water and sucrose.

A glucosyltransferase gene, SdoGtf7, was identified from *Streptococcus downei* MFe28. The nucleic acid sequence of this gene (positions 16 to 2375 of GENBANK Accession No. AB476746) is set forth in SEQ ID NO:15 and encodes the protein sequence of SEQ ID NO:16 (GENBANK Accession No. ZP_08549987.1). At the N-terminus of the SdoGtf7 protein (SEQ ID NO:16) is a signal peptide of 44 amino acids, as predicted by the SIGNALP 4.0 program. This indicates that SdoGtf7 protein (SEQ ID NO:16) is a secreted protein. The mature, secreted form of the SdoGtf7 protein is herein referred to as 2921 gtf, and is set forth in SEQ ID NO:17.

The nucleotide sequence encoding 2921 gtf was optimized for expression in *B. subtilis*. The optimized sequence (SEQ ID NO:18) was synthesized by Generay (Shanghai, China), and inserted into plasmid p2JM103BBI, resulting in plasmid pZZHB585 (FIG. 2D). Plasmid pZZHB585 contains an aprE promoter operably linked to a sequence encoding (i) an aprE signal sequence used to direct heterologous protein (2921 gtf in this case) secretion in *B. subtilis*, (ii) Ala-Gly-Lys to facilitate the secretion, and (iii) 2921 gtf (SEQ ID NO:17) (i-iii are fused together in the amino-to-carboxy direction).

Plasmid pZZHB585 was transformed into *B. subtilis* cells for 2921 gtf expression and purification (see General Methods).

The activity of 2921 gtf (SEQ ID NO:17) was determined in a 250-mL reaction at room temperature comprising 100 g/L sucrose, 20 mM sodium phosphate buffer (pH 5.5), and 6.25 mL of enzyme stock. The reaction was carried out at room temperature with shaking (150 rpm) for 8 days.

Samples (100 μL) were taken from the reaction at the reaction start and on 1, 2, 3, 6, 7 and 8 day time points, respectively. Enzyme was deactivated by heating each sample at 80° C. for 10 minutes. Samples were diluted 10-fold with water and centrifuged at 14000 rpm for 5 minutes. Supernatant (200 μL) was used for HPLC analysis.

The concentrations of sucrose, leucrose, glucose, fructose and oligosaccharides (DP2-DP7) in the gtf reaction were determined using HPLC procedures as described in Example 3. About 43% sucrose remained in the reaction on day 8. Aside from a viscous dextran product, 2921 gtf (SEQ ID NO:17) produced mostly fructose (~31%), leucrose (~6%), and glucose (~3%). No obvious production of DP2-DP7 oligosaccharides was observed.

Thus, reactions comprising water, sucrose and an enzyme comprising SEQ ID NO:17 synthesized a gelling product, which is believed to be a dextran polymer. This product can be used to prepare oxidized dextran as presently disclosed. Experimental results demonstrated that gtf 2921 likely has glucosyltransferase activity.

Example 7 (Comparative)

Production of Dextran Using Commercially Available Dextran Sucrase

This Example describes synthesizing dextran using a commercially available dextran sucrase in reactions comprising water and sucrose. The dextran produced in this was analyzed in Example 8 in comparison to the gelling dextran products synthesized in Examples 1-6.

Reagents for preparing dextran sucrase reaction:
Sucrose (Sigma Prod. No. S-9378). 400 g/L stock solution was prepared.
Sodium phosphate buffer stock (200 mM) (pH 5.5): prepare 250 mL in water using sodium phosphate monobasic monohydrate (Sigma Prod. No. S9638) and sodium phosphate dibasic heptahydrate (Sigma Prod. No. S9390), accordingly.
Dextran sucrase, lyophilized powder, ≥100 units/mg protein, from *Leuconostoc mesenteroides* (Sigma Prod. No. D9909).

A 50-mL reaction was prepared containing 20 mM sodium phosphate (pH 5.5), 110 g/L sucrose, and 10 units of dextran sucrase from Sigma-Aldrich. The dextran sucrase was added last when preparing the reaction. The reaction was carried out in a 125-mL capped shake flask at 26° C. with shaking (100 rpm) for 7 days. Samples (100 μL) of the reaction were taken at 0, 3, 6, 24, 48 and 168 hours, respectively. The dextran sucrase was deactivated in each sample by heating at 80° C. for 10 minutes. Each sample was then diluted 10-fold with water and centrifuged at 14,000 rpm for 5 minutes, afterwhich 200 μl of supernatant was used for HPLC analysis to measure sucrose consumption during the reaction.

The following HPLC conditions were applied for analyzing each sample: column (AMINEX HPX-87C carbohydrate column, 300×7.8 mm, Bio-Rad, No. 125-0095), eluent (water), flow rate (0.6 mL/min), temperature (85° C.), refractive index detector. HPLC analysis of the samples indicated sucrose consumption during the dextran sucrase reaction (FIG. 3). It is notable that the sucrose consumption rate by the commercial dextran sucrase was much slower compared to the sucrose consumption rate of gtf 0768 (Example 2). Specifically, while gtf 0768 depleted most sucrose after about 17-18 hours of reaction time (FIG. 1), commercial dextran sucrase depleted only about 20% of sucrose within this same time period, and required about 168 hours to deplete all or most sucrose.

HPLC was also used to analyze other products of the reaction. Dextran yield was back-calculated by subtracting the amount of all other saccharides left in the reaction from the amount of the starting sucrose. The back-calculated number was consistent with dextran dry weight analysis. Sucrose, leucrose, glucose, fructose, and DP2-7 disaccharides were quantified by HPLC as described in Example 2. These HPLC analyses indicated that the saccharide products of the commercial dextran sucrase reaction consisted of 49% dextran, 0.3% sucrose, 44% fructose, 1% glucose, 5% leucrose, and 1% DP2-7 oligosaccharides.

The dextran produced in this Example was analyzed in Example 8 in comparison to the gelling dextran products synthesized in Examples 1-6.

Example 8

Viscosity of Dextran Samples

This Example describes measuring the viscosities of the dextran polymers produced in Examples 1-7, as well as the viscosity of dextran obtained from a commercial source. Viscosity measurements were made at various shear rates.

Dextran polymer samples were prepared as described in Examples 1-7. Specifically, enzymatic reactions were conducted, afterwhich polymer was methanol-precipitated and washed with methanol (100%) four times, and then dried. Solutions (2 wt % and/or 3 wt %) of each sample were prepared by adding the appropriate amount of polymer to de-ionized (DI) water. Each preparation was then mixed using a bench top vortexer until polymer was fully in solution. Each of these samples is referred to in Tables 2 and 3 (below) as "After PPT" (after precipitation). A 2 wt % solution of dextran ($M_w$=956978) obtained from TCI America (Portland, Oreg.; catalogue No. D0061) was similarly prepared; this dextran is referred to below as "commercial dextran".

To determine the viscosity of each polymer solution at various shear rates, each solution was subjected to various shear rates using a viscometer while the temperature was held constant at 20° C. Also, polymer samples obtained directly, without precipitation, from each of the enzymatic reactions described in Examples 1-7 were subjected to various shear rates (referred to in Tables 2 and 3 as "Before PPT"). The shear rate was increased using a gradient program which increased from 0-10 rpm and the shear rate was increased by 0.17 (1/s) every 30 seconds. The results of this experiment are listed in Table 2.

TABLE 2

Viscosity of Certain Dextran Solutions at Various Shear Rates

| Dextran Sample[a] | Viscosity (cPs) @ 0.17 rpm | Viscosity (cPs) @ 1.03 rpm | Viscosity (cPs) @ 2.62 rpm | Viscosity (cPs) @ 4.22 rpm |
|---|---|---|---|---|
| Gtf 0768 (SEQ ID NO: 1) Before PPT (Example 2, 100 g/L sucrose reaction)) | 47976.13 | 11376.70 | 12956.11 | 14390.76 |
| Gtf 0768 (SEQ ID NO: 1) After PPT - 3 wt % (Example 2, 100 g/L sucrose reaction)) | | 15778.40 | 6245.31[b] | 4119.58[b] |
| Gtf 0768 (SEQ ID NO: 1) After PPT - 2 wt % (Example 2, 100 g/L sucrose reaction)) | | 4091.84 | 3417.10 | 2874.10 |
| Gtf 2918 (SEQ ID NO: 9) Before PPT (Example 4) | | n/a[b] | n/a[b] | n/a[b] |
| Gtf 2919 (SEQ ID NO: 5) Before PPT (Example 3) | | 98864 | 38671 | 25580 |
| Gtf 2920 (SEQ ID NO: 13) Before PPT (Example 5) | | 3874.85 | 4205.66 | 4119.58[b] |
| Gtf 2920 (SEQ ID NO: 13) After PPT - 3 wt % (Example 5) | | 6168.76 | 3294.43 | 2288.24 |
| Gtf 2921 (SEQ ID NO: 17) Before PPT (Example 6) | | 3533.86 | 2143.72 | 1748.95 |
| Gtf 2921 (SEQ ID NO: 17) After PPT - 3 wt % (Example 6) | | 4634.32 | 2780.4 | 1984.89 |
| Commercial dextran sucrase Before PPT (Example 7) | 16759.42 | | | |

[a]Polymer samples are listed according to the respective enzyme used to synthesize the sample.
[b]Measurement was outside the specification limits of the viscometer.

Polymer samples were also subjected to various higher shear rates using a viscometer while the temperature was held constant at 20° C. The shear rate was increased using a gradient program which increased from 10-250 rpm and the shear rate was increased by 7.36 (1/s) every 20 seconds. The results of this experiment are listed in Table 3.

TABLE 3

Viscosity of Certain Dextran Solutions at Various Shear Rates

| Dextran Sample[a] | Viscosity (cPs) @ 14.72 rpm | Viscosity (cPs) @ 102.9 rpm | Viscosity (cPs) @ 250 rpm |
|---|---|---|---|
| Gtf 2918 (SEQ ID NO: 9) After PPT - 3 wt % (Example 4) | 149.95 | 69.68 | 48.97 |
| Gtf 2919 (SEQ ID NO: 5) After PPT - 3 wt % (Example 3) | 80.82 | 41.23 | 29.49 |
| 2 wt % Commercial dextran | 241.41 | 105.28 | 68.88 |
| Commercial dextran sucrase After PPT - 2 wt % (Example 7) | 11.09[b] | 10.31[b] | 8.27 |

| | Viscosity (cPs) @ 14.11 rpm | Viscosity (cPs) @ 98.69 rpm | Viscosity (cPs) @ 162.1 rpm |
|---|---|---|---|
| Gtf 0768 (SEQ ID NO: 1) After PPT - 2 wt % (Example 2, 400 g/L sucrose reaction) | 49.89 | 23.61 | 18.32 |
| Gtf 0768 (SEQ ID NO: 1) After PPT - 2 wt % (Example 2, 800 g/L sucrose reaction) | 5.44 | 2.72 | 1.58 |

[a]Polymer samples are listed according to the respective enzyme used to synthesize the sample. Alternatively, dextran obtained from a commercial source was analyzed ("Commercial dextran").
[b]Measurement was outside the specification limits of the viscometer.

These data demonstrate that solutions of the dextran product of a glucosyltransferase comprising SEQ ID NO:1 can in most cases exhibit increased viscosity even after precipitation and resolution, as compared to the viscosities of commercially obtained dextran and the dextran product of a commercially obtained dextran sucrase. This observation also appears to apply to the respective polymer products of glucosyltransferases comprising SEQ ID NO:5, 9, 13, or 17.

It is also noteworthy that, based on Tables 2-3, as the amount of sucrose in a gtf 0768 reaction is decreased from 800 g/L to 100 g/L, the viscosity of the dextran product appears to increase. Specifically, Table 3 indicates (at 14.11 rpm/2 wt % loading) viscosities of 5.44 cPs and 49.89 cPs for dextran products of reactions comprising 800 and 400 g/L sucrose, respectively, and Table 2 (gtf 0768, 2 wt % loading) may indicate a viscosity of about 957 cPs (exponential extrapolated at a rotation of 14.11 rpm) for dextran product of a reaction comprising 100 g/L sucrose. This result suggests that the viscosity of a dextran product can be controlled by modifying the level of sucrose initially provided to reaction.

Example 9

Further Production and Analysis of Dextran Synthesized by Gtf 0768

This Example is in addition to Example 2, describing another reaction comprising water, sucrose and gtf 0768. Also, this Example provides additional linkage and molecular weight analyses of the gelling product synthesized by gtf 0768, showing that this product is a type of dextran.

Reagents for preparing gtf reaction:
Sucrose (Sigma Prod. No. S-9378).
Sodium phosphate buffer stock (1 M, pH 6.5, Teknova Cat No: S0276).
Gtf 0768 enzyme solution (cell lysate as prepared in Example 1).
Gtf reaction conditions:
A 50-mL reaction was prepared containing 20 mM sodium phosphate buffer (buffer was diluted 50-fold with ddH2O from 1 M stock, pH 6.5), 100 g/L sucrose, and 0.1 mL of gtf 0768 enzyme solution. The reaction was shaken at 100 rpm in an incubator shaker (Innova, Model 4000) at 26° C. for 43 hours; the reaction became viscous after about 24 hours.

The gtf enzyme was deactivated by heating the reaction at 80° C. for 10 minutes. The deactivated viscous reaction was then mixed with 75 mL of 100% methanol to precipitate the viscous product. A white precipitate was formed. After carefully decanting the supernatant, the white precipitate was washed twice with 75 mL of 100% methanol. The solid product was dried at 45° C. under vacuum in an oven for 48 hours.

Samples (1 mL) of the reaction were taken at 0, 0.5, 1, 2, and 24 hours, respectively. The gtf enzyme was deactivated in each sample by heating at 80° C. for 10 minutes. Each sample was then diluted 10-fold with sterile water. 500 µL of diluted sample was transferred into a centrifuge tube filter (SPIN-X, 0.45-µm Nylon, 2.0 mL Polypropylene Tube, Costar #8170) and centrifuged at 12,000 rpm in a table centrifuge for 60 minutes, after which 200 µL of flowthrough was used for HPLC analysis to measure sucrose consumption during the reaction. The following HPLC conditions were applied for analyzing each sample: column (AMINEX HPX-87C carbohydrate column, 300×7.8 mm, Bio-Rad, No. 125-0095), eluent (water), flow rate (0.6 mL/min), temperature (85° C.), refractive index detector. HPLC analysis of the samples indicated substantial sucrose consumption during the 0768 gtf reaction.

HPLC was also used to analyze other products of the reaction. Polymer yield was back-calculated by subtracting the amount of all other saccharides left in the reaction from the amount of the starting sucrose. The back-calculated number was consistent with the viscous product dry weight analysis. Sucrose, leucrose, glucose and fructose were quantified by HPLC with an HPX-87C column (HPLC conditions as described above). DP2-7 oligosaccharides were quantified by HPLC with the following conditions: column (AMINEX HPX-42A carbohydrate column, 300×7.8 mm, Bio-Rad, No. 125-0097), eluent (water), flow rate (0.6 mL/min), temperature (85° C.), refractive index detector. These HPLC analyses indicated that the glucosyl-containing saccharide products of the 0768 gtf reaction consisted of 92.3% polymer product, 1.3% glucose, 5.0% leucrose, and 1.4% DP2-7 oligosaccharides.

A sample of dry dextran powder product (~0.2 g) of the above reaction was used for molecular weight analysis. Molecular weight was determined by a flow injection chromatographic method using an Alliance™ 2695 separation module from Waters Corporation (Milford, Mass.) coupled with three online detectors: a differential refractometer 2414 from Waters, a Heleos™-2 18-angle multiangle light scattering (MALS) photometer with quasielastic light scattering (QELS) detector from Wyatt Technologies (Santa Barbara, Calif.), and a ViscoStar™ differential capillary viscometer from Wyatt. The dry dextran powder was dissolved at 0.5 mg/mL in aqueous Tris (Tris[hydroxymethyl]aminomethane) buffer (0.075 M) containing 200 ppm NaN$_3$. The dissolution of dextran was achieved by shaking overnight at 50° C. Two AQUAGEL-OH GUARD columns from Agilent Technologies (Santa Clara, Calif.) were used to separate the dextran polymer peak from the injection peak. The mobile base for this procedure was the same as the dextran solvent, the flow rate was 0.2 mL/min, the injection volume was 0.1 mL, and the column temperature was 30° C. Empower™ version 3 software from Waters was used for data acquisition, and Astra™ version 6 software from Wyatt was used for multidetector data reduction. It was determined from this work that the dextran polymer product had a weight-average molecular weight (Mw) of 1.022 (+/−0.025)×10$^8$ g/mol (i.e., roughly 100 million Daltons) (from MALS analysis), a z-average radius of gyration of 243.33 (+/−0.42) nm (from MALS analysis), and a z-average hydrodynamic radius of 215 nm (from QELS analysis). It was also determined from QELS analysis that the dextran has a standard deviation of particle size distribution (PSD) of about 0.259, indicating that the dextran likely is polydisperse in terms of hydrodynamic size.

For glycosidic linkage analysis purposes, a 50-mL gtf reaction was prepared as described above in this Example, except that the reaction time was 24 hours (reaction had become viscous). The gtf enzyme was deactivated by heating the reaction at 80° C. for 10 minutes. The deactivated viscous reaction was then placed into a regenerated cellulose sturdy dialysis tubing with a molecular weight cut-off (MWCO) of 12-14 kDa (Spectra/Por® 4 Dialysis Tubing, Part No. 132706, Spectrum Laboratories, Inc.) and dialyzed against 4 L of filter water at room temperature over one week. Water was exchanged every day during this dialysis. The dialyzed viscous reaction was then precipitated and dried as described above in this Example. About 0.2 g of dry powder was submitted for GC/MS linkage analysis.

Linkage analysis was performed according to methods described by Pettolino et al. (*Nature Protocols* 7:1590-1607), which is incorporated herein by reference. Briefly, a dry dextran sample was dissolved in dimethyl sulfoxide (DMSO) or 5% lithium chloride in DMSO, then all free hydroxyl groups were methylated by sequential addition of a sodium hydroxide/DMSO slurry followed by iodomethane. The methylated polymer was then extracted into methylene chloride and hydrolyzed to monomeric units using aqueous trifluoroacetic acid (TFA) at 120° C. The TFA was then evaporated from the sample and reductive ring opening was done using sodium borodeuteride, which also labeled the reducing end with a deuterium atom. The hydroxyl groups created by hydrolyzing the glycosidic linkages were then acetylated by treating with acetyl chloride and TFA at a temperature of 50° C. Finally, the derivatizing reagents were evaporated and the resulting methylated/acetylated monomers were reconstituted in acetonitrile and analyzed by gas chromatography with mass spectrometry (GC/MS) using a biscyanopropyl cyanopropylphenyl polysiloxane column. The relative positioning of the methyl and acetyl functionalities, along with the deuterium label, yielded species that have distinctive retention time indices and mass spectra that can be compared to published databases. In this way, the derivatives of the monomeric units indicated how each monomer was originally linked in the dextran polymer and whether the monomer was a branch point. The results of analyzing these samples (dextran initially dissolved in DMSO or DMSO/5% LiCl) are provided in Table 4.

TABLE 4

Linkage Profile of Gtf 0768 Dextran Product

| | Wt %/Mol % of Glucose Monomers in Dextran | | | | |
|---|---|---|---|---|---|
| Sample | 3-glc [a] | 6-glc [b] | 4-glc [c] | 3,6-glc [d] | 2,6- + 4,6-glc [e] |
| DMSO | 0.4 | 90.2 | 0.4 | 8.3 | 0.7 |
| DMSO/5% LiCl | 0.9 | 89.3 | 0.4 | 8.0 | 1.4 |

[a] Glucose monomer linked at carbon positions 1 and 3.
[b] Glucose monomer linked at carbon positions 1 and 6.
[c] Glucose monomer linked at carbon positions 1 and 4.
[d] Glucose monomer linked at carbon positions 1, 3 and 6.
[e] Glucose monomer linked at carbon positions 1, 2 and 6, or 1, 4 and 6.

In general, the results in Table 4 indicate that the dextran product analyzed above comprises:
(i) about 87-93 wt % glucose linked only at positions 1 and 6;
(ii) about 0.1-1.2 wt % glucose linked only at positions 1 and 3;
(iii) about 0.1-0.7 wt % glucose linked only at positions 1 and 4;
(iv) about 7.7-8.6 wt % glucose linked only at positions 1, 3 and 6; and
(v) about 0.4-1.7 wt % glucose linked only at (a) positions 1, 2 and 6, or (b) positions 1, 4 and 6.

Based on this information and some other studies (data not shown), it is contemplated that this product is a branched structure in which there are long chains (containing mostly or all alpha-1,6-linkages) of about 20 DP in length (average) that iteratively branch from each other (e.g., a long chain can be a branch from another long chain, which in turn can itself be a branch from another long chain, and so on). The branched structure also appears to comprise short branches from the long chains; these short chains are believed to be 1-3 DP in length and mostly comprise alpha-1,3 and -1,4 linkages, for example. Branch points in the dextran, whether from a long chain branching from another long chain, or a short chain branching from a long chain, appear to comprise alpha-1,3, -1,4, or -1,2 linkages off of a glucose involved in alpha-1,6 linkage. Roughly 25% of all the branch points of the dextran branched into a long chain.

Thus, reactions comprising water, sucrose and an enzyme comprising SEQ ID NO:1 synthesized a very large gelling dextran product, as determined by the product's high Mw and predominant alpha-1,6 glucosidic linkage profile. The dextran produced in this Example can be used to prepare oxidized dextran compounds as presently disclosed.

Example 10

Preparation of Oxidized Dextran at Room Temperature

This Example describes producing oxidized dextran in a reaction held at room temperature using a periodate compound. While the dextran product disclosed in Example 2 was used in this Example, the dextran product of Example 9 can similarly be used in the following oxidation procedure.

3 g of dextran as produced in Example 2 was dissolved in 100 mL of de-ionized (DI) water using a magnetic stir bar in a 500-mL capacity Erlenmeyer flask fitted with a thermocouple for temperature monitoring, a rubber stopper, and a magnetic stir bar. 6.9 g of sodium periodate was added to this preparation, which was then stirred for 48 hours at room temperature (20-25° C.). The reaction was quenched by adding 15 g of ethylene glycol. Excess methanol was added to precipitate any dissolved solid. Solid material (periodate-oxidized dextran, sample product no. 240) was then collected by vacuum filtration, washed with 95% ethanol, and dried under vacuum.

Thus, oxidized dextran was prepared and isolated from a reaction maintained at room temperature. A periodate compound was used as an oxidant in these reactions.

Example 11

Preparation of Oxidized Dextran at Room Temperature Using a Two-Step Reaction Process This Example describes producing oxidized dextran using a two-step reaction process held at room temperature. A first oxidation was performed with a periodate compound, after-which a second oxidation was performed with an N-oxoammonium salt. While the dextran product disclosed in Example 2 was used in this Example, the dextran product of Example 9 can similarly be used in the following oxidation procedure.

4.7 g of sodium periodate was dissolved in 41.9 g of DI water in a 500-mL capacity Erlenmeyer flask fitted with a thermocouple for temperature monitoring, a rubber stopper, and a magnetic stir bar. 5 g of dextran (dissolved in 45 g of DI water) as produced in Example 2 was added to this preparation, which was then stirred for 5 hours at room temperature (20-25° C.). The reaction was quenched by adding 11 g of ethylene glycol. Excess methanol was added to precipitate any dissolved solid. Solid material (periodate-oxidized dextran) was then collected by vacuum filtration, washed with 95% ethanol, and dried under vacuum.

1 g of periodate-oxidized dextran (prepared above) was added to 100 mL of sodium acetate buffer (1.64 g of sodium acetate dissolved in 100 mL of 5% acetic acid and adjusted to pH 4.6 with sodium hydroxide) in a 500-mL capacity Erlenmeyer flask fitted with a thermocouple for temperature monitoring, a rubber stopper, and a magnetic stir bar. Sodium chlorite (0.68 g) and 4-acetamido-TEMPO (0.096 g, Sigma-Aldrich, St. Louis, Mo.) were then added to this preparation. Sodium hypochlorite (0.74 g) was next added to the preparation, which was then stirred for 48 hours at room temperature (20-25° C.). The reaction was quenched by adding an excess amount of ethanol, thereby precipitating solid oxidized dextran product. The solid (sample product no. 173) thus formed was collected by vacuum filtration, washed with ethanol (95%) four times, and dried under a vacuum at 20-25° C.

An additional two-step reaction at room temperature was carried out using different reaction conditions (Table 5), thereby preparing sample product 245.

Thus, oxidized dextran was prepared and isolated using two-step oxidation reactions maintained at room temperature. A periodate compound and an N-oxoammonium salt were used as oxidizing agents in these reactions.

Example 12

Oxidized Dextran has Builder Activity

This Example discloses testing whether oxidized dextran has builder activity. This activity was determined by measuring the calcium dispersing capacity of oxidized dextran material under aqueous conditions.

For each assay, oxidized dextran (as prepared in Examples 10-11) was dissolved into 100 mL of water with stirring using a magnetic stir bar. The exact mass of the oxidized dextran that dissolved was recorded, after which the pH was adjusted to 8 using 4.5% sodium hydroxide. To this solution 10 g of 2% sodium carbonate was added and the pH was then adjusted to 11 using sodium hydroxide (if needed). The turbidity of the solution was measured using a turbidity meter. A 4.4% calcium acetate solution was titrated into the oxidized dextran solution using a glass burette, with samples taken out for turbidity measurements after each addition. When the percent transmittance of the solution decreased, such decrease indicated that the oxidized dextran was no longer dispersing the calcium carbonate. The amount of calcium acetate added during the assay was used to determine the calcium dispersing capacity of the oxidized dextran. The calcium dispersing capacity of each sample of oxidized dextran is listed in Table 6.

TABLE 6

Calcium Dispersing Capacity of Oxidized Dextran

| Sample Product Designation | Mass (g) Dissolved | Calcium Acetate (mL) | CCDC[a] of sample (g calcium carbonate/g polymer) |
|---|---|---|---|
| 173 | 0.1493 | 0.93 | 274.1 |
| 240 | 0.2919 | 0.6 | 90.44 |
| 245 | 0.0245 | 0.66 | 1185.3 |

[a]CCDC, calcium carbonate dispersing capacity.

Each sample of oxidized dextran exhibited the ability to delay precipitation of calcium carbonate in this assay, thereby indicating that oxidized dextran has builder activity. Such builder activity is contemplated to be useful in various applications that benefit from the use of a builder, such as in fabric care compositions.

TABLE 5

Preparation of Oxidized Dextran by Two-Step Reaction

| Sample Product Designation | Substrate[a] | Sodium Periodate | TEMPO[b] | Sodium Chlorite | Sodium Hypochlorite | Reaction Time |
|---|---|---|---|---|---|---|
| 245 | 1 g | 6.9 g | 0.1 g | 1.2 g | 5 g | 72 hr. |

[a]Starting amount of dextran entered into the two step reaction.
[b]4-acetamido-TEMPO.

Example 13

Adsorption of Oxidized Dextran on Various Fabrics

This Example discloses how one could test the degree of adsorption of oxidized dextran herein, such as produced above, on different types of fabric.

First, calibration curves were prepared that could be useful for determining the relative level of adsorption of oxidized dextran onto fabric surfaces.

Solutions of known concentration (ppm) were made using Direct Red 80 and Toluidine Blue 0 dyes. The absorbance of these solutions were measured using a LAMOTTE SMART2 Colorimeter at either 520 or 620 nm. The absorption information was plotted in order that it can be used to determine dye concentration of solutions exposed to fabric samples. The concentration and absorbance of each calibration curve are provided in Tables 7 and 8.

TABLE 7

Direct Red 80 Dye Calibration Curve Data

| Dye Concentration (ppm) | Average Absorbance @520 nm |
|---|---|
| 25 | 0.823333333 |
| 22.5 | 0.796666667 |
| 20 | 0.666666667 |
| 15 | 0.51 |
| 10 | 0.37 |
| 5 | 0.2 |

TABLE 8

Toluidine Blue O Dye Calibration Curve Data

| Dye Concentration (ppm) | Average Absorbance @620 nm |
|---|---|
| 12.5 | 1.41 |
| 10 | 1.226666667 |
| 7 | 0.88 |
| 5 | 0.676666667 |
| 3 | 0.44 |
| 1 | 0.166666667 |

These calibration curves may be useful for determining the relative level of adsorption of oxidized dextran on fabric surfaces, such as by following the below methodology.

0.07 wt % or 0.25 wt % solutions of an oxidized dextran compound in deionized water are made. Each solution is divided into several aliquots with different concentrations of compound (Table 9). Other components are added such as acid (dilute hydrochloric acid) or base (sodium hydroxide) to modify pH, or NaCl salt.

TABLE 9

Oxidized Dextran Compound Solutions Useful in Fabric Adsorption Studies

| Amount of NaCl (g) | Amount of Solution (g) | Compound Concentration (wt %) | Final pH |
|---|---|---|---|
| 0 | 15 | 0.07 | ~7 |
| 0.15 | 14.85 | 0.0693 | ~7 |
| 0.3 | 14.7 | 0.0686 | ~7 |
| 0.45 | 14.55 | 0.0679 | ~7 |
| 0 | 9.7713 | 0.0683 | ~3 |
| 0 | 9.7724 | 0.0684 | ~5 |
| 0 | 10.0311 | 0.0702 | ~9 |
| 0 | 9.9057 | 0.0693 | ~11 |
| 0 | 15 | 0.25 | ~7 |
| 0.15 | 14.85 | 0.2475 | ~7 |
| 0.3 | 14.7 | 0.245 | ~7 |
| 0.45 | 14.55 | 0.2425 | ~7 |
| 0 | 9.8412 | 0.2459 | ~3 |
| 0 | 9.4965 | 0.2362 | ~5 |
| 0 | 9.518 | 0.2319 | ~9 |
| 0 | 9.8811 | 0.247 | ~11 |

Four different fabric types (cretonne, polyester, 65:35 polyester/cretonne, bleached cotton) are cut into 0.17 g pieces. Each piece is placed in a 2-mL well in a 48-well cell culture plate. Each fabric sample is exposed to 1 mL of each of the above compound solutions (Table 9) (a control solution with no compound is included for each fabric test). The fabric samples are allowed to sit for at least 30 minutes in the compound solutions. The fabric samples are removed from the compound solutions and rinsed in DI water for at least one minute to remove any unbound compound. The fabric samples are then dried at 60° C. for at least 30 minutes until constant dryness is achieved. The fabric samples are weighed after drying and individually placed in 2-mL wells in a clean 48-well cell culture plate. The fabric samples are then exposed to 1 mL of a 250 ppm Direct Red 80 dye solution or a 250 ppm Toluidine Blue dye solution. The samples are left in the dye solution for at least 15 minutes. Each fabric sample is removed from the dye solution, after which the dye solution is diluted 10×.

The absorbance of the diluted solutions is measured compared to a control sample. A relative measure of oxidized dextran compound adsorbed to the fabric is calculated based on the calibration curve created above for Direct Red 80 and/or Toluidine Blue dye, as appropriate. Specifically, the difference in UV absorbance for the fabric samples exposed to the oxidized compound compared to the controls (fabric not exposed to compound) represents a relative measure of compound adsorbed to the fabric. This difference in UV absorbance could also be expressed as the amount of dye bound to the fabric (over the amount of dye bound to control), which is calculated using the calibration curve (i.e., UV absorbance is converted to ppm dye). A positive value represents the dye amount that is in excess to the dye amount bound to the control fabric, whereas a negative value represents the dye amount that is less than the dye amount bound to the control fabric. A positive value would reflect that the oxidized dextran compound adsorbed to the fabric surface.

It is believed that this assay would demonstrate that oxidized dextran can adsorb to various types of fabric under different salt and pH conditions. This adsorption would suggest that oxidized dextran compounds are useful in detergents for fabric care (e.g., as anti-redeposition agents).

Example 14

Oxidation of Dextran with Peroxide

This Example describes how one can produce oxidized dextran in a reaction comprising a peroxide compound. In particular, hydrogen peroxide could be used to oxidize dextran as presently disclosed.

3.6 g of dextran is added to 116.4 mL of DI water and adjusted to pH 7.0 in a 250-mL glass reaction vessel. Next, 360 mg of 30% hydrogen peroxide is added to this preparation to achieve a 3% w/w addition of hydrogen peroxide based on the dextran content. The preparation is mixed thoroughly, sealed in the glass reaction vessel and autoclaved for 60 minutes at 121° C. The reaction is cooled to room temperature following this treatment, and is contemplated to comprise oxidized dextran.

Thus, oxidized dextran can be prepared and isolated from reactions containing a peroxide compound.

What is claimed is:

1. A composition comprising an oxidized dextran compound, wherein the oxidized dextran compound is produced by contacting dextran under aqueous conditions with at least one N-oxoammonium salt, at least one periodate compound, and/or at least one peroxide compound, wherein the dextran is a product of an isolated glucosyltransferase enzyme comprising an amino acid sequence selected from one with at least 90% identity to SEQ ID NO:1 or SEQ ID NO:2.

2. The composition of claim 1, wherein the dextran is contacted with the periodate compound.

3. The composition of claim 1, wherein the dextran is first contacted with the periodate compound, and then contacted with the N-oxoammonium salt.

4. The composition of claim 1, wherein the N-oxoammonium salt comprises a TEMPO oxoammonium salt.

5. The composition of claim 1, wherein the composition is a personal care product, industrial product, pharmaceutical product, or food product.

6. The composition of claim 1, wherein the composition is a household product.

7. The composition of claim 1, wherein the composition is a detergent composition.

8. The composition of claim 1, wherein the composition is a fabric care product.

9. The composition of claim 1, wherein the composition is a dishwashing detergent composition.

10. The composition of claim 9, wherein the dishwashing detergent composition is an automatic dishwashing detergent composition.

11. The composition of claim 9, wherein the dishwashing detergent composition is a hand washing dish detergent composition.

12. The composition of claim 1, wherein the isolated glucosyltransferase enzyme comprises an amino acid sequence selected from one with at least 95% identity to SEQ ID NO:1 or SEQ ID NO:2.

13. The composition of claim 1, wherein the composition is an aqueous composition.

14. A method of treating a material, said method comprising:
contacting the material with a composition according to claim 13.

15. The method of claim 14, wherein the material comprises fabric.

16. The method of claim 15, wherein the fabric comprises (i) natural fiber, (ii) synthetic fiber, or a combination of both (i) and (ii).

17. The method of claim 14, wherein the material is a pot, pan, baking dish, or tableware.

18. The method of claim 17, wherein the material is tableware selected from the group consisting of dishes, glasses, utensils, and flatware, wherein the flatware is made from ceramic material, china, metal, glass, or plastic.

19. A method of producing an oxidized dextran compound, the method comprising:
contacting dextran under aqueous conditions with at least one N-oxoammonium salt, at least one periodate compound, and/or at least one peroxide compound, wherein the dextran is a product of an isolated glucosyltransferase enzyme comprising an amino acid sequence selected from one with at least 90% identity to SEQ ID NO:1 or SEQ ID NO:2;
wherein the dextran is oxidized by the N-oxoammonium salt, periodate compound, and/or peroxide compound thereby producing the oxidized dextran compound.

20. A method of increasing the builder capacity and/or anti-redeposition capacity of an aqueous composition, wherein the method comprises:

contacting an oxidized dextran compound according to claim 1 with the aqueous composition, wherein the builder and/or anti-redeposition capacity of the aqueous composition is increased by the oxidized dextran compound compared to the builder and/or anti-redeposition capacity of the aqueous composition before the contacting step.

21. The method of claim 19, wherein the isolated glucosyltransferase enzyme comprises an amino acid sequence selected from one with at least 95% identity to SEQ ID NO:1 or SEQ ID NO:2.

\* \* \* \* \*

SEQUENCE LISTING

```
<160> NUMBER OF SEQ ID NOS: 18

<210> SEQ ID NO 1
<211> LENGTH: 1447
<212> TYPE: PRT
<213> ORGANISM: Leuconostoc pseudomesenteroides
<220> FEATURE:
<221> NAME/KEY: MISC_FEATURE
<222> LOCATION: (1)..(1447)
<223> OTHER INFORMATION: mature 0768 gtf

<400> SEQUENCE: 1

Asp Gln Asn Val Asn Asp Pro Ser Val Ala Thr Thr Gln Asn Val
1               5                   10                  15

Val Thr Asp Gln Asp Thr Ser Ile Asp Ala Ser Val Ala Thr Thr Val
            20                  25                  30

Asn Pro Asn Leu Asp Asp Thr Gln Ala Asp Asn Thr Asn Ile Gln Thr
            35                  40                  45

Pro Thr Asp Gln Asn Asp Glu Ser Lys Asp Thr Thr Pro Lys Val Glu
        50                  55                  60

Thr Gly Asp Thr Thr Asn Ser Gln Ser Thr Glu Ala Gln Glu Thr Thr
65                  70                  75                  80

Ala Gln Thr Asn Asn Asp Val Glu Thr Pro Gln Asn Ser Asp Ala Ala
                85                  90                  95

Ile Glu Thr Gly Leu Leu Thr Thr Asn Asn Gln Ile Arg Tyr Val Asn
            100                 105                 110

Pro Asp Gly Thr Val Leu Thr Gly Ala Tyr Lys Thr Ile Asn Gly Asn
            115                 120                 125

Thr Tyr Tyr Phe Asp Asp Ser Gly Val Ala Leu Val Gly Leu His
130                 135                 140

Lys Ile Gly Asp Thr Leu Lys Gly Phe Ser Leu Asn Gly Val Gln Val
145                 150                 155                 160

Lys Gly Asp Tyr Leu Thr Ala Ala Asn Gly Asp Lys Tyr Tyr Phe Asp
                165                 170                 175

Ser Asn Gly Asn Ala Val Ser Gly Val Gln Gln Ile Asn Gly Lys Thr
            180                 185                 190

Tyr Tyr Phe Asp Ser Thr Gly Lys Leu Met Lys Gly Tyr Thr Ala Val
            195                 200                 205

Leu Asn Gly Val Val Thr Phe Phe Asn Ser Thr Thr Gly Glu Ala Asp
        210                 215                 220

Asn Thr Asp Ala Ser Thr Ile Lys Thr Gly Val Thr Ile Asp Asn Ser
225                 230                 235                 240

Asp Tyr Thr Val His Asn Ala Ala Tyr Asp Asn Thr Ala Ala Ser Phe
                245                 250                 255

Asp Asn Ile Asn Gly Tyr Leu Thr Ala Glu Ser Trp Tyr Arg Pro Lys
            260                 265                 270

Glu Ile Leu Glu Asn Gly Glu Ser Trp Arg Pro Ser Thr Ala Glu Asp
            275                 280                 285

Lys Arg Pro Ile Leu Ile Thr Trp Gln Pro Asp Ile Val Thr Glu Val
```

-continued

```
              290                 295                 300
Asn Tyr Leu Asn Met Met Ala Ala Asn Gly Leu Leu Ser Ile Asn Ala
305                 310                 315                 320

Pro Phe Thr Thr Ala Ser Asp Leu Ala Ile Met Asn Asp Ala Val Arg
                325                 330                 335

Ala Val Gln Lys Asn Ile Glu Met Arg Ile Ser Gln Glu Lys Ser Thr
                340                 345                 350

Asp Trp Leu Lys Ala Leu Met Thr Gln Phe Ile Asn Thr Gln Pro Gln
                355                 360                 365

Trp Asn Glu Val Ser Glu Ser Pro Ser Asn Asp His Leu Gln Gly Gly
            370                 375                 380

Ala Leu Thr Tyr Val Asn Ser Pro Leu Thr Pro Asp Ala Asn Ser Asn
385                 390                 395                 400

Phe Arg Leu Leu Asn Arg Thr Pro Thr Asn Gln Ser Gly Thr Thr Arg
                405                 410                 415

Tyr Asp Thr Asp Lys Ser Lys Gly Gly Phe Glu Leu Leu Leu Ala Asn
                420                 425                 430

Asp Val Asp Asn Ser Asn Pro Val Val Gln Ala Glu Gln Leu Asn Trp
            435                 440                 445

Leu Tyr Tyr Leu Met Asn Phe Gly Ser Ile Thr Ala Asn Asp Pro Thr
            450                 455                 460

Ala Asn Phe Asp Gly Ile Arg Val Asp Ala Val Asp Asn Val Asp Ala
465                 470                 475                 480

Asp Leu Leu Gln Ile Ala Ser Asp Tyr Phe Lys Leu Ala Tyr Gly Thr
                485                 490                 495

Ser Leu Ser Asp Thr Asn Ala Asn Gln His Leu Ser Ile Leu Glu Asp
                500                 505                 510

Trp Ser Ala Asn Asp Ala Glu Tyr Met Ser Lys Thr Gly Ser Asn Gln
            515                 520                 525

Leu Thr Met Asp Thr Tyr Thr Gln Gln Leu Leu Phe Ser Leu Thr
            530                 535                 540

Lys Gln Val Gly Asn Arg Ala Asp Met Arg Arg Phe Leu Glu Tyr Phe
545                 550                 555                 560

Met Ile Asn Arg Ala Asn Asp Ser Thr Glu Asn Val Ala Thr Pro Asn
                565                 570                 575

Tyr Ser Phe Val Arg Ala His Asp Ser Glu Val Gln Thr Val Ile Ala
                580                 585                 590

Thr Ile Ile Lys Asp Leu His Pro Asp Val Val Asn Ser Leu Ala Pro
                595                 600                 605

Thr Gln Ala Gln Leu Glu Glu Ala Phe Ala Val Tyr Asn Ala Asp Met
            610                 615                 620

Asn Arg Val Asp Lys Gln Tyr Thr Gln Tyr Asn Met Pro Ser Ala Tyr
625                 630                 635                 640

Ala Met Leu Leu Thr Asn Lys Asp Thr Ile Pro Arg Val Tyr Tyr Gly
                645                 650                 655

Asp Leu Tyr Thr Asp Asp Gly Glu Tyr Met Gly Thr Gln Thr Pro Tyr
                660                 665                 670

Tyr Asp Ala Ile Val Asn Leu Leu Gln Ser Arg Val Lys Tyr Val Ala
                675                 680                 685

Gly Gly Gln Ser Met Ala Val Asp Gln His Asp Ile Leu Thr Ser Val
            690                 695                 700

Arg Tyr Gly Lys Asn Leu Ala Asp Ala Asn Ala Thr Ser Asp Asp Leu
705                 710                 715                 720
```

```
Thr Ser Ile Asn Ser Gly Ile Gly Val Ile Ser Asn Asn Pro Asn
            725                 730                 735

Leu Ser Leu Ala Ser Gly Glu Thr Val Val Leu His Met Gly Ile Ala
            740                 745                 750

His Ala Asn Gln Val Tyr Arg Glu Ile Leu Glu Thr Thr Asp Asn Gly
            755                 760                 765

Ile Ala Asn Asn Thr Asp Ile Phe Lys Thr Thr Asp Ser Asn Gly Asp
            770                 775                 780

Leu Ile Phe Thr Ala Ser Glu Ile His Gly Tyr Ser Asn Val Gln Val
785                 790                 795                 800

Ser Gly Phe Leu Ser Val Trp Ala Pro Lys Asp Ala Thr Asp Asp Gln
            805                 810                 815

Asp Val Arg Thr Ala Ala Ser Glu Ser Thr Ser Asn Asp Gly Asn Thr
            820                 825                 830

Leu His Ser Asn Ala Ala Leu Asp Ser Asn Leu Ile Tyr Glu Gly Phe
            835                 840                 845

Ser Asn Phe Gln Ser Thr Pro Gln Ser Glu Ser Glu Phe Ala Asn Val
            850                 855                 860

Lys Ile Ala Ala Asn Val Asn Leu Phe Lys Ser Trp Gly Val Thr Ser
865                 870                 875                 880

Phe Gln Met Ala Pro Gln Tyr Arg Ser Ser Thr Asp Thr Ser Phe Leu
            885                 890                 895

Asp Ser Ile Ile Gln Asn Gly Tyr Ala Phe Thr Asp Arg Tyr Asp Leu
            900                 905                 910

Gly Phe Glu Thr Pro Thr Lys Tyr Gly Thr Asp Gln Gln Leu Arg Asp
            915                 920                 925

Ala Ile Lys Ala Leu His Ala Asn Gly Ile Gln Ala Met Ala Asp Phe
            930                 935                 940

Val Pro Asp Gln Ile Tyr Asn Leu Pro Gln Thr Glu Leu Val Ser Val
945                 950                 955                 960

Ser Arg Thr Asp Ser Leu Gly Asn Gln Ser Ala Asn Ser Asn Ala Ala
            965                 970                 975

Asn Val Leu Tyr Val Ser His Thr Val Gly Gly Gly Tyr Gln Ser
            980                 985                 990

Lys Tyr Gly Gly Glu Phe Leu Ala  Ile Ile Lys Ser Lys  Tyr Pro Ser
            995                1000               1005

Leu Phe Lys Thr Ile Gln Val  Ser Thr Gly Leu Pro  Ile Asp Asp
       1010                1015               1020

Ser Thr Lys Ile Lys Glu Trp  Ser Ala Lys Tyr Phe  Asn Gly Ser
       1025                1030               1035

Asn Ile Gln Gly Arg Gly Phe  Gly Tyr Val Leu Ser  Asp Gly Gly
       1040                1045               1050

Thr Gln Asn Tyr Phe Lys Val  Ile Ser Asn Ser Thr  Asp Asp Asp
       1055                1060               1065

Phe Leu Pro Asn Gln Leu Thr  Gly Lys Pro Thr Met  Thr Gly Phe
       1070                1075               1080

Glu Gln Thr Ser Lys Gly Ile  Val Tyr Tyr Ser Lys  Ser Gly Ile
       1085                1090               1095

Gln Ala Lys Asn Gln Phe Val  Lys Asp Asp Val Ser  Gly Asn Tyr
       1100                1105               1110

Tyr Tyr Phe Asn Lys Asn Gly  Leu Met Thr Val Gly  Ser Lys Thr
       1115                1120               1125
```

Ile Asn Gly Lys Asn Tyr Met Phe Leu Pro Asn Gly Val Glu Leu
1130            1135                1140

Arg Gly Ser Phe Leu Gln Thr Ala Asp Gly Thr Val Asn Tyr Tyr
1145            1150                1155

Ala Thr Asn Gly Ala Gln Val Gln Asp Ser Tyr Val Thr Asp Thr
1160            1165                1170

Glu Gly Asn Ser Tyr Tyr Phe Asp Gly Asp Gly Glu Met Val Thr
1175            1180                1185

Gly Thr Tyr Thr Val Asp Gly His Ala Gln Tyr Phe Asp Val Asn
1190            1195                1200

Gly Val Gln Thr Lys Gly Ala Ile Ile Thr Leu Gly Gly Val Gln
1205            1210                1215

Arg Tyr Tyr Gln Ala Gly Asn Gly Asn Leu Ala Thr Asn Gln Tyr
1220            1225                1230

Val Ser Tyr Asn Asn Ser Trp Tyr Tyr Ala Asn Thr Lys Gly Glu
1235            1240                1245

Leu Val Thr Gly Val Gln Ser Ile Asn Gly Asn Val Gln Tyr Phe
1250            1255                1260

Ala Ser Asn Gly Gln Gln Ile Lys Gly Gln Ile Val Val Thr Gly
1265            1270                1275

Asn Gln Lys Ser Tyr Tyr Asp Ala Asn Thr Gly Asn Leu Ile Lys
1280            1285                1290

Asn Asp Phe Leu Thr Pro Asp Gln Gly Lys Thr Trp Tyr Tyr Ala
1295            1300                1305

Asp Gln Asp Gly Asn Leu Val Val Gly Ala Gln Glu Val Asn Gly
1310            1315                1320

His Lys Leu Tyr Phe Asp Asn Gly Ile Gln Ile Lys Asp Gln
1325            1330                1335

Ile Ile Ser Asn Asp Gly Gln Gln Tyr Tyr Gln Gly Gly Asn
1340            1345                1350

Gly Asp Leu Val Thr Asn Arg Tyr Ile Ser Tyr Asn Asp Ser Trp
1355            1360                1365

Tyr Tyr Ala Asp Ala Thr Gly Val Leu Val Thr Gly Gln Gln Ile
1370            1375                1380

Ile Asn Gly Glu Thr Gln Tyr Phe Arg Thr Asp Gly Arg Gln Val
1385            1390                1395

Lys Gly Gln Ile Ile Ala Asp Gly Asp Lys Gln His Tyr Tyr Asp
1400            1405                1410

Ala Asp Ser Gly Asn Leu Val Lys Asn Asn Phe Val Thr Val Asp
1415            1420                1425

Gln Gly Lys Thr Trp Tyr Tyr Ala Asp Gln Asp Gly Asn Leu Ser
1430            1435                1440

Leu Val Asp Arg
1445

<210> SEQ ID NO 2
<211> LENGTH: 1457
<212> TYPE: PRT
<213> ORGANISM: Artificial sequence
<220> FEATURE:
<223> OTHER INFORMATION: 0768 gtf mature protein with start codon and
      other added sequences

<400> SEQUENCE: 2

Met Ala Ser Ala Asp Gln Asn Val Asn Asp Pro Ser Val Ala Thr Thr
1               5                   10                  15

Thr Gln Asn Val Val Thr Asp Gln Asp Thr Ser Ile Asp Ala Ser Val
                20                  25                  30

Ala Thr Thr Val Asn Pro Asn Leu Asp Asp Thr Gln Ala Asp Asn Thr
            35                  40                  45

Asn Ile Gln Thr Pro Thr Asp Gln Asn Asp Glu Ser Lys Asp Thr Thr
50                  55                  60

Pro Lys Val Glu Thr Gly Asp Thr Thr Asn Ser Gln Ser Thr Glu Ala
65                  70                  75                  80

Gln Glu Thr Thr Ala Gln Thr Asn Asn Asp Val Glu Thr Pro Gln Asn
                85                  90                  95

Ser Asp Ala Ala Ile Glu Thr Gly Leu Leu Thr Thr Asn Asn Gln Ile
            100                 105                 110

Arg Tyr Val Asn Pro Asp Gly Thr Val Leu Thr Gly Ala Tyr Lys Thr
            115                 120                 125

Ile Asn Gly Asn Thr Tyr Tyr Phe Asp Asp Ser Gly Val Ala Leu
130                 135                 140

Val Gly Leu His Lys Ile Gly Asp Thr Leu Lys Gly Phe Ser Leu Asn
145                 150                 155                 160

Gly Val Gln Val Lys Gly Asp Tyr Leu Thr Ala Ala Asn Gly Asp Lys
                165                 170                 175

Tyr Tyr Phe Asp Ser Asn Gly Asn Ala Val Ser Gly Val Gln Gln Ile
            180                 185                 190

Asn Gly Lys Thr Tyr Tyr Phe Asp Ser Thr Gly Lys Leu Met Lys Gly
            195                 200                 205

Tyr Thr Ala Val Leu Asn Gly Val Val Thr Phe Phe Asn Ser Thr Thr
            210                 215                 220

Gly Glu Ala Asp Asn Thr Asp Ala Ser Thr Ile Lys Thr Gly Val Thr
225                 230                 235                 240

Ile Asp Asn Ser Asp Tyr Thr Val His Asn Ala Ala Tyr Asp Asn Thr
                245                 250                 255

Ala Ala Ser Phe Asp Asn Ile Asn Gly Tyr Leu Thr Ala Glu Ser Trp
            260                 265                 270

Tyr Arg Pro Lys Glu Ile Leu Glu Asn Gly Ser Trp Arg Pro Ser
            275                 280                 285

Thr Ala Glu Asp Lys Arg Pro Ile Leu Ile Thr Trp Gln Pro Asp Ile
290                 295                 300

Val Thr Glu Val Asn Tyr Leu Asn Met Met Ala Ala Asn Gly Leu Leu
305                 310                 315                 320

Ser Ile Asn Ala Pro Phe Thr Thr Ala Ser Asp Leu Ala Ile Met Asn
            325                 330                 335

Asp Ala Val Arg Ala Val Gln Lys Asn Ile Glu Met Arg Ile Ser Gln
            340                 345                 350

Glu Lys Ser Thr Asp Trp Leu Lys Ala Leu Met Thr Gln Phe Ile Asn
            355                 360                 365

Thr Gln Pro Gln Trp Asn Glu Val Ser Glu Ser Ser Asn Asp His
            370                 375                 380

Leu Gln Gly Gly Ala Leu Thr Tyr Val Asn Ser Pro Leu Thr Pro Asp
385                 390                 395                 400

Ala Asn Ser Asn Phe Arg Leu Leu Asn Arg Thr Pro Thr Asn Gln Ser
            405                 410                 415

Gly Thr Thr Arg Tyr Asp Thr Asp Lys Ser Lys Gly Gly Phe Glu Leu
            420                 425                 430

-continued

```
Leu Leu Ala Asn Asp Val Asp Asn Ser Asn Pro Val Gln Ala Glu
            435                 440                 445
Gln Leu Asn Trp Leu Tyr Tyr Leu Met Asn Phe Gly Ser Ile Thr Ala
450                 455                 460
Asn Asp Pro Thr Ala Asn Phe Asp Gly Ile Arg Val Asp Ala Val Asp
465                 470                 475                 480
Asn Val Asp Ala Asp Leu Leu Gln Ile Ala Ser Asp Tyr Phe Lys Leu
                485                 490                 495
Ala Tyr Gly Thr Ser Leu Ser Asp Thr Asn Ala Asn Gln His Leu Ser
                500                 505                 510
Ile Leu Glu Asp Trp Ser Ala Asn Asp Ala Glu Tyr Met Ser Lys Thr
            515                 520                 525
Gly Ser Asn Gln Leu Thr Met Asp Thr Tyr Thr Gln Gln Gln Leu Leu
530                 535                 540
Phe Ser Leu Thr Lys Gln Val Gly Asn Arg Ala Asp Met Arg Arg Phe
545                 550                 555                 560
Leu Glu Tyr Phe Met Ile Asn Arg Ala Asn Asp Ser Thr Glu Asn Val
                565                 570                 575
Ala Thr Pro Asn Tyr Ser Phe Val Arg Ala His Asp Ser Glu Val Gln
                580                 585                 590
Thr Val Ile Ala Thr Ile Ile Lys Asp Leu His Pro Asp Val Val Asn
            595                 600                 605
Ser Leu Ala Pro Thr Gln Ala Gln Leu Glu Glu Ala Phe Ala Val Tyr
            610                 615                 620
Asn Ala Asp Met Asn Arg Val Asp Lys Gln Tyr Thr Gln Tyr Asn Met
625                 630                 635                 640
Pro Ser Ala Tyr Ala Met Leu Leu Thr Asn Lys Asp Thr Ile Pro Arg
                645                 650                 655
Val Tyr Tyr Gly Asp Leu Tyr Thr Asp Asp Gly Glu Tyr Met Gly Thr
                660                 665                 670
Gln Thr Pro Tyr Tyr Asp Ala Ile Val Asn Leu Leu Gln Ser Arg Val
            675                 680                 685
Lys Tyr Val Ala Gly Gly Gln Ser Met Ala Val Asp Gln His Asp Ile
690                 695                 700
Leu Thr Ser Val Arg Tyr Gly Lys Asn Leu Ala Asp Ala Asn Ala Thr
705                 710                 715                 720
Ser Asp Asp Leu Thr Ser Ile Asn Ser Gly Ile Gly Val Ile Val Ser
                725                 730                 735
Asn Asn Pro Asn Leu Ser Leu Ala Ser Gly Glu Thr Val Val Leu His
            740                 745                 750
Met Gly Ile Ala His Ala Asn Gln Val Tyr Arg Glu Ile Leu Glu Thr
            755                 760                 765
Thr Asp Asn Gly Ile Ala Asn Asn Thr Asp Ile Phe Lys Thr Thr Asp
770                 775                 780
Ser Asn Gly Asp Leu Ile Phe Thr Ala Ser Glu Ile His Gly Tyr Ser
785                 790                 795                 800
Asn Val Gln Val Ser Gly Phe Leu Ser Val Trp Ala Pro Lys Asp Ala
                805                 810                 815
Thr Asp Asp Gln Asp Val Arg Thr Ala Ala Ser Glu Ser Thr Ser Asn
            820                 825                 830
Asp Gly Asn Thr Leu His Ser Asn Ala Ala Leu Asp Ser Asn Leu Ile
            835                 840                 845
Tyr Glu Gly Phe Ser Asn Phe Gln Ser Thr Pro Gln Ser Glu Ser Glu
```

```
            850                 855                 860
    Phe Ala Asn Val Lys Ile Ala Ala Asn Val Asn Leu Phe Lys Ser Trp
    865                 870                 875                 880

Gly Val Thr Ser Phe Gln Met Ala Pro Gln Tyr Arg Ser Ser Thr Asp
                        885                 890                 895

Thr Ser Phe Leu Asp Ser Ile Ile Gln Asn Gly Tyr Ala Phe Thr Asp
                    900                 905                 910

Arg Tyr Asp Leu Gly Phe Glu Thr Pro Thr Lys Tyr Gly Thr Asp Gln
                915                 920                 925

Gln Leu Arg Asp Ala Ile Lys Ala Leu His Ala Asn Gly Ile Gln Ala
            930                 935                 940

Met Ala Asp Phe Val Pro Asp Gln Ile Tyr Asn Leu Pro Gln Thr Glu
    945                 950                 955                 960

Leu Val Ser Val Ser Arg Thr Asp Ser Leu Gly Asn Gln Ser Ala Asn
                        965                 970                 975

Ser Asn Ala Ala Asn Val Leu Tyr Val Ser His Thr Val Gly Gly Gly
                    980                 985                 990

Glu Tyr Gln Ser Lys Tyr Gly Gly  Glu Phe Leu Ala Ile  Ile Lys Ser
                995                 1000                1005

Lys Tyr  Pro Ser Leu Phe Lys  Thr Ile Gln Val Ser  Thr Gly Leu
        1010                 1015                 1020

Pro Ile  Asp Asp Ser Thr Lys  Ile Lys Glu Trp Ser  Ala Lys Tyr
        1025                 1030                 1035

Phe Asn  Gly Ser Asn Ile Gln  Gly Arg Gly Phe Gly  Tyr Val Leu
        1040                 1045                 1050

Ser Asp  Gly Gly Thr Gln Asn  Tyr Phe Lys Val Ile  Ser Asn Ser
        1055                 1060                 1065

Thr Asp  Asp Asp Phe Leu Pro  Asn Gln Leu Thr Gly  Lys Pro Thr
        1070                 1075                 1080

Met Thr  Gly Phe Glu Gln Thr  Ser Lys Gly Ile Val  Tyr Tyr Ser
        1085                 1090                 1095

Lys Ser  Gly Ile Gln Ala Lys  Asn Gln Phe Val Lys  Asp Asp Val
        1100                 1105                 1110

Ser Gly  Asn Tyr Tyr Tyr Phe  Asn Lys Asn Gly Leu  Met Thr Val
        1115                 1120                 1125

Gly Ser  Lys Thr Ile Asn Gly  Lys Asn Tyr Met Phe  Leu Pro Asn
        1130                 1135                 1140

Gly Val  Glu Leu Arg Gly Ser  Phe Leu Gln Thr Ala  Asp Gly Thr
        1145                 1150                 1155

Val Asn  Tyr Tyr Ala Thr Asn  Gly Ala Gln Val Gln  Asp Ser Tyr
        1160                 1165                 1170

Val Thr  Asp Thr Glu Gly Asn  Ser Tyr Tyr Phe Asp  Gly Asp Gly
        1175                 1180                 1185

Glu Met  Val Thr Gly Thr Tyr  Thr Val Asp Gly His  Ala Gln Tyr
        1190                 1195                 1200

Phe Asp  Val Asn Gly Val Gln  Thr Lys Gly Ala Ile  Ile Thr Leu
        1205                 1210                 1215

Gly Gly  Val Gln Arg Tyr Tyr  Gln Ala Gly Asn Gly  Asn Leu Ala
        1220                 1225                 1230

Thr Asn  Gln Tyr Val Ser Tyr  Asn Asn Ser Trp Tyr  Tyr Ala Asn
        1235                 1240                 1245

Thr Lys  Gly Glu Leu Val Thr  Gly Val Gln Ser Ile  Asn Gly Asn
        1250                 1255                 1260
```

| | | | | | | | | | | |
|---|---|---|---|---|---|---|---|---|---|---|
|Val|Gln|Tyr|Phe|Ala|Ser|Asn|Gly|Gln|Gln|Ile|Lys|Gly|Gln|Ile|
|1265| | | | |1270| | | | |1275| | | | |

Val Val Thr Gly Asn Gln Lys Ser Tyr Tyr Asp Ala Asn Thr Gly
1280                     1285                    1290

Asn Leu Ile Lys Asn Asp Phe Leu Thr Pro Asp Gln Gly Lys Thr
1295                     1300                    1305

Trp Tyr Tyr Ala Asp Gln Asp Gly Asn Leu Val Val Gly Ala Gln
1310                     1315                    1320

Glu Val Asn Gly His Lys Leu Tyr Phe Asp Asp Asn Gly Ile Gln
1325                     1330                    1335

Ile Lys Asp Gln Ile Ile Ser Asn Asp Gly Gln Gln Tyr Tyr Tyr
1340                     1345                    1350

Gln Gly Gly Asn Gly Asp Leu Val Thr Asn Arg Tyr Ile Ser Tyr
1355                     1360                    1365

Asn Asp Ser Trp Tyr Tyr Ala Asp Ala Thr Gly Val Leu Val Thr
1370                     1375                    1380

Gly Gln Gln Ile Ile Asn Gly Glu Thr Gln Tyr Phe Arg Thr Asp
1385                     1390                    1395

Gly Arg Gln Val Lys Gly Gln Ile Ile Ala Asp Gly Asp Lys Gln
1400                     1405                    1410

His Tyr Tyr Asp Ala Asp Ser Gly Asn Leu Val Lys Asn Asn Phe
1415                     1420                    1425

Val Thr Val Asp Gln Gly Lys Thr Trp Tyr Tyr Ala Asp Gln Asp
1430                     1435                    1440

Gly Asn Leu Ser Leu Val Asp Arg His His His His His His
1445                     1450                    1455

<210> SEQ ID NO 3
<211> LENGTH: 4347
<212> TYPE: DNA
<213> ORGANISM: Weissella cibaria

<400> SEQUENCE: 3

```
atgtacaagt ccggaaagtt ttgggtagct gccggtgctt tgtttgttgg gctggcattc      60
gctggtaaca cgcaggctga tactgtatta ccaagtgaac aacgtgcaac ggagacgaca     120
cagacgacac agaccagtga agacacgtcc gccactaaga cgccggcatc ggcgtcgact     180
tcaagctcag tcaatgttga cacgagtgac ctgcctgaca gttcaagtac ggtagttgat     240
agtacaagtg caagtgcaag cgtagtgagt gatagcgtcg ctgtgccaga tactggatca     300
caatttacga gttcgtcagg gtcaatgtca tcatcatttg ttaagtcatc actagcggca     360
acaactagtg atgcttctgg cagtcagtcg gcggcggtga ctagcgcaac cgttagttcg     420
gtggccacga gtagttcagc atcttcagtg acaacagcca caagcgaatc agcagtgata     480
agcagcgccg tgtcagatgg ttaccatgat gaaggtggtg attgggtcta ttatcgagct     540
ggaaaaaagt tagtcggtcg acaaacgatt gatacgtttg cggtttactt tgacgccgat     600
ggcaaacaag tcaagggtga ttggcgtgaa agtgatggta accgtgcgta ttatgatgga     660
caagaaggac gagcattaac gcaaacgcaa gcagtcaatg gcgttatcta cggttttaat     720
caaagcggct atcaaatcaa gaatgatttc ggccaaacag cgaatcgaga tacgtattat     780
ttcgacgcac aaggtcatgt tgtcacggga atccaaacaa ttgcaaacaa ggtttatgat     840
tttgatgagc aaggtcgaat gctgaaaggc attgccacgt cagttgatga caagatgatg     900
tattttgatg atcaaacagg tgttggacaa ccggctgatc atcctgaatt caaccctgaa     960
```

-continued

```
acggaaccgg ttcctgacga caatatcaaa cataatgcag cacatggtac gacaccagca    1020
gattttgatt cgatggctgg ctacctgacg gctgatactt ggtatcgccc aaccgatatt    1080
ttggaaaatg gtgagacgtg gcgcgaatcg caaccaactg aatttcgacc actgttagca    1140
acttggtggc caacaaaaca aactcaggcc gattacgtga actacatgaa tcacgcatta    1200
gatatgtcaa atgcaagtgt gtcagctgcc gattcagaag ccacgctaac tgcggcaacc    1260
gatgctattc aagcggccgt tgagcaccaa attacggtgc gccaatcaac ggcctggtta    1320
cgtgaattaa tggccgcgtt tgttgtgaca cagccacagt ggaataaaac cagtgaagat    1380
gttaatgatg atcatttgca aggtggggcg ctaacatttg agaataacgg cgacacagac    1440
gctaattcgg attatcgcct catgaatcgc acgccaacaa atcagactgg tgaacgcttg    1500
tatcacattg atgactcgct tggcggttac gaattattgc tggcaaatga cgttgacaat    1560
tcaaatccac aagttcaggc agaacaattg aattggttgt actacttgat gcattttggg    1620
gatattacag ctgatgatcc ggatgcaaat tttgatgcca tacggattga tgcggtcgat    1680
aatgtcgatg ctgatttact tcaactagca gctcagtatt ccgtgatgc ctatggcatg    1740 gccacgactg acgcgacatc aaataagcat ctttcaatac ttgaggattg gagccataac    1800
gatccggcgt atatgcaagc acacggcaat gatcaattaa cgatggatga ttatatgcac    1860
acacagttga tttggtcatt aaccaagcca gaggcacaac gtggcaccat ggcacgcttt    1920
atggacttct atctcaccaa ccgtgctaat gatgatacag aaaacacggc gcaacctagt    1980
tactcgtttg tgcgtgccca tgatagcgaa gtgcaaacag tcattgctga aatcgtgacg    2040
aagctacatc cagaagcagg aaacgggtta atgcctacgg aagaacaaat ggcagaagcg    2100
tttaagattt acaatgcgga ccaaaagaag gccgttaaaa cttacacgca ctacaatatg    2160
ccatctgcat acgccatgct gttaacgaac aaggatgtta ttccacgaat ttactatggt    2220
gacttgtaca ctgacgatgg gcaattcatg gcgacaaaat caccctatt tgatgcgatt    2280 tcggctatgt tacaagcgcg cacgaagtat gtagctggtg gacaaacgat ggcggttgac    2340
cagcacgacg tcttgactag cgttcggttt ggtaagggtg ccatgacggc cagtgattta    2400
ggaaatgctg agactcggac tgagggtgtg ggattaatta ttagcaacaa cccaaagttg    2460
caattgggac aacaagataa cgtggtgtta cacatgggac ttgcgcacgc gaatcaagca    2520
ttccgagcag ttgtactaac gaccgcgacc ggattaacca tttataatga cgatgatgct    2580
ccaattcgtt ataccgataa taagggtgat ttaattttca ataaccatga cgtatatggc    2640
gtgttgaatc cacaagtgtc aggcttcttg gcaatgtggg tgccaactgg tgcaccagcg    2700
aaccaggatg cgcgatctac tgcgtcaacc aacagttcaa cggatggatc tgcctaccat    2760
tctaatgcgc ctttagatag tcaagtcatc tttgaatcat tttcgaattt ccaggctatg    2820
ccaacaagcc atgacacgta caccaacgtt gtgttagcca atcatgctga ccagttacac    2880
gattggggaa taacttcggt acagttagcg ccacaatacc ggtcttcaac cgacggaacc    2940
tttttggatg cgattattca aaatggctat gccttcactg accgttatga tttagggttt    3000
ggtacgccaa ctaagtatgg ggatgatacg gatttgcgga acgtcatcaa agcattgcat    3060
gcaaatggca tgcaagtaat ggctgatttt gtgccggatc aattgtatac attaccaggt    3120
aaggaattgg tacaagtcac ccgaacaaac aatatgggtg agccagatac acactctgac    3180
atccaacata ttttatatgt gacgagcact cggggtggcg gtgagtatca gaaacagtac    3240
ggtggtgagt tccttgagcg gttacgtgcg ctctaccctg atttatttac gacacgtcaa    3300
```

```
atttcaaccg gacaaaccat tgatgattca gtaaaaatta agaatggtc agctaagtat      3360 ttgaatggta ccgcaattca aggccgtgga gctggctatg tgctacgtga taatggtaca      3420
aatgcttatt acaaggtgac ggcaaatgac ggtaatgtga acttaccaaa gcaattactc      3480
ggacaaccag tgatgaccgg attctatcac gaggcagatg gttatcattt tgaaacattg      3540
agtggtacgt cggccaaaga tgccttcatt atgggtgacg atgggcgct gtattatttt       3600 gatgatcagg gcgtcatggt aacgggtaag caacgtgtgc accaagacca gtatttcttc      3660
ctaccaaacg gtattgctct gacggatgcg tttgtacaaa gtgcggatgg tcaacgtcag      3720
tactatgata aaacaggtcg cctggtcatt aatcaatatg tgactgacca ccaagcaaat      3780
gcgttccggg ttgatgcaga cggtaacgtt gttcgtaacc aagctttgac tgttgacggc      3840
catgaacaat atttcggcac aaacggtgtc caagcgaaag cagtgctcat tcgaactgac      3900
gataatcagg cacggtacta cgaagccaat agtggtaatc tcgtgaagca acagtttatt      3960
cttgatacag atggacattg gttgtacgcc gatgctgcag gagacttggc acgcggacaa      4020
attacggttg gccaagacac gttgtatttt gatgataata atcatcaggt aaaagatgat      4080
tttgtctatg atactaacgg tgtgcattat tttaatggca acaggcgc tgaaatcaaa        4140 caagattacg cgtttcatga tggcaaatgg tactattttg atgatttggg acgaatggta      4200
accggtttgc agcgtattaa tggtgagtat cgctattttg atgctaatgg tgtgcaacta      4260
aagggtggta ccgtgaccga tccactaacg caccaaacgt acacttttga tgcgcaaact      4320
ggtgttggta cgttggtgac gttttaa                                         4347

<210> SEQ ID NO 4
<211> LENGTH: 1448
<212> TYPE: PRT
<213> ORGANISM: Weissella cibaria

<400> SEQUENCE: 4

Met Tyr Lys Ser Gly Lys Phe Trp Val Ala Ala Gly Ala Leu Phe Val
1               5                   10                  15

Gly Leu Ala Phe Ala Gly Asn Thr Gln Ala Asp Thr Val Leu Pro Ser
            20                  25                  30

Glu Gln Arg Ala Thr Glu Thr Thr Gln Thr Thr Gln Thr Ser Glu Asp
        35                  40                  45

Thr Ser Ala Thr Lys Thr Pro Ala Ser Ala Ser Thr Ser Ser Ser Val
    50                  55                  60

Asn Val Asp Thr Ser Asp Leu Pro Asp Ser Ser Thr Val Val Asp
65                  70                  75                  80

Ser Thr Ser Ala Ser Ala Ser Val Val Ser Asp Ser Val Ala Val Pro
                85                  90                  95

Asp Thr Gly Ser Gln Phe Thr Ser Ser Gly Ser Met Ser Ser Ser
            100                 105                 110

Phe Val Lys Ser Ser Leu Ala Ala Thr Thr Ser Asp Ala Ser Gly Ser
        115                 120                 125

Gln Ser Ala Ala Val Thr Ser Ala Thr Val Ser Ser Val Ala Thr Ser
    130                 135                 140

Ser Ser Ala Ser Ser Val Thr Thr Ala Thr Ser Glu Ser Ala Val Ile
145                 150                 155                 160

Ser Ser Ala Val Ser Asp Gly Tyr His Asp Glu Gly Gly Asp Trp Val
                165                 170                 175

Tyr Tyr Arg Ala Gly Lys Lys Leu Val Gly Arg Gln Thr Ile Asp Thr
            180                 185                 190
```

```
Phe Ala Val Tyr Phe Asp Ala Asp Gly Lys Gln Val Lys Gly Asp Trp
            195                 200                 205
Arg Glu Ser Asp Gly Asn Arg Ala Tyr Tyr Asp Gly Gln Glu Gly Arg
            210                 215                 220
Ala Leu Thr Gln Thr Gln Ala Val Asn Gly Val Ile Tyr Gly Phe Asn
225                 230                 235                 240
Gln Ser Gly Tyr Gln Ile Lys Asn Asp Phe Gly Gln Thr Ala Asn Arg
                245                 250                 255
Asp Thr Tyr Tyr Phe Asp Ala Gln Gly His Val Val Thr Gly Ile Gln
                260                 265                 270
Thr Ile Ala Asn Lys Val Tyr Asp Phe Asp Glu Gln Gly Arg Met Leu
            275                 280                 285
Lys Gly Ile Ala Thr Ser Val Asp Asp Lys Met Met Tyr Phe Asp Asp
            290                 295                 300
Gln Thr Gly Val Gly Gln Pro Ala Asp His Pro Glu Phe Asn Pro Glu
305                 310                 315                 320
Thr Glu Pro Val Pro Asp Asn Ile Lys His Asn Ala Ala His Gly
                325                 330                 335
Thr Thr Pro Ala Asp Phe Asp Ser Met Ala Gly Tyr Leu Thr Ala Asp
            340                 345                 350
Thr Trp Tyr Arg Pro Thr Asp Ile Leu Glu Asn Gly Glu Thr Trp Arg
            355                 360                 365
Glu Ser Gln Pro Thr Glu Phe Arg Pro Leu Leu Ala Thr Trp Trp Pro
            370                 375                 380
Thr Lys Gln Thr Gln Ala Asp Tyr Val Asn Tyr Met Asn His Ala Leu
385                 390                 395                 400
Asp Met Ser Asn Ala Ser Val Ser Ala Ala Asp Ser Glu Ala Thr Leu
                405                 410                 415
Thr Ala Ala Thr Asp Ala Ile Gln Ala Ala Val Glu His Gln Ile Thr
                420                 425                 430
Val Arg Gln Ser Thr Ala Trp Leu Arg Glu Leu Met Ala Ala Phe Val
            435                 440                 445
Val Thr Gln Pro Gln Trp Asn Lys Thr Ser Glu Asp Val Asn Asp Asp
            450                 455                 460
His Leu Gln Gly Gly Ala Leu Thr Phe Glu Asn Asn Gly Asp Thr Asp
465                 470                 475                 480
Ala Asn Ser Asp Tyr Arg Leu Met Asn Arg Thr Pro Thr Asn Gln Thr
                485                 490                 495
Gly Glu Arg Leu Tyr His Ile Asp Asp Ser Leu Gly Gly Tyr Glu Leu
            500                 505                 510
Leu Leu Ala Asn Asp Val Asp Asn Ser Asn Pro Gln Val Gln Ala Glu
            515                 520                 525
Gln Leu Asn Trp Leu Tyr Tyr Leu Met His Phe Gly Asp Ile Thr Ala
            530                 535                 540
Asp Asp Pro Asp Ala Asn Phe Asp Ala Ile Arg Ile Asp Ala Val Asp
545                 550                 555                 560
Asn Val Asp Ala Asp Leu Leu Gln Leu Ala Ala Gln Tyr Phe Arg Asp
                565                 570                 575
Ala Tyr Gly Met Ala Thr Thr Asp Ala Thr Ser Asn Lys His Leu Ser
                580                 585                 590
Ile Leu Glu Asp Trp Ser His Asn Asp Pro Ala Tyr Met Gln Ala His
            595                 600                 605
```

```
Gly Asn Asp Gln Leu Thr Met Asp Asp Tyr Met His Thr Gln Leu Ile
610                 615                 620

Trp Ser Leu Thr Lys Pro Glu Ala Gln Arg Gly Thr Met Ala Arg Phe
625                 630                 635                 640

Met Asp Phe Tyr Leu Thr Asn Arg Ala Asn Asp Thr Glu Asn Thr
                645                 650                 655

Ala Gln Pro Ser Tyr Ser Phe Val Arg Ala His Asp Ser Glu Val Gln
                660                 665                 670

Thr Val Ile Ala Glu Ile Val Thr Lys Leu His Pro Glu Ala Gly Asn
            675                 680                 685

Gly Leu Met Pro Thr Glu Glu Gln Met Ala Glu Ala Phe Lys Ile Tyr
            690                 695                 700

Asn Ala Asp Gln Lys Lys Ala Val Lys Thr Tyr Thr His Tyr Asn Met
705                 710                 715                 720

Pro Ser Ala Tyr Ala Met Leu Leu Thr Asn Lys Asp Val Ile Pro Arg
                725                 730                 735

Ile Tyr Tyr Gly Asp Leu Tyr Thr Asp Asp Gly Gln Phe Met Ala Thr
            740                 745                 750

Lys Ser Pro Tyr Phe Asp Ala Ile Ser Ala Met Leu Gln Ala Arg Thr
            755                 760                 765

Lys Tyr Val Ala Gly Gln Thr Met Ala Val Asp Gln His Asp Val
770                 775                 780

Leu Thr Ser Val Arg Phe Gly Lys Gly Ala Met Thr Ala Ser Asp Leu
785                 790                 795                 800

Gly Asn Ala Glu Thr Arg Thr Glu Gly Val Gly Leu Ile Ile Ser Asn
                805                 810                 815

Asn Pro Lys Leu Gln Leu Gly Gln Gln Asp Asn Val Val Leu His Met
                820                 825                 830

Gly Leu Ala His Ala Asn Gln Ala Phe Arg Ala Val Val Leu Thr Thr
            835                 840                 845

Ala Thr Gly Leu Thr Ile Tyr Asn Asp Asp Ala Pro Ile Arg Tyr
            850                 855                 860

Thr Asp Asn Lys Gly Asp Leu Ile Phe Asn Asn His Asp Val Tyr Gly
865                 870                 875                 880

Val Leu Asn Pro Gln Val Ser Gly Phe Leu Ala Met Trp Val Pro Thr
                885                 890                 895

Gly Ala Pro Ala Asn Gln Asp Ala Arg Ser Thr Ala Ser Thr Asn Ser
                900                 905                 910

Ser Thr Asp Gly Ser Ala Tyr His Ser Asn Ala Ala Leu Asp Ser Gln
            915                 920                 925

Val Ile Phe Glu Ser Phe Ser Asn Phe Gln Ala Met Pro Thr Ser His
            930                 935                 940

Asp Thr Tyr Thr Asn Val Val Leu Ala Asn His Ala Asp Gln Leu His
945                 950                 955                 960

Asp Trp Gly Ile Thr Ser Val Gln Leu Ala Pro Gln Tyr Arg Ser Ser
                965                 970                 975

Thr Asp Gly Thr Phe Leu Asp Ala Ile Ile Gln Asn Gly Tyr Ala Phe
            980                 985                 990

Thr Asp Arg Tyr Asp Leu Gly Phe Gly Thr Pro Thr Lys Tyr Gly Asp
            995                 1000                1005

Asp Thr Asp Leu Arg Asn Val Ile Lys Ala Leu His Ala Asn Gly
            1010                1015                1020

Met Gln Val Met Ala Asp Phe Val Pro Asp Gln Leu Tyr Thr Leu
```

-continued

|  | 1025 |  |  | 1030 |  |  | 1035 |  |  |  |
| --- | --- | --- | --- | --- | --- | --- | --- | --- | --- | --- |

Pro Gly Lys Glu Leu Val Gln Val Thr Arg Thr Asn Asn Met Gly
                1040                1045                1050

Glu Pro Asp Thr His Ser Asp Ile Gln His Ile Leu Tyr Val Thr
                1055                1060                1065

Ser Thr Arg Gly Gly Gly Glu Tyr Gln Lys Gln Tyr Gly Gly Glu
                1070                1075                1080

Phe Leu Glu Arg Leu Arg Ala Leu Tyr Pro Asp Leu Phe Thr Thr
                1085                1090                1095

Arg Gln Ile Ser Thr Gly Gln Thr Ile Asp Asp Ser Val Lys Ile
                1100                1105                1110

Lys Glu Trp Ser Ala Lys Tyr Leu Asn Gly Thr Ala Ile Gln Gly
                1115                1120                1125

Arg Gly Ala Gly Tyr Val Leu Arg Asp Asn Gly Thr Asn Ala Tyr
                1130                1135                1140

Tyr Lys Val Thr Ala Asn Asp Gly Asn Val Asn Leu Pro Lys Gln
                1145                1150                1155

Leu Leu Gly Gln Pro Val Met Thr Gly Phe Tyr His Glu Ala Asp
                1160                1165                1170

Gly Tyr His Phe Glu Thr Leu Ser Gly Thr Ser Ala Lys Asp Ala
                1175                1180                1185

Phe Ile Met Gly Asp Gly Ala Leu Tyr Tyr Phe Asp Asp Gln
                1190                1195                1200

Gly Val Met Val Thr Gly Lys Gln Arg Val His Gln Asp Gln Tyr
                1205                1210                1215

Phe Phe Leu Pro Asn Gly Ile Ala Leu Thr Asp Ala Phe Val Gln
                1220                1225                1230

Ser Ala Asp Gly Gln Arg Gln Tyr Tyr Asp Lys Thr Gly Arg Leu
                1235                1240                1245

Val Ile Asn Gln Tyr Val Thr Asp His Gln Ala Asn Ala Phe Arg
                1250                1255                1260

Val Asp Ala Asp Gly Asn Val Arg Asn Gln Ala Leu Thr Val
                1265                1270                1275

Asp Gly His Glu Gln Tyr Phe Gly Thr Asn Gly Val Gln Ala Lys
                1280                1285                1290

Ala Val Leu Ile Arg Thr Asp Asp Asn Gln Ala Arg Tyr Tyr Glu
                1295                1300                1305

Ala Asn Ser Gly Asn Leu Val Lys Gln Gln Phe Ile Leu Asp Thr
                1310                1315                1320

Asp Gly His Trp Leu Tyr Ala Asp Ala Ala Gly Asp Leu Ala Arg
                1325                1330                1335

Gly Gln Ile Thr Val Gly Gln Asp Thr Leu Tyr Phe Asp Asp Asn
                1340                1345                1350

Asn His Gln Val Lys Asp Asp Phe Val Tyr Asp Thr Asn Gly Val
                1355                1360                1365

His Tyr Phe Asn Gly Thr Thr Gly Ala Glu Ile Lys Gln Asp Tyr
                1370                1375                1380

Ala Phe His Asp Gly Lys Trp Tyr Tyr Phe Asp Asp Leu Gly Arg
                1385                1390                1395

Met Val Thr Gly Leu Gln Arg Ile Asn Gly Glu Tyr Arg Tyr Phe
                1400                1405                1410

Asp Ala Asn Gly Val Gln Leu Lys Gly Gly Thr Val Thr Asp Pro
                1415                1420                1425

-continued

```
Leu Thr His Gln Thr Tyr Thr Phe Asp Ala Gln Thr Gly Val Gly
    1430                1435                1440

Thr Leu Val Thr Phe
    1445

<210> SEQ ID NO 5
<211> LENGTH: 1422
<212> TYPE: PRT
<213> ORGANISM: Weissella cibaria
<220> FEATURE:
<221> NAME/KEY: MISC_FEATURE
<222> LOCATION: (1)..(1422)
<223> OTHER INFORMATION: mature 2919 gtf

<400> SEQUENCE: 5

Asp Thr Val Leu Pro Ser Glu Gln Arg Ala Thr Glu Thr Thr Gln Thr
1               5                   10                  15

Thr Gln Thr Ser Glu Asp Thr Ser Ala Thr Lys Thr Pro Ala Ser Ala
            20                  25                  30

Ser Thr Ser Ser Ser Val Asn Val Asp Thr Ser Asp Leu Pro Asp Ser
        35                  40                  45

Ser Ser Thr Val Val Asp Ser Thr Ser Ala Ser Ala Ser Val Val Ser
    50                  55                  60

Asp Ser Val Ala Val Pro Asp Thr Gly Ser Gln Phe Thr Ser Ser Ser
65                  70                  75                  80

Gly Ser Met Ser Ser Ser Phe Val Lys Ser Ser Leu Ala Ala Thr Thr
                85                  90                  95

Ser Asp Ala Ser Gly Ser Gln Ser Ala Ala Val Thr Ser Ala Thr Val
            100                 105                 110

Ser Ser Val Ala Thr Ser Ser Ser Ala Ser Ser Val Thr Thr Ala Thr
        115                 120                 125

Ser Glu Ser Ala Val Ile Ser Ser Ala Val Ser Asp Gly Tyr His Asp
    130                 135                 140

Glu Gly Gly Asp Trp Val Tyr Tyr Arg Ala Gly Lys Lys Leu Val Gly
145                 150                 155                 160

Arg Gln Thr Ile Asp Thr Phe Ala Val Tyr Phe Asp Ala Asp Gly Lys
                165                 170                 175

Gln Val Lys Gly Asp Trp Arg Glu Ser Asp Gly Asn Arg Ala Tyr Tyr
            180                 185                 190

Asp Gly Gln Glu Gly Arg Ala Leu Thr Gln Thr Gln Ala Val Asn Gly
        195                 200                 205

Val Ile Tyr Gly Phe Asn Gln Ser Gly Tyr Gln Ile Lys Asn Asp Phe
    210                 215                 220

Gly Gln Thr Ala Asn Arg Asp Thr Tyr Tyr Phe Asp Ala Gln Gly His
225                 230                 235                 240

Val Val Thr Gly Ile Gln Thr Ile Ala Asn Lys Val Tyr Asp Phe Asp
                245                 250                 255

Glu Gln Gly Arg Met Leu Lys Gly Ile Ala Thr Ser Val Asp Asp Lys
            260                 265                 270

Met Met Tyr Phe Asp Asp Gln Thr Gly Val Gly Gln Pro Ala Asp His
        275                 280                 285

Pro Glu Phe Asn Pro Glu Thr Glu Pro Val Pro Asp Asp Asn Ile Lys
    290                 295                 300

His Asn Ala Ala His Gly Thr Thr Pro Ala Asp Phe Asp Ser Met Ala
305                 310                 315                 320
```

-continued

```
Gly Tyr Leu Thr Ala Asp Thr Trp Tyr Arg Pro Thr Asp Ile Leu Glu
                325                 330                 335

Asn Gly Glu Thr Trp Arg Glu Ser Gln Pro Thr Glu Phe Arg Pro Leu
            340                 345                 350

Leu Ala Thr Trp Trp Pro Thr Lys Gln Thr Gln Ala Asp Tyr Val Asn
        355                 360                 365

Tyr Met Asn His Ala Leu Asp Met Ser Asn Ala Ser Val Ser Ala Ala
    370                 375                 380

Asp Ser Glu Ala Thr Leu Thr Ala Ala Thr Asp Ala Ile Gln Ala Ala
385                 390                 395                 400

Val Glu His Gln Ile Thr Val Arg Gln Ser Thr Ala Trp Leu Arg Glu
                405                 410                 415

Leu Met Ala Ala Phe Val Val Thr Gln Pro Gln Trp Asn Lys Thr Ser
            420                 425                 430

Glu Asp Val Asn Asp Asp His Leu Gln Gly Gly Ala Leu Thr Phe Glu
        435                 440                 445

Asn Asn Gly Asp Thr Asp Ala Asn Ser Asp Tyr Arg Leu Met Asn Arg
    450                 455                 460

Thr Pro Thr Asn Gln Thr Gly Glu Arg Leu Tyr His Ile Asp Asp Ser
465                 470                 475                 480

Leu Gly Gly Tyr Glu Leu Leu Leu Ala Asn Asp Val Asp Asn Ser Asn
                485                 490                 495

Pro Gln Val Gln Ala Glu Gln Leu Asn Trp Leu Tyr Tyr Leu Met His
            500                 505                 510

Phe Gly Asp Ile Thr Ala Asp Asp Pro Asp Ala Asn Phe Asp Ala Ile
        515                 520                 525

Arg Ile Asp Ala Val Asp Asn Val Asp Ala Asp Leu Leu Gln Leu Ala
    530                 535                 540

Ala Gln Tyr Phe Arg Asp Ala Tyr Gly Met Ala Thr Thr Asp Ala Thr
545                 550                 555                 560

Ser Asn Lys His Leu Ser Ile Leu Glu Asp Trp Ser His Asn Asp Pro
                565                 570                 575

Ala Tyr Met Gln Ala His Gly Asn Asp Gln Leu Thr Met Asp Asp Tyr
            580                 585                 590

Met His Thr Gln Leu Ile Trp Ser Leu Thr Lys Pro Glu Ala Gln Arg
        595                 600                 605

Gly Thr Met Ala Arg Phe Met Asp Phe Tyr Leu Thr Asn Arg Ala Asn
    610                 615                 620

Asp Asp Thr Glu Asn Thr Ala Gln Pro Ser Tyr Ser Phe Val Arg Ala
625                 630                 635                 640

His Asp Ser Glu Val Gln Thr Val Ile Ala Glu Ile Val Thr Lys Leu
                645                 650                 655

His Pro Glu Ala Gly Asn Gly Leu Met Pro Thr Glu Glu Gln Met Ala
            660                 665                 670

Glu Ala Phe Lys Ile Tyr Asn Ala Asp Gln Lys Ala Val Lys Thr
        675                 680                 685

Tyr Thr His Tyr Asn Met Pro Ser Ala Tyr Ala Met Leu Leu Thr Asn
    690                 695                 700

Lys Asp Val Ile Pro Arg Ile Tyr Tyr Gly Asp Leu Tyr Thr Asp Asp
705                 710                 715                 720

Gly Gln Phe Met Ala Thr Lys Ser Pro Tyr Phe Asp Ala Ile Ser Ala
                725                 730                 735

Met Leu Gln Ala Arg Thr Lys Tyr Val Ala Gly Gly Gln Thr Met Ala
```

-continued

```
            740                 745                 750
Val Asp Gln His Asp Val Leu Thr Ser Val Arg Phe Gly Lys Gly Ala
            755                 760                 765
Met Thr Ala Ser Asp Leu Gly Asn Ala Glu Thr Arg Thr Glu Gly Val
            770                 775                 780
Gly Leu Ile Ile Ser Asn Asn Pro Lys Leu Gln Leu Gly Gln Gln Asp
785                 790                 795                 800
Asn Val Val Leu His Met Gly Leu Ala His Ala Asn Gln Ala Phe Arg
                805                 810                 815
Ala Val Val Leu Thr Thr Ala Thr Gly Leu Thr Ile Tyr Asn Asp Asp
                820                 825                 830
Asp Ala Pro Ile Arg Tyr Thr Asp Asn Lys Gly Asp Leu Ile Phe Asn
            835                 840                 845
Asn His Asp Val Tyr Gly Val Leu Asn Pro Gln Val Ser Gly Phe Leu
            850                 855                 860
Ala Met Trp Val Pro Thr Gly Ala Pro Ala Asn Gln Asp Ala Arg Ser
865                 870                 875                 880
Thr Ala Ser Thr Asn Ser Ser Thr Asp Gly Ser Ala Tyr His Ser Asn
                885                 890                 895
Ala Ala Leu Asp Ser Gln Val Ile Phe Glu Ser Phe Ser Asn Phe Gln
                900                 905                 910
Ala Met Pro Thr Ser His Asp Thr Tyr Thr Asn Val Val Leu Ala Asn
            915                 920                 925
His Ala Asp Gln Leu His Asp Trp Gly Ile Thr Ser Val Gln Leu Ala
            930                 935                 940
Pro Gln Tyr Arg Ser Ser Thr Asp Gly Thr Phe Leu Asp Ala Ile Ile
945                 950                 955                 960
Gln Asn Gly Tyr Ala Phe Thr Asp Arg Tyr Asp Leu Gly Phe Gly Thr
                965                 970                 975
Pro Thr Lys Tyr Gly Asp Asp Thr Asp Leu Arg Asn Val Ile Lys Ala
                980                 985                 990
Leu His Ala Asn Gly Met Gln Val Met Ala Asp Phe Val Pro Asp Gln
            995                1000                1005
Leu Tyr Thr Leu Pro Gly Lys Glu Leu Val Gln Val Thr Arg Thr
            1010                1015                1020
Asn Asn Met Gly Glu Pro Asp Thr His Ser Asp Ile Gln His Ile
            1025                1030                1035
Leu Tyr Val Thr Ser Thr Arg Gly Gly Gly Glu Tyr Gln Lys Gln
            1040                1045                1050
Tyr Gly Gly Glu Phe Leu Glu Arg Leu Arg Ala Leu Tyr Pro Asp
            1055                1060                1065
Leu Phe Thr Thr Arg Gln Ile Ser Thr Gly Gln Thr Ile Asp Asp
            1070                1075                1080
Ser Val Lys Ile Lys Glu Trp Ser Ala Lys Tyr Leu Asn Gly Thr
            1085                1090                1095
Ala Ile Gln Gly Arg Gly Ala Gly Tyr Val Leu Arg Asp Asn Gly
            1100                1105                1110
Thr Asn Ala Tyr Tyr Lys Val Thr Ala Asn Asp Gly Asn Val Asn
            1115                1120                1125
Leu Pro Lys Gln Leu Leu Gly Gln Pro Val Met Thr Gly Phe Tyr
            1130                1135                1140
His Glu Ala Asp Gly Tyr His Phe Glu Thr Leu Ser Gly Thr Ser
            1145                1150                1155
```

| Ala | Lys | Asp | Ala | Phe | Ile | Met | Gly | Asp | Asp | Gly | Ala | Leu | Tyr | Tyr |
|  | 1160 |  |  |  | 1165 |  |  |  | 1170 |  |  |  |  |  |

| Phe | Asp | Asp | Gln | Gly | Val | Met | Val | Thr | Gly | Lys | Gln | Arg | Val | His |
| 1175 |  |  |  |  | 1180 |  |  |  |  | 1185 |  |  |  |  |

| Gln | Asp | Gln | Tyr | Phe | Phe | Leu | Pro | Asn | Gly | Ile | Ala | Leu | Thr | Asp |
| 1190 |  |  |  |  | 1195 |  |  |  |  | 1200 |  |  |  |  |

| Ala | Phe | Val | Gln | Ser | Ala | Asp | Gly | Gln | Arg | Gln | Tyr | Tyr | Asp | Lys |
| 1205 |  |  |  |  | 1210 |  |  |  |  | 1215 |  |  |  |  |

| Thr | Gly | Arg | Leu | Val | Ile | Asn | Gln | Tyr | Val | Thr | Asp | His | Gln | Ala |
| 1220 |  |  |  |  | 1225 |  |  |  |  | 1230 |  |  |  |  |

| Asn | Ala | Phe | Arg | Val | Asp | Ala | Asp | Gly | Asn | Val | Val | Arg | Asn | Gln |
| 1235 |  |  |  |  | 1240 |  |  |  |  | 1245 |  |  |  |  |

| Ala | Leu | Thr | Val | Asp | Gly | His | Glu | Gln | Tyr | Phe | Gly | Thr | Asn | Gly |
| 1250 |  |  |  |  | 1255 |  |  |  |  | 1260 |  |  |  |  |

| Val | Gln | Ala | Lys | Ala | Val | Leu | Ile | Arg | Thr | Asp | Asp | Asn | Gln | Ala |
| 1265 |  |  |  |  | 1270 |  |  |  |  | 1275 |  |  |  |  |

| Arg | Tyr | Tyr | Glu | Ala | Asn | Ser | Gly | Asn | Leu | Val | Lys | Gln | Gln | Phe |
| 1280 |  |  |  |  | 1285 |  |  |  |  | 1290 |  |  |  |  |

| Ile | Leu | Asp | Thr | Asp | Gly | His | Trp | Leu | Tyr | Ala | Asp | Ala | Ala | Gly |
| 1295 |  |  |  |  | 1300 |  |  |  |  | 1305 |  |  |  |  |

| Asp | Leu | Ala | Arg | Gly | Gln | Ile | Thr | Val | Gly | Gln | Asp | Thr | Leu | Tyr |
| 1310 |  |  |  |  | 1315 |  |  |  |  | 1320 |  |  |  |  |

| Phe | Asp | Asp | Asn | Asn | His | Gln | Val | Lys | Asp | Asp | Phe | Val | Tyr | Asp |
| 1325 |  |  |  |  | 1330 |  |  |  |  | 1335 |  |  |  |  |

| Thr | Asn | Gly | Val | His | Tyr | Phe | Asn | Gly | Thr | Thr | Gly | Ala | Glu | Ile |
| 1340 |  |  |  |  | 1345 |  |  |  |  | 1350 |  |  |  |  |

| Lys | Gln | Asp | Tyr | Ala | Phe | His | Asp | Gly | Lys | Trp | Tyr | Tyr | Phe | Asp |
| 1355 |  |  |  |  | 1360 |  |  |  |  | 1365 |  |  |  |  |

| Asp | Leu | Gly | Arg | Met | Val | Thr | Gly | Leu | Gln | Arg | Ile | Asn | Gly | Glu |
| 1370 |  |  |  |  | 1375 |  |  |  |  | 1380 |  |  |  |  |

| Tyr | Arg | Tyr | Phe | Asp | Ala | Asn | Gly | Val | Gln | Leu | Lys | Gly | Gly | Thr |
| 1385 |  |  |  |  | 1390 |  |  |  |  | 1395 |  |  |  |  |

| Val | Thr | Asp | Pro | Leu | Thr | His | Gln | Thr | Tyr | Thr | Phe | Asp | Ala | Gln |
| 1400 |  |  |  |  | 1405 |  |  |  |  | 1410 |  |  |  |  |

| Thr | Gly | Val | Gly | Thr | Leu | Val | Thr | Phe |
| 1415 |  |  |  |  | 1420 |  |  |  |

<210> SEQ ID NO 6
<211> LENGTH: 4269
<212> TYPE: DNA
<213> ORGANISM: Artificial sequence
<220> FEATURE:
<223> OTHER INFORMATION: 2919 gtf with heterologous signal sequence

<400> SEQUENCE: 6

```
gacacagtcc ttccgtcaga acaaagagcc acggagacga cacagacaac acaaacaagc      60
gaagacacaa gcgccacaaa gacgcctgct agcgcttcaa cgagcagctc agtgaacgtg     120
gacacatcag atcttccgga cagctcaagc acggtggtgg attcaacgtc agcctcagca     180
agcgtcgtgt cagactcagt cgctgtccct gatacgggat cacagttcac atcatcaagc     240
ggcagcatgt caagcagctt tgttaaaagc tcactggcag ctacgacgtc agatgcttca     300
ggctcacaaa gcgccgctgt gacatcagca acagtttcaa gcgtggcgac gagctcatca     360
gcgtcatcag ttacaacagc cacgagcgaa tcagcggtta ttagctcagc agttagcgat     420
```

```
ggctatcacg atgaaggagg cgattgggtt tactacagag ctggcaaaaa actggttggc    480
agacaaacga ttgatacatt tgccgtttac ttcgatgcag atggaaaaca ggttaaagga    540
gactggagag agtcagacgg aaacagagcg tactatgatg gccaagaagg cagagccctt    600
acgcaaacac aggcagttaa cggagtcatc tatggattta atcaatcagg atatcagatt    660
aagaacgatt tcggccagac ggctaacaga gacacgtatt actttgatgc tcaaggacat    720
gtggttacgg gcatccagac aattgcaaat aaagtttatg atttcgatga acaaggaaga    780
atgctgaaag gaattgccac gtcagtcgac gataaaatga tgtatttcga cgaccaaacg    840
ggcgtgggcc aacctgccga ccaccctgag tttaatccgg aaacggagcc ggtcccggat    900
gacaacatta acataacgc tgcgcacgga acgacacctg ctgattttga tagcatggcc     960
ggatacctta cggcggatac atggtataga cctacagaca ttctggagaa tggcgaaaca    1020
tggagagaaa gccagcctac ggagttcaga ccgcttcttg ccacatggtg gcctacgaaa    1080
caaacgcaag cagattatgt taattacatg aaccatgctc tggatatgtc aaatgcgagc    1140
gtgagcgctg ccgatagcga ggcaacactt acagccgcga cggatgccat ccaagctgca    1200
gtcgaacatc aaattacagt gagacagtca acggcatggc ttagagaact tatgcgggca    1260
tttgtcgtga cgcaaccgca gtggaataaa acatcagagg atgtcaacga cgatcacctg    1320
caaggaggag cgcttacatt cgaaaataac ggcgatacgg acgcaaatag cgattacaga    1380
cttatgaata gaacgcctac aaaccaaaca ggagaaagac tttaccacat tgacgactca    1440
cttggaggat acgaactgct tctggccaac gatgttgata acagcaatcc tcaagtgcag    1500
gctgagcaac ttaattggct ttattacctg atgcattttg gcgatattac agctgacgac    1560
cctgacgcca acttcgacgc gattagaatc gatgcggtcg ataatgtcga cgcagacctt    1620
cttcaactgg ctgctcaata tttcagagac gcatacggaa tggcaacaac agacgctaca    1680
agcaataaac atctgtcaat tcttgaagac tggtcacata atgatccggc gtacatgcaa    1740
gctcatggaa acgatcaact tacgatggat gactatatgc acacacaact tatttggtca    1800
ctgacaaaac cggaggctca aagaggaaca atggctagat ttatggactt ttatcttaca    1860
aatagagcga acgatgatac agaaaatacg gctcaacctt catattcatt cgttagagca    1920
catgattcag aagttcaaac agtgattgca gaaattgtta caaaactgca tcctgaggcg    1980
ggcaatggac tgatgccgac agaagagcaa atggcagaag cctttaagat ctataatgcc    2040
gatcagaaaa aagcagtgaa acatatatca cactacaata tgccttcagc ttatgcaatg    2100
ctgcttacga ataaagacgt cattcctaga atttactatg gagatcttta tacagatgat    2160
ggacaattca tggctacaaa gtcaccttat tttgacgcta tcagcgcgat gctgcaagcg    2220
agaacgaagt atgtcgcagg cggccagacg atggcagtgg atcagcacga cgtgcttaca    2280
agcgtgagat ttggcaaagg cgcaatgaca gcatcagacc tgggcaatgc agagacaaga    2340
acggagggag ttggccttat catttcaaat aatccgaaac tgcaactggg ccagcaggat    2400
aacgtcgttc ttcatatggg cctggcgcac gcaaaccagg cctttagagc agttgttctt    2460
acaacagcga cgggcctgac aatctacaat gacgatgatg caccgattag atatacagac    2520
aataaaggcg acctgatttt caacaaccat gatgtctacg cgtcctgaa  cccgcaggtt    2580
tcaggcttcc tggccatgtg ggttcctaca ggcgcacctg ctaaccaaga tgctagatca    2640
acagcaagca caaactcatc aacggatggc tcagcatatc attcaaatgc tgcgctggat    2700
tcacaagtta ttttcgaatc attctcaaat ttccaagcaa tgccgacgtc acatgacaca    2760
tacacgaatg tggttctggc caaccacgcc gaccagcttc acgattgggg cattacatca    2820
```

```
gtgcagctgg caccgcagta tagaagctca acagacggca cgttcctgga tgcaattatc    2880
cagaatggct atgccttcac agatagatac gatcttggct ttggcacacc tacaaaatac    2940
ggcgacgaca cggatctgag aaatgtgatt aaggcgcttc atgccaacgg catgcaggtt    3000
atggccgact tcgtcccgga ccaactttat acacttccgg gaaagagct ggtgcaagtc     3060 acgagaacga ataacatggg cgaacctgat acacactcag acattcaaca tattctgtac    3120
gttacgtcaa cgagaggcgg aggagaatat caaaaacagt atggcggcga gtttcttgaa    3180
agactgagag cactgtaccc tgaccttttt acgacaagac aaattagcac aggccaaaca    3240
attgacgatt cagtgaagat caaagagtgg tcagctaagt acctgaacgg cacagctatc    3300
caaggaagag gcgcaggcta tgttctgaga gataatggca caaatgccta ctacaaagtt    3360
acagcgaatg atggaaatgt caatcttcct aaacaacttc ttggacagcc ggttatgacg    3420
ggcttctacc acgaggccga tggatatcac ttcgagacac tgtcaggaac atcagccaag    3480
gatgcgttta tcatgggaga tgacggagcg ctttattact ttgatgacca aggcgttatg    3540
gtgacaggaa aacagagagt tcatcaagac cagtacttct ttctgcctaa cggaattgct    3600
ctgacagacg cgttcgttca atcagcagac ggacaaagac agtattatga caaaacggga    3660
agacttgtta tcaaccagta tgtgacagat caccaagcta atgcttttag agtcgatgct    3720
gatggcaacg tggttagaaa ccaagcactt acagttgatg gacacgaaca atatttcgga    3780
acaaatggag tccaggctaa agcggttctg attagaacag atgataatca agcgagatat    3840
tacgaagcta actcaggcaa tctggttaag caacaattca ttcttgacac agatggccac    3900
tggctgtacg ccgatgcagc cggagatctt gctagaggac agattacagt gggacaggat    3960
acactgtatt tcgacgataa taaccaccaa gttaaggatg attttgtcta tgatacaaac    4020
ggcgttcatt atttcaatgg aacgacagga gctgagatta acaagatta cgcatttcac     4080 gacggcaaat ggtactactt cgatgatctg ggaagaatgg ttacaggact gcaaagaatt    4140
aacggcgaat atagatattt tgacgctaat ggcgtccaac ttaagggagg aacagtcacg    4200
gaccctctta cacatcaaac atatacattt gatgctcaaa caggcgttgg aacgctggtc    4260
acgttttga                                                            4269
```

<210> SEQ ID NO 7
<211> LENGTH: 4392
<212> TYPE: DNA
<213> ORGANISM: Lactobacillus fermentum

<400> SEQUENCE: 7

```
ttgcaagacg agtcacagaa gtttagaaaa aagatgtata agtccggaaa gttttgggta      60
gctgccggtg cttttgtttgt tgggctggca ttcgctggta acgcgcaggc agatactgta    120
ttaccaagtg aacaacgtgc aacacagacg acacagacga cacagaccag tgaagacacg    180
tccgccacta agacgccggc atcggcgtcg acttcaagct cagacaatgt tgacacgagt    240
gacctgcctg acagtgcaag tgcggtggtt gatagtgcag ttacaagtac aagtacaagt    300
gcaagtgtag tgagtgatag cgtcgccgtg ccagatactg gatcacaatt tatgagttcg    360
tcagcgccac cgtcatcagc gtttgttaaa ccgtcactaa cgtcaacaac tagtggtgct    420
tccggcagtc agtcatcagc ggtgactagc gcaaacgata gttcggtggc aactagtagt    480
tcagcatctt cagtgacaac agccacaagt gaatcggctg tggtaagcag cgccgtgtca    540
gatggttacc atgatgaagg tggtgattgg gtctattatc gagctgggaa aaagttactc    600
```

```
ggtcgacaaa cgattgatac gtttgcggtt tactttgacg ccgatggcaa acaagtcaag      660
ggtgattggc gtgaaagtga tggtaaacgt gcgtattatg atgggcaaga aggacgagca      720
ttaacgcaaa cgcaagcagt caatggcgtt atctacggtt ttaatcaaag cggctatcaa      780
atcaagaatg atttcggcca aacagcgaat cgagatacgt attatttcga cgcacaaggt      840
catgttgtca cgggaatcca aacaattgca aacaaggttt atgattttga tgagcaaggt      900
cgaatgctga aaggcattgc cacgtcagtt gatgacaaga tgatgtattt tgatgatcaa      960
acaggtgttg acaaccggc tgatcatcct gaattcaacc ctgaaacgga accggttcct     1020
gacgacaata tcaaacataa tgcagcacat ggtacgacac cagaagattt tgattcgatg     1080
gctgactacc tgacggctga tacttggtat cgcccaaccg atattttgga aaatggtgag     1140
acgtggcgcg aatcgcaacc aactgaattt cgaccactgt tagcaacttg gtggccaaca     1200
aaacaaaccc aggccgatta cgtgaactac atgaatcacg cattagatat ggcaaatgca     1260
ggtgtgtcag ctgctgattc agaagccacg ttaactgcgg caaccgatgc tattcaagcg     1320
gttgttgagc accaaatcac ggtgcgtcaa tcaacggctt ggttacgtga attaatggcc     1380
gcatttgttg tgacacagcc acagtggaat aaaacaagtg aagatgtgaa tgatgatcat     1440
ttgcaaggtg gggcattaac atttgaaaat aacggcgaca cagacgctaa ttcggattat     1500
cgcctcatga accgcacgcc aacaaatcag actggcgaac gcttgtacca cattgatgac     1560
tcacttggtg gttacgaatt attgctggca atgacgttg acaattcaaa tccacaagtt     1620
caggcagaac aattgaattg gttgtactac ttaatgcatt ttgggatat tacagctgat     1680 gatccggacg caaattttga tgccatacgg attgatgcgg tcgataatgt cgatgctgat     1740
ttacttcaac tagcagccca gtatttccgg gatgcctatg catggctac aactgacgca     1800 acatcaaata gcatctttc aattcttgag gattggagcc ataacgatcc ggcgtatatg     1860
caagcacacg gcaatgatca attaacgatg gatgattata tgcacacaca gttgatttgg     1920
tcattaacca agcccgaggc acaacgcggg accatggcac gctttatgga cttctatctc     1980
accaaccgtg ctaatgatga tacagaaaac acggcgcaac ctagttactc gtttgtgcgt     2040
gcccatgata gcgaagtaca aacagtcatt gctgagatcg tgacgaagct gcatccagaa     2100
gcaggaaatg ggttaatgcc tacggaagaa caaatggcag aagcgtttaa gatttacaat     2160
gcggaccaaa agaaggccgt taagacttac acacattaca atatgccatc tgcatacgcc     2220
atgctgttaa cgaacaagga tgttattcca cgaatttact atggtgactt gtacactgat     2280
gatgggcaat tcatggcgac aaaatcacct tattttgatg cgatttcgac catgttacaa     2340
gcacgcacga agtatgtagc tggtggacag acgatggcgg ttgaccagca cgacgtcttg     2400
actagcgttc ggtttggtaa gggggccatg acggccaatg attaggggga tgctgagacc     2460
cggactgagg gtgtgggatt aattattagc aacaacccaa agttgcaatt gggacaacaa     2520
gacaacgtgg tgttacacat gggacttgcg cacgcgaatc aggcattccg cgcagtcgta     2580
ctaacgaccg cgaccggatt aaccatttat aatgacgatg atgctccgat tcgttatacc     2640
gataataagg gtgatttaat tttcactaac catgacgtat atggcgtgtt gaatccacaa     2700
gtgtcaggct tcttggcaat gtgggtgcca actggtgcac cagcgaacca ggatgcgcga     2760
tctactgcgt caaccaacat gtcaacggat ggatctgcct accattctaa tgcggctttg     2820
gatagtcaag taatctttga atcattttcg aatttccagg ctatgccaac aagtcatgac     2880
acatacacca cgttgtgtt agccaatcat gctgaccagt tgcacgattg gggaataact     2940
tcggtacagt tagcaccaca ataccggtct tcaaccgacg gtacctttt agacgcgatt     3000
```

-continued

```
attcaaaatg gctatgcctt cactgaccgt tatgatttag ggtttggtac gccaactaaa    3060
tacggggatg atacggattt gcggaacgtc atcaaagcat tgcatgcaaa tggcatgcaa    3120
gtaatggctg attttgtgcc ggatcaattg tatacattac caggtaagga attggtacaa    3180
gtcacccgaa caaacaatat gggtgagcca gatacgcatt ctgacatcca acatatttta    3240
tatgtgacga gcactcgtgg tggtggtgac tatcagaaac agtacggtgg tgagttcctt    3300
gcacgattgc gtgaacgata cccagattta tttacgcacg tcaaatttc gaccggacaa     3360
acaattgatg attcagtaaa aattaaagaa tggtcagcta agtatttgaa tggtaccgca    3420
attcaaggac gtggagctgg ctatgtgctg cgtgataatg gtacaaatgc ttattacaag    3480
gtgacagcaa atgacggtaa tgtgaactta ccaaagcaat tactcggcca accggtgatg    3540
accggattct atcacgaggc agatggttat cattttgaaa cattgagtgg tacgtcggcc    3600
aaagatgcct ttattatggg cgacgatggg gcactgtatt attttgatga tcagggtgtt    3660
atggtaacgg gtaagcaacg tgtgcaccaa gatcagtatt tcttcctgcc aaatggtatt    3720
gctttgacag atgctttcgt acaaactgct gatggtcaac gtcagtacta tgataaaaca    3780
ggtcgtctgg tcattaatca atatgtgact gaccaccaag cgaatgcgtt ccgggttgat    3840
gcagacggta acgttgtccg caatcaagct ttgactgttg acggccatga acaatatttc    3900
ggcacaaacg tgtccaagc gaaagcagtg ctcattcgaa ctgacgataa tcaggcgcgc    3960
tactacgaag ccaatagtgg taatctcgtg aagcaacagt ttattcttga tacagatgga    4020
cattggttgt acgcggatgc tgcaggtgac ttggcacgcg gacaaattac aattggccaa    4080
gacacgttgt attttgatga taataatcac caggtaaaag atgatttcgt ctatgatact    4140
aacggtgtgc attatttaa tggcacaaca ggcgctgaaa tcaaacaaga ttacgcgttt    4200
catgatggca aatggtacta ttttgatgat ttgggacgaa tggtaaccgg cttgcagcgt    4260
attaatggtg agtatcgcta ttttgatgct aatggtgtgc aactaaaggg cggtaccgtg    4320
accgatccac taacgcacca aacgtacact tttgatgcga aaactggtgc tggtacgttg    4380
gtgacgattt aa                                                        4392
```

<210> SEQ ID NO 8
<211> LENGTH: 1463
<212> TYPE: PRT
<213> ORGANISM: Lactobacillus fermentum

<400> SEQUENCE: 8

```
Met Gln Asp Glu Ser Gln Lys Phe Arg Lys Lys Met Tyr Lys Ser Gly
1               5                   10                  15

Lys Phe Trp Val Ala Ala Gly Ala Leu Phe Val Gly Leu Ala Phe Ala
                20                  25                  30

Gly Asn Ala Gln Ala Asp Thr Val Leu Pro Ser Glu Gln Arg Ala Thr
            35                  40                  45

Gln Thr Thr Gln Thr Thr Gln Thr Ser Glu Asp Thr Ser Ala Thr Lys
        50                  55                  60

Thr Pro Ala Ser Ala Ser Thr Ser Ser Asp Asn Val Asp Thr Ser
65                  70                  75                  80

Asp Leu Pro Asp Ser Ala Ser Ala Val Val Asp Ser Ala Val Thr Ser
                85                  90                  95

Thr Ser Thr Ser Ala Ser Val Val Ser Asp Ser Val Ala Val Pro Asp
            100                 105                 110

Thr Gly Ser Gln Phe Met Ser Ser Ser Ala Pro Ala Ser Ser Ala Phe
```

```
            115                 120                 125
Val Lys Pro Ser Leu Thr Ser Thr Ser Gly Ala Gly Ser Gln
130                 135                 140

Ser Ser Ala Val Thr Ser Ala Asn Asp Ser Ser Val Ala Thr Ser Ser
145                 150                 155                 160

Ser Ala Ser Ser Val Thr Thr Ala Thr Ser Glu Ser Ala Val Val Ser
                165                 170                 175

Ser Ala Val Ser Asp Gly Tyr His Asp Glu Gly Gly Asp Trp Val Tyr
                180                 185                 190

Tyr Arg Ala Gly Lys Lys Leu Leu Gly Arg Gln Thr Ile Asp Thr Phe
                195                 200                 205

Ala Val Tyr Phe Asp Ala Asp Gly Lys Gln Val Lys Gly Asp Trp Arg
                210                 215                 220

Glu Ser Asp Gly Lys Arg Ala Tyr Tyr Asp Gly Gln Glu Gly Arg Ala
225                 230                 235                 240

Leu Thr Gln Thr Gln Ala Val Asn Gly Val Ile Tyr Gly Phe Asn Gln
                245                 250                 255

Ser Gly Tyr Gln Ile Lys Asn Asp Phe Gly Gln Thr Ala Asn Arg Asp
                260                 265                 270

Thr Tyr Tyr Phe Asp Ala Gln Gly His Val Val Thr Gly Ile Gln Thr
                275                 280                 285

Ile Ala Asn Lys Val Tyr Asp Phe Asp Glu Gln Gly Arg Met Leu Lys
290                 295                 300

Gly Ile Ala Thr Ser Val Asp Asp Lys Met Met Tyr Phe Asp Asp Gln
305                 310                 315                 320

Thr Gly Val Gly Gln Pro Ala Asp His Pro Glu Phe Asn Pro Glu Thr
                325                 330                 335

Glu Pro Val Pro Asp Asp Asn Ile Lys His Asn Ala Ala His Gly Thr
                340                 345                 350

Thr Pro Glu Asp Phe Asp Ser Met Ala Asp Tyr Leu Thr Ala Asp Thr
                355                 360                 365

Trp Tyr Arg Pro Thr Asp Ile Leu Glu Asn Gly Glu Thr Trp Arg Glu
                370                 375                 380

Ser Gln Pro Thr Glu Phe Arg Pro Leu Leu Ala Thr Trp Trp Pro Thr
385                 390                 395                 400

Lys Gln Thr Gln Ala Asp Tyr Val Asn Tyr Met Asn His Ala Leu Asp
                405                 410                 415

Met Ala Asn Ala Gly Val Ser Ala Ala Asp Ser Glu Ala Thr Leu Thr
                420                 425                 430

Ala Ala Thr Asp Ala Ile Gln Ala Val Val Glu His Gln Ile Thr Val
                435                 440                 445

Arg Gln Ser Thr Ala Trp Leu Arg Glu Leu Met Ala Ala Phe Val Val
                450                 455                 460

Thr Gln Pro Gln Trp Asn Lys Thr Ser Glu Asp Val Asn Asp Asp His
465                 470                 475                 480

Leu Gln Gly Gly Ala Leu Thr Phe Glu Asn Asn Gly Asp Thr Asp Ala
                485                 490                 495

Asn Ser Asp Tyr Arg Leu Met Asn Arg Thr Pro Thr Asn Gln Thr Gly
                500                 505                 510

Glu Arg Leu Tyr His Ile Asp Asp Ser Leu Gly Gly Tyr Glu Leu Leu
                515                 520                 525

Leu Ala Asn Asp Val Asp Asn Ser Asn Pro Gln Val Gln Ala Glu Gln
530                 535                 540
```

```
Leu Asn Trp Leu Tyr Tyr Leu Met His Phe Gly Asp Ile Thr Ala Asp
545                 550                 555                 560

Asp Pro Asp Ala Asn Phe Asp Ala Ile Arg Ile Asp Ala Val Asp Asn
                565                 570                 575

Val Asp Ala Asp Leu Leu Gln Leu Ala Ala Gln Tyr Phe Arg Asp Ala
            580                 585                 590

Tyr Gly Met Ala Thr Thr Asp Ala Thr Ser Asn Lys His Leu Ser Ile
            595                 600                 605

Leu Glu Asp Trp Ser His Asn Asp Pro Ala Tyr Met Gln Ala His Gly
        610                 615                 620

Asn Asp Gln Leu Thr Met Asp Asp Tyr Met His Thr Gln Leu Ile Trp
625                 630                 635                 640

Ser Leu Thr Lys Pro Glu Ala Gln Arg Gly Thr Met Ala Arg Phe Met
                645                 650                 655

Asp Phe Tyr Leu Thr Asn Arg Ala Asn Asp Asp Thr Glu Asn Thr Ala
            660                 665                 670

Gln Pro Ser Tyr Ser Phe Val Arg Ala His Asp Ser Glu Val Gln Thr
            675                 680                 685

Val Ile Ala Glu Ile Val Thr Lys Leu His Pro Glu Ala Gly Asn Gly
690                 695                 700

Leu Met Pro Thr Glu Glu Gln Met Ala Glu Ala Phe Lys Ile Tyr Asn
705                 710                 715                 720

Ala Asp Gln Lys Lys Ala Val Lys Thr Tyr Thr His Tyr Asn Met Pro
                725                 730                 735

Ser Ala Tyr Ala Met Leu Leu Thr Asn Lys Asp Val Ile Pro Arg Ile
            740                 745                 750

Tyr Tyr Gly Asp Leu Tyr Thr Asp Asp Gly Gln Phe Met Ala Thr Lys
            755                 760                 765

Ser Pro Tyr Phe Asp Ala Ile Ser Thr Met Leu Gln Ala Arg Thr Lys
        770                 775                 780

Tyr Val Ala Gly Gly Gln Thr Met Ala Val Asp Gln His Asp Val Leu
785                 790                 795                 800

Thr Ser Val Arg Phe Gly Lys Gly Ala Met Thr Ala Asn Asp Leu Gly
                805                 810                 815

Asp Ala Glu Thr Arg Thr Glu Gly Val Gly Leu Ile Ile Ser Asn Asn
            820                 825                 830

Pro Lys Leu Gln Leu Gly Gln Gln Asp Asn Val Val Leu His Met Gly
        835                 840                 845

Leu Ala His Ala Asn Gln Ala Phe Arg Ala Val Val Leu Thr Thr Ala
        850                 855                 860

Thr Gly Leu Thr Ile Tyr Asn Asp Asp Ala Pro Ile Arg Tyr Thr
865                 870                 875                 880

Asp Asn Lys Gly Asp Leu Ile Phe Thr Asn His Asp Val Tyr Gly Val
            885                 890                 895

Leu Asn Pro Gln Val Ser Gly Phe Leu Ala Met Trp Val Pro Thr Gly
            900                 905                 910

Ala Pro Ala Asn Gln Asp Ala Arg Ser Thr Ala Ser Thr Asn Met Ser
            915                 920                 925

Thr Asp Gly Ser Ala Tyr His Ser Asn Ala Ala Leu Asp Ser Gln Val
        930                 935                 940

Ile Phe Glu Ser Phe Ser Asn Phe Gln Ala Met Pro Thr Ser His Asp
945                 950                 955                 960
```

Thr Tyr Thr Asn Val Val Leu Ala Asn His Ala Asp Gln Leu His Asp
        965                 970                 975

Trp Gly Ile Thr Ser Val Gln Leu Ala Pro Gln Tyr Arg Ser Ser Thr
        980                 985                 990

Asp Gly Thr Phe Leu Asp Ala Ile Ile Gln Asn Gly Tyr Ala Phe Thr
        995                 1000                1005

Asp Arg Tyr Asp Leu Gly Phe Gly Thr Pro Thr Lys Tyr Gly Asp
        1010                1015                1020

Asp Thr Asp Leu Arg Asn Val Ile Lys Ala Leu His Ala Asn Gly
        1025                1030                1035

Met Gln Val Met Ala Asp Phe Val Pro Asp Gln Leu Tyr Thr Leu
        1040                1045                1050

Pro Gly Lys Glu Leu Val Gln Val Thr Arg Thr Asn Asn Met Gly
        1055                1060                1065

Glu Pro Asp Thr His Ser Asp Ile Gln His Ile Leu Tyr Val Thr
        1070                1075                1080

Ser Thr Arg Gly Gly Asp Tyr Gln Lys Gln Tyr Gly Gly Glu
        1085                1090                1095

Phe Leu Ala Arg Leu Arg Glu Arg Tyr Pro Asp Leu Phe Thr Thr
        1100                1105                1110

Arg Gln Ile Ser Thr Gly Gln Thr Ile Asp Asp Ser Val Lys Ile
        1115                1120                1125

Lys Glu Trp Ser Ala Lys Tyr Leu Asn Gly Thr Ala Ile Gln Gly
        1130                1135                1140

Arg Gly Ala Gly Tyr Val Leu Arg Asp Asn Gly Thr Asn Ala Tyr
        1145                1150                1155

Tyr Lys Val Thr Ala Asn Asp Gly Asn Val Asn Leu Pro Lys Gln
        1160                1165                1170

Leu Leu Gly Gln Pro Val Met Thr Gly Phe Tyr His Glu Ala Asp
        1175                1180                1185

Gly Tyr His Phe Glu Thr Leu Ser Gly Thr Ser Ala Lys Asp Ala
        1190                1195                1200

Phe Ile Met Gly Asp Asp Gly Ala Leu Tyr Tyr Phe Asp Asp Gln
        1205                1210                1215

Gly Val Met Val Thr Gly Lys Gln Arg Val His Gln Asp Gln Tyr
        1220                1225                1230

Phe Phe Leu Pro Asn Gly Ile Ala Leu Thr Asp Ala Phe Val Gln
        1235                1240                1245

Thr Ala Asp Gly Gln Arg Gln Tyr Tyr Asp Lys Thr Gly Arg Leu
        1250                1255                1260

Val Ile Asn Gln Tyr Val Thr Asp His Gln Ala Asn Ala Phe Arg
        1265                1270                1275

Val Asp Ala Asp Gly Asn Val Val Arg Asn Gln Ala Leu Thr Val
        1280                1285                1290

Asp Gly His Glu Gln Tyr Phe Gly Thr Asn Gly Val Gln Ala Lys
        1295                1300                1305

Ala Val Leu Ile Arg Thr Asp Asn Gln Ala Arg Tyr Tyr Glu
        1310                1315                1320

Ala Asn Ser Gly Asn Leu Val Lys Gln Gln Phe Ile Leu Asp Thr
        1325                1330                1335

Asp Gly His Trp Leu Tyr Ala Asp Ala Ala Gly Asp Leu Ala Arg
        1340                1345                1350

Gly Gln Ile Thr Ile Gly Gln Asp Thr Leu Tyr Phe Asp Asp Asn

```
            1355                1360                1365

Asn His Gln Val Lys Asp Asp Phe Val Tyr Asp Thr Asn Gly Val
        1370                1375                1380

His Tyr Phe Asn Gly Thr Thr Gly Ala Glu Ile Lys Gln Asp Tyr
    1385                1390                1395

Ala Phe His Asp Gly Lys Trp Tyr Tyr Phe Asp Asp Leu Gly Arg
1400                1405                1410

Met Val Thr Gly Leu Gln Arg Ile Asn Gly Glu Tyr Arg Tyr Phe
    1415                1420                1425

Asp Ala Asn Gly Val Gln Leu Lys Gly Gly Thr Val Thr Asp Pro
        1430                1435                1440

Leu Thr His Gln Thr Tyr Thr Phe Asp Ala Lys Thr Gly Ala Gly
            1445                1450                1455

Thr Leu Val Thr Ile
        1460

<210> SEQ ID NO 9
<211> LENGTH: 1426
<212> TYPE: PRT
<213> ORGANISM: Lactobacillus fermentum
<220> FEATURE:
<221> NAME/KEY: MISC_FEATURE
<222> LOCATION: (1)..(1426)
<223> OTHER INFORMATION: mature 2918 gtf

<400> SEQUENCE: 9

Asp Thr Val Leu Pro Ser Glu Gln Arg Ala Thr Gln Thr Thr Gln Thr
1               5                   10                  15

Thr Gln Thr Ser Glu Asp Thr Ser Ala Thr Lys Thr Pro Ala Ser Ala
            20                  25                  30

Ser Thr Ser Ser Ser Asp Asn Val Asp Thr Ser Asp Leu Pro Asp Ser
        35                  40                  45

Ala Ser Ala Val Val Asp Ser Ala Val Thr Ser Thr Ser Thr Ser Ala
    50                  55                  60

Ser Val Val Ser Asp Ser Val Ala Val Pro Asp Thr Gly Ser Gln Phe
65                  70                  75                  80

Met Ser Ser Ser Ala Pro Ala Ser Ser Ala Phe Val Lys Pro Ser Leu
                85                  90                  95

Thr Ser Thr Thr Ser Gly Ala Gly Ser Gln Ser Ser Ala Val Thr
            100                 105                 110

Ser Ala Asn Asp Ser Ser Val Ala Thr Ser Ser Ser Ala Ser Ser Val
        115                 120                 125

Thr Thr Ala Thr Ser Glu Ser Ala Val Val Ser Ser Ala Val Ser Asp
    130                 135                 140

Gly Tyr His Asp Glu Gly Gly Asp Trp Val Tyr Tyr Arg Ala Gly Lys
145                 150                 155                 160

Lys Leu Leu Gly Arg Gln Thr Ile Asp Thr Phe Ala Val Tyr Phe Asp
                165                 170                 175

Ala Asp Gly Lys Gln Val Lys Gly Asp Trp Arg Glu Ser Asp Gly Lys
            180                 185                 190

Arg Ala Tyr Tyr Asp Gly Gln Glu Gly Arg Ala Leu Thr Gln Thr Gln
        195                 200                 205

Ala Val Asn Gly Val Ile Tyr Gly Phe Asn Gln Ser Gly Tyr Gln Ile
    210                 215                 220

Lys Asn Asp Phe Gly Gln Thr Ala Asn Arg Asp Thr Tyr Tyr Phe Asp
225                 230                 235                 240
```

```
Ala Gln Gly His Val Thr Gly Ile Gln Thr Ile Ala Asn Lys Val
            245                 250                 255

Tyr Asp Phe Asp Glu Gln Gly Arg Met Leu Lys Gly Ile Ala Thr Ser
        260                 265                 270

Val Asp Asp Lys Met Met Tyr Phe Asp Gln Thr Gly Val Gly Gln
        275                 280                 285

Pro Ala Asp His Pro Glu Phe Asn Pro Glu Thr Glu Pro Val Pro Asp
    290                 295                 300

Asp Asn Ile Lys His Asn Ala Ala His Gly Thr Thr Pro Glu Asp Phe
305                 310                 315                 320

Asp Ser Met Ala Asp Tyr Leu Thr Ala Asp Thr Trp Tyr Arg Pro Thr
            325                 330                 335

Asp Ile Leu Glu Asn Gly Glu Thr Trp Arg Glu Ser Gln Pro Thr Glu
        340                 345                 350

Phe Arg Pro Leu Leu Ala Thr Trp Trp Pro Thr Lys Gln Thr Gln Ala
        355                 360                 365

Asp Tyr Val Asn Tyr Met Asn His Ala Leu Asp Met Ala Asn Ala Gly
    370                 375                 380

Val Ser Ala Ala Asp Ser Glu Ala Thr Leu Thr Ala Ala Thr Asp Ala
385                 390                 395                 400

Ile Gln Ala Val Val Glu His Gln Ile Thr Val Arg Gln Ser Thr Ala
            405                 410                 415

Trp Leu Arg Glu Leu Met Ala Ala Phe Val Val Thr Gln Pro Gln Trp
        420                 425                 430

Asn Lys Thr Ser Glu Asp Val Asn Asp His Leu Gln Gly Gly Ala
        435                 440                 445

Leu Thr Phe Glu Asn Asn Gly Asp Thr Asp Ala Asn Ser Asp Tyr Arg
    450                 455                 460

Leu Met Asn Arg Thr Pro Thr Asn Gln Thr Gly Glu Arg Leu Tyr His
465                 470                 475                 480

Ile Asp Asp Ser Leu Gly Gly Tyr Glu Leu Leu Ala Asn Asp Val
            485                 490                 495

Asp Asn Ser Asn Pro Gln Val Gln Ala Glu Gln Leu Asn Trp Leu Tyr
        500                 505                 510

Tyr Leu Met His Phe Gly Asp Ile Thr Ala Asp Pro Asp Ala Asn
        515                 520                 525

Phe Asp Ala Ile Arg Ile Asp Ala Val Asp Asn Val Asp Ala Asp Leu
    530                 535                 540

Leu Gln Leu Ala Ala Gln Tyr Phe Arg Asp Ala Tyr Gly Met Ala Thr
545                 550                 555                 560

Thr Asp Ala Thr Ser Asn Lys His Leu Ser Ile Leu Glu Asp Trp Ser
            565                 570                 575

His Asn Asp Pro Ala Tyr Met Gln Ala His Gly Asn Asp Gln Leu Thr
        580                 585                 590

Met Asp Asp Tyr Met His Thr Gln Leu Ile Trp Ser Leu Thr Lys Pro
        595                 600                 605

Glu Ala Gln Arg Gly Thr Met Ala Arg Phe Met Asp Phe Tyr Leu Thr
    610                 615                 620

Asn Arg Ala Asn Asp Asp Thr Glu Asn Thr Ala Gln Pro Ser Tyr Ser
625                 630                 635                 640

Phe Val Arg Ala His Asp Ser Glu Val Gln Thr Val Ile Ala Glu Ile
            645                 650                 655
```

-continued

Val Thr Lys Leu His Pro Glu Ala Gly Asn Gly Leu Met Pro Thr Glu
            660                 665                 670

Glu Gln Met Ala Glu Ala Phe Lys Ile Tyr Asn Ala Asp Gln Lys Lys
            675                 680                 685

Ala Val Lys Thr Tyr Thr His Tyr Asn Met Pro Ser Ala Tyr Ala Met
            690                 695                 700

Leu Leu Thr Asn Lys Asp Val Ile Pro Arg Ile Tyr Tyr Gly Asp Leu
705                 710                 715                 720

Tyr Thr Asp Asp Gly Gln Phe Met Ala Thr Lys Ser Pro Tyr Phe Asp
            725                 730                 735

Ala Ile Ser Thr Met Leu Gln Ala Arg Thr Lys Tyr Val Ala Gly Gly
            740                 745                 750

Gln Thr Met Ala Val Asp Gln His Asp Val Leu Thr Ser Val Arg Phe
            755                 760                 765

Gly Lys Gly Ala Met Thr Ala Asn Asp Leu Gly Asp Ala Glu Thr Arg
            770                 775                 780

Thr Glu Gly Val Gly Leu Ile Ser Asn Asn Pro Lys Leu Gln Leu
785                 790                 795                 800

Gly Gln Gln Asp Asn Val Val Leu His Met Gly Leu Ala His Ala Asn
            805                 810                 815

Gln Ala Phe Arg Ala Val Val Leu Thr Thr Ala Thr Gly Leu Thr Ile
            820                 825                 830

Tyr Asn Asp Asp Ala Pro Ile Arg Tyr Thr Asp Asn Lys Gly Asp
            835                 840                 845

Leu Ile Phe Thr Asn His Asp Val Tyr Gly Val Leu Asn Pro Gln Val
850                 855                 860

Ser Gly Phe Leu Ala Met Trp Val Pro Thr Gly Ala Pro Ala Asn Gln
865                 870                 875                 880

Asp Ala Arg Ser Thr Ala Ser Thr Asn Met Ser Thr Asp Gly Ser Ala
            885                 890                 895

Tyr His Ser Asn Ala Ala Leu Asp Ser Gln Val Ile Phe Glu Ser Phe
            900                 905                 910

Ser Asn Phe Gln Ala Met Pro Thr Ser His Asp Thr Tyr Thr Asn Val
            915                 920                 925

Val Leu Ala Asn His Ala Asp Gln Leu His Asp Trp Gly Ile Thr Ser
930                 935                 940

Val Gln Leu Ala Pro Gln Tyr Arg Ser Ser Thr Asp Gly Thr Phe Leu
945                 950                 955                 960

Asp Ala Ile Ile Gln Asn Gly Tyr Ala Phe Thr Asp Arg Tyr Asp Leu
            965                 970                 975

Gly Phe Gly Thr Pro Thr Lys Tyr Gly Asp Asp Thr Asp Leu Arg Asn
            980                 985                 990

Val Ile Lys Ala Leu His Ala Asn Gly Met Gln Val Met Ala Asp Phe
            995                 1000                1005

Val Pro Asp Gln Leu Tyr Thr Leu Pro Gly Lys Glu Leu Val Gln
            1010                1015                1020

Val Thr Arg Thr Asn Asn Met Gly Glu Pro Asp Thr His Ser Asp
            1025                1030                1035

Ile Gln His Ile Leu Tyr Val Thr Ser Thr Arg Gly Gly Gly Asp
            1040                1045                1050

Tyr Gln Lys Gln Tyr Gly Gly Glu Phe Leu Ala Arg Leu Arg Glu
            1055                1060                1065

Arg Tyr Pro Asp Leu Phe Thr Thr Arg Gln Ile Ser Thr Gly Gln

```
                1070                1075                1080

Thr Ile Asp Asp Ser Val Lys Ile Lys Glu Trp Ser Ala Lys Tyr
        1085                1090                1095

Leu Asn Gly Thr Ala Ile Gln Gly Arg Gly Ala Gly Tyr Val Leu
        1100                1105                1110

Arg Asp Asn Gly Thr Asn Ala Tyr Tyr Lys Val Thr Ala Asn Asp
        1115                1120                1125

Gly Asn Val Asn Leu Pro Lys Gln Leu Leu Gly Gln Pro Val Met
        1130                1135                1140

Thr Gly Phe Tyr His Glu Ala Asp Gly Tyr His Phe Glu Thr Leu
        1145                1150                1155

Ser Gly Thr Ser Ala Lys Asp Ala Phe Ile Met Gly Asp Asp Gly
        1160                1165                1170

Ala Leu Tyr Tyr Phe Asp Asp Gln Gly Val Met Val Thr Gly Lys
        1175                1180                1185

Gln Arg Val His Gln Asp Gln Tyr Phe Phe Leu Pro Asn Gly Ile
        1190                1195                1200

Ala Leu Thr Asp Ala Phe Val Gln Thr Ala Asp Gly Gln Arg Gln
        1205                1210                1215

Tyr Tyr Asp Lys Thr Gly Arg Leu Val Ile Asn Gln Tyr Val Thr
        1220                1225                1230

Asp His Gln Ala Asn Ala Phe Arg Val Asp Ala Asp Gly Asn Val
        1235                1240                1245

Val Arg Asn Gln Ala Leu Thr Val Asp Gly His Glu Gln Tyr Phe
        1250                1255                1260

Gly Thr Asn Gly Val Gln Ala Lys Ala Val Leu Ile Arg Thr Asp
        1265                1270                1275

Asp Asn Gln Ala Arg Tyr Tyr Glu Ala Asn Ser Gly Asn Leu Val
        1280                1285                1290

Lys Gln Gln Phe Ile Leu Asp Thr Asp Gly His Trp Leu Tyr Ala
        1295                1300                1305

Asp Ala Ala Gly Asp Leu Ala Arg Gly Gln Ile Thr Ile Gly Gln
        1310                1315                1320

Asp Thr Leu Tyr Phe Asp Asp Asn Asn His Gln Val Lys Asp Asp
        1325                1330                1335

Phe Val Tyr Asp Thr Asn Gly Val His Tyr Phe Asn Gly Thr Thr
        1340                1345                1350

Gly Ala Glu Ile Lys Gln Asp Tyr Ala Phe His Asp Gly Lys Trp
        1355                1360                1365

Tyr Tyr Phe Asp Asp Leu Gly Arg Met Val Thr Gly Leu Gln Arg
        1370                1375                1380

Ile Asn Gly Glu Tyr Arg Tyr Phe Asp Ala Asn Gly Val Gln Leu
        1385                1390                1395

Lys Gly Gly Thr Val Thr Asp Pro Leu Thr His Gln Thr Tyr Thr
        1400                1405                1410

Phe Asp Ala Lys Thr Gly Ala Gly Thr Leu Val Thr Ile
        1415                1420                1425
```

<210> SEQ ID NO 10
<211> LENGTH: 4281
<212> TYPE: DNA
<213> ORGANISM: Artificial sequence
<220> FEATURE:
<223> OTHER INFORMATION: 2918 gtf with heterologous signal sequence

<400> SEQUENCE: 10

```
gatacagtgc tgcctagcga gcaaagagca acacagacga cacaaacaac gcagacatca    60
gaggatacga gcgcgacgaa gacaccggca agcgcatcaa cgtcaagcag cgataacgtg   120
gatacgtcag atcttccgga tagcgccagc gcagttgtcg attcagcggt tacatcaaca   180
agcacgtcag cctcagtggt gagcgatagc gttgcagtcc cggatacggg atcacaattt   240
atgtcatcat cagctcctgc gagcagcgcg tttgttaaac ctagccttac gtcaacgacg   300
tcaggagcga gcggctcaca gagctcagca gtgacaagcg ccaatgattc aagcgtcgct   360
acaagctcat cagcttcatc agttacgaca gcaacaagcg agtcagccgt tgtctcaagc   420
gcggtctcag acggctatca tgacgaagga ggagattggg tttactacag agcaggaaaa   480
aaactgcttg gaagacagac aattgatacg tttgctgttt actttgatgc tgacggaaaa   540
caagtgaaag gcgactggag agaatcagat ggaaagagag cgtattatga tggacaagaa   600
ggaagagccc ttacgcaaac gcaagccgtt aatggagtga tctatggatt caatcaatca   660
ggataccaga tcaaaaacga ttttggccag acagcgaaca gagatacata ctacttcgac   720
gcacaaggcc atgtggttac aggcatccaa acaatcgcga taaagtttta tgacttcgat   780
gaacaaggca gaatgcttaa aggaattgcc acatcagtcg atgacaagat gatgtatttt   840
gacgatcaaa caggcgtggg acaacctgca gatcaccctg agtttaaccc ggaaacagaa   900
ccggtgcctg acgataacat caagcataat gcagcccacg gcacaacacc tgaagatttt   960
gatagcatgg cggactatct gacagctgat acatggtata gacctacaga tattctggag  1020
aatggagaaa catggagaga gagccaaccg acggaattta gaccgctgct ggcaacgtgg  1080
tggcctacaa aacagacaca agcagattat gtgaactata tgaaccacgc acttgacatg  1140
gctaatgctg gcgttagcgc tgcggattca gaggcaacac ttacagcggc tacgatgcc   1200
attcaggctg ttgttgagca ccaaattacg gttagacaaa gcacggcctg gcttagagaa  1260
cttatggcgg cttttgttgt tacacaacct caatggaata agacgagcga agatgtcaat  1320
gatgatcacc ttcaaggagg cgcactgaca tttgagaata acggagacac agatgcaaat  1380
agcgattata gacttatgaa tagaacaccg acaaatcaaa cgggcgagag actttatcat  1440
attgatgact cactgggagg ctacgagctg cttcttgcaa acgatgtgga caactcaaac  1500
ccgcaggttc aggcggaaca acttaactgg ctttactatc ttatgcattt cggagatatt  1560
acagccgatg acccggatgc taactttgac gcgatcagaa ttgacgccgt tgataatgtc  1620
gacgctgacc tgcttcagct tgctgcccaa tactttagag atgcatatgg aatggccaca  1680
acagacgcca cgagcaataa acacctttca atccttgagg attggagcca taacgatcct  1740
gcttatatgc aggcacatgg aaatgaccag cttacaatgg atgactacat gcacacacaa  1800
ctgatttggt cactgacgaa accggaagca caaagaggaa cgatggcaag atttatggac  1860
ttttatctta caaatagagc taacgatgat acagaaaaca cagcgcaacc ttcatattca  1920
tttgttagag cacacgactc agaagtgcag acagttattg cagaaattgt tacgaaactt  1980
cacccggagg caggcaacgg ccttatgcct acggaggaac agatggcaga ggcgtttaag  2040
atctacaatg cagaccaaaa gaaagcggtg aaaacatata cacactataa catgccttca  2100
gcctacgcta tgctgctgac aaataaggat gtgattccta gaatctacta cggcgatctt  2160
tacacgacg acggccagtt catggcaaca aagtcaccgt atttcgatgc aatttcaaca  2220
atgctgcaag caagaacaaa atatgttgca ggcgacaaa cgatggcggt tgaccaacat  2280
gatgtcctga cgagcgtgag atttggcaaa ggcgcgatga cagcaaatga ccttggagac  2340
```

```
gcggaaacga gaacagaggg cgtgggactg atcatcagca acaaccctaa gctgcaactg    2400
ggacagcagg ataacgtggt ccttcatatg ggcctggcac acgcgaatca ggctttcaga    2460
gcagtcgtgc ttacaacagc cacaggactg acgatctaca acgacgatga cgctcctatt    2520
agatatacgg acaataaggg cgacctgatc tttacgaatc acgatgttta cggcgttctg    2580
aacccgcagg ttagcggctt ccttgctatg tgggttccga cgggcgcacc tgccaatcaa    2640
gacgcaagaa gcacggcttc aacgaatatg tcaacggatg gatcagctta tcattcaaac    2700
gcagctctgg attcacaagt tatctttgag tcatttagca acttttcaagc aatgccgaca    2760 tcacacgata catacacgaa tgttgtcctt gcaaaccatg cagaccaact tcacgattgg    2820
ggaattacgt cagtgcaact tgcaccgcaa tatagatcaa gcacagacgg aacgtttctg    2880
gatgcaatta ttcaaaatgg atatgctttt acagatagat atgatcttgg ctttggaaca    2940
cctacgaagt acggcgacga cacggacctg agaaatgtga tcaaagccct tcatgcaaac    3000
ggcatgcaag tcatggcaga tttttgttcct gatcaactgt acacacttcc gggcaaagaa    3060
ctggttcaag tgacaagaac aaataacatg ggcgaaccgg atacacacag cgatattcaa    3120
cacatcctgt atgttacatc aacaagagga ggcggagact atcagaaaca atatggcggc    3180
gaatttctgg ctagacttag agaaagatac ccggaccttt ttacgacgag acaaattagc    3240
acaggccaaa caattgacga cagcgttaag attaaggagt ggtcagcgaa atatctgaac    3300
ggcacagcaa ttcaaggcag aggcgctggc tatgttctga gagataatgg aacgaatgca    3360
tactataaag ttacgccaa tgatggaaac gtcaatcttc ctaagcaact gctgggccag    3420
ccggttatga caggcttcta tcacgaagca gacggctacc acttcgagac actgtcaggc    3480
acatcagcca aggacgcatt tatcatggga gatgatggcg cactgtacta tttcgatgac    3540
caaggcgtga tggttacagg aaaacaaaga gttcatcagg atcaatactt ttttctgccg    3600
aatggcatcg ctctgacgga cgctttcgtt caaacagctg atggacagag acagtactac    3660
gataaaacag gcagactggt tattaaccaa tatgtgacag accatcaggc gaatgccttc    3720
agagttgatg cggacggaaa tgtcgttaga aaccaagcac ttacagtgga cggacatgaa    3780
cagtatttcg gcacgaacgg agtgcaggca aaagcagttc tgattagaac ggacgataat    3840
caagcgagat attatgaggc aaattcaggc aatctggtga acaacaatt tatccttgac    3900 acagatggcc actggctgta cgcagacgca gcaggcgatc ttgctagagg ccagattaca    3960
atcggccagg atacgctgta ttttgatgat aacaatcacc aagttaaaga tgacttcgtt    4020
tatgatacga atggagtcca ttactttaat ggcacaacag gagcagagat taaacaagat    4080
tacgcattcc atgacggcaa atggtactac ttcgacgacc tgggaagaat ggtcacggga    4140
cttcaaagaa ttaatggaga gtatagatac tttgacgcga acggcgtcca actgaaagga    4200
ggcacagtga cggatcctct gacacatcaa acatatacat ttgatgcaaa aacgggagcc    4260
ggcacgcttg ttacaatttg a                                              4281
```

<210> SEQ ID NO 11
<211> LENGTH: 4521
<212> TYPE: DNA
<213> ORGANISM: Streptococcus sobrinus

<400> SEQUENCE: 11

```
atggaaagaa aattgcatta caaattacac aaggtaaaaa aacagtgggt aacgattgcc      60
gttgcctctg ctggtttggc tagcattgtt ggtgctggtt cattaagcca aactgtttct    120
```

```
gccgatgact tagccaagga acaagctgcg gctagtcaac aaaaggcagc agccaatcag      180
aatgaggacg aagtggcttc tgatgcagct gatactgcta gtgcaaaagc gacttccgaa      240
aaagaagttg tccaatcttc tgatacaaat tcagaaacta accaagttga aactaaagat      300
caagctagcg ctaaggaaag tgctgacgca gtagccaagc aagcaccaca agctggccct      360
gcaaccacta gccaggttgc aagctcagaa agcagctctg tagcgcctag caaggaagct      420
gataaggcag ctgctggatc agttagccaa aatgaagaag aagcagccct atcgcttgcc      480
aatattaaaa agattgatgg taagtattac tatgttatgg cagacggttc ttataagaag      540
aactttgcca ttacagttga tggtcaaatg ctttactttg atgccaaaac aggtgccctg      600
tcttcaacct ctacctattc tttcagtcaa ggtttgacac caattgtttc tgatttctca      660
gtcaacaaca aggcttttcga ttcttctgaa aagagttttg aattggttga tggctatttg      720
acagctgaaa gctggtaccg tcctgctaag attcttgaaa atggtaaaac ttgggttgat      780
tctaaagaaa ctgacctacg cccagttctg atgagctggt ggccaaacaa ggatacgcaa      840
gttgcctacc ttaactacat gagcaaggca cttggtggca aggaagaatt cacaactgaa      900
acctcccaat tgaccttgaa tacagccgct gagttgattc aagctaaaat tgaagctcgc      960
gtttctaaag aacaaggaac aaagtggttg cgtgaagcta tggcagcctt cgttgctacc     1020
caatctcgtt ggaataagga cagcgaacaa tacgataagg ctgaccacct gcaaggcgga     1080
gccctgctct ataccaataa caacttgaca gagtgggcaa attcaaactg cgcgcctgctt     1140 aaccgtaccc caactcgtca agatggtaaa acccattact ctaaggctga caaatacggt     1200
ggttatgaat tcctcttggc caacgacgtg gataactcta acccagtcgt tcaagcggaa     1260
atgctcaacc aaatccacta cctcatgaac tggggtgaaa ttgtgatggg tgataagaat     1320
gccaactttg atggtattcg tgtcgatgcc gtggataacg tcaatgcaga tactctgcaa     1380
ctctacacca actactttaa ttctgtttat ggtgtcaaca agtctgaagc ccaagccctg     1440
gctcacatct cagtcttgga agcatggtct tacaatgata tgactataa ccaagacacc     1500 aacgggggctg ccctggctat ggacaatggt ctacgctttt ccctgcttta taccttgacc     1560
cgtccgatca atgaacggac acctggtatg tcaaccctga ttaaatcaga atatggtttg     1620
actgaccgga ctaagaatga taagtatgga gatacccaac catcttatgt ttttgttcgg     1680
gcgcatgact cagaagtgca aaccgttatt gcacaaatca tcaaggaaaa aattgatcca     1740
acaaccgatg gtttccacctt caccttggac caattgaaac aggcctttga aatctacaac     1800
aaggatatga atagtgttaa caagcactat acccactata atatcccagc agcctacgct     1860
gtcatgttgt ctaatatgga atccgtaacc cgggtttact atggtgacct cttcaccgat     1920
gatggtcaat acatggcatc taaatctcca tattatgatg ccatcaacac tctcttgcgg     1980
gctcgcattc gttacgcagc cggtggtcaa attatggaac acaattccta caaaccatca     2040
gcagccatga aggcagctca tccagatgct ggtaatgtcc ttggtaacag cgaagtcttg     2100
gtatcggttc gtttcggtca agatgtcatg tctgccgatg atatgactgg tggtaagctg     2160
gctaagacct ctggtatgtt caccctgatt tctaacaacc ctgaattgga attggatgtc     2220
aatgaagaaa tcaaggttaa cgttggtaaa atccatgctg ccaagcccta ccgtcccttg     2280
cttttgacaa ctgataaggg tctgcaaaag tatctcaatg attctgatac caagttgacc     2340
aagattgctg acaaggatgg tttcattacc ttcaagggta gcgaaatcaa gggttacaaa     2400
caagtcgaag tcaatggtta cctctcagtt tgggtaccag ttggtgctaa ggctgaccaa     2460
gacattcgtg tggccccttc aacagcggct aagggtgaaa aggccaagac ttacacagct     2520
```

| | | |
|---|---|---|
| agccaagctt tggaatcgca attaatctac gaaggcttct caaacttcca agattttgtt | 2580 |
| caaaaagatt cccaatacac caacaagaag attgctgaaa atactgacct cttcaaggct | 2640 |
| tggggtgtta cctcatttga atggcacca caatacgttt cagcaaccga tggaaccttc | 2700 |
| ctggattcta tcattgaaaa cggttatgcc ttcaccgacc gttatgacct tgccatgagc | 2760 |
| aagaacaata atacggttc taaggaagat ttggccaacg ccctcaaggc ccttcacgca | 2820 |
| gctggtattc aagccattgc tgactgggta ccagaccaaa tttaccaact gcctggtaag | 2880 |
| gaagttgtta ccgctagccg ggttgacaac tacggtcgtg tgaaagttga ccaaccacta | 2940 |
| gttgaaaaac tttatctggc caacaccaag agctcaggaa aagatttcca agctaaatac | 3000 |
| ggtggtgaat tcttagcaga actgcaaaag aaatatcctg aaatgttcac gactaagatg | 3060 |
| atttcaactg gtaaaaccat tgatccatct gtcaaattga agaatggtc tgctaagtac | 3120 |
| ttcaacggaa ccaacgtcct tgatcgtggt acggactata tcctcagtga tgaaggtact | 3180 |
| ggtaaatact ttaccgtcaa tgaaaaaggt gacttcttac ctgcctcatt gactggtaat | 3240 |
| aaggatgcca agactggttt ctacaacgat ggtaagggca ttgtttacta cacaaccgcc | 3300 |
| ggtaacaagg ctagatcagc cttcgtaaca gaagcaggta ataccatta cttcgactac | 3360 |
| accggccata tggtaacagg ccctaacgtt attaacacta aattctatta cttcttgcca | 3420 |
| aatggtatca tgcttaagga tgctattaag caggatgaaa aaggtcgttc cgtatactac | 3480 |
| ggtaagactg gtgttatgta caagggtggc cgcgataatg aatggttcgc catgacagac | 3540 |
| tctaagggtc aaatgcgttt ccgtcactt gacaggtacg gcttcatgtc tatcggtttg | 3600 |
| gtaaccatca accaaaatgt tcagtattat gatgaaaatg gtttccaagt taaaggtgaa | 3660 |
| tttgtaaccg atcaggatgg acaaacccgt tacttcgacc aaggttcagg taacttggtt | 3720 |
| aagggacaat tcctcaacaa ggatggcaac tggtactacc ttgatgacca agggctagtt | 3780 |
| gctaaaggag ctcagacaat taaggtcaa aagctttact ttgacacaaa accggtgtc | 3840 |
| caagttaaag gggattttgt aacggataaa gatggcaata ccttctttta cagtggagat | 3900 |
| actggcgatt taatccttgg tcagttcttc tcaactggaa ataacgcttg gttctatgct | 3960 |
| gatgaaaatg gtcatgtcgc taaggagct aagactatca gaggtcagaa gctctacttt | 4020 |
| gatacaaaa caggtcagca agctaaggga cgctttatcc gtgatgacaa gggggttcgt | 4080 |
| tactatgatg ctgacacagg taccttggta accaacgctt tccttgaaac taaggctggt | 4140 |
| tctaaccaat ggtattacat gggagcagat ggttatgctg tcaaggggaa ccagaccata | 4200 |
| aaaaatcagc acatgtattt tgatgctgaa actggccaac aagctaaggg aattatagtg | 4260 |
| acagatgcca atggtcgcaa gtatttctat gatacttta ctggcagtcg tgttgtaaac | 4320 |
| caatttgttt tggttaatgg aaattggtat ttctttggtt atgatggagc tgcagtaaca | 4380 |
| ggtttccatg atatcaaggg acaacacctt tacttcaatt ccgatggaac acaggccaaa | 4440 |
| gggactacgg taaaaattgg caatcgcagc tatacctttg atgctcacac tggtgagctg | 4500 |
| acatctgttc attatggctg a | 4521 |

<210> SEQ ID NO 12
<211> LENGTH: 1506
<212> TYPE: PRT
<213> ORGANISM: Streptococcus sobrinus

<400> SEQUENCE: 12

Met Glu Arg Lys Leu His Tyr Lys Leu His Lys Val Lys Lys Gln Trp
1               5                   10                  15

```
Val Thr Ile Ala Val Ala Ser Ala Gly Leu Ala Ser Ile Val Gly Ala
         20                  25                  30

Gly Ser Leu Ser Gln Thr Val Ser Ala Asp Asp Leu Ala Lys Glu Gln
         35                  40                  45

Ala Ala Ala Ser Gln Gln Lys Ala Ala Ala Asn Gln Asn Glu Asp Glu
 50                  55                  60

Val Ala Ser Asp Ala Ala Asp Thr Ala Ser Ala Lys Ala Thr Ser Glu
 65                  70                  75                  80

Lys Glu Val Val Gln Ser Ser Asp Thr Asn Ser Glu Thr Asn Gln Val
                     85                  90                  95

Glu Thr Lys Asp Gln Ala Ser Ala Lys Glu Ser Ala Asp Ala Val Ala
                100                 105                 110

Lys Gln Ala Pro Gln Ala Gly Pro Ala Thr Thr Ser Gln Val Ala Ser
            115                 120                 125

Ser Glu Ser Ser Ser Val Ala Pro Ser Lys Glu Ala Asp Lys Ala Ala
    130                 135                 140

Ala Gly Ser Val Ser Gln Asn Glu Glu Glu Ala Ala Leu Ser Leu Ala
145                 150                 155                 160

Asn Ile Lys Lys Ile Asp Gly Lys Tyr Tyr Tyr Val Met Ala Asp Gly
                    165                 170                 175

Ser Tyr Lys Lys Asn Phe Ala Ile Thr Val Asp Gly Gln Met Leu Tyr
            180                 185                 190

Phe Asp Ala Lys Thr Gly Ala Leu Ser Ser Thr Ser Thr Tyr Ser Phe
        195                 200                 205

Ser Gln Gly Leu Thr Pro Ile Val Ser Asp Phe Ser Val Asn Asn Lys
    210                 215                 220

Ala Phe Asp Ser Ser Glu Lys Ser Phe Glu Leu Val Asp Gly Tyr Leu
225                 230                 235                 240

Thr Ala Glu Ser Trp Tyr Arg Pro Ala Lys Ile Leu Glu Asn Gly Lys
                    245                 250                 255

Thr Trp Val Asp Ser Lys Glu Thr Asp Leu Arg Pro Val Leu Met Ser
            260                 265                 270

Trp Trp Pro Asn Lys Asp Thr Gln Val Ala Tyr Leu Asn Tyr Met Ser
        275                 280                 285

Lys Ala Leu Gly Gly Lys Glu Glu Phe Thr Thr Glu Thr Ser Gln Leu
    290                 295                 300

Thr Leu Asn Thr Ala Ala Glu Leu Ile Gln Ala Lys Ile Glu Ala Arg
305                 310                 315                 320

Val Ser Lys Glu Gln Gly Thr Lys Trp Leu Arg Glu Ala Met Ala Ala
                    325                 330                 335

Phe Val Thr Gln Ser Arg Trp Asn Lys Asp Ser Glu Gln Tyr Asp
            340                 345                 350

Lys Ala Asp His Leu Gln Gly Gly Ala Leu Leu Tyr Thr Asn Asn Asn
        355                 360                 365

Leu Thr Glu Trp Ala Asn Ser Asn Trp Arg Leu Leu Asn Arg Thr Pro
    370                 375                 380

Thr Arg Gln Asp Gly Lys Thr His Tyr Ser Lys Ala Asp Lys Tyr Gly
385                 390                 395                 400

Gly Tyr Glu Phe Leu Leu Ala Asn Asp Val Asp Asn Ser Asn Pro Val
                    405                 410                 415

Val Gln Ala Glu Met Leu Asn Gln Ile His Tyr Leu Met Asn Trp Gly
            420                 425                 430
```

Glu Ile Val Met Gly Asp Lys Asn Ala Asn Phe Asp Gly Ile Arg Val
                435                 440                 445

Asp Ala Val Asp Asn Val Asn Ala Asp Thr Leu Gln Leu Tyr Thr Asn
450                 455                 460

Tyr Phe Asn Ser Val Tyr Gly Val Asn Lys Ser Glu Ala Gln Ala Leu
465                 470                 475                 480

Ala His Ile Ser Val Leu Glu Ala Trp Ser Tyr Asn Asp Asn Asp Tyr
                485                 490                 495

Asn Gln Asp Thr Asn Gly Ala Ala Leu Ala Met Asp Asn Gly Leu Arg
                500                 505                 510

Phe Ser Leu Leu Tyr Thr Leu Thr Arg Pro Ile Asn Glu Arg Thr Pro
                515                 520                 525

Gly Met Ser Thr Leu Ile Lys Ser Glu Tyr Gly Leu Thr Asp Arg Thr
                530                 535                 540

Lys Asn Asp Lys Tyr Gly Asp Thr Gln Pro Ser Tyr Val Phe Val Arg
545                 550                 555                 560

Ala His Asp Ser Glu Val Gln Thr Val Ile Ala Gln Ile Ile Lys Glu
                565                 570                 575

Lys Ile Asp Pro Thr Thr Asp Gly Phe Thr Phe Thr Leu Asp Gln Leu
                580                 585                 590

Lys Gln Ala Phe Glu Ile Tyr Asn Lys Asp Met Asn Ser Val Asn Lys
                595                 600                 605

His Tyr Thr His Tyr Asn Ile Pro Ala Ala Tyr Ala Val Met Leu Ser
                610                 615                 620

Asn Met Glu Ser Val Thr Arg Val Tyr Tyr Gly Asp Leu Phe Thr Asp
625                 630                 635                 640

Asp Gly Gln Tyr Met Ala Ser Lys Ser Pro Tyr Tyr Asp Ala Ile Asn
                645                 650                 655

Thr Leu Leu Arg Ala Arg Ile Arg Tyr Ala Ala Gly Gly Gln Ile Met
                660                 665                 670

Glu His Asn Ser Tyr Lys Pro Ser Ala Ala Met Lys Ala Ala His Pro
                675                 680                 685

Asp Ala Gly Asn Val Leu Gly Asn Ser Glu Val Leu Val Ser Val Arg
690                 695                 700

Phe Gly Gln Asp Val Met Ser Ala Asp Met Thr Gly Gly Lys Leu
705                 710                 715                 720

Ala Lys Thr Ser Gly Met Phe Thr Leu Ile Ser Asn Asn Pro Glu Leu
                725                 730                 735

Glu Leu Asp Val Asn Glu Glu Ile Lys Val Asn Val Gly Lys Ile His
                740                 745                 750

Ala Gly Gln Ala Tyr Arg Pro Leu Leu Leu Thr Thr Asp Lys Gly Leu
                755                 760                 765

Gln Lys Tyr Leu Asn Asp Ser Asp Thr Lys Leu Thr Lys Ile Ala Asp
                770                 775                 780

Lys Asp Gly Phe Ile Thr Phe Lys Gly Ser Glu Ile Lys Gly Tyr Lys
785                 790                 795                 800

Gln Val Glu Val Asn Gly Tyr Leu Ser Val Trp Val Pro Val Gly Ala
                805                 810                 815

Lys Ala Asp Gln Asp Ile Arg Val Ala Pro Ser Thr Ala Ala Lys Gly
                820                 825                 830

Glu Lys Ala Lys Thr Tyr Thr Ala Ser Gln Ala Leu Glu Ser Gln Leu
                835                 840                 845

Ile Tyr Glu Gly Phe Ser Asn Phe Gln Asp Phe Val Gln Lys Asp Ser

```
            850                 855                 860
Gln Tyr Thr Asn Lys Lys Ile Ala Glu Asn Thr Asp Leu Phe Lys Ala
865                 870                 875                 880

Trp Gly Val Thr Ser Phe Glu Met Ala Pro Gln Tyr Val Ser Ala Thr
                    885                 890                 895

Asp Gly Thr Phe Leu Asp Ser Ile Ile Glu Asn Gly Tyr Ala Phe Thr
                900                 905                 910

Asp Arg Tyr Asp Leu Ala Met Ser Lys Asn Asn Lys Tyr Gly Ser Lys
            915                 920                 925

Glu Asp Leu Ala Asn Ala Leu Lys Ala Leu His Ala Ala Gly Ile Gln
        930                 935                 940

Ala Ile Ala Asp Trp Val Pro Asp Gln Ile Tyr Gln Leu Pro Gly Lys
945                 950                 955                 960

Glu Val Val Thr Ala Ser Arg Val Asp Asn Tyr Gly Arg Val Lys Val
                    965                 970                 975

Asp Gln Pro Leu Val Glu Lys Leu Tyr Leu Ala Asn Thr Lys Ser Ser
                980                 985                 990

Gly Lys Asp Phe Gln Ala Lys Tyr Gly Gly Glu Phe Leu Ala Glu Leu
            995                 1000                1005

Gln Lys Lys Tyr Pro Glu Met Phe Thr Thr Lys Met Ile Ser Thr
        1010                1015                1020

Gly Lys Thr Ile Asp Pro Ser Val Lys Leu Lys Glu Trp Ser Ala
        1025                1030                1035

Lys Tyr Phe Asn Gly Thr Asn Val Leu Asp Arg Gly Thr Asp Tyr
        1040                1045                1050

Ile Leu Ser Asp Glu Gly Thr Gly Lys Tyr Phe Thr Val Asn Glu
        1055                1060                1065

Lys Gly Asp Phe Leu Pro Ala Ser Leu Thr Gly Asn Lys Asp Ala
        1070                1075                1080

Lys Thr Gly Phe Tyr Asn Asp Gly Lys Gly Ile Val Tyr Tyr Thr
        1085                1090                1095

Thr Ala Gly Asn Lys Ala Arg Ser Ala Phe Val Thr Glu Ala Gly
        1100                1105                1110

Asn Thr Tyr Tyr Phe Asp Tyr Thr Gly His Met Val Thr Gly Pro
        1115                1120                1125

Asn Val Ile Asn Thr Lys Phe Tyr Tyr Phe Leu Pro Asn Gly Ile
        1130                1135                1140

Met Leu Lys Asp Ala Ile Lys Gln Asp Glu Lys Gly Arg Ser Val
        1145                1150                1155

Tyr Tyr Gly Lys Thr Gly Val Met Tyr Lys Gly Gly Arg Asp Asn
        1160                1165                1170

Glu Trp Phe Ala Met Thr Asp Ser Lys Gly Gln Met Arg Phe Arg
        1175                1180                1185

His Phe Asp Arg Tyr Gly Phe Met Ser Ile Gly Leu Val Thr Ile
        1190                1195                1200

Asn Gln Asn Val Gln Tyr Tyr Asp Glu Asn Gly Phe Gln Val Lys
        1205                1210                1215

Gly Glu Phe Val Thr Asp Gln Asp Gly Gln Thr Arg Tyr Phe Asp
        1220                1225                1230

Gln Gly Ser Gly Asn Leu Val Lys Gly Gln Phe Leu Asn Lys Asp
        1235                1240                1245

Gly Asn Trp Tyr Tyr Leu Asp Asp Gln Gly Leu Val Ala Lys Gly
        1250                1255                1260
```

```
Ala Gln Thr Ile Lys Gly Gln Lys Leu Tyr Phe Asp Thr Lys Thr
    1265                1270                1275

Gly Val Gln Val Lys Gly Asp Phe Val Thr Asp Lys Asp Gly Asn
    1280                1285                1290

Thr Phe Phe Tyr Ser Gly Asp Thr Gly Asp Leu Ile Leu Gly Gln
    1295                1300                1305

Phe Phe Ser Thr Gly Asn Asn Ala Trp Phe Tyr Ala Asp Glu Asn
    1310                1315                1320

Gly His Val Ala Lys Gly Ala Lys Thr Ile Arg Gly Gln Lys Leu
    1325                1330                1335

Tyr Phe Asp Thr Lys Thr Gly Gln Gln Ala Lys Gly Arg Phe Ile
    1340                1345                1350

Arg Asp Asp Lys Gly Val Arg Tyr Tyr Asp Ala Asp Thr Gly Thr
    1355                1360                1365

Leu Val Thr Asn Ala Phe Leu Glu Thr Lys Ala Gly Ser Asn Gln
    1370                1375                1380

Trp Tyr Tyr Met Gly Ala Asp Gly Tyr Ala Val Lys Gly Asn Gln
    1385                1390                1395

Thr Ile Lys Asn Gln His Met Tyr Phe Asp Ala Glu Thr Gly Gln
    1400                1405                1410

Gln Ala Lys Gly Ile Ile Val Thr Asp Ala Asn Gly Arg Lys Tyr
    1415                1420                1425

Phe Tyr Asp Thr Phe Thr Gly Ser Arg Val Val Asn Gln Phe Val
    1430                1435                1440

Leu Val Asn Gly Asn Trp Tyr Phe Phe Gly Tyr Asp Gly Ala Ala
    1445                1450                1455

Val Thr Gly Phe His Asp Ile Lys Gly Gln His Leu Tyr Phe Asn
    1460                1465                1470

Ser Asp Gly Thr Gln Ala Lys Gly Thr Thr Val Lys Ile Gly Asn
    1475                1480                1485

Arg Ser Tyr Thr Phe Asp Ala His Thr Gly Glu Leu Thr Ser Val
    1490                1495                1500

His Tyr Gly
    1505

<210> SEQ ID NO 13
<211> LENGTH: 1465
<212> TYPE: PRT
<213> ORGANISM: Streptococcus sobrinus
<220> FEATURE:
<221> NAME/KEY: MISC_FEATURE
<222> LOCATION: (1)..(1465)
<223> OTHER INFORMATION: mature 2920 gtf

<400> SEQUENCE: 13

Asp Asp Leu Ala Lys Glu Gln Ala Ala Ser Gln Gln Lys Ala Ala
1               5                   10                  15

Ala Asn Gln Asn Glu Asp Glu Val Ala Ser Asp Ala Asp Thr Ala
                20                  25                  30

Ser Ala Lys Ala Thr Ser Glu Lys Glu Val Val Gln Ser Ser Asp Thr
                35                  40                  45

Asn Ser Glu Thr Asn Gln Val Glu Thr Lys Asp Gln Ala Ser Ala Lys
    50                  55                  60

Glu Ser Ala Asp Ala Val Ala Lys Gln Ala Pro Gln Ala Gly Pro Ala
65                  70                  75                  80
```

-continued

```
Thr Thr Ser Gln Val Ala Ser Ser Glu Ser Ser Val Ala Pro Ser
            85                  90                  95

Lys Glu Ala Asp Lys Ala Ala Gly Ser Val Ser Gln Asn Glu Glu
        100                 105                 110

Glu Ala Ala Leu Ser Leu Ala Asn Ile Lys Lys Ile Asp Gly Lys Tyr
            115                 120                 125

Tyr Tyr Val Met Ala Asp Gly Ser Tyr Lys Lys Asn Phe Ala Ile Thr
        130                 135                 140

Val Asp Gly Gln Met Leu Tyr Phe Asp Ala Lys Thr Gly Ala Leu Ser
145                 150                 155                 160

Ser Thr Ser Thr Tyr Ser Phe Ser Gln Gly Leu Thr Pro Ile Val Ser
                165                 170                 175

Asp Phe Ser Val Asn Asn Lys Ala Phe Asp Ser Ser Glu Lys Ser Phe
            180                 185                 190

Glu Leu Val Asp Gly Tyr Leu Thr Ala Glu Ser Trp Tyr Arg Pro Ala
        195                 200                 205

Lys Ile Leu Glu Asn Gly Lys Thr Trp Val Asp Ser Lys Glu Thr Asp
210                 215                 220

Leu Arg Pro Val Leu Met Ser Trp Trp Pro Asn Lys Asp Thr Gln Val
225                 230                 235                 240

Ala Tyr Leu Asn Tyr Met Ser Lys Ala Leu Gly Gly Lys Glu Glu Phe
                245                 250                 255

Thr Thr Glu Thr Ser Gln Leu Thr Leu Asn Thr Ala Ala Glu Leu Ile
            260                 265                 270

Gln Ala Lys Ile Glu Ala Arg Val Ser Lys Glu Gln Gly Thr Lys Trp
        275                 280                 285

Leu Arg Glu Ala Met Ala Ala Phe Val Ala Thr Gln Ser Arg Trp Asn
290                 295                 300

Lys Asp Ser Glu Gln Tyr Asp Lys Ala Asp His Leu Gln Gly Gly Ala
305                 310                 315                 320

Leu Leu Tyr Thr Asn Asn Asn Leu Thr Glu Trp Ala Asn Ser Asn Trp
                325                 330                 335

Arg Leu Leu Asn Arg Thr Pro Thr Arg Gln Asp Gly Lys Thr His Tyr
            340                 345                 350

Ser Lys Ala Asp Lys Tyr Gly Gly Tyr Glu Phe Leu Leu Ala Asn Asp
        355                 360                 365

Val Asp Asn Ser Asn Pro Val Val Gln Ala Glu Met Leu Asn Gln Ile
        370                 375                 380

His Tyr Leu Met Asn Trp Gly Glu Ile Val Met Gly Asp Lys Asn Ala
385                 390                 395                 400

Asn Phe Asp Gly Ile Arg Val Asp Ala Val Asp Asn Val Asn Ala Asp
                405                 410                 415

Thr Leu Gln Leu Tyr Thr Asn Tyr Phe Asn Ser Val Tyr Gly Val Asn
            420                 425                 430

Lys Ser Glu Ala Gln Ala Leu Ala His Ile Ser Val Leu Glu Ala Trp
        435                 440                 445

Ser Tyr Asn Asp Asn Asp Tyr Asn Gln Asp Thr Asn Gly Ala Ala Leu
        450                 455                 460

Ala Met Asp Asn Gly Leu Arg Phe Ser Leu Leu Tyr Thr Leu Thr Arg
465                 470                 475                 480

Pro Ile Asn Glu Arg Thr Pro Gly Met Ser Thr Leu Ile Lys Ser Glu
                485                 490                 495

Tyr Gly Leu Thr Asp Arg Thr Lys Asn Asp Lys Tyr Gly Asp Thr Gln
```

-continued

```
                500                 505                 510
Pro Ser Tyr Val Phe Val Arg Ala His Asp Ser Glu Val Gln Thr Val
            515                 520                 525
Ile Ala Gln Ile Ile Lys Glu Lys Ile Asp Pro Thr Thr Asp Gly Phe
            530                 535                 540
Thr Phe Thr Leu Asp Gln Leu Lys Gln Ala Phe Glu Ile Tyr Asn Lys
545                 550                 555                 560
Asp Met Asn Ser Val Asn Lys His Tyr Thr His Tyr Asn Ile Pro Ala
                565                 570                 575
Ala Tyr Ala Val Met Leu Ser Asn Met Glu Ser Val Thr Arg Val Tyr
                580                 585                 590
Tyr Gly Asp Leu Phe Thr Asp Gly Gln Tyr Met Ala Ser Lys Ser
            595                 600                 605
Pro Tyr Tyr Asp Ala Ile Asn Thr Leu Leu Arg Ala Arg Ile Arg Tyr
            610                 615                 620
Ala Ala Gly Gly Gln Ile Met Glu His Asn Ser Tyr Lys Pro Ser Ala
625                 630                 635                 640
Ala Met Lys Ala Ala His Pro Asp Ala Gly Asn Val Leu Gly Asn Ser
                645                 650                 655
Glu Val Leu Val Ser Val Arg Phe Gly Gln Asp Val Met Ser Ala Asp
                660                 665                 670
Asp Met Thr Gly Gly Lys Leu Ala Lys Thr Ser Gly Met Phe Thr Leu
            675                 680                 685
Ile Ser Asn Asn Pro Glu Leu Glu Leu Asp Val Asn Glu Glu Ile Lys
            690                 695                 700
Val Asn Val Gly Lys Ile His Ala Gly Gln Ala Tyr Arg Pro Leu Leu
705                 710                 715                 720
Leu Thr Thr Asp Lys Gly Leu Gln Lys Tyr Leu Asn Asp Ser Asp Thr
                725                 730                 735
Lys Leu Thr Lys Ile Ala Asp Lys Asp Gly Phe Ile Thr Phe Lys Gly
            740                 745                 750
Ser Glu Ile Lys Gly Tyr Lys Gln Val Glu Val Asn Gly Tyr Leu Ser
            755                 760                 765
Val Trp Val Pro Val Gly Ala Lys Ala Asp Gln Asp Ile Arg Val Ala
770                 775                 780
Pro Ser Thr Ala Lys Gly Glu Lys Ala Lys Thr Tyr Thr Ala Ser
785                 790                 795                 800
Gln Ala Leu Glu Ser Gln Leu Ile Tyr Glu Gly Phe Ser Asn Phe Gln
                805                 810                 815
Asp Phe Val Gln Lys Asp Ser Gln Tyr Thr Asn Lys Lys Ile Ala Glu
                820                 825                 830
Asn Thr Asp Leu Phe Lys Ala Trp Gly Val Thr Ser Phe Glu Met Ala
            835                 840                 845
Pro Gln Tyr Val Ser Ala Thr Asp Gly Thr Phe Leu Asp Ser Ile Ile
            850                 855                 860
Glu Asn Gly Tyr Ala Phe Thr Asp Arg Tyr Asp Leu Ala Met Ser Lys
865                 870                 875                 880
Asn Asn Lys Tyr Gly Ser Lys Glu Asp Leu Ala Asn Ala Leu Lys Ala
                885                 890                 895
Leu His Ala Ala Gly Ile Gln Ala Ile Ala Asp Trp Val Pro Asp Gln
            900                 905                 910
Ile Tyr Gln Leu Pro Gly Lys Glu Val Val Thr Ala Ser Arg Val Asp
            915                 920                 925
```

-continued

```
Asn Tyr Gly Arg Val Lys Val Asp Gln Pro Leu Val Glu Lys Leu Tyr
    930                 935                 940
Leu Ala Asn Thr Lys Ser Ser Gly Lys Asp Phe Gln Ala Lys Tyr Gly
945                 950                 955                 960
Gly Glu Phe Leu Ala Glu Leu Gln Lys Lys Tyr Pro Glu Met Phe Thr
                965                 970                 975
Thr Lys Met Ile Ser Thr Gly Lys Thr Ile Asp Pro Ser Val Lys Leu
            980                 985                 990
Lys Glu Trp Ser Ala Lys Tyr Phe Asn Gly Thr Asn Val Leu Asp Arg
        995                 1000                1005
Gly Thr Asp Tyr Ile Leu Ser Asp Glu Thr Gly Lys Tyr Phe
    1010                1015                1020
Thr Val Asn Glu Lys Gly Asp Phe Leu Pro Ala Ser Leu Thr Gly
    1025                1030                1035
Asn Lys Asp Ala Lys Thr Gly Phe Tyr Asn Asp Gly Lys Gly Ile
    1040                1045                1050
Val Tyr Tyr Thr Thr Ala Gly Asn Lys Ala Arg Ser Ala Phe Val
    1055                1060                1065
Thr Glu Ala Gly Asn Thr Tyr Tyr Phe Asp Tyr Thr Gly His Met
    1070                1075                1080
Val Thr Gly Pro Asn Val Ile Asn Thr Lys Phe Tyr Tyr Phe Leu
    1085                1090                1095
Pro Asn Gly Ile Met Leu Lys Asp Ala Ile Lys Gln Asp Glu Lys
    1100                1105                1110
Gly Arg Ser Val Tyr Tyr Gly Lys Thr Gly Val Met Tyr Lys Gly
    1115                1120                1125
Gly Arg Asp Asn Glu Trp Phe Ala Met Thr Asp Ser Lys Gly Gln
    1130                1135                1140
Met Arg Phe Arg His Phe Asp Arg Tyr Gly Phe Met Ser Ile Gly
    1145                1150                1155
Leu Val Thr Ile Asn Gln Asn Val Gln Tyr Tyr Asp Glu Asn Gly
    1160                1165                1170
Phe Gln Val Lys Gly Glu Phe Val Thr Asp Gln Asp Gly Gln Thr
    1175                1180                1185
Arg Tyr Phe Asp Gln Gly Ser Gly Asn Leu Val Lys Gly Gln Phe
    1190                1195                1200
Leu Asn Lys Asp Gly Asn Trp Tyr Tyr Leu Asp Asp Gln Gly Leu
    1205                1210                1215
Val Ala Lys Gly Ala Gln Thr Ile Lys Gly Gln Lys Leu Tyr Phe
    1220                1225                1230
Asp Thr Lys Thr Gly Val Gln Val Lys Gly Asp Phe Val Thr Asp
    1235                1240                1245
Lys Asp Gly Asn Thr Phe Tyr Ser Gly Asp Thr Gly Asp Leu
    1250                1255                1260
Ile Leu Gly Gln Phe Phe Ser Thr Gly Asn Asn Ala Trp Phe Tyr
    1265                1270                1275
Ala Asp Glu Asn Gly His Val Ala Lys Gly Ala Lys Thr Ile Arg
    1280                1285                1290
Gly Gln Lys Leu Tyr Phe Asp Thr Lys Thr Gly Gln Gln Ala Lys
    1295                1300                1305
Gly Arg Phe Ile Arg Asp Asp Lys Gly Val Arg Tyr Tyr Asp Ala
    1310                1315                1320
```

| | | | | | | | | | | | |
|---|---|---|---|---|---|---|---|---|---|---|---|
| Asp | Thr | Gly | Thr | Leu | Val | Thr | Asn | Ala | Phe | Leu | Glu | Thr | Lys | Ala |
| | 1325 | | | | 1330 | | | | 1335 | | |

Asp Thr Gly Thr Leu Val Thr Asn Ala Phe Leu Glu Thr Lys Ala
    1325                1330                1335

Gly Ser Asn Gln Trp Tyr Tyr Met Gly Ala Asp Gly Tyr Ala Val
    1340                1345                1350

Lys Gly Asn Gln Thr Ile Lys Asn Gln His Met Tyr Phe Asp Ala
    1355                1360                1365

Glu Thr Gly Gln Gln Ala Lys Gly Ile Ile Val Thr Asp Ala Asn
    1370                1375                1380

Gly Arg Lys Tyr Phe Tyr Asp Thr Phe Thr Gly Ser Arg Val Val
    1385                1390                1395

Asn Gln Phe Val Leu Val Asn Gly Asn Trp Tyr Phe Phe Gly Tyr
    1400                1405                1410

Asp Gly Ala Ala Val Thr Gly Phe His Asp Ile Lys Gly Gln His
    1415                1420                1425

Leu Tyr Phe Asn Ser Asp Gly Thr Gln Ala Lys Gly Thr Thr Val
    1430                1435                1440

Lys Ile Gly Asn Arg Ser Tyr Thr Phe Asp Ala His Thr Gly Glu
    1445                1450                1455

Leu Thr Ser Val His Tyr Gly
    1460                1465

<210> SEQ ID NO 14
<211> LENGTH: 4398
<212> TYPE: DNA
<213> ORGANISM: Artificial sequence
<220> FEATURE:
<223> OTHER INFORMATION: 2920 gtf with heterologous signal sequence

<400> SEQUENCE: 14

```
gatgacctgg cgaaggaaca agcagccgcc tcacagcaaa aagcagcggc taaccagaat      60
gaagacgaag ttgcatcaga tgcagccgat acagctagcg ccaaagccac gtcagagaaa     120
gaagtggttc agtcaagcga tacaaactca gaaacaaatc aggttgagac gaaagaccaa     180
gcatcagcta aggagagcgc agacgcagtc gcgaaacaag ctcctcaagc aggaccggca     240
acaacgtcac aggtcgccag ctcagagagc agcagcgtgg caccgagcaa ggaggctgac     300
aaggctgccg caggctcagt ctcacagaac gaggaggagg cagccctttc acttgccaac     360
atcaagaaga ttgacggaaa atactattac gttatggccg atggaagcta caagaaaaac     420
tttgcgatta cggttgatgg acagatgctt tactttgacg caaaaacagg cgcactttca     480
tcaacgagca cgtatagctt ttcacaaggc ctgacgccga ttgtctcaga ctttagcgtg     540
aacaataagg ctttcgattc atcagaaaag tcatttgaac ttgtggacgg ctacctgaca     600
gccgaaagct ggtacagacc ggccaaaatc tggaaaacg gaaagacgtg ggtcgactca     660
aaagaaacag atcttagacc tgtcctgatg tcatggtggc gaacaaaga cacacaagtc     720
gcatatctga attacatgtc aaaagctctg ggaggcaaag aagagtttac gacagagaca     780
tcacaactga cactgaatac agcggcagaa cttatccagg cgaagatcga agctagagtg     840
agcaaagagc agggcacaaa atggctgaga gaagcaatgg cagcatttgt ggcgacgcaa     900
tcaagatgga ataagaattc agagcaatat gataaagcag atcatcttca aggcggagct     960
ctgctgtaca caaacaacaa ccttacagaa tgggctaatt caaattggag actgcttaat    1020
agaacaccga cgagacagga tggaaaaaca cattactcaa aggcagataa gtatggcgga    1080
tatgagtttc tgctggctaa tgatgtcgat aactcaaatc cggttgtcca agctgaaatg    1140
cttaaccaaa ttcattatct tatgaattgg ggcgaaattg ttatgggcga taagaatgct    1200
```

```
aacttcgacg gaatcagagt tgatgcagtt gacaacgtta atgcagatac actgcagctt   1260
tatacaaatt actttaatag cgtttatgga gtcaacaagt cagaagcaca ggcccttgca   1320
catatttcag tccttgaggc atggtcatat aatgataacg actataatca ggatacgaat   1380
ggcgcagcac ttgcgatgga taatggcctg agattctcac ttctgtatac gcttacaaga   1440
ccgattaatg aaagaacgcc tggcatgagc acactgatta agagcgaata cggactgacg   1500
gatagaacga aaaacgacaa gtacggcgac acgcaaccta gctatgtctt cgttagagca   1560
catgatagcg aggttcaaac ggttattgcc caaattatca aggagaaaat cgatcctaca   1620
acagatggct ttacatttac gctggatcaa ctgaagcaag ccttcgaaat ctataacaag   1680
gacatgaact cagtgaataa gcactacacg cattacaata ttcctgctgc atacgctgtt   1740
atgctgagca acatggaaag cgtgacaaga gtgtactacg gcgaccttt tacgatgac    1800
ggccagtata tggcaagcaa gtcaccttat tatgatgcta tcaatacact tcttagagcg   1860
agaattagat acgccgctgg aggacaaatc atggaacata attcatataa gccgagcgcc   1920
gcaatgaaag ctgcacaccc ggacgccggc aacgtcctgg gcaattcaga ggtcctggtc   1980
tcagtgagat tcggccaaga cgtgatgtca gcagatgata tgacaggcgg aaaacttgcg   2040
aaaacatcag gcatgtttac gcttattagc aataacccgg aactggaact tgacgttaat   2100
gaggagatca aagtgaatgt gggcaaaatc catgctggac aagcttatag accgcttctg   2160
cttacaacag ataagggact tcagaagtac cttaatgatt cagacacaaa actgacgaag   2220
atcgctgaca agacggatt cattacattc aaaggatcag aaattaaggg ctataaacaa    2280
gttgaggtta atggctacct ttcagtttgg gtcccggttg gcgctaaagc agaccaagat   2340
attagagttg ccccgagcac agccgcaaaa ggagaaaagg ctaaaacgta tacagcatca   2400
caggctctgg aatcacagct tatctatgaa ggcttctcaa actttcaaga ctttgttcaa   2460
aaagatagcc aatatacgaa taagaaaatt gcagagaaca cagacctgtt taaagcatgg   2520
ggagttacgt cattcgagat ggctcctcaa tatgttagcg caacggatgg cacattcctg   2580
gattcaatca ttgaaaacgg ctatgcattc acagacagat acgaccttgc tatgagcaag   2640
aataacaaat atggatcaaa agaggatctg gctaacgcac ttaaggcact tcacgcagct   2700
ggcattcaag ctattgcgga ttgggtgcct gaccaaatct accaactgcc gggcaaagag   2760
gttgtgacag ccagcagagt ggataactat ggcagagtta aggtggacca gccgcttgtc   2820
gagaagctgt atctggcgaa tacgaaatca tcaggaaaag atttccaggc taagtacggc   2880
ggagagttcc ttgcggagct gcagaagaaa tacccggaga tgttcacgac aaaaatgatc   2940
agcacaggaa agacaatcga cccgtcagtg aagctgaaag agtggtcagc caagtacttc   3000
aatgaacga acgtgctgga tagaggcaca gactatattc ttagcgatga gggaacggga   3060
aagtatttca cagtcaacga gaagggcgat ttcctgcctg cgagccttac aggcaacaag   3120
gatgccaaaa caggctttta caatgacgga aaaggaattg tttactacac aacagctgga   3180
aacaaggcta aagcgcgtt cgtgacagag gctggcaaca catactattt cgactatacg    3240
ggccacatgg tgacaggacc gaatgttatc aacacgaagt tctattactt tcttcctaac   3300
ggcatcatgc tgaaggacgc aattaagcaa gatgaaaagg gaagagcgt ttattacggc    3360
aagacaggag ttatgtacaa gggcggcaga gataacgaat ggtttgcaat gacagactca   3420
aagggacaga tgagatttag acatttcgat agatatggct tcatgtcaat tggacttgtt   3480
acaatcaacc agaatgttca atactatgat gagaatggct ttcaggtgaa aggcgaattt   3540
```

| | |
|---|---:|
| gtcacagatc aggatggaca acgagatac ttcgaccaag gctcaggcaa tcttgttaaa | 3600 |
| ggacagtttc ttaacaaaga tggaaattgg tattatctgg atgatcaagg actggttgct | 3660 |
| aaaggagctc aaacgattaa aggccaaaaa ctgtattttg atacgaagac gggcgtgcag | 3720 |
| gttaagggag attttgtgac ggacaaggac ggcaatacat tcttctatag cggagatacg | 3780 |
| ggagatctga ttctgggaca attctttca acgggcaata atgcatggtt ttatgcggac | 3840 |
| gagaacggac acgtcgccaa aggcgcaaaa acaatcagag acagaagct ttacttcgat | 3900 |
| acaaaaacgg acaacaagc caagggcaga ttcatcagag acgacaaggg agtcagatac | 3960 |
| tacgatgcag acacgggcac actggttaca aacgcatttc tggagacgaa ggcgggaagc | 4020 |
| aatcagtggt actacatggg cgctgatgga tatgccgtga agggaaacca gacgatcaag | 4080 |
| aaccagcata tgtactttga cgctgaaaca ggacagcaag ctaagggaat catcgttacg | 4140 |
| gacgcgaacg gcagaaaata cttctatgac acgtttacgg gctcaagagt tgttaatcaa | 4200 |
| ttcgttcttg tgaacggaaa ctggtacttt tttggatacg atggagcagc agttacagga | 4260 |
| ttccacgata tcaagggcca acatctttat ttcaactcag acgaacgca agcgaaaggc | 4320 |
| acgacagtta agatcggaaa tagaagctac acattcgacg cacacacagg cgagcttaca | 4380 |
| tcagtccatt acggatga | 4398 |

<210> SEQ ID NO 15
<211> LENGTH: 4360
<212> TYPE: DNA
<213> ORGANISM: Streptococcus downei

<400> SEQUENCE: 15

| | |
|---|---:|
| atgattttca tggaaagaaa attacattac aaattacaca aggtcaagaa gcagtgggtg | 60 |
| accatcgctg tcgcctctgc tggtttggcc agcgtagtcg gtgctggctc cttgagccaa | 120 |
| accgtttctg ctgacgatct tgctaaggac caagcggcag cgactgagca aaaggcatca | 180 |
| gccaatcagg aaaagaaga agtagttct gatcaggttg acacgaccag tgccaaagca | 240 |
| acctctgaga aggaagttgc tcaagcttcg acactagtt cagaagccaa ccaagttcca | 300 |
| gcccaagaag aaaagaaggc tgaaaaggca gctgctcctg cgacagcgac accagctcca | 360 |
| cagactggtg caaaaaacag ccaaacagct agttcagaag caccagcgac aagcaatcaa | 420 |
| gcaagtgaga cagctgaaac tggtgcctta agccaaaaag aagaagcagc agttctttcg | 480 |
| cttgataata tcaagaagat tgatggaaag tattactatg ttatggcaga cggctcttat | 540 |
| aagaagaact ttgccattac tgttgatggg caaatgcttt actttgatgc caaaacaggt | 600 |
| gccctgtctt caacctctac ctattctttc agtcaaggtt tgacaccaat tgtttctgat | 660 |
| ttctcagtca acaataaggc tttcgattct tctgaaaaga gttttgaact ggtagatggt | 720 |
| tacctgacag ctgaaagctg gtaccgtcct gctaagattc ttgaaaatgg caagacctgg | 780 |
| gtggactcca agaaactga ccttcgtcca gttctcatga gctggtggcc aaacaaggat | 840 |
| acccaagttg cctacctcaa ctatatgtcc aaggcgcttg gtggcaagga agagttaca | 900 |
| acagaaacct ctcaaacaac cttgaataca gctgctgagt tgattcaaac caagattgaa | 960 |
| gctcgtattt ctaaggaaca agggaccaaa tggcttcgtg aagctatggc tgctttttgta | 1020 |
| gcgactcagt ctcgttggag ttacgctagt gagcaatttg ataaaaacga ccacttgcaa | 1080 |
| ggtggtgctc tccttttatac taataataaa ttgacccaat gggcagattc taactatcgt | 1140 |
| ttgcttaacc gcacccctac ccgacaggat ggcaagcctc attattctaa agctgacgaa | 1200 |
| tacggtggtt acgaattcct cttggctaat gacgtggata actccaaccc agtcgttcaa | 1260 |

```
gcggaaatgc tcaaccaaat ccactacctg atgaactggg gctctattgt catgaatgac    1320
aaggatgcca actttgatgg tatccgtgtg atgcggtgg ataatgtcaa tgcggatacc    1380
ctgcaactct acactaacta ttttaattcg gtttatggtg tcaacaagtc agaagcccaa    1440
gccctagctc acatttcagt attagaagct tggtcttata tgataatga ctataaccaa    1500 gataccaatg gtgcggcctt ggctatggac aatggtctac gcttctccct gctttatacc    1560
ctgacacgtc cacttaatga gcggactcct ggtatgtcaa ccttgattaa gtcacaatat    1620
ggtttgactg accggaccaa ggatgacaag tatggcgata ctcagccatc ctatgtcttt    1680
gttcgggctc atgactcaga agtgcaaacc gttattgcgc aaatcatcaa gaaaaaaatt    1740
gatccaacga ctgatggctt taccttcacc ttggaccaat tgaaacaggc ctttgacatc    1800
tacaataagg atatgaatag tgttgataag cactataccc actacaatat tccagcagcc    1860
tacgctgtta tgttgtccaa catggaatca gtaactcggg tttactatgg agacctcttt    1920
accgatgatg gtcaatacat ggaaaccaag tctccttact acgatgctat caataccctc    1980
cttagggccc ggattcgtta cgccgctggt ggtcaaacca tggaacacaa ttcctataag    2040
gcatcagcag ctatgaaagc taaaaatcct gatagtggta gtgtgcttgg caacagcgaa    2100
gttcttgtct ctgttcgttt tggtcaagat gtgatgtctg ctgacgatat gactggtggt    2160
aagctggcta aaacctctgg tatgttcagc ctgatttcca acaaccctga attagaattg    2220
gatgccaatg aagaaatcag ggtcaatgtt ggtaagattc atgctggtca aacctaccgt    2280
ccattgcttt tgacaaccga taagggtctg caaaagtacc tcaatgattc tgatactaag    2340
ctgaccaagg ttgccgataa ggatggttat atcaccttca agggcagtga atcaagggc    2400 tacaagcagg ttgaagtcaa tggttaccttt tctgtttggg taccagtcgg cgcaaaggca    2460
gatcaagata ttcgtgtggc agcttcaact aaggttaatg gtaaggatga caagacttat    2520
acagctagtc aagccttaga atcacaatta atctacgaag gtttctcaaa cttccaagat    2580
ttcgttaaga aggactccca atataccaat aagaagattg ctgaaaatac cgacctcttt    2640
aaggcctggg gcgtgacctc atttgaaatg gcgccacaat acgtttccgc aactgatggt    2700
accttcctgg attctattat tgaaaatggt tatgccttca ccgaccgtta tgaccttgcc    2760
atgagcaaga caacaagta cggttctaag gaagacttgg ccaatgctct taaggccctc    2820
cacgctgctg gtatccaagc tatcgcagac tgggttccag accaaattta ccaactccca    2880
ggtaaggaag tggtaactgc aagtcgtgtt gataactatg ccgtgttaa gattgaccaa    2940 ccattggttg aaaaacttta cttggccaat accaagagct caggaaaaga cttccaggct    3000
aaatatggtg gtgaattctt agaagacctg caaaagcaat accctgaaat gtttaccgct    3060
aagatgattt caaccggtaa aaccattgat ccatctgtca aattgaagga atggtcagct    3120
aagtacttga acggaacaaa tgttctgggt cgtggtacag actatgtcct cagcgatgaa    3180
ggaactggca atacttcac tgttaatgaa aagggtgact tcctaccagc agccctgaca    3240
ggtgataggg aagccaagac tggtttctac aatgatggta agggaatgac ctactataca    3300
acggctggta acaaggctaa atctgccttt gtaaccgtag ctggaaatac ctattacttt    3360
gactatactg gttatatggt aacaggacca aacacgatta cagcaaatt ctattacttc    3420 ctgccaaatg gggtaatgct caaggatgct attaagcaag atgagttggg ccgttcggtt    3480
tactatggta aaactggtac catgtacaag gcgacagata atctcaatg gtttgccatg    3540 accgactcta agggtcaaca acgcttccgt cactttgacc gcttcggtat catgtctgta    3600
```

-continued

```
ggactggtta ccatcaatgg tagtgttcaa tattacgatg aagaaggctt ccaagttaag    3660
ggcgaatttg tcactgataa ggatggtcaa acccgttact ttgacgaagg ttctggtaat    3720
ctggttaagg accgcttcct caataaggat ggcaagtggt actatcttga tgataaaggc    3780
ttgctggtca aggggctca aaccattaag ggtcaaaaac tctactttga caccaagacc    3840
ggtgcccaag tcaagggtga ctttgttgcc gacaaggatg caacctgac cttctatagt    3900 ggtgatagtg tcaaatggt tcaaagtgat ttcttctcaa caggaaataa tgcttggttc    3960
tatgccgatg aaaatggtca tgtcgctaag ggagctaaga ctatcagagg tcagaagctc    4020
tactttgata caaaaacagg tcagcaagct aagggacgct ttatccgtga tgacaagggg    4080
gttcgttact atgatgctga cacaggtgcc ttggtaacca acgctttcct tgaaactaag    4140
gctggttcta accatggta ttacatggga gcagatggtt atgctgtcaa ggggaaccag    4200
accataaaaa atcagcacat gtattttgat gctgaaactg gccaacaagc taagggaatt    4260
atagtgacag atgccaatgg tcgcaagtat ttctatgata cttttactgg cagtcgtgtt    4320
gtaaaccaat ttgttttggt taatggaaat tggtatttct                         4360

<210> SEQ ID NO 16
<211> LENGTH: 1453
<212> TYPE: PRT
<213> ORGANISM: Streptococcus downei

<400> SEQUENCE: 16

Met Ile Phe Met Glu Arg Lys Leu His Tyr Lys Leu His Lys Val Lys
1               5                   10                  15

Lys Gln Trp Val Thr Ile Ala Val Ala Ser Ala Gly Leu Ala Ser Val
                20                  25                  30

Val Gly Ala Gly Ser Leu Ser Gln Thr Val Ser Ala Asp Asp Leu Ala
            35                  40                  45

Lys Asp Gln Ala Ala Ala Thr Glu Gln Lys Ala Ser Ala Asn Gln Glu
        50                  55                  60

Lys Glu Glu Val Val Ser Asp Gln Val Asp Thr Thr Ser Ala Lys Ala
65                  70                  75                  80

Thr Ser Glu Lys Glu Val Ala Gln Ala Ser Asp Thr Ser Glu Ala
                85                  90                  95

Asn Gln Val Pro Ala Gln Glu Glu Lys Lys Ala Glu Lys Ala Ala
                100                 105                 110

Pro Ala Thr Ala Thr Pro Ala Pro Gln Thr Gly Ala Lys Asn Ser Gln
            115                 120                 125

Thr Ala Ser Ser Glu Ala Pro Ala Thr Ser Asn Gln Ala Ser Glu Thr
        130                 135                 140

Ala Glu Thr Gly Ala Leu Ser Gln Lys Glu Glu Ala Ala Val Leu Ser
145                 150                 155                 160

Leu Asp Asn Ile Lys Lys Ile Asp Gly Lys Tyr Tyr Tyr Val Met Ala
                165                 170                 175

Asp Gly Ser Tyr Lys Lys Asn Phe Ala Ile Thr Val Asp Gly Gln Met
            180                 185                 190

Leu Tyr Phe Asp Ala Lys Thr Gly Ala Leu Ser Ser Thr Ser Thr Tyr
        195                 200                 205

Ser Phe Ser Gln Gly Leu Thr Pro Ile Val Ser Asp Phe Ser Val Asn
    210                 215                 220

Asn Lys Ala Phe Asp Ser Ser Glu Lys Ser Phe Glu Leu Val Asp Gly
225                 230                 235                 240
```

```
Tyr Leu Thr Ala Glu Ser Trp Tyr Arg Pro Ala Lys Ile Leu Glu Asn
            245                 250                 255

Gly Lys Thr Trp Val Asp Ser Lys Glu Thr Asp Leu Arg Pro Val Leu
            260                 265                 270

Met Ser Trp Trp Pro Asn Lys Asp Thr Gln Val Ala Tyr Leu Asn Tyr
            275                 280                 285

Met Ser Lys Ala Leu Gly Gly Lys Glu Glu Phe Thr Thr Glu Thr Ser
            290                 295                 300

Gln Thr Thr Leu Asn Thr Ala Ala Glu Leu Ile Gln Thr Lys Ile Glu
305                 310                 315                 320

Ala Arg Ile Ser Lys Glu Gln Gly Thr Lys Trp Leu Arg Glu Ala Met
            325                 330                 335

Ala Ala Phe Val Ala Thr Gln Ser Arg Trp Ser Tyr Ala Ser Glu Gln
            340                 345                 350

Phe Asp Lys Asn Asp His Leu Gln Gly Gly Ala Leu Leu Tyr Thr Asn
            355                 360                 365

Asn Lys Leu Thr Gln Trp Ala Asp Ser Asn Tyr Arg Leu Leu Asn Arg
            370                 375                 380

Thr Pro Thr Arg Gln Asp Gly Lys Pro His Tyr Ser Lys Ala Asp Glu
385                 390                 395                 400

Tyr Gly Gly Tyr Glu Phe Leu Leu Ala Asn Asp Val Asp Asn Ser Asn
            405                 410                 415

Pro Val Val Gln Ala Glu Met Leu Asn Gln Ile His Tyr Leu Met Asn
            420                 425                 430

Trp Gly Ser Ile Val Met Asn Asp Lys Asp Ala Asn Phe Asp Gly Ile
            435                 440                 445

Arg Val Asp Ala Val Asp Asn Val Asn Ala Asp Thr Leu Gln Leu Tyr
            450                 455                 460

Thr Asn Tyr Phe Asn Ser Val Tyr Gly Val Asn Lys Ser Glu Ala Gln
465                 470                 475                 480

Ala Leu Ala His Ile Ser Val Leu Glu Ala Trp Ser Tyr Asn Asp Asn
            485                 490                 495

Asp Tyr Asn Gln Asp Thr Asn Gly Ala Ala Leu Ala Met Asp Asn Gly
            500                 505                 510

Leu Arg Phe Ser Leu Leu Tyr Thr Leu Thr Arg Pro Leu Asn Glu Arg
            515                 520                 525

Thr Pro Gly Met Ser Thr Leu Ile Lys Ser Gln Tyr Gly Leu Thr Asp
            530                 535                 540

Arg Thr Lys Asp Asp Lys Tyr Gly Asp Thr Gln Pro Ser Tyr Val Phe
545                 550                 555                 560

Val Arg Ala His Asp Ser Glu Val Gln Thr Val Ile Ala Gln Ile Ile
            565                 570                 575

Lys Lys Lys Ile Asp Pro Thr Thr Asp Gly Phe Thr Phe Thr Leu Asp
            580                 585                 590

Gln Leu Lys Gln Ala Phe Asp Ile Tyr Asn Lys Asp Met Asn Ser Val
            595                 600                 605

Asp Lys His Tyr Thr His Tyr Asn Ile Pro Ala Ala Tyr Ala Val Met
            610                 615                 620

Leu Ser Asn Met Glu Ser Val Thr Arg Val Tyr Tyr Gly Asp Leu Phe
625                 630                 635                 640

Thr Asp Asp Gly Gln Tyr Met Glu Thr Lys Ser Pro Tyr Tyr Asp Ala
            645                 650                 655

Ile Asn Thr Leu Leu Arg Ala Arg Ile Arg Tyr Ala Ala Gly Gly Gln
```

-continued

```
                660                 665                 670
Thr Met Glu His Asn Ser Tyr Lys Ala Ser Ala Ala Met Lys Ala Lys
            675                 680                 685

Asn Pro Asp Ser Gly Ser Val Leu Gly Asn Ser Glu Val Leu Val Ser
        690                 695                 700

Val Arg Phe Gly Gln Asp Val Met Ser Ala Asp Met Thr Gly Gly
705                 710                 715                 720

Lys Leu Ala Lys Thr Ser Gly Met Phe Ser Leu Ile Ser Asn Asn Pro
                725                 730                 735

Glu Leu Glu Leu Asp Ala Asn Glu Glu Ile Arg Val Asn Val Gly Lys
            740                 745                 750

Ile His Ala Gly Gln Thr Tyr Arg Pro Leu Leu Thr Thr Asp Lys
        755                 760                 765

Gly Leu Gln Lys Tyr Leu Asn Asp Ser Asp Thr Lys Leu Thr Lys Val
    770                 775                 780

Ala Asp Lys Asp Gly Tyr Ile Thr Phe Lys Gly Ser Glu Ile Lys Gly
785                 790                 795                 800

Tyr Lys Gln Val Glu Val Asn Gly Tyr Leu Ser Val Trp Val Pro Val
                805                 810                 815

Gly Ala Lys Ala Asp Gln Asp Ile Arg Val Ala Ala Ser Thr Lys Val
            820                 825                 830

Asn Gly Lys Asp Lys Thr Tyr Thr Ala Ser Gln Ala Leu Glu Ser
        835                 840                 845

Gln Leu Ile Tyr Glu Gly Phe Ser Asn Phe Gln Asp Phe Val Lys Lys
    850                 855                 860

Asp Ser Gln Tyr Thr Asn Lys Lys Ile Ala Glu Asn Thr Asp Leu Phe
865                 870                 875                 880

Lys Ala Trp Gly Val Thr Ser Phe Glu Met Ala Pro Gln Tyr Val Ser
                885                 890                 895

Ala Thr Asp Gly Thr Phe Leu Asp Ser Ile Ile Glu Asn Gly Tyr Ala
            900                 905                 910

Phe Thr Asp Arg Tyr Asp Leu Ala Met Ser Lys Asn Asn Lys Tyr Gly
        915                 920                 925

Ser Lys Glu Asp Leu Ala Asn Ala Leu Lys Ala Leu His Ala Ala Gly
    930                 935                 940

Ile Gln Ala Ile Ala Asp Trp Val Pro Asp Gln Ile Tyr Gln Leu Pro
945                 950                 955                 960

Gly Lys Glu Val Val Thr Ala Ser Arg Val Asp Asn Tyr Gly Arg Val
                965                 970                 975

Lys Ile Asp Gln Pro Leu Val Glu Lys Leu Tyr Leu Ala Asn Thr Lys
            980                 985                 990

Ser Ser Gly Lys Asp Phe Gln Ala Lys Tyr Gly Gly Glu Phe Leu Glu
        995                 1000                1005

Asp Leu Gln Lys Gln Tyr Pro Glu Met Phe Thr Ala Lys Met Ile
    1010                1015                1020

Ser Thr Gly Lys Thr Ile Asp Pro Ser Val Lys Leu Lys Glu Trp
    1025                1030                1035

Ser Ala Lys Tyr Leu Asn Gly Thr Asn Val Leu Gly Arg Gly Thr
    1040                1045                1050

Asp Tyr Val Leu Ser Asp Glu Gly Thr Gly Lys Tyr Phe Thr Val
    1055                1060                1065

Asn Glu Lys Gly Asp Phe Leu Pro Ala Ala Leu Thr Gly Asp Arg
    1070                1075                1080
```

Glu Ala Lys Thr Gly Phe Tyr Asn Asp Gly Lys Gly Met Thr Tyr
1085            1090                1095

Tyr Thr Thr Ala Gly Asn Lys Ala Lys Ser Ala Phe Val Thr Val
1100            1105                1110

Ala Gly Asn Thr Tyr Tyr Phe Asp Tyr Thr Gly Tyr Met Val Thr
1115            1120                1125

Gly Pro Asn Thr Ile Asn Ser Lys Phe Tyr Tyr Phe Leu Pro Asn
1130            1135                1140

Gly Val Met Leu Lys Asp Ala Ile Lys Gln Asp Glu Leu Gly Arg
1145            1150                1155

Ser Val Tyr Tyr Gly Lys Thr Gly Thr Met Tyr Lys Ala Thr Asp
1160            1165                1170

Lys Ser Gln Trp Phe Ala Met Thr Asp Ser Lys Gly Gln Gln Arg
1175            1180                1185

Phe Arg His Phe Asp Arg Phe Gly Ile Met Ser Val Gly Leu Val
1190            1195                1200

Thr Ile Asn Gly Ser Val Gln Tyr Tyr Asp Glu Glu Gly Phe Gln
1205            1210                1215

Val Lys Gly Glu Phe Val Thr Asp Lys Asp Gly Gln Thr Arg Tyr
1220            1225                1230

Phe Asp Glu Gly Ser Gly Asn Leu Val Lys Asp Arg Phe Leu Asn
1235            1240                1245

Lys Asp Gly Lys Trp Tyr Tyr Leu Asp Asp Lys Gly Leu Leu Val
1250            1255                1260

Lys Gly Ala Gln Thr Ile Lys Gly Gln Lys Leu Tyr Phe Asp Thr
1265            1270                1275

Lys Thr Gly Ala Gln Val Lys Gly Asp Phe Val Ala Asp Lys Asp
1280            1285                1290

Gly Asn Leu Thr Phe Tyr Ser Gly Asp Ser Gly Gln Met Val Gln
1295            1300                1305

Ser Asp Phe Phe Ser Thr Gly Asn Asn Ala Trp Phe Tyr Ala Asp
1310            1315                1320

Glu Asn Gly His Val Ala Lys Gly Ala Lys Thr Ile Arg Gly Gln
1325            1330                1335

Lys Leu Tyr Phe Asp Thr Lys Thr Gly Gln Gln Ala Lys Gly Arg
1340            1345                1350

Phe Ile Arg Asp Asp Lys Gly Val Arg Tyr Tyr Asp Ala Asp Thr
1355            1360                1365

Gly Ala Leu Val Thr Asn Ala Phe Leu Glu Thr Lys Ala Gly Ser
1370            1375                1380

Asn Gln Trp Tyr Tyr Met Gly Ala Asp Gly Tyr Ala Val Lys Gly
1385            1390                1395

Asn Gln Thr Ile Lys Asn Gln His Met Tyr Phe Asp Ala Glu Thr
1400            1405                1410

Gly Gln Gln Ala Lys Gly Ile Ile Val Thr Asp Ala Asn Gly Arg
1415            1420                1425

Lys Tyr Phe Tyr Asp Thr Phe Thr Gly Ser Arg Val Val Asn Gln
1430            1435                1440

Phe Val Leu Val Asn Gly Asn Trp Tyr Phe
1445            1450

<210> SEQ ID NO 17
<211> LENGTH: 1409

```
<212> TYPE: PRT
<213> ORGANISM: Streptococcus downei
<220> FEATURE:
<221> NAME/KEY: MISC_FEATURE
<222> LOCATION: (1)..(1409)
<223> OTHER INFORMATION: mature 2921 gtf

<400> SEQUENCE: 17
```

| | | | | | | | | | | | | | | | |
|---|---|---|---|---|---|---|---|---|---|---|---|---|---|---|---|
| Asp | Asp | Leu | Ala | Lys | Asp | Gln | Ala | Ala | Ala | Thr | Glu | Gln | Lys | Ala | Ser |
| 1 | | | | 5 | | | | | 10 | | | | | 15 | |
| Ala | Asn | Gln | Glu | Lys | Glu | Val | Val | Ser | Asp | Gln | Val | Asp | Thr | Thr | |
| | | | 20 | | | | | 25 | | | | | 30 | | |
| Ser | Ala | Lys | Ala | Thr | Ser | Glu | Lys | Glu | Val | Ala | Gln | Ala | Ser | Asp | Thr |
| | | 35 | | | | | 40 | | | | | 45 | | | |
| Ser | Ser | Glu | Ala | Asn | Gln | Val | Pro | Ala | Gln | Glu | Glu | Lys | Lys | Ala | Glu |
| | 50 | | | | | 55 | | | | | 60 | | | | |
| Lys | Ala | Ala | Ala | Pro | Ala | Thr | Ala | Thr | Pro | Ala | Pro | Gln | Thr | Gly | Ala |
| 65 | | | | | 70 | | | | | 75 | | | | | 80 |
| Lys | Asn | Ser | Gln | Thr | Ala | Ser | Ser | Glu | Ala | Pro | Ala | Thr | Ser | Asn | Gln |
| | | | | 85 | | | | | 90 | | | | | 95 | |
| Ala | Ser | Glu | Thr | Ala | Glu | Thr | Gly | Ala | Leu | Ser | Gln | Lys | Glu | Glu | Ala |
| | | | 100 | | | | | 105 | | | | | 110 | | |
| Ala | Val | Leu | Ser | Leu | Asp | Asn | Ile | Lys | Lys | Ile | Asp | Gly | Lys | Tyr | Tyr |
| | | 115 | | | | | 120 | | | | | 125 | | | |
| Tyr | Val | Met | Ala | Asp | Gly | Ser | Tyr | Lys | Lys | Asn | Phe | Ala | Ile | Thr | Val |
| | 130 | | | | | 135 | | | | | 140 | | | | |
| Asp | Gly | Gln | Met | Leu | Tyr | Phe | Asp | Ala | Lys | Thr | Gly | Ala | Leu | Ser | Ser |
| 145 | | | | | 150 | | | | | 155 | | | | | 160 |
| Thr | Ser | Thr | Tyr | Ser | Phe | Ser | Gln | Gly | Leu | Thr | Pro | Ile | Val | Ser | Asp |
| | | | | 165 | | | | | 170 | | | | | 175 | |
| Phe | Ser | Val | Asn | Asn | Lys | Ala | Phe | Asp | Ser | Ser | Glu | Lys | Ser | Phe | Glu |
| | | | 180 | | | | | 185 | | | | | 190 | | |
| Leu | Val | Asp | Gly | Tyr | Leu | Thr | Ala | Glu | Ser | Trp | Tyr | Arg | Pro | Ala | Lys |
| | | 195 | | | | | 200 | | | | | 205 | | | |
| Ile | Leu | Glu | Asn | Gly | Lys | Thr | Trp | Val | Asp | Ser | Lys | Glu | Thr | Asp | Leu |
| | 210 | | | | | 215 | | | | | 220 | | | | |
| Arg | Pro | Val | Leu | Met | Ser | Trp | Trp | Pro | Asn | Lys | Asp | Thr | Gln | Val | Ala |
| 225 | | | | | 230 | | | | | 235 | | | | | 240 |
| Tyr | Leu | Asn | Tyr | Met | Ser | Lys | Ala | Leu | Gly | Gly | Lys | Glu | Glu | Phe | Thr |
| | | | | 245 | | | | | 250 | | | | | 255 | |
| Thr | Glu | Thr | Ser | Gln | Thr | Thr | Leu | Asn | Thr | Ala | Ala | Glu | Leu | Ile | Gln |
| | | | 260 | | | | | 265 | | | | | 270 | | |
| Thr | Lys | Ile | Glu | Ala | Arg | Ile | Ser | Lys | Glu | Gln | Gly | Thr | Lys | Trp | Leu |
| | | 275 | | | | | 280 | | | | | 285 | | | |
| Arg | Glu | Ala | Met | Ala | Ala | Phe | Val | Ala | Thr | Gln | Ser | Arg | Trp | Ser | Tyr |
| | 290 | | | | | 295 | | | | | 300 | | | | |
| Ala | Ser | Glu | Gln | Phe | Asp | Lys | Asn | Asp | His | Leu | Gln | Gly | Gly | Ala | Leu |
| 305 | | | | | 310 | | | | | 315 | | | | | 320 |
| Leu | Tyr | Thr | Asn | Asn | Lys | Leu | Thr | Gln | Trp | Ala | Asp | Ser | Asn | Tyr | Arg |
| | | | | 325 | | | | | 330 | | | | | 335 | |
| Leu | Leu | Asn | Arg | Thr | Pro | Thr | Arg | Gln | Asp | Gly | Lys | Pro | His | Tyr | Ser |
| | | | 340 | | | | | 345 | | | | | 350 | | |
| Lys | Ala | Asp | Glu | Tyr | Gly | Gly | Tyr | Glu | Phe | Leu | Leu | Ala | Asn | Asp | Val |
| | | 355 | | | | | 360 | | | | | 365 | | | |
| Asp | Asn | Ser | Asn | Pro | Val | Val | Gln | Ala | Glu | Met | Leu | Asn | Gln | Ile | His |

```
            370                 375                 380
Tyr Leu Met Asn Trp Gly Ser Ile Val Met Asn Asp Lys Asp Ala Asn
385                 390                 395                 400

Phe Asp Gly Ile Arg Val Asp Ala Val Asp Asn Val Asn Ala Asp Thr
                405                 410                 415

Leu Gln Leu Tyr Thr Asn Tyr Phe Asn Ser Val Tyr Gly Val Asn Lys
            420                 425                 430

Ser Glu Ala Gln Ala Leu Ala His Ile Ser Val Leu Glu Ala Trp Ser
        435                 440                 445

Tyr Asn Asp Asn Asp Tyr Asn Gln Asp Thr Asn Gly Ala Ala Leu Ala
    450                 455                 460

Met Asp Asn Gly Leu Arg Phe Ser Leu Leu Tyr Thr Leu Thr Arg Pro
465                 470                 475                 480

Leu Asn Glu Arg Thr Pro Gly Met Ser Thr Leu Ile Lys Ser Gln Tyr
                485                 490                 495

Gly Leu Thr Asp Arg Thr Lys Asp Lys Tyr Gly Asp Thr Gln Pro
            500                 505                 510

Ser Tyr Val Phe Val Arg Ala His Asp Ser Glu Val Gln Thr Val Ile
        515                 520                 525

Ala Gln Ile Ile Lys Lys Ile Asp Pro Thr Thr Asp Gly Phe Thr
    530                 535                 540

Phe Thr Leu Asp Gln Leu Lys Gln Ala Phe Asp Ile Tyr Asn Lys Asp
545                 550                 555                 560

Met Asn Ser Val Asp Lys His Tyr Thr His Tyr Asn Ile Pro Ala Ala
                565                 570                 575

Tyr Ala Val Met Leu Ser Asn Met Glu Ser Val Thr Arg Val Tyr Tyr
            580                 585                 590

Gly Asp Leu Phe Thr Asp Asp Gly Gln Tyr Met Glu Thr Lys Ser Pro
        595                 600                 605

Tyr Tyr Asp Ala Ile Asn Thr Leu Leu Arg Ala Arg Ile Arg Tyr Ala
    610                 615                 620

Ala Gly Gly Gln Thr Met Glu His Asn Ser Tyr Lys Ala Ser Ala Ala
625                 630                 635                 640

Met Lys Ala Lys Asn Pro Asp Ser Gly Ser Val Leu Gly Asn Ser Glu
                645                 650                 655

Val Leu Val Ser Val Arg Phe Gly Gln Asp Val Met Ser Ala Asp Asp
            660                 665                 670

Met Thr Gly Gly Lys Leu Ala Lys Thr Ser Gly Met Phe Ser Leu Ile
        675                 680                 685

Ser Asn Asn Pro Glu Leu Glu Leu Asp Ala Asn Glu Glu Ile Arg Val
    690                 695                 700

Asn Val Gly Lys Ile His Ala Gly Gln Thr Tyr Arg Pro Leu Leu Leu
705                 710                 715                 720

Thr Thr Asp Lys Gly Leu Gln Lys Tyr Leu Asn Asp Ser Asp Thr Lys
                725                 730                 735

Leu Thr Lys Val Ala Asp Lys Asp Gly Tyr Ile Thr Phe Lys Gly Ser
            740                 745                 750

Glu Ile Lys Gly Tyr Lys Gln Val Glu Val Asn Gly Tyr Leu Ser Val
        755                 760                 765

Trp Val Pro Val Gly Ala Lys Ala Asp Gln Asp Ile Arg Val Ala Ala
    770                 775                 780

Ser Thr Lys Val Asn Gly Lys Asp Asp Lys Thr Tyr Thr Ala Ser Gln
785                 790                 795                 800
```

```
Ala Leu Glu Ser Gln Leu Ile Tyr Glu Gly Phe Ser Asn Phe Gln Asp
            805                 810                 815

Phe Val Lys Lys Asp Ser Gln Tyr Thr Asn Lys Lys Ile Ala Glu Asn
            820                 825                 830

Thr Asp Leu Phe Lys Ala Trp Gly Val Thr Ser Phe Glu Met Ala Pro
            835                 840                 845

Gln Tyr Val Ser Ala Thr Asp Gly Thr Phe Leu Asp Ser Ile Ile Glu
            850                 855                 860

Asn Gly Tyr Ala Phe Thr Asp Arg Tyr Asp Leu Ala Met Ser Lys Asn
865                 870                 875                 880

Asn Lys Tyr Gly Ser Lys Glu Asp Leu Ala Asn Ala Leu Lys Ala Leu
            885                 890                 895

His Ala Ala Gly Ile Gln Ala Ile Ala Asp Trp Val Pro Asp Gln Ile
            900                 905                 910

Tyr Gln Leu Pro Gly Lys Glu Val Val Thr Ala Ser Arg Val Asp Asn
            915                 920                 925

Tyr Gly Arg Val Lys Ile Asp Gln Pro Leu Val Glu Lys Leu Tyr Leu
            930                 935                 940

Ala Asn Thr Lys Ser Ser Gly Lys Asp Phe Gln Ala Lys Tyr Gly Gly
945                 950                 955                 960

Glu Phe Leu Glu Asp Leu Gln Lys Gln Tyr Pro Glu Met Phe Thr Ala
            965                 970                 975

Lys Met Ile Ser Thr Gly Lys Thr Ile Asp Pro Ser Val Lys Leu Lys
            980                 985                 990

Glu Trp Ser Ala Lys Tyr Leu Asn Gly Thr Asn Val Leu Gly Arg Gly
            995                 1000                1005

Thr Asp Tyr Val Leu Ser Asp Glu Gly Thr Gly Lys Tyr Phe Thr
        1010                1015                1020

Val Asn Glu Lys Gly Asp Phe Leu Pro Ala Ala Leu Thr Gly Asp
        1025                1030                1035

Arg Glu Ala Lys Thr Gly Phe Tyr Asn Asp Gly Lys Gly Met Thr
        1040                1045                1050

Tyr Tyr Thr Thr Ala Gly Asn Lys Ala Lys Ser Ala Phe Val Thr
        1055                1060                1065

Val Ala Gly Asn Thr Tyr Tyr Phe Asp Tyr Thr Gly Tyr Met Val
        1070                1075                1080

Thr Gly Pro Asn Thr Ile Asn Ser Lys Phe Tyr Tyr Phe Leu Pro
        1085                1090                1095

Asn Gly Val Met Leu Lys Asp Ala Ile Lys Gln Asp Glu Leu Gly
        1100                1105                1110

Arg Ser Val Tyr Tyr Gly Lys Thr Gly Thr Met Tyr Lys Ala Thr
        1115                1120                1125

Asp Lys Ser Gln Trp Phe Ala Met Thr Asp Ser Lys Gly Gln Gln
        1130                1135                1140

Arg Phe Arg His Phe Asp Arg Phe Gly Ile Met Ser Val Gly Leu
        1145                1150                1155

Val Thr Ile Asn Gly Ser Val Gln Tyr Tyr Asp Glu Glu Gly Phe
        1160                1165                1170

Gln Val Lys Gly Glu Phe Val Thr Asp Lys Asp Gly Gln Thr Arg
        1175                1180                1185

Tyr Phe Asp Glu Gly Ser Gly Asn Leu Val Lys Asp Arg Phe Leu
        1190                1195                1200
```

| | | | | | | | | | |
|---|---|---|---|---|---|---|---|---|---|
Asn Lys Asp Gly Lys Trp Tyr Tyr Leu Asp Asp Lys Gly Leu Leu
1205 1210 1215

Val Lys Gly Ala Gln Thr Ile Lys Gly Gln Lys Leu Tyr Phe Asp
1220 1225 1230

Thr Lys Thr Gly Ala Gln Val Lys Gly Asp Phe Val Ala Asp Lys
1235 1240 1245

Asp Gly Asn Leu Thr Phe Tyr Ser Gly Asp Ser Gly Gln Met Val
1250 1255 1260

Gln Ser Asp Phe Phe Ser Thr Gly Asn Asn Ala Trp Phe Tyr Ala
1265 1270 1275

Asp Glu Asn Gly His Val Ala Lys Gly Ala Lys Thr Ile Arg Gly
1280 1285 1290

Gln Lys Leu Tyr Phe Asp Thr Lys Thr Gly Gln Gln Ala Lys Gly
1295 1300 1305

Arg Phe Ile Arg Asp Asp Lys Gly Val Arg Tyr Tyr Asp Ala Asp
1310 1315 1320

Thr Gly Ala Leu Val Thr Asn Ala Phe Leu Glu Thr Lys Ala Gly
1325 1330 1335

Ser Asn Gln Trp Tyr Tyr Met Gly Ala Asp Gly Tyr Ala Val Lys
1340 1345 1350

Gly Asn Gln Thr Ile Lys Asn Gln His Met Tyr Phe Asp Ala Glu
1355 1360 1365

Thr Gly Gln Gln Ala Lys Gly Ile Ile Val Thr Asp Ala Asn Gly
1370 1375 1380

Arg Lys Tyr Phe Tyr Asp Thr Phe Thr Gly Ser Arg Val Val Asn
1385 1390 1395

Gln Phe Val Leu Val Asn Gly Asn Trp Tyr Phe
1400 1405

<210> SEQ ID NO 18
<211> LENGTH: 4230
<212> TYPE: DNA
<213> ORGANISM: Artificial sequence
<220> FEATURE:
<223> OTHER INFORMATION: 2921 gtf with heterologous signal sequence

<400> SEQUENCE: 18

```
gatgatctgg caaaggacca agcggctgcc acggaacaga aggcatcagc gaatcaagaa      60
aaggaggaag ttgtttcaga tcaagttgat acgacaagcg ccaaagcaac gtcagaaaaa     120
gaggtggcac aggctagcga tacatcatca gaggccaacc aggttccggc ccaagaggaa     180
aagaaagccg agaaggccgc agcacctgcg acagctacgc cggcaccgca aacgggagcc     240
aaaaatagcc aaacagcctc aagcgaggca ccggctacat caaatcaagc atcagaaacg     300
gcggaaacag gcgcactgtc acaaaaggaa gaagcagctg tcctttcact tgataatatc     360
aaaaagattg acggaaaata ctactatgtt atggctgatg gatcatataa gaaaaacttt     420
gcgattacag tcgatggcca aatgctgtat tttgatgcaa aacaggagc tctttcaagc     480
acatcaacat attcatttc acaaggcctg acaccgattg ttagcgactt ctcagtcaat     540
aacaaggcat tgatagcag cgagaaatca ttcgaacttg tggatggata tcttacggcc     600
gagagctggt acagaccggc aaaaattctg gagaatggaa agacgtgggt tgattcaaaa     660
gagacggacc ttagaccggt gctgatgtca tggtggccga ataaggatac gcaggttgcc     720
tacctgaact atatgtcaaa agcacttggc ggcaaagagg agtttacaac ggagacatca     780
caaacgacac ttaacacggc tgctgaactt atccagacga agatcgaggc aagaattagc     840
```

```
aaagaacaag gaacgaagtg gcttagagaa gctatggccg catttgttgc tacgcagtca    900
agatggtcat atgcgtcaga gcagttcgat aaaaacgatc accttcaagg cggagcactt    960
ctgtacacaa ataataagct gacacaatgg gctgactcaa actatagact gcttaacaga   1020
acgcctacga gacaggatgg aaaacctcat tacagcaaag cagacgagta tggaggctat   1080
gagttcctgc ttgcaaatga cgtcgataac tcaaatccgg tggttcaggc agagatgctt   1140
aatcaaattc actatcttat gaactggggc tcaattgtta tgaatgataa ggacgcgaat   1200
ttcgatggaa ttagagtgga tgcggttgac aatgttaatg cggacacact tcaactgtat   1260
acgaattact ttaactcagt ttacggcgtt aacaaatcag aagctcaggc acttgctcat   1320
atcagcgttc ttgaagcatg gagctacaac gacaatgatt acaatcagga tacaaatggc   1380
gctgcactgg ccatggataa tggacttaga ttcagccttc tttacacact gacaagaccg   1440
cttaacgaga gaacacctgg catgtcaaca cttattaagt cacaatatgg ccttacagac   1500
agaacaaaag acgataagta cggcgacacg caaccgtcat acgtgtttgt tagagctcac   1560
gacagcgaag ttcaaacagt tattgctcag attattaaga gaaaattga tccgacaaca    1620
gacggattca catttacact ggaccaactt aaacaagcct tcgatatcta taacaaagat   1680
atgaatagcg ttgataaaca ttacacgcac tacaatattc ctgcagcata cgctgtcatg   1740
ctgtcaaaca tggaatcagt tacaagagtc tattatggcg acctgtttac agatgacggc   1800
caatatatgg aaacaaaatc accgtactat gacgccatta atacactgct gagagccaga   1860
atcagatatg cagctggcgg acaaacaatg gaacacaaca gctataaggc gtcagctgcg   1920
atgaaggcga aaaccctga tagcggctca gtccttggca attcagaagt tctggttagc   1980
gttagatttg acaagatgt gatgagcgct gacgatatga caggaggcaa acttgctaag   2040
acgtcaggaa tgttctcact gatttcaaat aatccggaac tggaacttga cgctaatgaa   2100
gagatcagag tgaatgttgg aaaaatccat gccggccaaa cgtacagacc tcttctgctt   2160
acgacagata agggcctgca aaagtatctt aatgactcag acacgaaact tacgaaggtt   2220
gcagataaag atggctatat tacatttaag ggctcagaga ttaaaggcta taaacaggtt   2280
gaagttaatg gctacctgag cgtctgggtg ccggttggcg ctaaagcaga ccaagacatc   2340
agagtcgcag cttcaacaaa agtcaatgga aaggatgata agacgtacac ggcaagccaa   2400
gcacttgagt cacagcttat ttacgagggc ttctcaaatt ccaagatttt cgttaagaaa   2460
gattcacaat atacaaataa gaaaatcgcg gaaaatacag atcttttcaa agcatggggc   2520
gttacatcat ttgaaatggc gcctcagtat gttagcgcaa cagatggcac atttctggat   2580
agcattatcg agaatggata tgcatttacg gatagatatg acctggccat gtcaaaaaac   2640
aacaaatacg gatcaaaaga ggatcttgct aatgcgctta agctctgca cgcagctggc   2700
attcaagcca ttgcggattg ggttcctgat caaatctacc aacttcctgg caaggaggtt   2760
gttacagcat caagagtcga caattacggc agagtgaaga tcgaccaacc tctggtggaa   2820
aagctgtatc tggctaacac aaagagctca ggcaaagatt ttcaggcgaa atatggcgga   2880
gaattcttg aagacctgca gaaacagtat cctgaaatgt ttacagcgaa aatgatttca   2940
acaggaaaaa cgattgatcc tagcgttaaa cttaaggagt ggtcagccaa atacctgaat   3000
ggaacaaacg tgctgggaag aggcacagat tatgttcttt cagatgaggg aacgggcaaa   3060
tactttacgg tcaatgagaa aggcgatttc ctgccggctg cacttacagg cgatagaaa   3120
gcaaagacag gattctataa tgacggcaaa ggcatgacgt attacacaac ggccggaaat   3180
```

```
aaggcgaaga gcgcgttcgt tacagtggcg ggcaacacat actactttga ttatacggga    3240
tatatggtta caggacctaa tacaattaac agcaagtttt actatttcct tcctaatggc    3300
gttatgctga aggatgcaat taagcaggat gaacttggaa gatcagtcta ctatggcaaa    3360
acgggaacaa tgtataaggc aacggataaa tcacagtggt tcgccatgac agatagcaag    3420
ggacaacaga gattcagaca ttttgataga ttcggaatca tgagcgttgg acttgtcacg    3480
attaatggaa gcgtccagta ttacgacgaa gaaggctttc aagttaaggg agagttcgtg    3540
acggacaaag atggacagac gagatatttt gacgagggaa gcggcaacct ggttaaggac    3600
agattcctga acaaggacgg aaagtggtat taccttgacg ataagggact gcttgtcaag    3660
ggagctcaaa caatcaaggg ccagaaactt tatttcgata caaaaacagg agcgcaagtc    3720
aaaggagact ttgtggctga taaggatgga aacctgacgt tttatagcgg cgattcagga    3780
caaatggtgc agtcagactt ctttagcaca ggcaacaatg catggtttta tgcagatgaa    3840
aacggacatg ttgcaaaagg cgcgaagaca atcagaggcc aaaaactgta cttcgacacg    3900
aagacgggac agcaggccaa gggcagattc attagagatg acaaaggcgt gagatactat    3960
gatgcagaca caggcgcact ggtcacaaat gctttcctgg aaacgaaggc tggctcaaat    4020
cagtggtact acatgggagc cgatggatac gcggtgaagg gcaaccagac gatcaagaat    4080
cagcacatgt actttgacgc ggagacgggc caacaagcta agggcatcat cgtcacagat    4140
gcaaatggca gaaagtactt ctatgacacg ttcacgggca gcagagttgt taaccaattt    4200
gttctggtga acggcaattg gtactttga                                      4230
```